United States Patent
Webb et al.

(10) Patent No.: US 9,682,993 B2
(45) Date of Patent: Jun. 20, 2017

(54) ANTICANCER COMPOUNDS

(71) Applicant: ST. JUDE CHILDREN'S RESEARCH HOSPITAL, Memphis, TN (US)

(72) Inventors: Thomas R Webb, Menlo Park, CA (US); Chandraiah Lagisetti, Collierville, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

(21) Appl. No.: 14/650,826

(22) PCT Filed: Dec. 9, 2013

(86) PCT No.: PCT/US2013/073925
§ 371 (c)(1),
(2) Date: Jun. 9, 2015

(87) PCT Pub. No.: WO2014/089571
PCT Pub. Date: Jun. 12, 2014

(65) Prior Publication Data
US 2016/0009728 A1    Jan. 14, 2016

Related U.S. Application Data

(60) Provisional application No. 61/735,054, filed on Dec. 9, 2012.

(51) Int. Cl.
*C07D 493/10*    (2006.01)
*C07D 309/10*    (2006.01)
*A61K 31/351*    (2006.01)

(52) U.S. Cl.
CPC .......... *C07D 493/10* (2013.01); *A61K 31/351* (2013.01); *C07D 309/10* (2013.01)

(58) Field of Classification Search
CPC ... C07D 493/10; C07D 309/10; A61K 31/351
See application file for complete search history.

(56) References Cited

U.S. PATENT DOCUMENTS

| | | |
|---|---|---|
| 2008/0096879 A1 | 4/2008 | Koide et al. |
| 2011/0178098 A1 | 7/2011 | Webb et al. |

FOREIGN PATENT DOCUMENTS

| | | |
|---|---|---|
| WO | WO 2009/031999 A1 | 3/2009 |
| WO | WO 2009/155606 A1 | 12/2009 |

OTHER PUBLICATIONS

Albert et al. (2007) Total syntheses, fragmentation studies, and antitumor/; antiproliferative activities of FR901464 and its low picomolar analogue. J. Am. Chem. Soc., 129: 2648-2659.
Beal, S. L. (2001) Ways to fit a PK model with some data below the quantification limit. *J. Pharmacokinet. Pharmacodyn.* 28: 481.
Chou and Talalay (1984) Quantitative analysis of dose-effect relationships: the combined effects of multiple drugs or enzyme inhibitors. *Adv. Enzyme Regul.* 22: 27.
Corey et al. (1965) Dimethyloxosulfonium methylide and dimethylsulfonium methylide. Formation and application to organic synthesis. J. Am. Chem. Soc., 87: 1353-1364.
Decker et al. (2009) Mammalian epoxide hydrolases in xenobiotic metabolism and signaling. *Arch. Toxicol.* 83: 297.
Fan et al. (2011) Sudemycins, novel small molecule analogues of FR901464, induce alternative gene splicing. *ACS Chem. Biol.* 6: 582.
Fishman et al. (1985) Medicine, 2d Ed., J. B. Lippincott Co., Philadelphia.
Golas, et al. (2003) Molecular Architecture of the Multiprotein Splicing Factor SF3b. Science, 300(5621): 980-984.
Grant No. CA014074 awarded by the National Institutes of Health (NIH).
Gundluru MK, et al. (2011) Design, synthesis and initial biological evaluation of a novel pladienolide analog scaffold. Med Chem Comm, 2(9): 904-908.
Hann et al. (2001) Building 'validated' mouse models of human cancer. *Curr. Opin. Cell Biol.* 13(6): 778-784.
Kaida, et al. (2007) Spliceostatin A targets SF3b and inhibits both splicing and nuclear ; retention of pre-mRNA. Nature Chemical Biology, 3: 576-583.
Kotake Y, et al. (2007) Splicing factor SF3b as a target or the antitumor natural product pladienolide. Nat Chem Biol, 3: 570-575.
Lagisetti et al. (2008) Antitumor Compounds Based on a Natural Product Consensus Pharmacophore. *J. Med. Chem.* 51: 6220-6224.
Lagisetti et al. (2009) Synthetic mRNA Splicing Modulator Compounds with in Vivo Antitumor Activity. *J. Med. Chem.* 52: 6979-6990.
Lagisetti C, et al. (2013) Optimization of Antitumor Modulators of Pre-mRNA Splicing. *J. Med. Chem.* 56: 10033.
Liu et al. (2009) Sorafenib has soluble epoxide hydrolase inhibitory activity, which contributes to its effect profile in vivo. *Mol. Cancer Ther.* 8: 2193.
LoPiccolo et al. (2008) Targeting the PI3K/Akt/mTOR pathway: effective combinations and clinical considerations. *Drug Resist Updat.* 11: 32.
Maione et al. (1991) Inhibition of tumor growth in mice by an analogue of platelet factor 4 that lacks affinity for heparin and retains potent angiostatic activity. *Cancer Res.* 51: 2077.
Maira et al. (2008) Identification and characterization of NVP-BEZ235, a new orally available dual phosphatidylinositol 3-kinase/mammalian target of rapamycin inhibitor with potent in vivo antitumor activity. *Mol. Cancer Ther.* 7: 1851.

(Continued)

Primary Examiner — Sarah Pihonak
(74) Attorney, Agent, or Firm — Ballard Spahr LLP

(57) ABSTRACT

In one aspect, the invention relates to compounds having anticancer activity; synthetic methods for making the compounds; pharmaceutical compositions comprising the compounds; and methods of treating disorders associated with uncontrolled cellular proliferation using the compounds and compositions. This abstract is intended to be used as a scanning tool for purposes of searching in the particular art and is not intended to be limiting of the present invention.

20 Claims, 11 Drawing Sheets

(56) References Cited

OTHER PUBLICATIONS

Malcovati L, et al. (2011) Clinical significance of SF3B1 mutations in myelodysplastic syndromes and myelodysplastic/myeloproliferative neoplasm. Blood, 118(24): 6229-6246.
Massad et al. (1983) A series of (2S)-2-O-protected-2-hydroxypropanals (L-lactaldehydes) suitable for use as optically active intermediates. *The Journal of Organic Chemistry* 48: 5180-5182.
Mitsunobu O. (1981) The use of diethyl azodicarboxylate and triphenylphosphine in synthesis and transformation of natural products. Synthesis, 1981(1): 1-28.
Mizui Y, et al. (2004) Pladienolides, new substances from culture of Streptomyces platenis Mer-11107. III. In vitro and in vivo antitumor activities. J. Antibiot., 57: 188-196.
Motoyoshi H, et al. (2004) Structure-activity relationship for FR901464: a versatile method for the conversion and preparation of biologically active biotinylated proves. Biosci. Biotechnol. Biochem., 68: 2178-2182.
Motoyoshi et al. (2006) Total synthesis of FR901464: second generation. *Tetrahedron* 62: 1378-1389.
Murphy et al. (1997) Informed Decisions: The Complete Book of Cancer Diagnosis, Treatment, and Recovery, Viking Penguin, Penguin Books U.S.A., Inc., United States of America.
Nagarajan S, et al. (1987) Chemistry of naturally occurring polyamines. 11. Unsaturated spermidine and spermine derivatives. J Org. Chem., 52: 5044-5046.
Nakajima H, et al. (1996) New antitumor substances, FR901463, FR901464 and FR901465. II. Activities against experimental tumors in mice and mechanism of action. J. Antibiot (Tokyo), 49(12): 1204-1211.
Nakajima H, et al. (1996) New antitumor substances, FR901463, FR901464 and FR901465. I. Taxonomy, fermentation, isolation, physicochemical properties and biological activities. J. Antibiot., 49: 1196-1203.
Nakajima H, et al. (1997) New antitumor substances, FR901463, FR901464 and FR901465. III. Structures of FR 901463, FR901464 and FR901465. J. Antibiot., 50: 96-99.
Ohta T, et al. (1995) Asymmetric Hydrogenation of Olefins with Aprotic Oxygen Functionalities Catalyzed by BINAP-RU(II) Complexes. J. Org. Chem., 60: 357-363.
Ouellet SG, et al. (2007) Enantioselective organocatalytic transfer hydrogenation reactions using Hantzsch esters. Acc. Chem. Res., 40: 1327-1339.
Pessah N, et al. (2004) Bioactivation of carbamate-based 20(S)-camptothecin prodrugs. Bioorg. Med. Chem., 12: 1859-1866.
Pharmacokinetics, Second Edition; Gibaldi, M.; Perrier, D., Eds.; $2^{nd}$ ed.; CRC Press, 1982.
Robbins and Angell (1976) Basic Pathology, 2d Ed., W.B. Saunders Co., Philadelphia, pp. 112-113.
Rymond B, et al. (2007) Targeting the spliceosome. Nature Chemical Biology, 3: 533-535.
Sage et al. (1995) Inhibition of endothelial cell proliferation by SPARC is mediated through a $Ca^{2+}$-binding EF-hand sequence. *J. Cell. Biochem.* 57: 127.
Thompson CF, et al. (2001) FR901464: total synthesis, proof of structure, and evaluation of synthetic analogues. J. Am. Chem. Soc., 123: 9974-9983.
Tolsma et al. (1993) Peptides derived from two separate domains of the matrix protein thrombospondin-1 have anti-angiogenic activity. *J. Cell Biol.* 122: 497.
Tripathi M, et al. (2012) Sudemycin Selectively Inhibits Growth of Primary Murine Hematopoietic Cells Expressing Mutant U2AF1. Oral and Poster Abstracts. Myelodysplastic Syndromes: Functional/Pathophysiologic studies of MDS. Monday, Dec. 10, 2012 Georgia World Congress Center.
Tuttle JB, et al. (2006) Organocatalytic Transfer Hydrogenation of Cyclic Enones. Journal of the American Chemical Society, 128: 12662-12663.
Valverde S, et al. (1987) The reaction of carbohydrate-derived alkoxyaldehydes with methoxycarbonylmethylenetriphenylphosphorane: stereoselective synthesis of β-unsaturated esters. Tetrahedron, 43: 1895-1901.
Yamanaka N, et al. (2001) Engraftment of tonsillar mononuclear cells in human skin/SCID mouse chimera—validation of a novel xenogeneic transplantation model for autoimmune diseases. Microbiol Immunol, 45(7): 507-514.
Yoon NM, et al. (1973) Selective reductions. XIX. Rapid reaction of carboxylic acides with ; borane-tetrahydrofuran. Remarkably convenient procedure for the selective conversion of carboxylic acids to the corresponding alcohols in the presence of other functional groups. J. Org. Chem., 38: 2786-2792.
International Preliminary Report on Patentability issued by the International Bureau on Dec. 21, 2010 for ; PCT/US2009/048167 filed Jun. 22, 2009 and published as WO 2009/155606 on Dec. 23, 2009 (Applicants 0 St. Jude Children's Research Hospital, et al.; Inventors—Webb, et al.; (10 pages).
International Search Report and Written Opinion issued by the International Bureau on Oct. 5, 2009 for PCT/US2009/048167 filed Jun. 22, 2009 and published as WO 2009/155606 on Dec. 23, 2009 (Applicants—St. Jude Children's Research Hospital, et al.; Inventors—Webb, et al.; (14 pages).
International Search Report mailed on Apr. 8, 2014 for PCT/US2013/73925 filed Dec. 9, 2013 and published as Wo 2014/089571 on Jun. 12, 2014 (Applicants—St. Jude Children's Research Hospital; Inventors—Webb et al.; (2 pages).
Written Opinion mailed on Apr. 8, 2014 for PCT/US2013/73925 filed Dec. 9, 2013 and published as WO 2014/089571 on Jun. 12, 2014 (Applicants—St. Jude Children's Research Hospital; Inventors—Webb et al.; (4 pages).

```
SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: PCR forward primer targeted to human MDM2
      proto-oncogene, E3 ubiquitin protein ligase (MDM2), transcript
      variant 1, mRNA,

<400> SEQUENCE: 1
ctggggagtc ttgagggacc                                              20

<210> SEQ ID NO 2
<211> LENGTH: 20
<212> TYPE: DNA
<213> ORGANISM: Artificial sequence
<220> FEATURE:
<223> OTHER INFORMATION: PCR reverse primer targeted to human MDM2
      proto-oncogene, E3 ubiquitin protein ligase (MDM2), transcript
      variant 1, mRNA,

<400> SEQUENCE: 2
caggttgtct aaattcctag                                              20

<210> SEQ ID NO 3
<211> LENGTH: 24
<212> TYPE: DNA
<213> ORGANISM: Artificial sequence
<220> FEATURE:
<223> OTHER INFORMATION: PCR forward primer targeting ubiquitin A-52
      residue ribosomal protein fusion product 1 (UBA52), transcript
      variant 1, mRNA.

<400> SEQUENCE: 3
acctgaccag cagcgtctga tatt                                         24

<210> SEQ ID NO 4
<211> LENGTH: 24
<212> TYPE: DNA
<213> ORGANISM: Artificial sequence
```

```
<220> FEATURE:
<223> OTHER INFORMATION: PCR reverse primer targeting ubiquitin A-52
      residue ribosomal protein fusion product 1 (UBA52), transcript
      variant 1, mRNA.

<400> SEQUENCE: 4
tcgcagttgt atttctgggc aagc                                          24
```

ANTICANCER COMPOUNDS

CROSS-REFERENCE TO RELATED APPLICATIONS

This Application claims the benefit of priority under 35 U.S.C. §371 of PCT/US2013/073925, filed on Dec. 9, 2013, which claims the benefit under 35 U.S.C. §119(e) of U.S. Provisional Application No. 61/735,054, filed on Dec. 9, 2012, which are incorporated herein by reference in their entireties.

STATEMENT REGARDING FEDERALLY SPONSORED RESEARCH

This invention was made in part with government support under grant number CA014074, awarded by the National Institutes of Health (NIH). The government has certain rights in the invention.

REFERENCE TO A SEQUENCE LISTING SUBMITTED AS A TEXT FILE VIA EFS-WEB

The Sequence Listing submitted herein as a text file named "19116_0018U2_ST25.txt," created on Sep. 22, 2015, and having a size of 1,620 bytes is hereby incorporated by reference pursuant to 37 C.F.R. §1.52(e)(5).

BACKGROUND

Diseases of uncontrolled cellular proliferation, including cancer, can affect people of all ages, including fetuses. Cancer alone is thought to be responsible for approximately 13% of all deaths worldwide. During 2007, about 7.8 million people died of cancer. The production of cancer cells can be caused by various genetic abnormalities, with risk factors including errors in cell replication, exposure to carcinogens, such as radiation, chemicals, or infectious agents. Cancer cells are typically characterized by hyperactive growth and division, protection against programmed cell death, loss of respect for normal tissue boundaries, and the ability to thrive in a diverse range of tissues. Although cancer research remains a burgeoning area of basic and clinical research, there still to date no cure for cancer.

Chemotherapeutic agents and radiation, which cause mutations in actively dividing cells, are intended to selectively kill the cancer cells while not effecting normal cells. Unfortunately, these cytotoxic agents, while effective in managing several types of cancer, are limited in their utility due to adverse side effects and lack of specificity for cancer cells. Advancement in the understanding of cell biology and cancer has led to the advent of new more selective treatments providing hope for cancer patients.

With the development of chemotherapy, survival and recovery rates of cancer patients have improved. However, anticancer agents are problematic in terms of being highly toxic and thus severely damaging to normal cells. To overcome such a side effect of anticancer agents, many recent studies have focused on developing alternative anticancer substances capable of specifically suppressing proliferation of tumor cells.

Unfortunately, however, due to the prevalence of many different types of cancers and due to the complexity of cancers, there still remains a need to develop new anticancer therapeutics, including the development of compounds displaying anticancer activity.

SUMMARY

In accordance with the purpose(s) of the invention, as embodied and broadly described herein, the invention, in one aspect, relates to compounds useful as anticancer agents, modulators of RNA splicing, modulators of the spliceosome, methods of making same, pharmaceutical compositions comprising same, methods of treating disorders using the compounds and compositions, and methods of treating disorders associated with a RNA splicing dysregulation.

Disclosed are compounds having a structure represented by a formula:

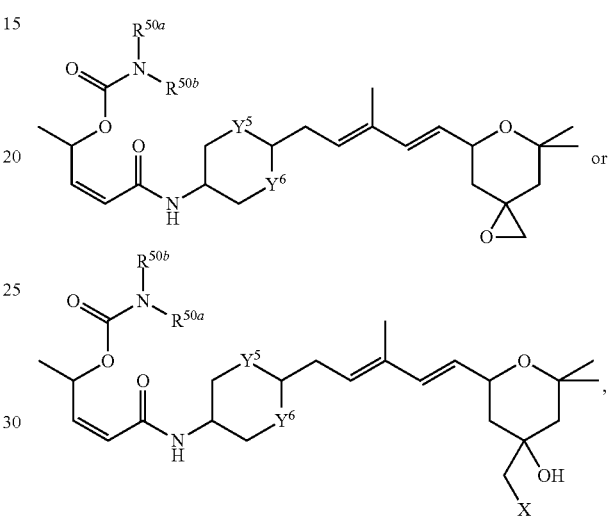

wherein each of $R^{50a}$ and $R^{50b}$ is independently selected from hydrogen, C1-C6 alkyl, C1-C6 monohaloalkyl, and C1-C6 polyhaloalkyl; wherein each of $Y^5$ and $Y^6$ is independently selected from —O— and —CH$_2$—; and wherein X is a leaving group; or a pharmaceutically acceptable salt, solvate, prodrug, or polymorph thereof.

Also disclosed are compounds having a structure represented by a formula:

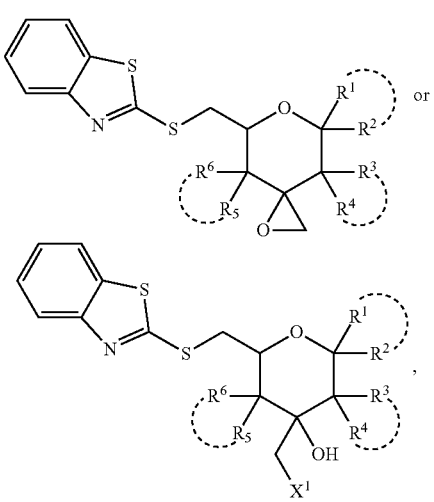

wherein each of $R^1$, $R^2$, $R^3$, $R^4$, $R^5$, and $R^6$ is independently selected from hydrogen, halogen, hydroxyl, amino, thiol, and an optionally substituted organic residue comprising 1 to 6 carbons, and wherein $X^1$ is a leaving group, or a salt or solvate thereof.

Also disclosed are methods of treating a disorder of uncontrolled cellular proliferation in a subject, comprising the step of administering to the subject a therapeutically effective amount of a compound having the structure represented by the formula:

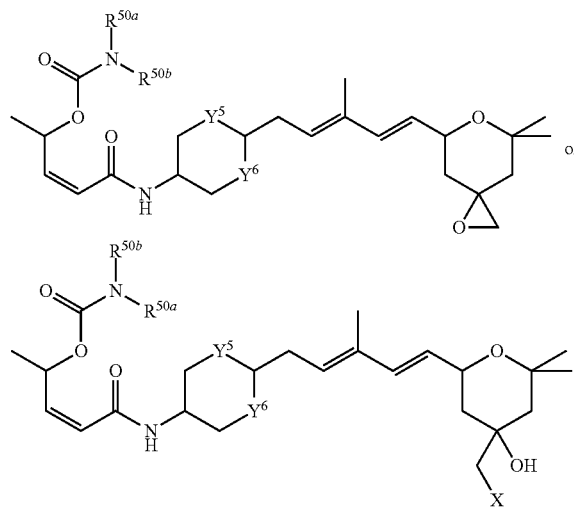

wherein each of $R^{50a}$ and $R^{50b}$ is independently selected from hydrogen, C1-C6 alkyl, C1-C6 monohaloalkyl, and C1-C6 polyhaloalkyl; wherein each of $Y^5$ and $Y^6$ is independently selected from —O— and —CH$_2$—; and wherein X is a leaving group; or a pharmaceutically acceptable salt, solvate, prodrug, or polymorph thereof.

Also disclosed are methods of treating a genetic disorder in a subject, comprising the step of administering to the subject a therapeutically effective amount of a compound having the structure represented by the formula:

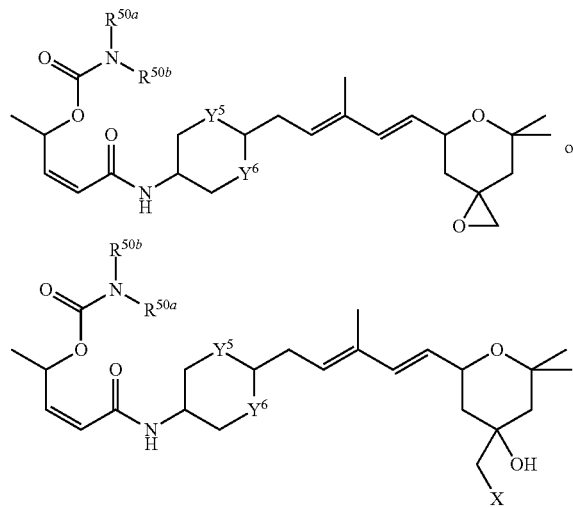

wherein each of $R^{50a}$ and $R^{50b}$ is independently selected from hydrogen, C1-C6 alkyl, C1-C6 monohaloalkyl, and C1-C6 polyhaloalkyl; wherein each of $Y^5$ and $Y^6$ is independently selected from —O— and —CH$_2$—; and wherein X is a leaving group; or a pharmaceutically acceptable salt, solvate, prodrug, or polymorph thereof.

Also disclosed are methods for inhibiting cell replication in at least one cell, comprising the step of contacting at least one cell with an effective amount of a compound having the structure represented by the formula:

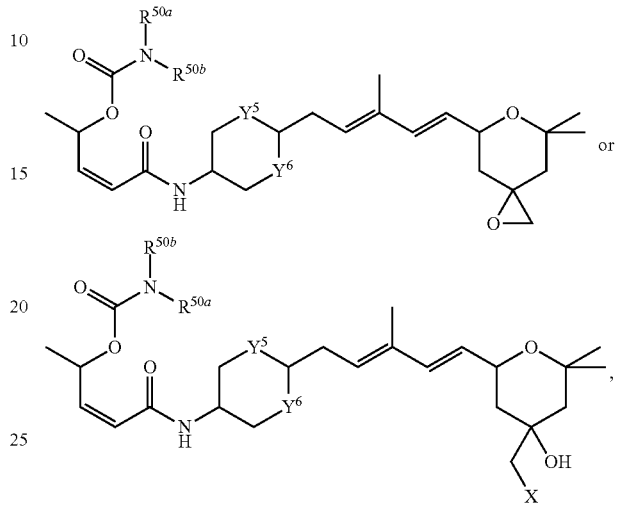

wherein each of $R^{50a}$ and $R^{50b}$ is independently selected from hydrogen, C1-C6 alkyl, C1-C6 monohaloalkyl, and C1-C6 polyhaloalkyl; wherein each of $Y^5$ and $Y^6$ is independently selected from —O— and —CH$_2$—; and wherein X is a leaving group; or a pharmaceutically acceptable salt, solvate, prodrug, or polymorph thereof.

Also disclosed are methods for modulating mRNA splicing in at least one cell, comprising the step of contacting the cell with an effective amount of a compound having the structure represented by the formula:

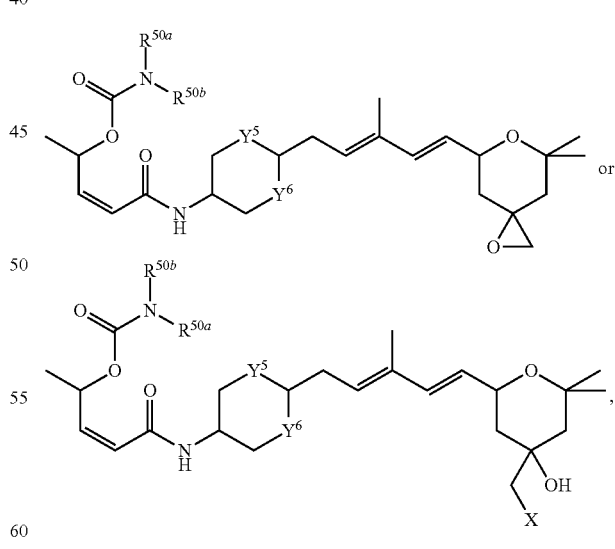

wherein each of $R^{50a}$ and $R^{50b}$ is independently selected from hydrogen, C1-C6 alkyl, C1-C6 monohaloalkyl, and C1-C6 polyhaloalkyl; wherein each of $Y^5$ and $Y^6$ is independently selected from —O— and —CH$_2$—; and wherein X is a leaving group; or a pharmaceutically acceptable salt, solvate, prodrug, or polymorph thereof.

Also disclosed are methods for modulating the activity of at least one spliceosome in at least one cell, comprising the step of contacting the cell with an effective amount of a compound having the structure represented by the formula:

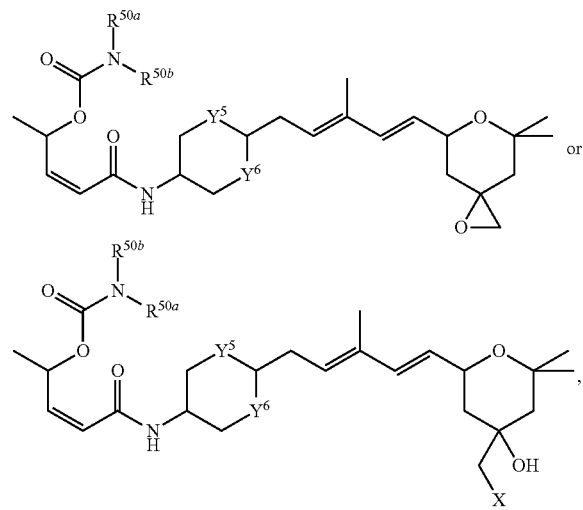

wherein each of $R^{50a}$ and $R^{50b}$ is independently selected from hydrogen, C1-C6 alkyl, C1-C6 monohaloalkyl, and C1-C6 polyhaloalkyl; wherein each of $Y^5$ and $Y^6$ is independently selected from —O— and —CH$_2$—; and wherein X is a leaving group; or a pharmaceutically acceptable salt, solvate, prodrug, or polymorph thereof.

Also kit comprising at least one compound having a structure represented by a formula:

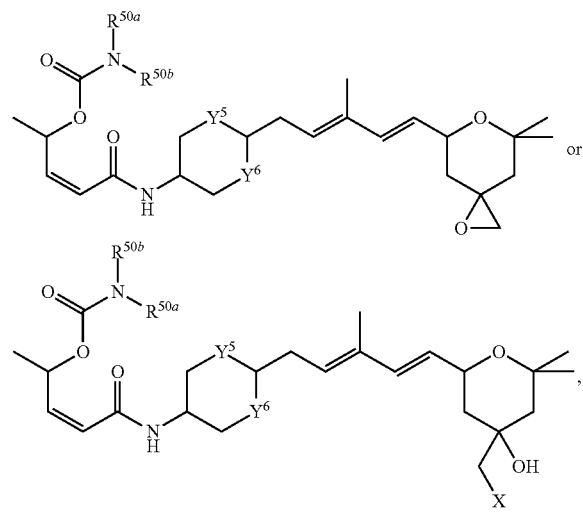

wherein each of $R^{50a}$ and $R^{50b}$ is independently selected from hydrogen, C1-C6 alkyl, C1-C6 monohaloalkyl, and C1-C6 polyhaloalkyl; wherein each of $Y^5$ and $Y^6$ is independently selected from —O— and —CH$_2$—; and wherein X is a leaving group; or a pharmaceutically acceptable salt, solvate, prodrug, or polymorph thereof; and one or more of: (a) at least one agent known to increase spliceosome activity; (b) at least one agent known to decrease spliceosome activity; (c) at least one agent known to treat a disorder of uncontrolled cellular proliferation; or (d) instructions for treating a disorder of uncontrolled cellular proliferation.

Also disclosed are pharmaceutical compositions comprising a therapeutically effective amount of one or more disclosed compounds, or a pharmaceutically acceptable salt, hydrate, solvate, or polymorph thereof, and a pharmaceutically acceptable carrier.

Also disclosed are uses of a disclosed compound, or a pharmaceutically acceptable salt, hydrate, solvate, or polymorph thereof.

Also disclosed are uses of a disclosed compound, or a pharmaceutically acceptable salt, hydrate, solvate, or polymorph thereof, in the manufacture of a medicament for the treatment of a disorder associated with a splicing dysfunction in a mammal.

Also disclosed are uses of a disclosed compound, or a pharmaceutically acceptable salt, hydrate, solvate, or polymorph thereof, in the manufacture of a medicament for the treatment of a disorder of uncontrolled cellular proliferation in a mammal.

Also disclosed are methods of making benzothiazole spiro epoxide derivatives, comprising the steps of: (a) providing a compound having a structure represented by a formula:

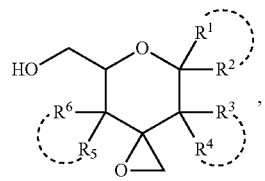

wherein each of $R^1$, $R^2$, $R^3$, $R^4$, $R^5$, and $R^6$ is independently selected from hydrogen, halogen, hydroxyl, amino, thiol, and an optionally substituted organic residue comprising 1 to 6 carbons; and (b) performing a coupling reaction with benzo[d]thiazole-2-thiol to yield the benzothiazole spiro epoxide derivative.

Also disclosed are methods of making (E)-5-(buta-1,3-dien-1-yl)-1,6-dioxaspiro[2.5]octane derivatives comprising the steps of: (a) providing a compound having a structure represented by a formula:

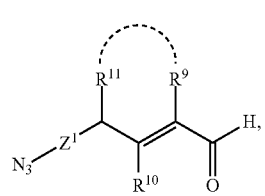

wherein each of $R^9$, $R^{10}$, and $R^{11}$ is independently selected from hydrogen, halogen, hydroxyl, amino, thiol, and an optionally substituted organic residue comprising 1 to 6 carbons; and wherein each ----- is an optional covalent bond; wherein $Z^1$ comprises an optionally substituted 3, 4, 5, 6, or 7 membered ring; and (b) performing a coupling reaction with a compound having a structure represented by a formula:

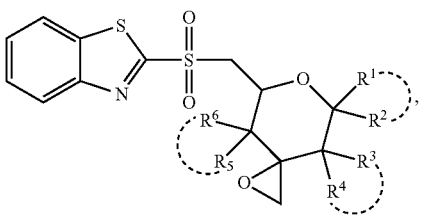

thereby yielding the (E)-5-(buta-1,3-dien-1-yl)-1,6-dioxaspiro[2.5]octane derivative having a structure represented by a formula:

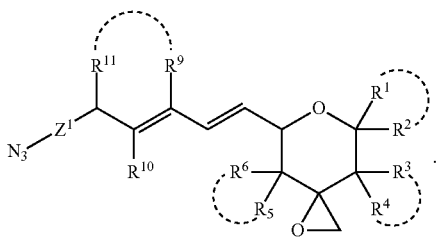

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
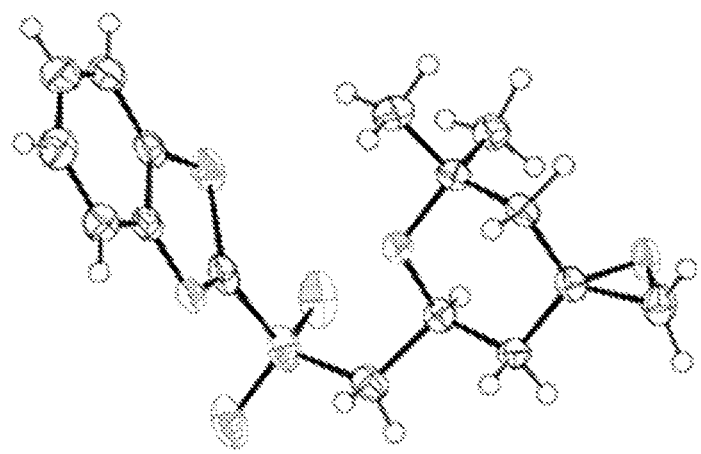
FIG. 1 shows a high resolution single crystal X-ray structure of compound 5.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "SAP130" and "SF3b3" can be used interchangeably and refer a protein encoded by the SF3B3 gene, which has a human gene map locus of 16q22.1, 16q22.1, and 16q22 as defined by Entrez Gene, Ensembl, and HGNC, respectively. These terms refer to a native protein that has 1,217 amino acids and a molecular weight of 135,577 Da. It is a component of splicing factor SF3B. The terms "SAP130" and "SF3b3" are inclusive of the splice isoforms, and also is inclusive of such alternative designations as: Pre-MRNA-Splicing Factor SF3b 130 KDa Subunit; Splicing Factor 3b, Subunit 3, 130 kD; Spliceosome-Associated Protein 130; SF3b130; STAF130; SAP 130; RSE1; Splicing Factor 3B Subunit 3; KIAA0017; and SF3B130, as used by those skilled in the art.

As used herein, the terms "SAP155" and "SF3b1" can be used interchangeably and refer a protein encoded by the SF3B1 gene, which has a gene map locus of 2q33.1 as defined by Entrez Gene, Ensembl, and HGN. These terms refer to a native protein that has 1,304 amino acids and a molecular weight of 145,830 Da. It is a component of splicing factor SF3B. The terms "SAP155" and "SF3b1" are inclusive of the splice isoforms, and also is inclusive of such alternative designations as: splicing factor 3b, subunit 1, 155 kDa; SAP155; SAP 155; spliceosome-associated protein 155; SF3b155; Hsh155; MDS; PRP10; PRPF10; pre-mRNA processing 10; pre-mRNA splicing factor SF3b, 155 kDa subunit; splicing factor 3B subunit 1; pre-mRNA splicing factor SF3b 155 kDa subunit; and SF3B155, as used by those skilled in the art.

As used herein, the terms "sudemycin D1" and "(S,Z)-5-(((1R,4R)-4-((2E,4E)-5-((3R,5S)-7,7-dimethyl-1,6-dioxaspiro[2.5]octan-5-yl)-3-methylpenta-2,4-dien-1-yl)cyclohexyl)amino)-5-oxopent-3-en-2-yl dimethylcarbamate" refer to the compound given by the formula: 1

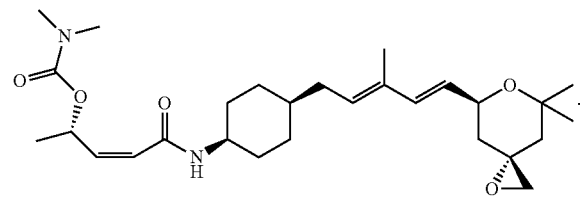 [SMILES: CC(/C=C/[C@@H]1C[C@]2(CO2)CC(C)(C)O1)=C\C[C@H]1CC[C@@H](NC(=O)/C=C\[C@H](C)OC(=O)N(C)C)CC1]

As used herein, the terms "sudemycin D6" and "(S,Z)-5-(((1R,4R)-4-((2E,4E)-5-((3R,5S)-7,7-dimethyl-1,6-dioxaspiro[2.5]octan-5-yl)-3-methylpenta-2,4-dien-1-yl)cyclohexyl)amino)-5-oxopent-3-en-2-yl methylcarbamate" refer to the compound given by the formula:

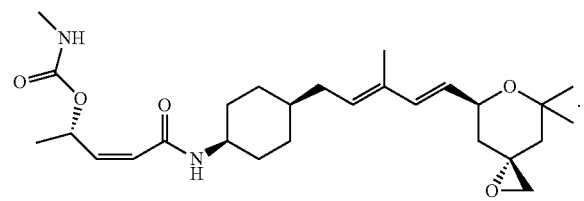 [SMILES: CNC(=O)O[C@@H](C)/C=C\C(=O)N[C@H]1CC[C@@H](C/C=C(C)/C=C/[C@@H]2C[C@]3(CO3)CC(C)(C)O2)CC1]

As used herein, the terms "optional" or "optionally" means that the subsequently described event or circumstance can or cannot occur, and that the description includes instances where said event or circumstance occurs and instances where it does not.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein below. The permissible substituents can be one or more and the same or different for appropriate organic compounds. For purposes of this disclosure, the heteroatoms such as nitrogen can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited to alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic residues, wherein the terms are defined elsewhere herein. Organic residues can preferably comprise 1 to 36 carbons, 1 to 26 carbons, 1 to 18 carbon atoms, 1 to 15 carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

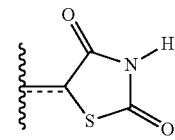

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, for example, 1 to 12 carbon atoms, 1 to 9 carbon atoms, 1 to 6 carbon atoms, 1 to 4 carbon atoms. Examples of alkyl include, but are not limited to methyl, ethyl, n propyl, isopropyl, n butyl, isobutyl, t butyl, pentyl, hexyl, heptyl, octyl, decyl, tetradecyl, hexadecyl, eicosyl, tetracosyl and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, halide, hydroxamate, hydroxy, ketone, nitro, silyl, sulfo-oxo, sulfonyl, sulfone, sulfoxide, or thiol, as described below. The term "halogenated alkyl" specifically refers to an alkyl group that is substituted with one or more halide, e.g., fluorine, chlorine, bromine, or iodine. A "lower alkyl" group is an alkyl group containing from one to six (e.g., from one to four, one to three, or one to two) carbon atoms.

The term "alkoxy" as used herein is an alkyl group bound through a single, terminal ether linkage; that is, an "alkoxy" group can be defined as —OA where A is alkyl as defined above.

The term "alkenyl" as used herein is a hydrocarbon group of from 2 to 24 carbon atoms with a structural formula containing at least one carbon-carbon double bond. Asymmetric structures such as (AB)C=C(CD) are intended to include both the E and Z isomers. This can be presumed in structural formulae herein wherein an asymmetric alkene is present, or it can be explicitly indicated by the bond symbol C=C.

The term "alkynyl" as used herein is a hydrocarbon group of 2 to 24 carbon atoms with a structural formula containing at least one carbon-carbon triple bond, i.e., C≡C.

The term "aryl" as used herein is any carbon-based aromatic group including, but not limited to, benzene, naphthalene, phenyl, biphenyl, etc. The term "aromatic" also includes "heteroaryl," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, halogenated alkyl, alkoxy, alkenyl, alkynyl, aryl, heteroaryl, aldehyde, amino, carboxylic acid, ester, halide, hydroxamate, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, halide, hydroxamate, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and contains at least one carbon-carbon double bound, C=C. Examples of cycloalkenyl groups include, but are not limited to, cyclopropenyl, cyclobutenyl, cyclopentenyl, cyclopentadienyl, cyclohexenyl, etc. The term "heterocycloalkenyl" is a cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, halide, hydroxamate, hydroxy, ketone, nitro, silyl, sulfo-oxo, sulfonyl, sulfone, sulfoxide, or thiol as described herein.

The term "heterocycle" as used herein is intended to include the following groups, which can be optionally substituted: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The term "heterocycle" as used herein is also intended to include, but is not limited to, the following groups which can be optionally substituted: methylenedioxyphenyl, imidazopyridyl, imidazopyrimidinyl, imidazopyridazinyl, imidazopyrazinyl, imidazotriazinyl, imidazothiopheyl, pyrazolopyridyl, pyrazolopyrimidinyl, pyrazolopyridazinyl, pyrazolopyrazinyl, pyrazolotriazinyl, pyrazolothiophenyl, triazolopyridyl, triazolopyrimidinyl, triazolopyridazinyl, triazolopyrazinyl, triazolothiophenyl, tetrahydroimidazopyridinyl, tetrahydropyrazolopyridinyl, tetrahydrotriazopyridinyl, tetrahydrotriazolopyridazinyl, and tetrahydroindazolyl.

The term "heterocycle" as used herein is also intended to include, but is not limited to, the following groups which can be optionally substituted: tetrahydroimidazopyrimidyl, tetrahydroimidazopyrazinyl, tetrahydroimidazopyridazinyl, tetrahydrotriazolopyrimidyl, tetrahydrotriazolopyrazinyl, tetrahydropyrazolopyrimidyl, tetrahydropyrazolopyrazinyl, imidazothiazolyl, and imidazothiadiazolyl.

The term "aldehyde" as used herein is represented by the formula —C(O)H.

The terms "amine" or "amino" as used herein are represented by the formula —NAA$^1$A$^2$, where A, A$^1$, and A$^2$ can be, independently, any suitable substituent, including hydrogen, alkyl, halogenated alkyl, alkenyl, alkynyl, aryl, heteroaryl, cycloalkyl, cycloalkenyl, heterocycloalkyl, or heteroalkenyl group described above. An amino group can be present as an N-oxide. An "N-oxide," as used herein is represented by a formula N(O)AA$^1$A$^2$, where A, A$^1$, and A$^2$ are as defined above. An "N-oxide" can comprise a dative bond, i.e., N→O, which is sometimes represented by the formula, N=O.

The term "carboxylic acid" as used herein is represented by the formula —C(O)OH.

The term "ester" as used herein is represented by the formula —C(O)OA, where A can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula AOA1, where A and A1 can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula —C(O)—.

The term "halide" as used herein refers to the halogens fluorine, chlorine, bromine, and iodine.

The term "hydroxamate" as used herein is represented by the formula —C(O)NHOH.

The term "hydroxyl" as used herein is represented by the formula —OH.

The term "nitro" as used herein is represented by the formula —NO$_2$.

The term "thiol" as used herein is represented by the formula —SH.

The term "cyano" as used herein is represented by the formula —CN.

The term "azide" as used herein is represented by the formula —N$_3$.

The term "carboxamido" as used herein is represented by the formula —C(O)NH—.

The term "trifluoromethyl" as used herein is represented by the formula —CF$_3$.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixtures.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

The term "substantially" as used herein can be applied to modify any quantitative representation which could permissibly vary without resulting in a change in the basic function to which it is related. For example, the term "substantially pure" is intended to refer to a mixture wherein the desired compound is present in from about 70% to about 100% parts by weight, e.g., 75%, 80%, 90%, 95%, 99%. The term "substantially enantiopure" is intended to refer to a mixture of chiral isomers (e.g., enantiomers, diastereomers, meso compounds, and the like) wherein one compound in the mixture is present in about 70%, or about 80%, or about 85%, or about 90%, or about 95% parts by weight.

The term "enantiomeric excess" is intended to refer to the absolute difference between the mole fraction of each enantiomer in an enantiomeric mixture. Thus, enantiomeric excess exists when one enantiomer in a mixture of enantiomers is present in a greater amount than the other(s). As an example, a sample with 70% of an R isomer and 30% of an S will have an enantiomeric excess of 40%. This can also be thought of as a mixture of 40% pure R with 60% of a racemic mixture (which contributes 30% R and 30% S to the overall composition).

The term "hydrolysable residue" is meant to refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis", T. W. Greene, P. G. M. Wuts, Wiley-Interscience, 1999).

The term "leaving group" is meant to refer to an atom (or a group of atoms) with electron withdrawing ability that can be displaced as a stable species, taking with it the bonding electrons. Examples of suitable leaving groups include sulfonate esters, including, but not limited to, triflate, mesylate, tosylate, brosylate, and halides.

Certain instances of the above defined terms can occur more than once in the structural formulae, and upon such occurrence each term shall be defined independently of the other. For example, if more than one compound is represented by a formula comprising an $R^1$ substituent, each $R^1$ of each formula shall be treated independently. Thus, if $R^1$ is defined as alkyl in one instance, $R^1$ is not necessarily alkyl in another instance.

As used herein, and without limitation, the term "derivative" is used to refer to any compound which has a structure derived from the structure of the compounds disclosed herein and whose structure is sufficiently similar to those disclosed herein and based upon that similarity, would be expected, by one skilled in the art, to exhibit the same or similar activities and utilities as the claimed compounds, or to induce, as a precursor, the same or similar activities and utilities as the claimed compounds. For example, a derivative can be a prodrug, a metabolite, or a pharmaceutically acceptable derivative.

The term "pharmaceutically acceptable" means a material that is not biologically or otherwise undesirable, i.e., without causing any undesirable biological effects or interacting in a deleterious manner.

The term "pharmaceutically acceptable derivative" refers to any homolog, analog, or fragment corresponding to the disclosed compounds which can modulate spliceosome activity. A "pharmaceutically acceptable derivative," for example, includes any pharmaceutically acceptable salt, ester, amide, salt of an ester or amide, or other derivative of a disclosed compound.

The term "modulate" or "modulating" refers to the ability of an agent to regulate a desired response, e.g., inhibiting cellular proliferation including cell killing. Modulate, as used herein, can refer to a process by which an agent elevates or reduces, or increases or decreases, a desired response. Modulate refers to the ability of an agent to regulate a response either directly or indirectly. Modulate can refer to a process by which an agent substantially inhibits, stabilizes, or prevents a response when a response would otherwise increase. Modulate can also refer to a process by which an agent substantially stabilizes, enhances, or maintains a response when a response would otherwise decrease. Thus, compounds disclosed herein as spliceosome modulators, can function as inhibitory agents, for example. Included within "inhibitory agents" is a preventative agent, i.e. a compound capable of eliminating uncontrolled cellular proliferation.

As used herein, a "spliceosome" is intended to refer to a ribonucleoprotein complex that removes introns from one or more pre-mRNA segments.

A "cytotoxic" substance is intended to refer to a substance that imparts a toxic effect on a cell. In one aspect, a toxic effect can be a splicing defect. In a further aspect, a splicing defect can result in a toxic effect, and vice versa. In a further aspect, a cytotoxic substance is toxic against a certain cell (e.g., a tumor cell) and non-toxic, or not as toxic, against other cells (e.g., non-tumor cells).

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein.

The term "contacting" as used herein refers to bringing a disclosed compound and a cell or other biological entity together in such a manner that the compound can affect the activity of the target (e.g., the cell, etc.), either directly; i.e., by interacting with the target itself, or indirectly; i.e., by interacting with another molecule, co-factor, factor, or protein on which the activity of the target is dependent.

As used herein, the term "cancer" means any condition characterized by cells displaying uncontrolled growth, invasion of normal tissue, and/or metastasis.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, "diagnosed" means having been subjected to a physical examination by a person of skill, for example, a physician, and found to have a condition that can be diagnosed or treated by the compounds, compositions, or methods disclosed herein. For example, "diagnosed with a disorder associated with uncontrolled cellular proliferation" means having been subjected to a physical examination by a person of skill, for example, a physician, and found to have a condition that can be diagnosed or treated by a compound or composition that can favorably affect uncontrolled cellular proliferation (e.g., a spliceosome modulator).

Disclosed are the components to be used to prepare the compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions. Thus, if there are a variety of additional steps that can be performed it is understood that each of these additional steps can be performed with any specific embodiment or combination of embodiments of the methods.

Certain materials, compounds, compositions, and components disclosed herein can be obtained commercially or synthesized using techniques generally known to those of skill in the art or by methods disclosed herein. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

B. Compounds

In accordance with the purpose(s) of the invention, as embodied and broadly described herein, the invention, in one aspect, relates to compounds useful as anticancer agents, modulators of RNA splicing, modulators of the spliceosome, methods of making same, pharmaceutical compositions comprising same, methods of treating disorders using the compounds and compositions, and methods of treating disorders associated with a RNA splicing dysregulation.

In various aspects, the disclosed compounds modulate the activity of a spliceosome. In a further aspect, the disclosed compounds destabilize the SF3b spliceosome subunit. In a still further aspect, the disclosed compounds interfere with the integration of the SF3b subunit into the U2 snRNP. In a yet further aspect, the disclosed compounds interfere with the U2 snRNP spliceosome recruitment.

In a further aspect, the disclosed compounds can bind to a protein of the SF3b subunit. In a still further aspect, the protein of the SF3b subunit that disclosed compounds can bind is selected from the SAP130 protein and the SAP155 protein. In a yet further aspects, the disclosed compounds can bind the SAP130 protein of the SF3b subunit. In an even further aspect, the disclosed compounds can bind the SAP155 protein of the SF3b subunit.

In various aspects, the disclosed compounds have cytotoxic activity on a cell. In a further aspect, the cell is a mammalian cell. In a still further aspect, the mammalian cell is human. In a yet further aspect, the mammalian cell is murine.

In a further aspect, the disclosed compounds are cytotoxic against at least one cancer cell line. In a still further aspect, the cancer cell line is selected from PC3, JeKo-1, JVM-2, and WIDr cells. In a yet further aspect, the cancer cell line is a leukemia cell. In an even further aspect, the leukemia cell line is JeKo-1. In a still further aspect, the cancer cell line is a lymphoma cell line. In a yet further aspect, lymphoma cell line is JVM-2 (ATCC CRL-3002).

In a further aspect, the disclosed compounds have cytotoxic activity on a cell associated with uncontrolled cellular proliferation. In a yet further aspect, the cell associated with uncontrolled cellular proliferation is a cancer cell. In an even further aspect, the cell is a cell cultured in vitro. In a still further aspect, the cell is in vivo.

In various aspects, the disclosed compounds disrupt or inhibit cellular processes such as cell replication. In a further aspect, the cellular process that is disrupt or inhibited is RNA splicing. In a still further aspect, the disclosed compounds are capable of inducing a splicing defect in at least one cell.

In various aspects, the disclosed compounds treat a genetic disorder, including, but not limited to, a genetic disorder associated with RNA splicing. In a further aspect, the genetic disorder is associated with a mutation.

It is understood that the disclosed compounds can be used in connection with the disclosed methods, compositions, kits, and uses. It is also contemplated that any one or more disclosed compound can be optionally omitted from the invention.

1. Structure

In one aspect, disclosed are compounds having a structure represented by a formula:

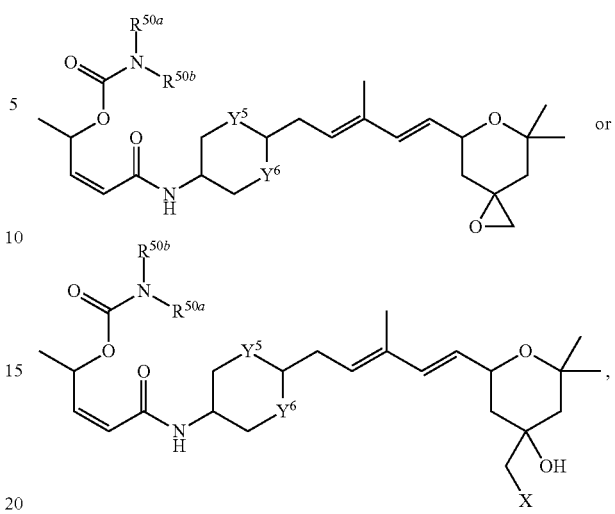

wherein each of $R^{50a}$ and $R^{50b}$ is independently selected from hydrogen, C1-C6 alkyl, C1-C6 monohaloalkyl, and C1-C6 polyhaloalkyl; wherein each of $Y^5$ and $Y^6$ is independently selected from —O— and —CH$_2$—; and wherein X is a leaving group; or a pharmaceutically acceptable salt, solvate, prodrug, or polymorph thereof.

In a further aspect, the compound has a structure represented by a formula listed below:

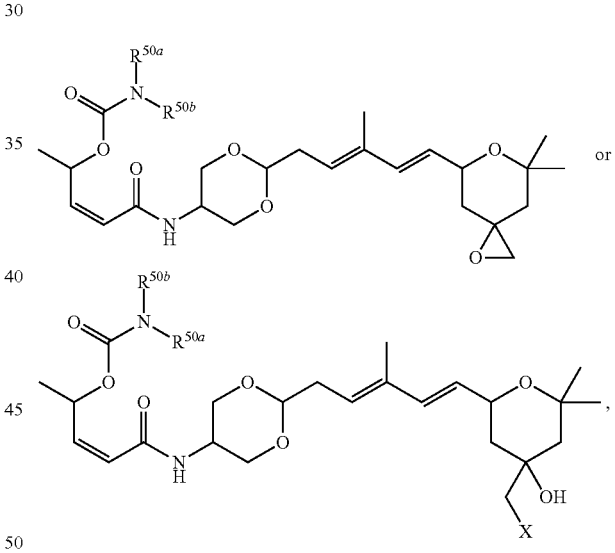

and wherein all variables are as defined herein.

In a further aspect, the compound has a structure represented by a formula listed below:

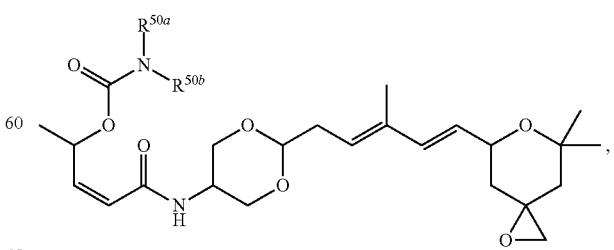

and wherein all variables are as defined herein.

In a further aspect, the compound has a structure represented by a formula listed below:

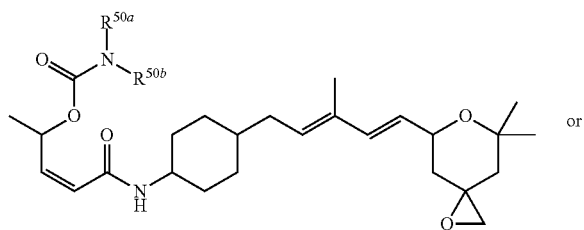

or

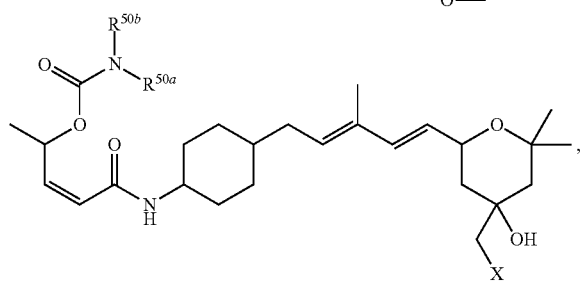

and wherein all variables are as defined herein.

In a further aspect, the compound has a structure represented by a formula listed below:

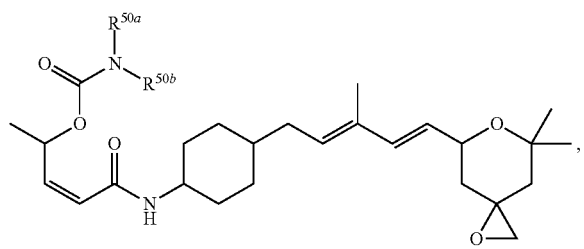

and wherein all variables are as defined herein.

In a further aspect, the compound has a structure represented by a formula listed below:

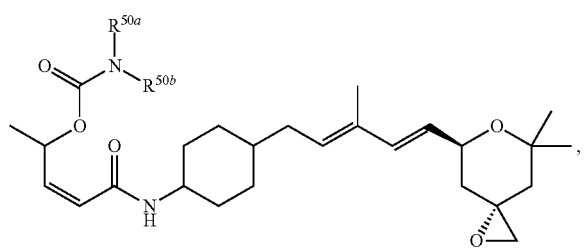

and wherein all variables are as defined herein.

In a further aspect, the compound has a structure represented by a formula listed below:

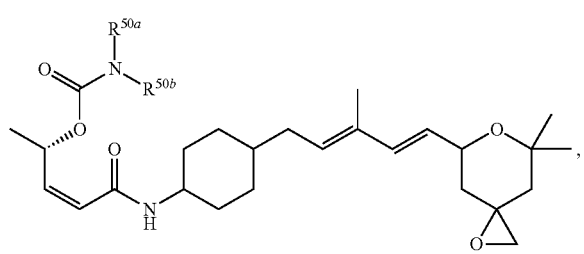

and wherein all variables are as defined herein.

In a further aspect, the compound has a structure represented by a formula listed below:

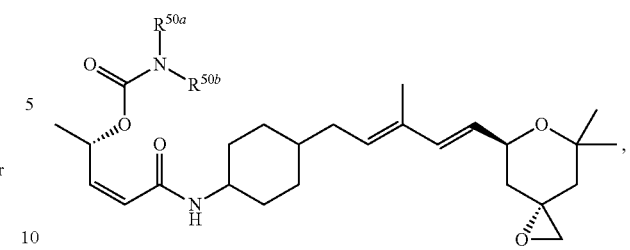

and wherein all variables are as defined herein.

In a further aspect, the compound has a structure represented by a formula listed below:

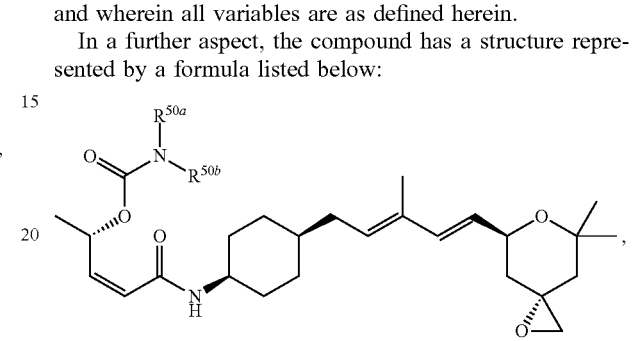

and wherein all variables are as defined herein.

In a further aspect, the compound has a structure represented by a formula listed below:

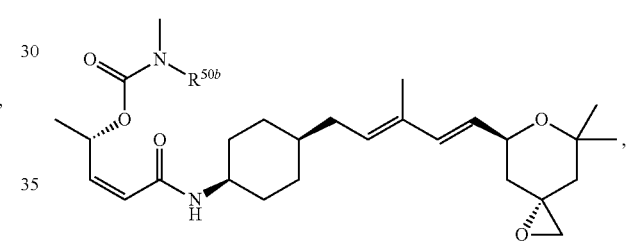

and wherein all variables are as defined herein.

In a further aspect, the compound has a structure represented by a formula listed below:

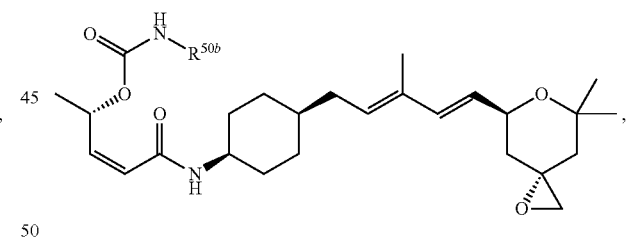

and wherein all variables are as defined herein.

In a further aspect, the compound has a structure represented by a formula listed below:

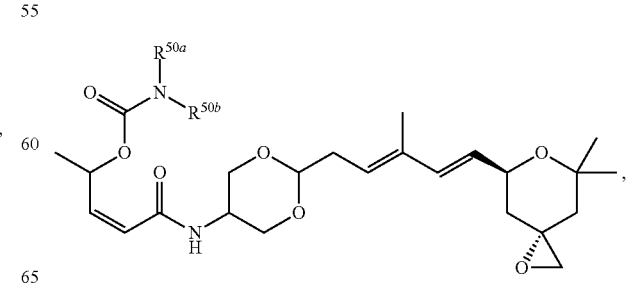

and wherein all variables are as defined herein.

In a further aspect, the compound has a structure represented by a formula listed below:

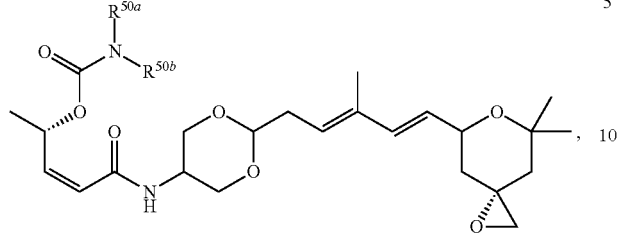

and wherein all variables are as defined herein.

In a further aspect, the compound has a structure represented by a formula listed below:

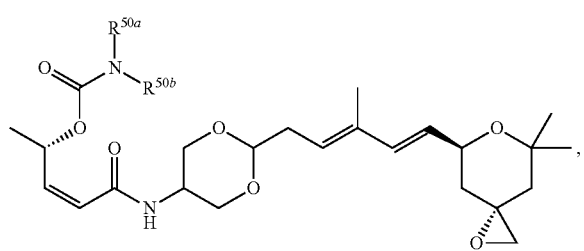

and wherein all variables are as defined herein.

In a further aspect, the compound has a structure represented by a formula listed below:

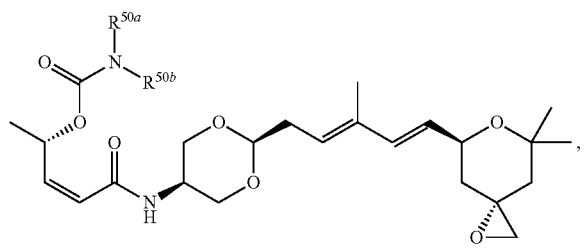

and wherein all variables are as defined herein.

In a further aspect, the compound has a structure represented by a formula listed below:

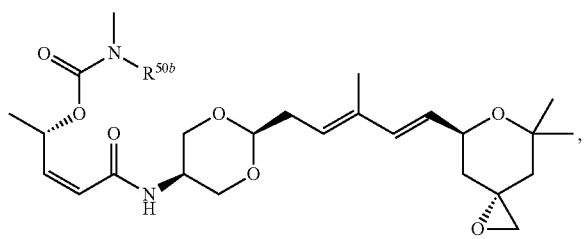

and wherein all variables are as defined herein.

In a further aspect, the compound has a structure represented by a formula listed below:

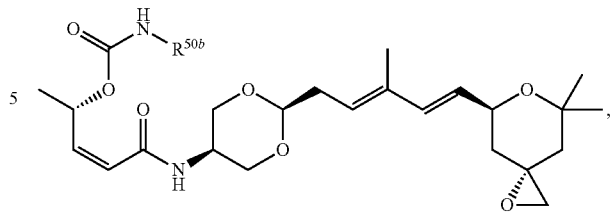

and wherein all variables are as defined herein.

In one aspect, a pyran derivative, as disclosed herein, can convert into a dioxaspiro derivative, as disclosed herein, which can be represented by the following reaction scheme:

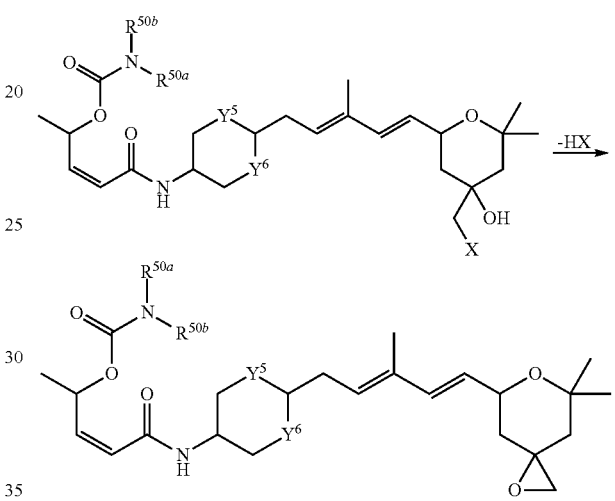

In a further aspect, a non-active pyran derivative can convert into an active dioxaspiro derivative. Thus, in this example, a pyran derivative, while not necessarily active, can function as a precursor, or prodrug, from which an active therapeutic agent can be generated.

In various aspects, the compound comprises a single diastereomer. For example, the compound can be substantially enantiopure.

Suitable substituents are described below.

a. $R^1$, $R^2$, $R^3$, $R^4$, $R^5$, and $R^6$ Groups

In one aspect, each of $R^1$, $R^2$, $R^3$, $R^4$, $R^5$, and $R^6$ is independently selected from hydrogen, halogen, hydroxyl, amino, thiol, and an optionally substituted organic residue comprising 1 to 6 carbons. In a further aspect, each of $R^1$, $R^2$, $R^3$, $R^4$, $R^5$, and $R^6$ is independently selected from hydrogen, halogen, hydroxyl, amino, thiol, and C1-C6 alkyl.

In a further aspect, neither $R^5$ nor $R^6$ is hydroxyl. In a still further aspect, at least one of $R^5$ and $R^6$ is hydroxyl.

In a further aspect, $R^1$ and $R^2$ is independently selected from hydroxyl, methyl, ethyl, propyl, or butyl, and each of $R^3$, $R^4$, $R^5$, and $R^6$ is hydrogen. In a still further aspect, each of $R^1$ and $R^2$ is methyl. In one aspect, at least one of $R^1$ and $R^2$ is hydroxyl.

In a further aspect, each of $R^1$, $R^2$, $R^3$, $R^4$, $R^5$, and $R^6$ is independently selected from hydrogen and an optionally substituted organic residue comprising 1 to 6 carbons. In a still further aspect, each of $R^1$, $R^2$, $R^3$, $R^4$, $R^5$, and $R^6$ is independently selected from hydrogen and C1-C6 alkyl. In a yet further aspect, each of $R^1$, $R^2$, $R^3$, $R^4$, $R^5$, and $R^6$ is independently selected from hydrogen, methyl, ethyl, propyl, and isopropyl. In an even further aspect, each of $R^1$, $R^2$, $R^3$, $R^4$, $R^5$, and $R^6$ is independently selected from hydrogen and methyl.

In a further aspect, each of $R^1$ and $R^2$ is independently selected from hydrogen and an optionally substituted organic residue comprising 1 to 6 carbons; and each of $R^3$, $R^4$, $R^5$, and $R^6$ is hydrogen. In a still further aspect, each of $R^1$ and $R^2$ is independently selected from hydrogen and C1-C6 alkyl; and each of $R^3$, $R^4$, $R^5$, and $R^6$ is hydrogen. In a yet further aspect, each of $R^1$ and $R^2$ is independently selected from hydrogen, methyl, ethyl, propyl, and isopropyl; and each of $R^3$, $R^4$, $R^5$, and $R^6$ is hydrogen. In an even further aspect, each of $R^1$ and $R^2$ is independently selected from hydrogen and methyl; and wherein each of $R^3$, $R^4$, $R^5$, and $R^6$ is hydrogen.

In a further aspect, each of $R^1$ and $R^2$ is methyl; and each of $R^3$, $R^4$, $R^5$, and $R^6$ is hydrogen.

b. $R^9$, $R^{10}$, and Groups

In one aspect, each of $R^9$, $R^{10}$, and $R^{11}$ is independently selected from hydrogen, halogen, hydroxyl, amino, thiol, and an optionally substituted organic residue comprising 1 to 6 carbons; and wherein each ----- is an optional covalent bond.

In a further aspect, each of $R^9$, $R^{10}$, and $R^{11}$ is independently selected from hydrogen and optionally substituted organic residue comprising from 1 to 4 carbons. In a still further aspect, $R^9$ is methyl. In a further aspect, each of $R^9$, $R^{10}$, and $R^{11}$ is hydrogen.

c. $R^{14}$ and $R^{15}$ Groups

In one aspect, each of $R^{14}$ and $R^{15}$ is independently selected from hydrogen and optionally substituted C1-C4 alkyl. In a further aspect, each of $R^{14}$ and $R^{15}$ is hydrogen.

In a further aspect, each of $R^{14}$ and $R^{15}$ is independently selected from hydrogen, methyl, ethyl, propyl, and isopropyl. In a still further aspect, each of $R^{14}$ and $R^{15}$ is independently selected from hydrogen, methyl, and ethyl. In a yet further aspect, each of $R^{14}$ and $R^{15}$ is independently selected from hydrogen and methyl.

In a further aspect, $R^{14}$ is hydrogen and $R^{15}$ is selected from hydrogen, methyl, ethyl, propyl, and isopropyl. In a still further aspect, $R^{14}$ is hydrogen and $R^{15}$ is selected from hydrogen, methyl, and ethyl. In a yet further aspect, $R^{14}$ is hydrogen and $R^{15}$ is selected from hydrogen and methyl. In an even further aspect, $R^{14}$ is hydrogen and $R^{15}$ is methyl. In a still further aspect, $R^{14}$ is hydrogen and $R^{15}$ is ethyl.

d. $R^{50a}$ and $R^{50b}$ Groups

In one aspect, each of $R^{50a}$ and $R^{50b}$ is independently selected from hydrogen, C1-C6 alkyl, C1-C6 monohaloalkyl, and C1-C6 polyhaloalkyl. In a further aspect, both of $R^{50a}$ and $R^{50b}$ are not simultaneously hydrogen.

In a further aspect, each of $R^{50a}$ and $R^{50b}$ is independently selected from hydrogen, C1-C4 alkyl, C1-C4 monohaloalkyl, and C1-C4 polyhaloalkyl. In a still further aspect, each of $R^{50a}$ and $R^{50b}$ is independently selected from hydrogen, methyl, ethyl, propyl, isopropyl, tert-butyl, sec-butyl, isobutyl, tert-butyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a yet further aspect, each of $R^{50a}$ and $R^{50b}$ is independently selected from hydrogen, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In an even further aspect, each of $R^{50a}$ and $R^{50b}$ is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, each of $R^{50a}$ and $R^{50b}$ is independently selected from hydrogen, methyl, ethyl, —CH$_2$F, —CH$_2$CH$_2$F, —CHF$_2$, —CF$_3$, —CH$_2$CHF$_2$, and —CH$_2$CF$_3$. In a yet further aspect, each of $R^{50a}$ and $R^{50b}$ is independently selected from hydrogen, methyl, —CH$_2$F, —CHF$_2$, and —CF$_3$.

In a further aspect, each of $R^{50a}$ and $R^{50b}$ is independently hydrogen, C1-C6 monohaloalkyl, and C1-C6 polyhaloalkyl. In a still further aspect, each of $R^{50a}$ is hydrogen and $R^{50b}$ is selected from hydrogen, C1-C4 monohaloalkyl, and C1-C4 polyhaloalkyl. In a yet further aspect, each of $R^{50a}$ and $R^{50b}$ is independently selected from hydrogen, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In an even further aspect, each of $R^{50a}$ and $R^{50b}$ is independently selected from hydrogen, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a still further aspect, each of $R^{50a}$ and $R^{50b}$ is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, each of $R^{50a}$ and $R^{50b}$ is independently selected from hydrogen, —CH$_2$F, —CH$_2$CH$_2$F, —CHF$_2$, —CF$_3$, —CH$_2$CHF$_2$, and —CH$_2$CF$_3$. In an even further aspect, each of $R^{50a}$ and $R^{50b}$ is independently selected from hydrogen, —CH$_2$F, —CHF$_2$, and —CF$_3$.

In a further aspect, each of $R^{50a}$ and $R^{50b}$ is independently selected from hydrogen and C1-C6 alkyl. In a still further aspect, each of $R^{50a}$ and $R^{50b}$ is independently selected from hydrogen and C1-C4 alkyl. In a yet further aspect, each of $R^{50a}$ and $R^{50b}$ is independently selected from hydrogen, methyl, ethyl, and propyl, and isopropyl. In an even further aspect, each of $R^{50a}$ and $R^{50b}$ is independently selected from hydrogen, methyl, and ethyl. In a still further aspect, each of $R^{50a}$ and $R^{50b}$ is independently selected from hydrogen and methyl. In a yet further aspect, each of $R^{50a}$ and $R^{50b}$ is independently selected from hydrogen and ethyl.

In a further aspect, each of $R^{50a}$ and $R^{50b}$ is independently selected from C1-C6 alkyl, C1-C6 monohaloalkyl, and C1-C6 polyhaloalkyl. In a still further aspect, each of $R^{50a}$ and $R^{50b}$ is independently selected from C1-C4 alkyl, C1-C4 monohaloalkyl, and C1-C4 polyhaloalkyl. In a yet further aspect, each of $R^{50a}$ and $R^{50b}$ is independently selected from methyl, ethyl, propyl, isopropyl, tert-butyl, sec-butyl, isobutyl, tert-butyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In an even further aspect, each of R$^{50a}$ and R$^{50b}$ is independently selected from methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a still further aspect, each of R$^{50a}$ and R$^{50b}$ is independently selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, each of R$^{50a}$ and R$^{50b}$ is independently selected from methyl, ethyl, —CH$_2$F, —CH$_2$CH$_2$F, —CHF$_2$, —CF$_3$, —CH$_2$CHF$_2$, and —CH$_2$CF$_3$. In an even further aspect, each of R$^{50a}$ and R$^{50b}$ is independently selected from methyl, —CH$_2$F, —CHF$_2$, and —CF$_3$.

In a further aspect, each of R$^{50a}$ and R$^{50b}$ is independently selected from C1-C6 monohaloalkyl and C1-C6 polyhaloalkyl. In a still further aspect, each of R$^{50a}$ and R$^{50b}$ is independently selected from C1-C4 monohaloalkyl and C1-C4 polyhaloalkyl. In a yet further aspect, each of R$^{50a}$ and R$^{50b}$ is independently selected from —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In an even further aspect, each of R$^{50a}$ and R$^{50b}$ is independently selected from —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a still further aspect, each of R$^{50a}$ and R$^{50b}$ is independently selected from —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, each of R$^{50a}$ and R$^{50b}$ is independently selected from —CH$_2$F, —CH$_2$CH$_2$F, —CHF$_2$, —CF$_3$, —CH$_2$CHF$_2$, and —CH$_2$CF$_3$. In an even further aspect, each of R$^{50a}$ and R$^{50b}$ is independently selected from —CH$_2$F, —CHF$_2$, and —CF$_3$.

In a further aspect, each of R$^{50a}$ and R$^{50b}$ is independently C1-C6 alkyl. In a still further aspect, each of R$^{50a}$ and R$^{50b}$ is independently C1-C4 alkyl. In a yet further aspect, each of R$^{50a}$ and R$^{50b}$ is independently selected from methyl, ethyl, and propyl, and isopropyl. In an even further aspect, each of R$^{50a}$ and R$^{50b}$ is independently selected from methyl and ethyl.

In a further aspect, each of R$^{50a}$ and R$^{50b}$ is hydrogen. In a still further aspect, each of R$^{50a}$ and R$^{50b}$ is ethyl. In a yet further aspect, each of R$^{50a}$ and R$^{50b}$ is methyl. In an even further aspect, each of R$^{50a}$ and R$^{50b}$ is —CH$_2$F. In a still further aspect, each of R$^{50a}$ and R$^{50b}$ is —CHF$_2$. In a yet further aspect, each of R$^{50a}$ and R$^{50b}$ is —CF$_3$.

In a further aspect, R$^{50a}$ is hydrogen and R$^{50b}$ is selected from hydrogen, C1-C6 alkyl, C1-C6 monohaloalkyl, and C1-C6 polyhaloalkyl. In a still further aspect, R$^{50a}$ is hydrogen and R$^{50b}$ is selected from hydrogen, C1-C4 alkyl, C1-C4 monohaloalkyl, and C1-C4 polyhaloalkyl. In a yet further aspect, R$^{50a}$ is hydrogen and R$^{50b}$ is selected from hydrogen, methyl, ethyl, propyl, isopropyl, tert-butyl, sec-butyl, isobutyl, tert-butyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In an even further aspect, R$^{50a}$ is hydrogen and R$^{50b}$ is selected from hydrogen, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a still further aspect, R$^{50a}$ is hydrogen and R$^{50b}$ is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, R$^{50a}$ is hydrogen and R$^{50b}$ is selected from hydrogen, methyl, ethyl, —CH$_2$F, —CH$_2$CH$_2$F, —CHF$_2$, —CF$_3$, —CH$_2$CHF$_2$, and —CH$_2$CF$_3$. In an even further aspect, R$^{50a}$ is hydrogen and R$^{50b}$ is selected from hydrogen, methyl, —CH$_2$F, —CHF$_2$, and —CF$_3$.

In a further aspect, R$^{50a}$ is hydrogen and R$^{50b}$ is selected from hydrogen, C1-C6 monohaloalkyl, and C1-C6 polyhaloalkyl. In a still further aspect, R$^{50a}$ is hydrogen and R$^{50b}$ is selected from hydrogen, C1-C4 monohaloalkyl, and C1-C4 polyhaloalkyl. In a yet further aspect, R$^{50a}$ is hydrogen and R$^{50b}$ is selected from hydrogen, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In an even further aspect, R$^{50a}$ is hydrogen and R$^{50b}$ is selected from hydrogen, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a still further aspect, R$^{50a}$ is hydrogen and R$^{50b}$ is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, R$^{50a}$ is hydrogen and R$^{50b}$ is selected from hydrogen, —CH$_2$F, —CH$_2$CH$_2$F, —CHF$_2$, —CF$_3$, —CH$_2$CHF$_2$, and —CH$_2$CF$_3$. In an even further aspect, R$^{50a}$ is hydrogen and R$^{50b}$ is selected from hydrogen, —CH$_2$F, —CHF$_2$, and —CF$_3$.

In a further aspect, R$^{50a}$ is hydrogen and R$^{50b}$ is selected from hydrogen and C1-C6 alkyl. In a still further aspect, R$^{50a}$ is hydrogen and R$^{50b}$ is selected from hydrogen and C1-C4 alkyl. In a yet further aspect, R$^{50a}$ is hydrogen and R$^{50b}$ is selected from hydrogen, methyl, ethyl, and propyl, and isopropyl. In an even further aspect, R$^{50a}$ is hydrogen and R$^{50b}$ is selected from hydrogen, methyl, and ethyl.

In a further aspect, R$^{50a}$ is hydrogen and R$^{50b}$ is selected from C1-C6 alkyl, C1-C6 monohaloalkyl, and C1-C6 polyhaloalkyl. In a still further aspect, R$^{50a}$ is hydrogen and R$^{50b}$ is selected from C1-C4 alkyl, C1-C4 monohaloalkyl, and C1-C4 polyhaloalkyl. In a yet further aspect, $R^{50a}$ is hydrogen and $R^{50b}$ is selected from methyl, ethyl, propyl, isopropyl, tert-butyl, sec-butyl, isobutyl, tert-butyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In an even further aspect, $R^{50a}$ is hydrogen and $R^{50b}$ is selected from methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a still further aspect, $R^{50a}$ is hydrogen and $R^{50b}$ is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, $R^{50a}$ is hydrogen and $R^{50b}$ is selected from methyl, ethyl, —CH$_2$F, —CH$_2$CH$_2$F, —CHF$_2$, —CF$_3$, —CH$_2$CHF$_2$, and —CH$_2$CF$_3$. In a still further aspect, $R^{50a}$ is hydrogen and $R^{50b}$ is selected from methyl, —CH$_2$F, —CHF$_2$, and —CF$_3$.

In a further aspect, $R^{50a}$ is hydrogen and $R^{50b}$ is selected from C1-C6 monohaloalkyl and C1-C6 polyhaloalkyl. In a still further aspect, $R^{50a}$ is hydrogen and $R^{50b}$ is selected from C1-C4 monohaloalkyl and C1-C4 polyhaloalkyl. In a yet further aspect, $R^{50a}$ is hydrogen and $R^{50b}$ is selected from —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In an even further aspect, $R^{50a}$ is hydrogen and $R^{50b}$ is selected from —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a still further aspect, $R^{50a}$ is hydrogen and $R^{50b}$ is selected from —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, $R^{50a}$ is hydrogen and $R^{50b}$ is selected from —CH$_2$F, —CH$_2$CH$_2$F, —CHF$_2$, —CF$_3$, —CH$_2$CHF$_2$, and —CH$_2$CF$_3$. In an even further aspect, $R^{50a}$ is hydrogen and $R^{50b}$ is selected from —CH$_2$F, —CHF$_2$, and —CF$_3$.

In a further aspect, $R^{50a}$ is hydrogen and $R^{50b}$ is C1-C6 alkyl. In a still further aspect, $R^{50a}$ is hydrogen and $R^{50b}$ is C1-C4 alkyl. In a yet further aspect, $R^{50a}$ is hydrogen and $R^{50b}$ is selected from methyl, ethyl, and propyl, and isopropyl. In an even further aspect, $R^{50a}$ is hydrogen and $R^{50b}$ is selected from methyl and ethyl.

In a further aspect, $R^{50a}$ is hydrogen and $R^{50b}$ is —CH$_2$F. In a still further aspect, $R^{50a}$ is hydrogen and $R^{50b}$ is —CHF$_2$. In a yet further aspect, $R^{50a}$ is hydrogen and $R^{50b}$ is —CF$_3$. In an even further aspect, $R^{50a}$ is hydrogen and $R^{50b}$ is ethyl. In a still further aspect, $R^{50a}$ is hydrogen and $R^{50b}$ is methyl.

e. X Groups

In one aspect, X is a leaving group. In a further aspect, X is selected from halogen and sulfonate ester.

In a further aspect, X is a halogen. In a still further aspect, X is selected from chloro, bromo, and iodo. In a yet further aspect, X is selected from chloro and bromo. In an even further aspect, X is chloro. In a still further aspect, X is bromo. In a yet further aspect, X is iodo.

In a further aspect, X is a sulfonate ester. In a still further aspect, X is selected from triflate, mesylate, tosylate, and brosylate. In a yet further aspect, X is triflate. In an even further aspect, X is mesylate. In an even further aspect, X is tosylate. In a still further aspect, X is brosylate.

f. $X^1$ Groups

In one aspect, $X^1$ is a leaving group. In a further aspect, $X^1$ is selected from halogen and sulfonate ester.

In a further aspect, $X^1$ is a halogen. In a still further aspect, $X^1$ is selected from chloro, bromo, and iodo. In a yet further aspect, $X^1$ is selected from chloro and bromo. In an even further aspect, $X^1$ is chloro. In a still further aspect, $X^1$ is bromo. In a yet further aspect, $X^1$ is iodo.

In a further aspect, $X^1$ is a sulfonate ester. In a still further aspect, $X^1$ is selected from triflate, mesylate, tosylate, and brosylate. In a yet further aspect, $X^1$ is triflate. In an even further aspect, $X^1$ is mesylate. In an even further aspect, $X^1$ is tosylate. In a still further aspect, $X^1$ is brosylate.

g. $Y^1$, $Y^2$, $Y^3$, and $Y^4$ Groups

In one aspect, each of $Y^1$, $Y^2$, $Y^3$, and $Y^4$ is independently selected from oxygen, optionally substituted carbon, and optionally substituted nitrogen; wherein the optionally substituted nitrogen has a structure represented by the formula, $NR^{14}R^{15}$; wherein each of $R^{14}$ and $R^{15}$ is independently selected from hydrogen and optionally substituted C1-C4 alkyl; and wherein is an optional covalent bond.

In a further aspect, each of $Y^1$ and $Y^4$ is —CH$_2$—; wherein each of $Y^2$ and $Y^3$ is independently selected from —O— and —CH$_2$—. In a still further aspect, each of $Y^2$ and $Y^3$ is —O—. In a yet further aspect, each of $Y^2$ and $Y^3$ is —CH$_2$—. In an even further aspect, each of $Y^2$ is —O— and $Y^3$ is —CH$_2$—.

In a further aspect, each of $Y^2$ and $Y^3$ is —CH$_2$—; wherein each of $Y^1$ and $Y^4$ is independently selected from —O— and —CH$_2$—. In a still further aspect, each of $Y^1$ and $Y^4$ is —O—. In a yet further aspect, each of $Y^1$ and $Y^4$ is —CH$_2$—. In an even further aspect, each of $Y^1$ is —O— and $Y^4$ is —CH$_2$—.

In a further aspect, each of $Y^1$, $Y^2$, $Y^3$, and $Y^4$ is —CH$_2$—.

h. $Y^5$ and $Y^6$ Groups

In one aspect, each of $Y^5$ and $Y^6$ is independently selected from —O— and —CH$_2$—. In a further aspect, each of $Y^5$ and $Y^6$ is —CH$_2$—. In a still further aspect, each of $Y^5$ and $Y^6$ is —O—. In a yet further aspect, $Y^5$ is —CH$_2$— and $Y^6$ is —O—.

i. $Z^1$ Groups

In one aspect, $Z^1$ comprises an optionally substituted 3, 4, 5, 6, or 7 membered ring. In a further aspect, $Z^1$ is an optionally substituted 3 membered ring. In a still further aspect, $Z^1$ is an optionally substituted 4 membered ring. In a yet further aspect, $Z^1$ is an optionally substituted 5 membered ring. In an even further aspect, $Z^1$ is an optionally substituted 6 membered ring. In a still further aspect, $Z^1$ is an optionally substituted 7 membered ring.

In a further aspect, $Z^1$ is a 1,4-cyclohexane residue. In a still further aspect, $Z^1$ is 1,4-dioxane residue. In a yet further aspect, $Z^1$ is a 1,4-tetrahydro-2H-pyran residue.

In a further aspect, $Z^1$ has a structure represented by a formula:

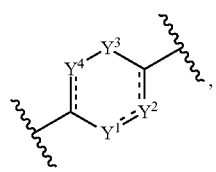

wherein $Y^1$, $Y^2$, $Y^3$, and $Y^4$ independently comprises oxygen, optionally substituted carbon, or optionally substituted nitrogen with a structure represented by the formula, $NR^{14}R^{15}$, wherein $R^{14}$ and $R^{15}$ independently comprises hydrogen or optionally substituted alkyl comprising from 1 to 4 carbons; and wherein ---- is an optional bond.

In a further aspect, $Z^1$ has a structure represented by a formula:

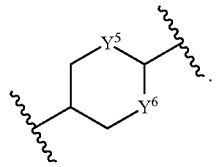

In a further aspect, $Z^1$ has a structure represented by a formula:

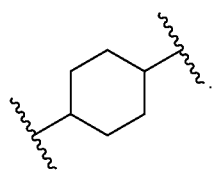 [SMILES: *C1CCC(*)CC1]

In a further aspect, $Z^1$ has a structure represented by a formula:

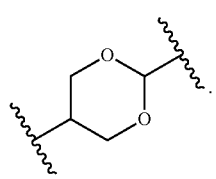 [SMILES: *C1COC(*)OC1]

In a further aspect, $Z^1$ has a structure represented by a formula:

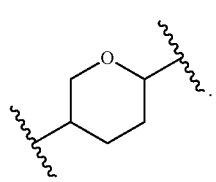 [SMILES: *C1CCC(*)OC1]

In a further aspect, $Z^1$ comprises a ring that can include but is not limited to:

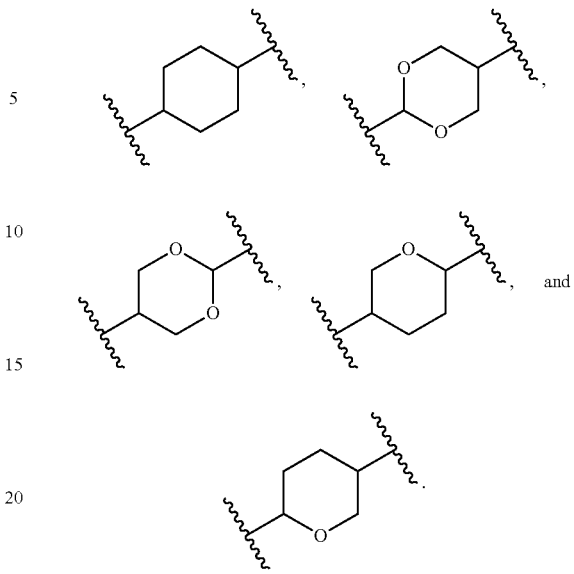

In a further aspect, $Z^1$ comprises a ring with no more than two chiral centers in the 3, 4, 5, 6, or 7 membered ring. For example, $Z^1$ can have two chiral centers in the 3, 4, 5, 6, or 7 membered ring. In a still further aspect, $Z^1$ can have two chiral centers in the 6 membered ring. In a yet further aspect, $Z^1$ comprises a ring with no more than three stereocenters.

A "stereocenter," as used herein can mean a geometrical center with restricted rotation, e.g., a ring, such as a constrained ring, or a double bond. In a further aspect, a "stereocenter" can mean a chiral center. Thus, as an non-limiting example, $Z^1$ would not comprise a ring with a structure represented by a formula:

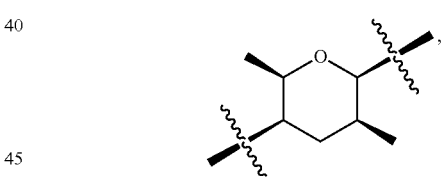

which, assuming the structural features beyond the connecting points are asymmetrical, would comprise a total of four stereocenters, which in this case are chiral centers.

In various aspects, $Z^1$ comprises optionally substituted cycloalkyl or cycloalkenyl or cycloalkynyl, an optionally substituted heterocycloalkyl or heterocycloalkenyl or heterocycloalkynyl, or optionally substituted aryl, or optionally substituted heteroaryl. In a further aspect, $Z^1$ comprises an optionally substituted cyclopropyl, cyclobutyl, cyclopentyl, cyclohexyl, cycloheptyl, heterocyclopropyl, heterocyclobutyl, heterocyclopentyl, heterocyclohexyl, heterocycloheptyl, furan, pyran, oxole, oxazine, thiophene, thiazole, oxathiolane, pyrrolidine, pyrazolidine, imidazolidine, triazolidine, perhydropyridine, azole, morpholine, pyridine, pyrimidine, or benzene.

2. Example Compounds

In one aspect, a compound can be present as one or more of the following structures:

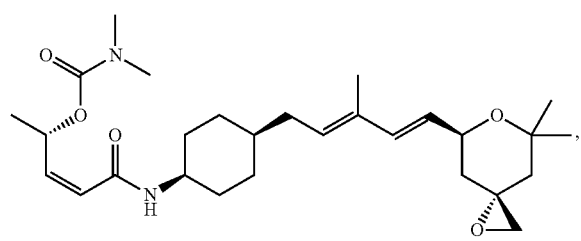
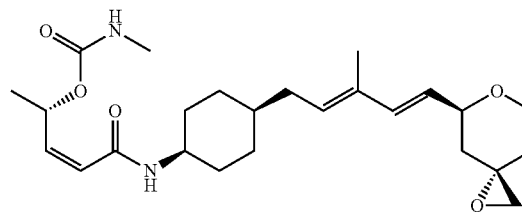
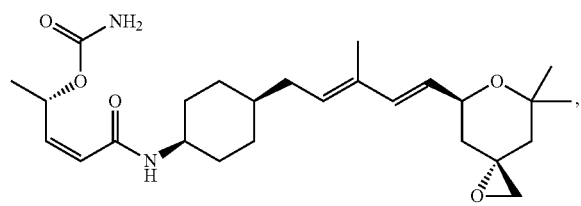
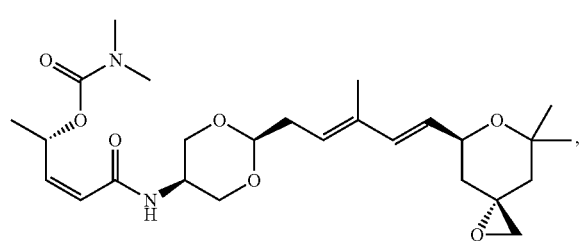
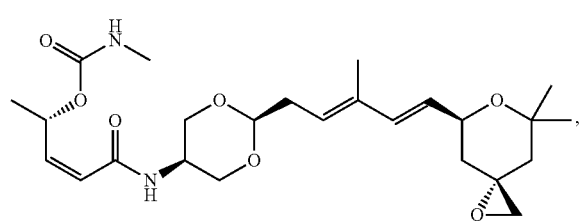
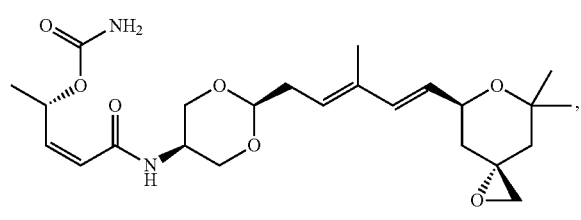
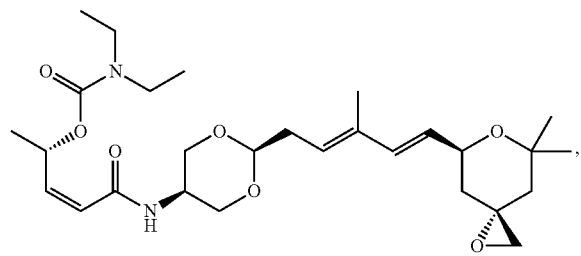
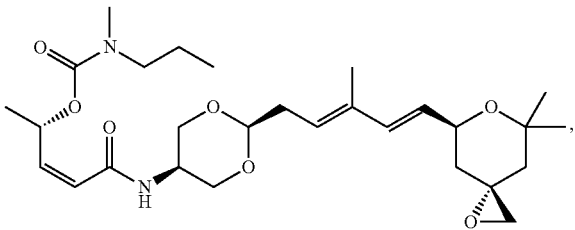
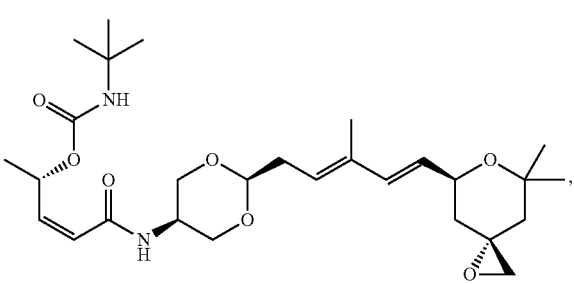
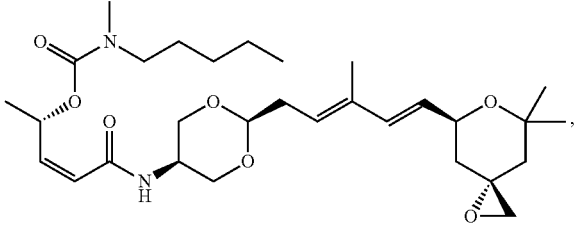
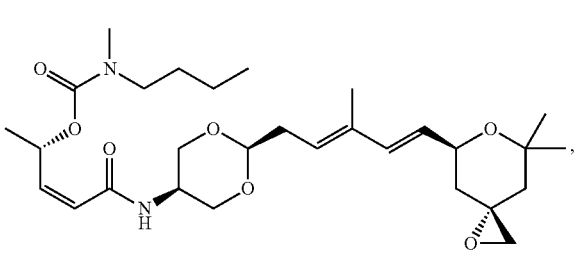
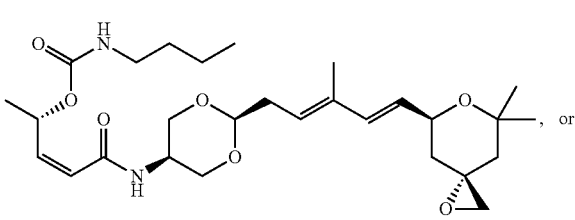
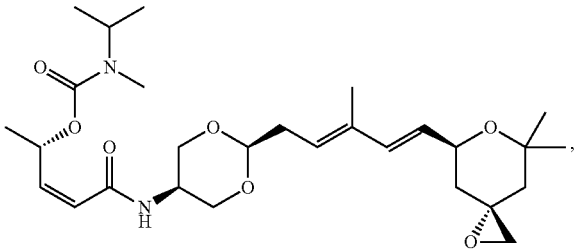 [SMILES: CC(/C=C/[C@@H]1C[C@]2(CO2)CC(C)(C)O1)=C\C[C@H]1OC[C@@H](NC(=O)/C=C\[C@H](C)OC(=O)N(C)C(C)C)CO1]
or a subgroup thereof.
In one aspect, a compound can be present as one or more of the following structures:

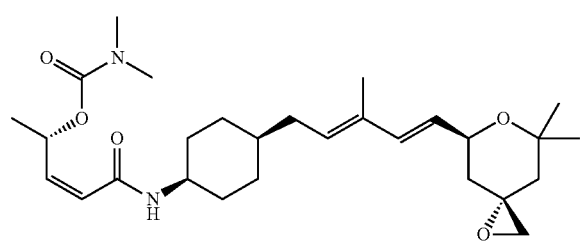
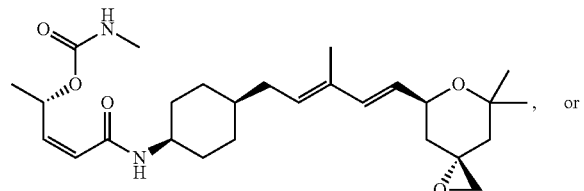
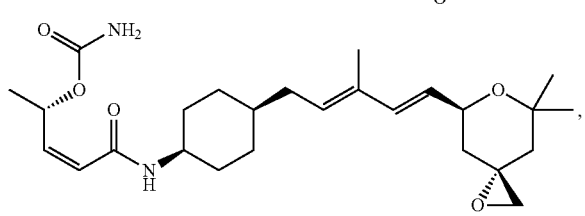
or a subgroup thereof.
In one aspect, a compound can be present as one or more of the following structures:
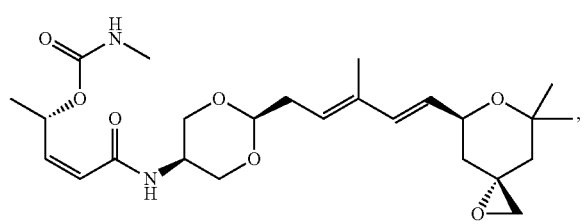
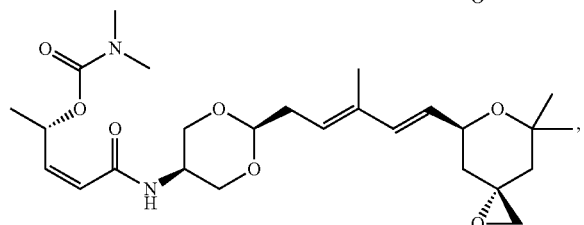
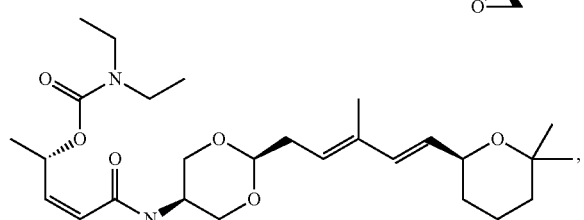
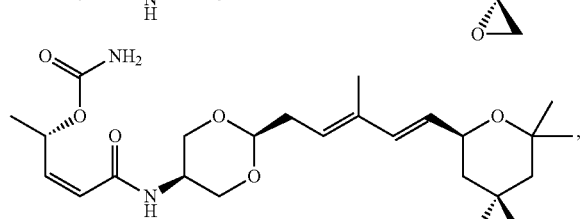
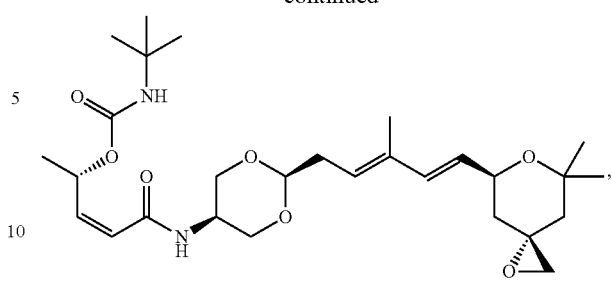
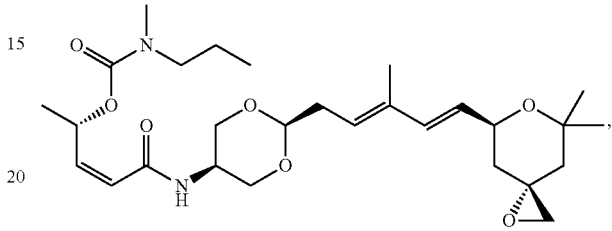
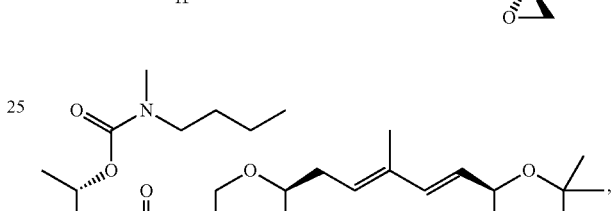
or a subgroup thereof.
In one aspect, a compound can be present as one or more of the following structures:

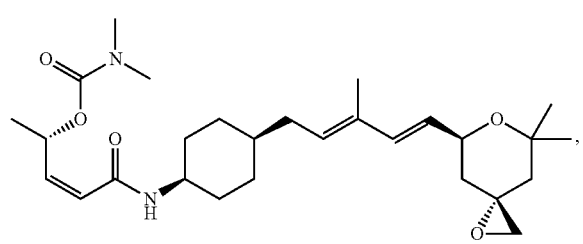 [SMILES: CC(/C=C/[C@@H]1C[C@]2(CO2)CC(C)(C)O1)=C\C[C@H]1CC[C@@H](NC(=O)/C=C\[C@H](C)OC(=O)N(C)C)CC1]
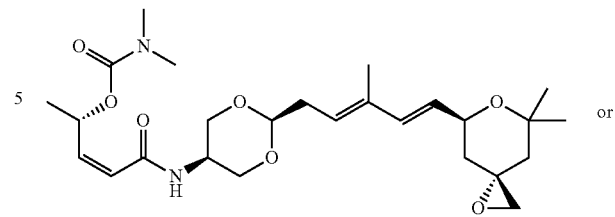
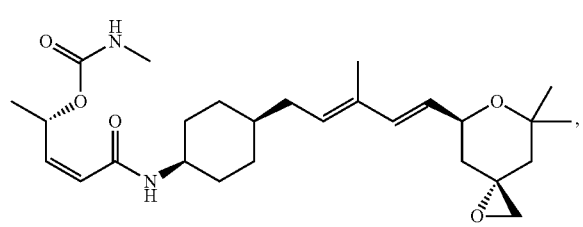
In one aspect, a compound can be present as:
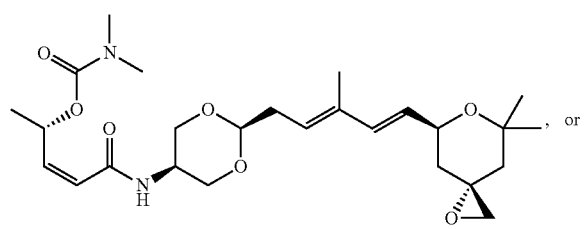
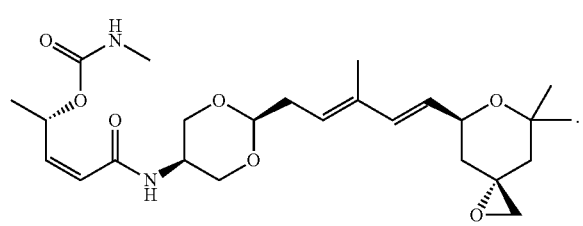
or a subgroup thereof.
In one aspect, a compound can be present as one or more of the following structures:
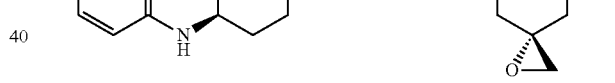
In one aspect, a compound can be present as:
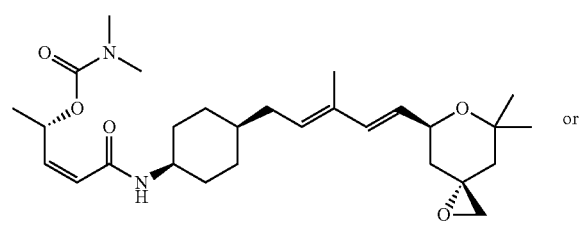
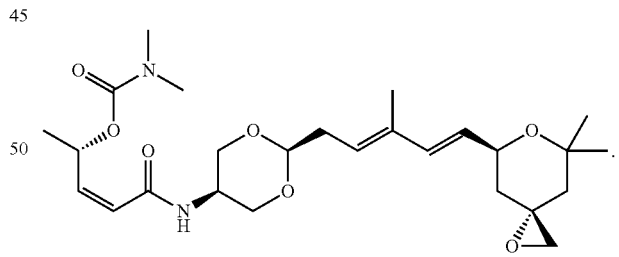
In one aspect, a compound can be present as:
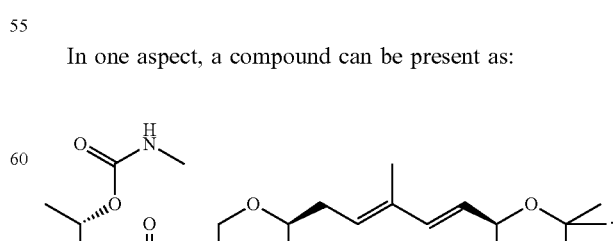
In one aspect, a compound can be present as:
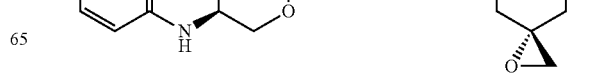
In one aspect, a compound can be present as one or more of the following structures:

It is contemplated that one or more compounds can optionally be omitted from the disclosed invention.

3. Anticancer Activity

The disclosed compounds can have anticancer activity, and thus can be effective at treating one or more cancers and/or related disorders. In one aspect, the compound is capable of inhibiting the proliferation of at least one cell (e.g., a cancer cell). A disclosed compound can also be cytotoxic against at least one cancer cell line (e.g., a lymphoma cell line or leukemia cell line). For example, the compound can be effective at treating proliferation of a lymphoma cell line such as JVM-2. In various further aspects, the compound can be effective at treating proliferation of a leukemia cell line such as JeKo-1.

The disclosed compounds can be efficacious against a variety of cancer cell types and cell lines derived from cancer cells. If a cell line is selected from Jeko-1 and JVM-2, for example, a compound disclosed herein can exhibit an $IC_{50}$ value of about 40, 50, 60, 70, 80, 90, or 100 nM against the cell line. In various aspects, the compound exhibits an $IC_{50}$ value of about 100 nM against a lymphoma cell line. In a further aspect, the compound exhibits an $IC_{50}$ value of about 100 nM against a leukemia cell line.

In various aspects, the disclosed compounds exhibit an $IC_{50}$ value of less than or equal to about 500 nM. In a further aspect, the disclosed compounds exhibit an $IC_{50}$ value of less than or equal to about 300 nM. In a still further aspect, the disclosed compounds exhibit an $IC_{50}$ value of less than or equal to about 100 nM. In an even further aspect, the $IC_{50}$ is determined using the Jeko-1 cell line. In a still further aspect, the $IC_{50}$ is determined using the JVM-2 cell line.

In a further aspect, based on a pharmacophore analysis, the compounds disclosed herein can act in a similar fashion as pladienolide series and/or FR series compounds. For example, a disclosed compound can be efficacious against a cancer cell line that a PD series and/or FR series compound is also efficacious against.

C. Methods of Making the Compounds

The compounds of this invention can be prepared by employing reactions as shown in the disclosed schemes, in addition to other standard manipulations that are known in the literature, exemplified in the experimental sections or clear to one skilled in the art. The following examples are provided so that the invention might be more fully understood, are illustrative only, and should not be construed as limiting. For clarity, examples having a fewer substituent can be shown where multiple substituents are allowed under the definitions disclosed herein.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed compositions, methods, kits, and uses.

1. Synthesis Route 1

In various aspects, benzothiazole spiro epoxide derivatives of the present invention can be prepared generically by the synthetic scheme as shown below.

SCHEME 1A

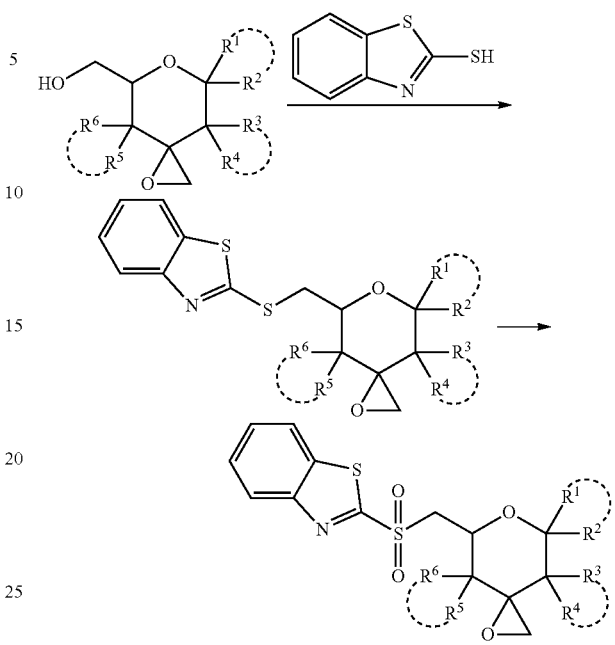

Compounds are represented in generic form, with substituents as noted in compound descriptions elsewhere herein. A more specific example is set forth below.

SCHEME 1B

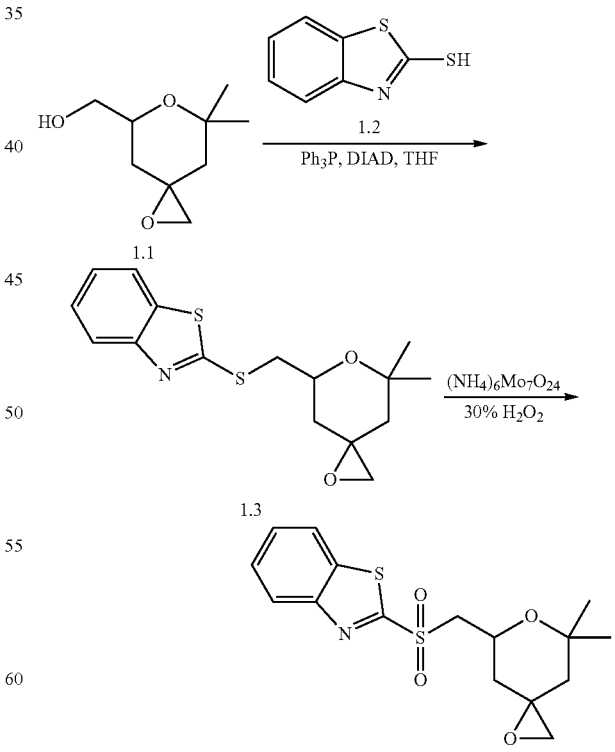

In various aspects, benzothiazole spiro epoxide derivatives, such as a compound of type 1.4, can be prepared starting from an appropriate spiro epoxide derivative, such as a compound of type 1.1. A coupling reaction comprising a compound of type 1.1, a benzothiazole, such as benzo[d]thiazole-2-thiol (1.2), triphenylphosphine, and DIAD, to yield a compound of type 1.3. Oxidation of the thioether using ammonium molybdate and hydrogen peroxide yields the desired sulfonyl, a compound of type 1.4.

Thus, in one aspect, the invention relates to a method of making benzothiazole spiro epoxide derivatives, comprising the steps of: (a) providing a compound having a structure represented by a formula:

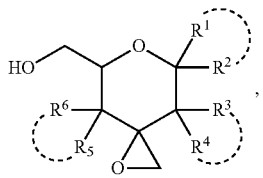

wherein each of $R^1$, $R^2$, $R^3$, $R^4$, $R^5$, and $R^6$ is independently selected from hydrogen, halogen, hydroxyl, amino, thiol, and an optionally substituted organic residue comprising 1 to 6 carbons; and (b) performing a coupling reaction with benzo[d]thiazole-2-thiol to yield the benzothiazole spiro epoxide derivative.

As used herein, the term "spiro epoxide," is intended to refer to the functional group:

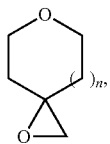

wherein n is an integer from 0-3. Thus, a spiro epoxide derivative can be a compound comprising the aforementioned spiro epoxide functional group. Moreover, a spiro epoxide derivative includes a compound having a structure represented by a formula:

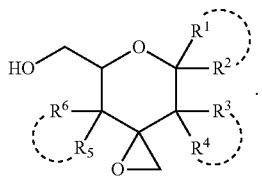

It is understood that a spiro epoxide is a subset of a "spiro" compound, which a bicyclic ring system, wherein two joined rings share only one common atom.

In a further aspect, the spiro epoxide derivative provided has a structure represented by a formula:

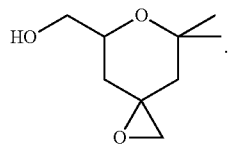

In a further aspect, the benzothiazole spiro epoxide derivative yielded by the reaction has a structure represented by a formula:

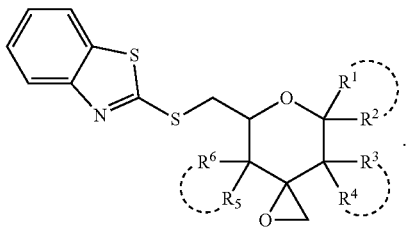

In a further aspect, the benzothiazole spiro epoxide derivative yielded is:

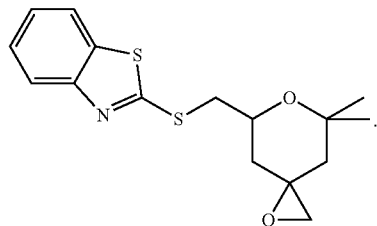 [SMILES: CC1(C)CC2(CO2)CC(CSc2nc3ccccc3s2)O1]

In various aspects, the coupling reaction is carried out using triphenyl phosphine and an azodicarboxylate. In a further aspect, the azodicarboxylate is selected from diethyl azodicarboxylate and diisopropyl azodicarboxylate. In a still further aspect, the azodicarboxylate is diisopropyl azodicarboxylate.

In a further aspect, the method of making further comprises the step of oxidation of the benzothiazole spiro epoxide derivative to provide a sulfonyl benzothiazole spiro epoxide derivative. In a still further aspect, the further step of oxidation is carried out using hydrogen peroxide and ammonium molybdate. In a yet further aspect, the further step of oxidation yields a sulfonyl benzothiazole spiro epoxide derivative having a structure represented by a formula:

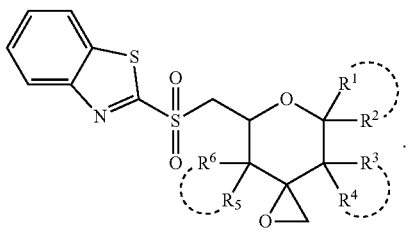

In an even further aspect, the sulfonyl benzothiazole spiro epoxide derivative yielded by the oxidation step is:

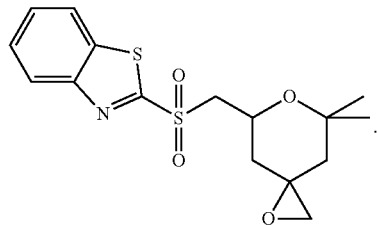 [SMILES: CC1(C)CC2(CO2)CC(CS(=O)(=O)c2nc3ccccc3s2)O1]

2. Synthesis Route 2

In various aspects, (E)-5-(buta-1,3-dien-1-yl)-1,6-dioxaspiro[2.5]octane derivatives of the present invention can be prepared generically by the synthetic scheme as shown below.

SCHEME 2A

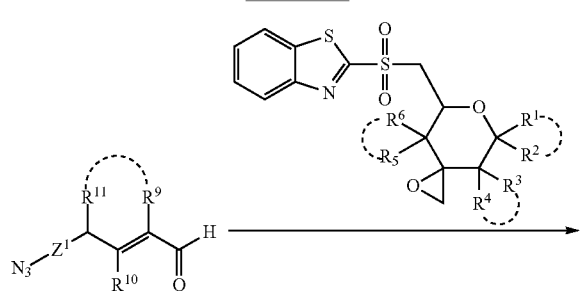

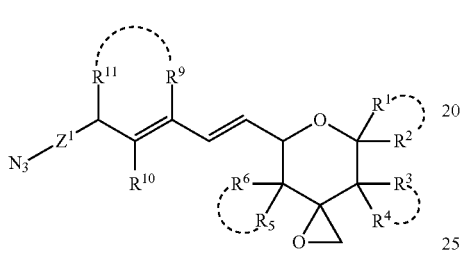

SCHEM 2B

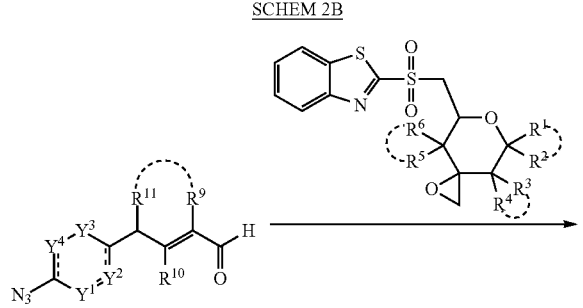

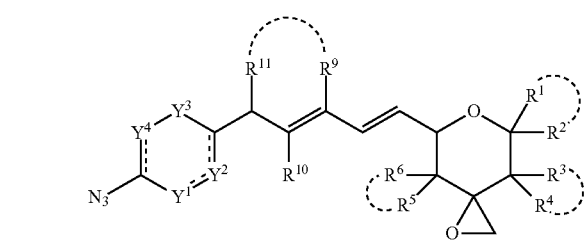

SCHEM 2C

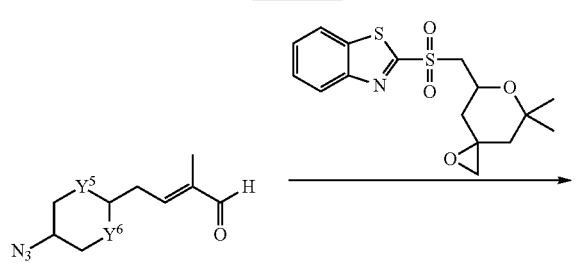

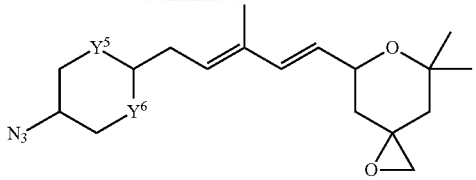

Compounds are represented in generic form, with substituents as noted in compound descriptions elsewhere herein. A more specific example is set forth below.

SCHEM 2D

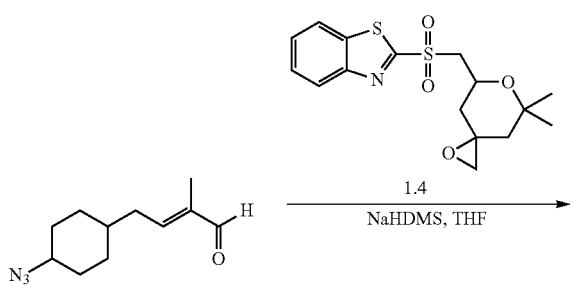

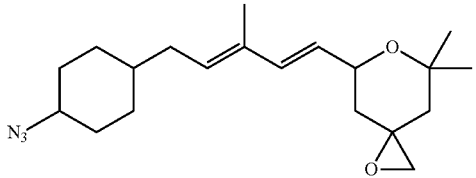

In one aspect, (E)-5-(buta-1,3-dien-1-yl)-1,6-dioxaspiro[2.5]octane derivatives of type 2.2 can be prepared starting with an appropriate azidocyclohexylbutenal compound, such as a compound of type 2.1. A coupling reaction is carried out with a compound of type 1.4, prepared as described hereinabove, and using a reagent such as sodium hexamethyldisilazide to yield the desired (E)-5-(buta-1,3-dien-1-yl)-1,6-dioxaspiro[2.5]octane derivative, a compound of type 2.2. The cyclic moiety can be varied, e.g. a 1,3-dioxyl moiety, to provide further examples of compounds consistent with the generic schemes disclosed hereinabove.

Thus, in one aspect, the invention relates to a method of making (E)-5-(buta-1,3-dien-1-yl)-1,6-dioxaspiro[2.5]octane derivatives comprising the steps of: (a) providing a compound having a structure represented by a formula:

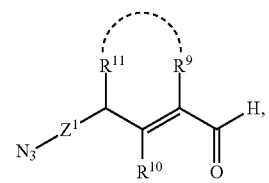

wherein each of $R^9$, $R^{10}$, and $R^{11}$ is independently selected from hydrogen, halogen, hydroxyl, amino, thiol, and an optionally substituted organic residue comprising 1 to 6 carbons; and wherein each ----- is an optional covalent bond; wherein $Z^1$ comprises an optionally substituted 3, 4, 5, 6, or 7 membered ring; and (b) performing a coupling reaction with a compound having a structure represented by a formula:

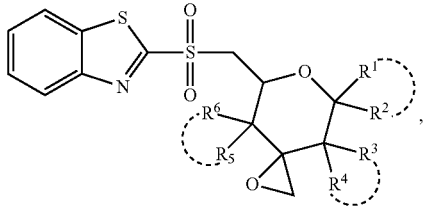

thereby yielding the (E)-5-(buta-1,3-dien-1-yl)-1,6-dioxaspiro[2.5]octane derivative having a structure represented by a formula:

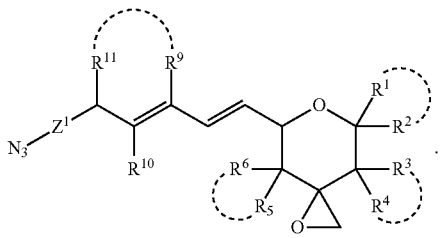

As used herein, the term "(E)-4-(4-azidocycle)-2-methybut-2-enal," is intended to refer to the functional group:

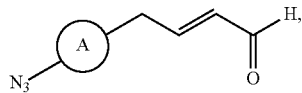

wherein A represents an optionally substituted 3, 4, 5, 6, or 7 membered ring. Thus, a "(E)-4-(4-azidocycle)-2-methybut-2-enal derivative can be a compound comprising the aforementioned spiro epoxide functional group. Moreover, a (E)-4-(4-azidocycle)-2-methybut-2-enal derivative includes a compound having a structure represented by a formula:

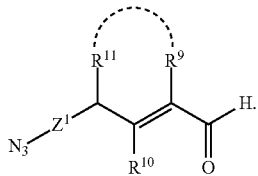

In a further aspect, the a (E)-4-(4-azidocycle)-2-methybut-2-enal derivative provided has a structure represented by a formula:

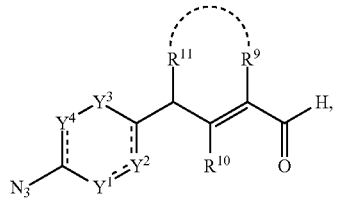

wherein each of $Y^1$, $Y^2$, $Y^3$, and $Y^4$ is independently selected from oxygen, optionally substituted carbon, and optionally substituted nitrogen; wherein the optionally substituted nitrogen has a structure represented by the formula, $NR^{14}R^{15}$; wherein each of $R^{14}$ and $R^{15}$ is independently selected from hydrogen and optionally substituted C1-C4 alkyl; and wherein ----- is an optional covalent bond.

In a further aspect, the a (E)-4-(4-azidocycle)-2-methybut-2-enal derivative provided has a structure represented by a formula:

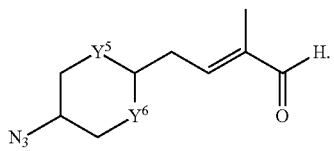

In a further aspect, the a (E)-4-(4-azidocycle)-2-methybut-2-enal derivative provided is:

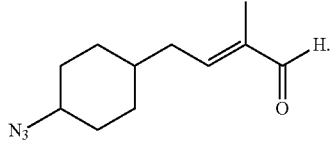

In a further aspect, the a (E)-4-(4-azidocycle)-2-methybut-2-enal derivative provided is:

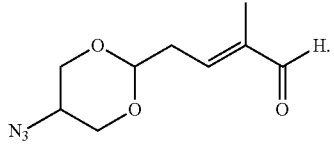

In a further aspect, the coupling reaction is performed with the compound:

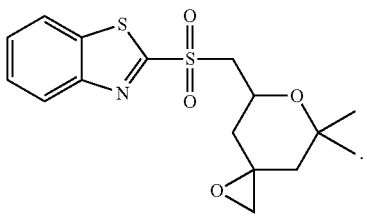 [SMILES: CC1(C)CC2(CO2)CC(CS(=O)(=O)c2nc3ccccc3s2)O1]

Also disclosed herein is the product of any of the disclosed methods. Thus, in one aspect, the invention pertains to compounds having a structure represented by a formula:

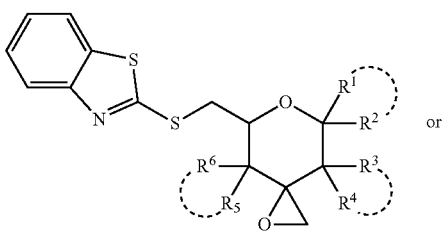

-continued

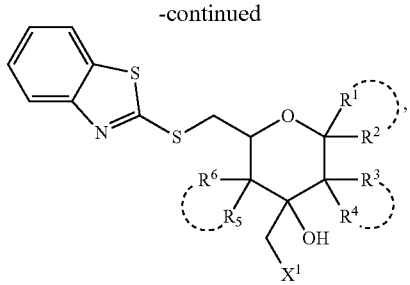

wherein each of $R^1$, $R^2$, $R^3$, $R^4$, $R^5$, and $R^6$ is independently selected from hydrogen, halogen, hydroxyl, amino, thiol, and an optionally substituted organic residue comprising 1 to 6 carbons, and wherein $X^1$ is a leaving group, or a salt or solvate thereof.

In a further aspect, the compound has a structure represented by a formula:

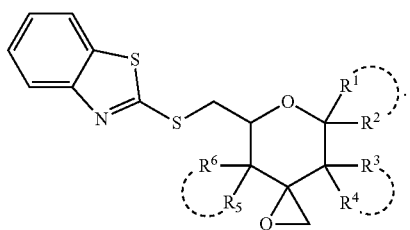

In a further aspect, the compound has a structure represented by a formula:

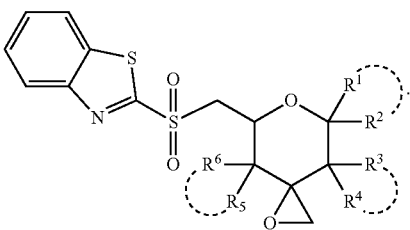

In a further aspect, the compound has a structure represented by a formula:

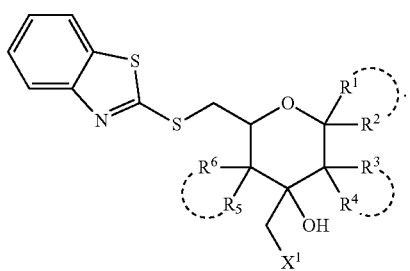

In a further aspect, the compound has a structure represented by a formula:

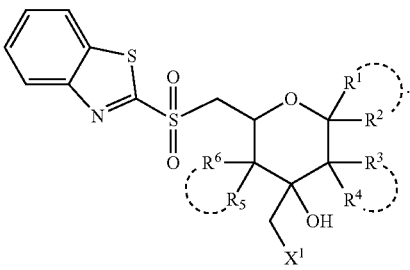

In a further aspect, the compound can be present as one or more of the following structures:

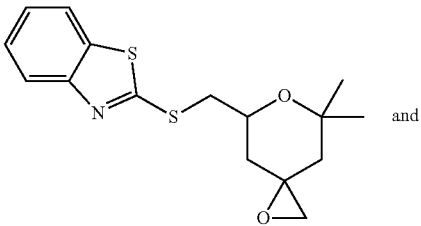

In a further aspect, the compound can be present as:

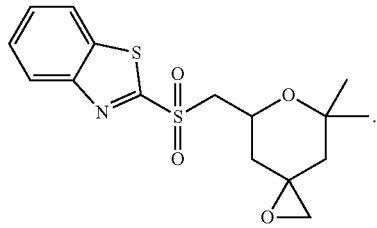

In a further aspect, the compound can be present as:

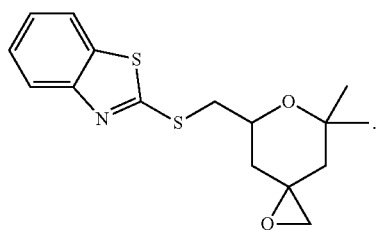 [SMILES: CC1(C)CC2(CO2)CC(CSc2nc3ccccc3s2)O1]

3. Synthesis Route 3

In various aspects, dioxaspiro methanol derivatives of the present invention can be prepared generically by the synthetic scheme as shown below.

Scheme 3A

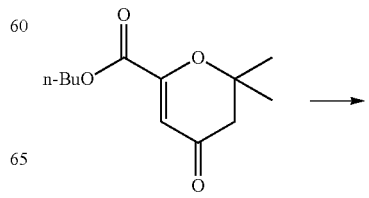

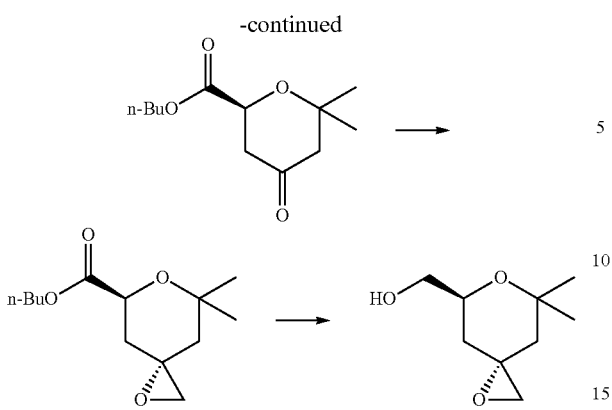

Compounds are represented in generic form, with substituents as noted in compound descriptions elsewhere herein. A more specific example is set forth below.

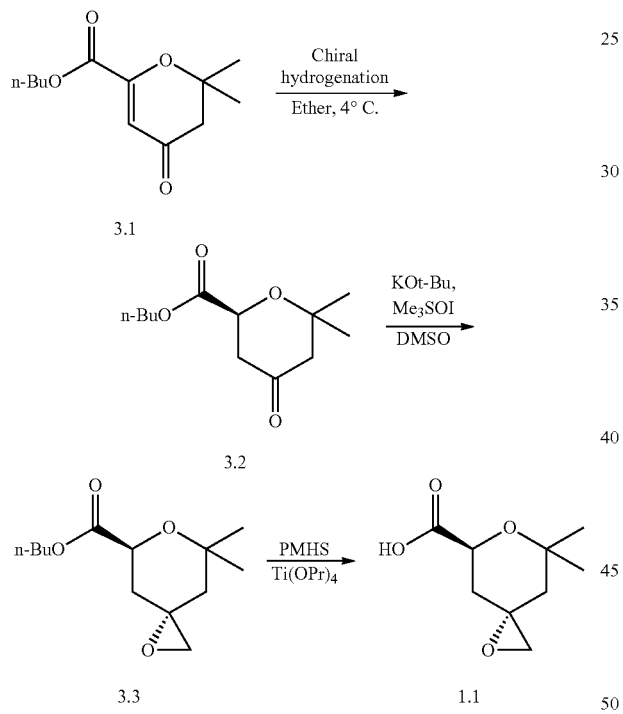

Dioxaspiro methanol derivatives (1.1) can be prepared starting with commercially available indalone (butyl 2,2-dimethyl-4-oxo-3,4-dihydro-2H-pyran-6-carboxylate; 3.1). A solution of indalone is prepared in a suitable solvent, e.g. anhydrous ether, and to this is sequentially added di-tert-buty-2,6-dimethyldicarboxylate and a suitable acid, e.g. trichloroacetic acid. The reaction is allowed to proceed at a suitable temperature, e.g. about 0-5° C., for a suitable period of time to ensure that the reaction is complete, e.g. about 4-8 days, to yield the desired product, a compound of type 3.2. The product is reacted with a suitable methylene transfer reagent, e.g. trimethylsulfoxonium iodide, and a suitable base, e.g. t-butoxide, and the reaction is carried out in a suitable solvent, e.g. DMSO, at suitable temperature, e.g. about 10-20° C., for a suitable period of time to ensure that the reaction is complete, e.g. about 30-180 minutes, to yield the yield the desired dioxaspiro ester (3.3). The dioxaspiro ester, dioxaspiro ester, 3.3, is reacted in the presence of a suitable reducing agent, e.g. polymethylhydrosiloxane, and a reductive cleavage agent, e.g. titanium isoproxide, and the reaction allowed to proceed at a suitable temperature, e.g. about 20-30° C., for a suitable period of time to ensure that the reaction is complete, e.g. about 12-24 hours, to yield the desired dioxaspiro methanol derivative (1.1).

4. Synthesis Route 4

In various aspects, 4-azidocycle-2-methylbut-2-enal derivatives of the present invention can be prepared generically by the synthetic scheme as shown below.

SCHEME 4A

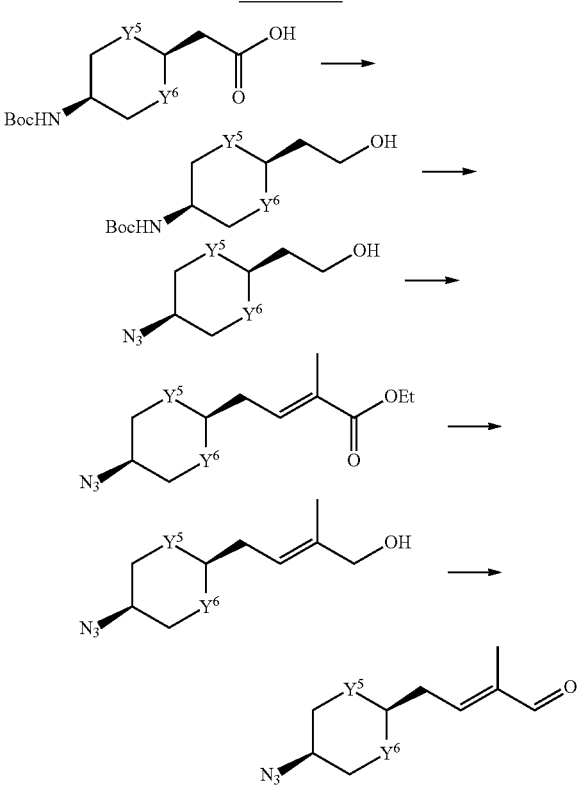

Compounds are represented in generic form, with substituents as noted in compound descriptions elsewhere herein. A more specific example is set forth below.

SCHEME 4B

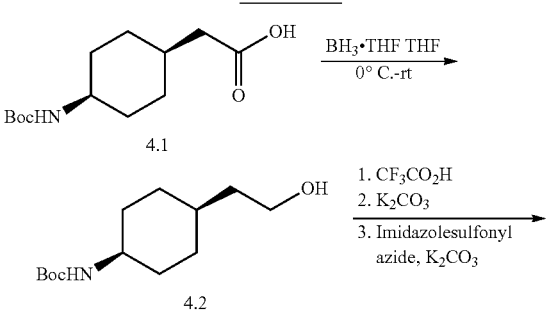

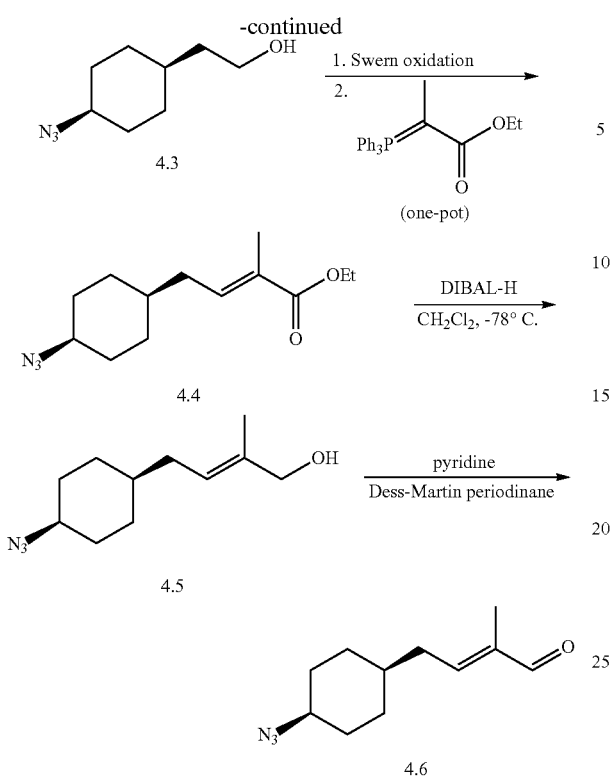

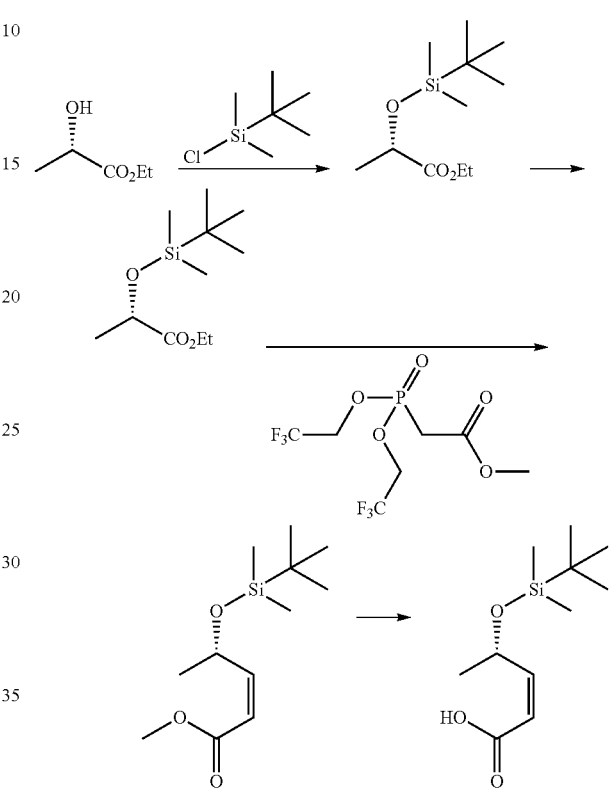

Suitable 4-azidocycle-2-methylbut-2-enal derivatives (4.6) can be prepared starting with the commercially available boc-protected 2-((1s,4s)-4-aminocyclohexyl)acetic acid (4.1), or alternatively the 2-((1s,4s)-4-aminocyclohexyl)acetic acid can be obtained commercially and protected by methods known to one skilled in the art. A solution of the starting compound (4.1) is prepared in a suitable solvent, e.g. anhydrous THF, and brought to a suitable temperature, e.g. about 0-4° C., and a suitable borane derivative is added, e.g. borane tetrahydrofuran complex solution, BH$_3$-THF, is added. Following reaction at a suitable temperature, e.g. about 20-30° C., for a suitable period of time to ensure that reaction is completed, e.g. about 2-5 hours, the desired product (4.2) is isolated.

The azido compound (4.3) is prepared by reaction of the previously prepared product by first reaction with a suitable acid, e.g. trifluoroacetic acid, at a suitable temperature, e.g. about 0-2° C. followed by allowing the reaction to come to a temperature of about 20-30° C., and reaction for a suitable period of time, e.g. about 2-6 hours. The residue is isolated, comprising the deprotected amine, by methods known to one skilled in the art, and the residue is resuspended in a suitable solvent, e.g. methanol, and a suitable base, e.g. potassium carbonate, and copper sulfate is added, followed by addition of a suitable diazo transfer reagent, e.g. 1H-imidazole-1-sulfonylazide HCl, is added.

The resulting product (4.3) is used in a suitable oxidation reaction and coupling reaction, which can be carried out in a single reaction vessel as shown hereinabove. For example, a Swern oxidation reaction is carried out following by coupling with a suitable stable ylide, e.g. ethyl 2-(triphenylphosphoranylidene)propanoate, is added to provide the desired azido ester derivative (4.4).

The azido ester derivative (4.4) is treated with a suitable reducing agent, e.g. diisobutylaluminium hydride (DIBAL-H), and the reaction carried out in a suitable solvent, e.g. methylene chloride, at a suitable temperature, e.g. −60-90° C., for a suitable period of time to complete the reaction, e.g. about 2-5 hours, to provide the desired alcohol derivative (4.5). The alcohol is converted to the desired aldehyde (4.6) by use of Dess-Martin periodinane, although other suitable methods are known to one skilled in the art.

5. Synthesis Route 5

In various aspects, (S,Z)-4-((tert-butyldimethylsilyl)oxy)pent-2-enoic acid derivatives of the present invention can be prepared generically by the synthetic scheme as shown below.

SCHEME 5A

Compounds are represented in generic form, with substituents as noted in compound descriptions elsewhere herein. A more specific example is set forth below.

SCHEME 5B

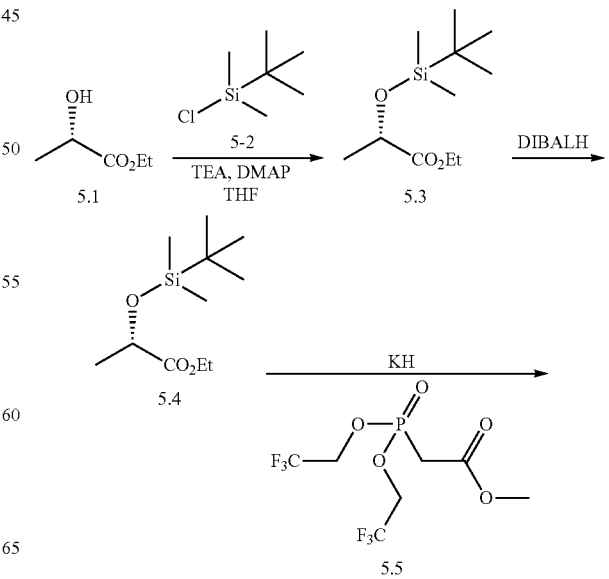

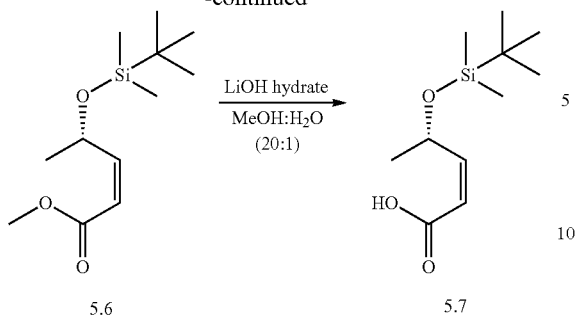

The above reactions can be carried out as generally outlined in the examples, although other suitable methods can be utilized as known to one skilled in the art.

6. Synthesis Route 6

In various aspects, substituted 7,7-dimethyl-1,6-dioxaspiro[2.5]octan-5-yl)-3-methylpenta-2,4-dien-1-yl)cyclohexyl)amino)-5-oxopent-3-en-2-yl carbamate analogues of the present invention can be prepared generically by the synthetic scheme as shown below.

SCHEME 6A

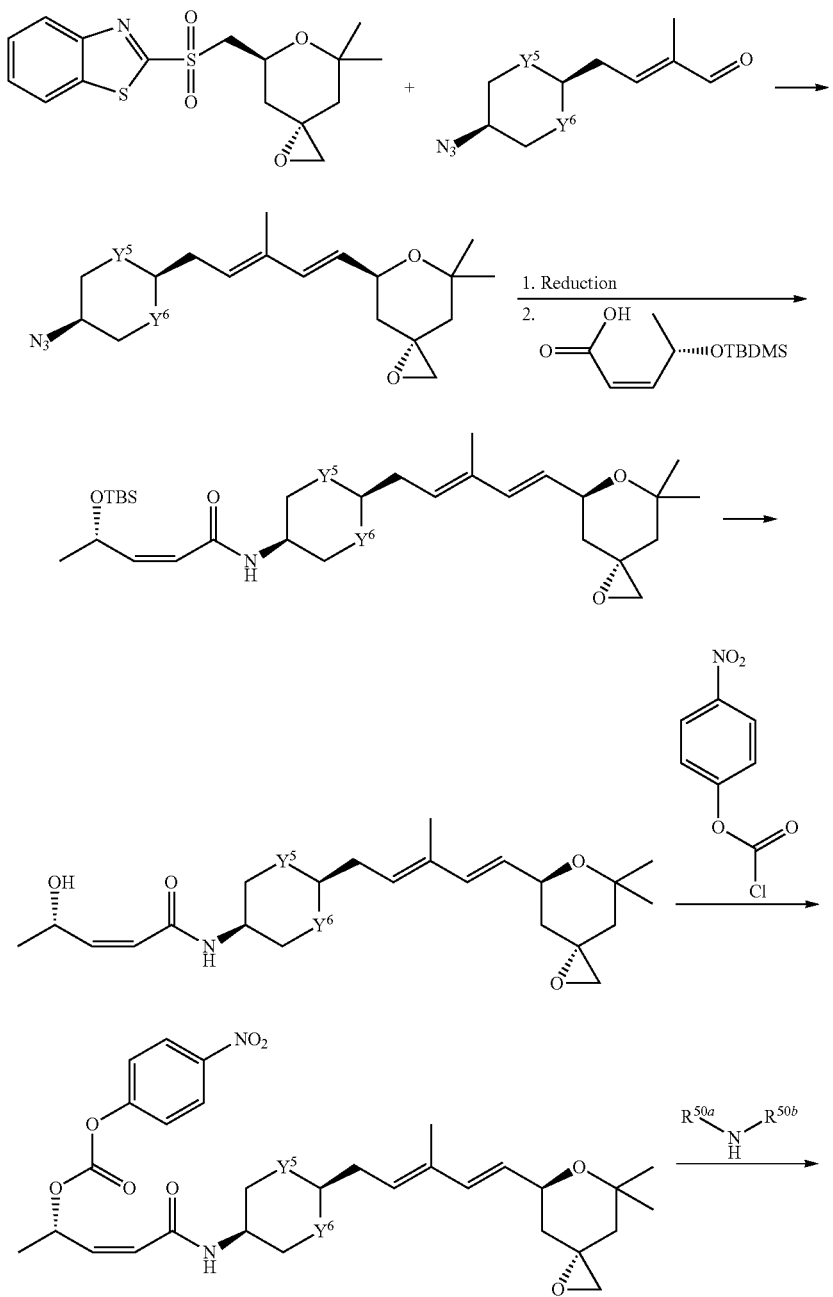

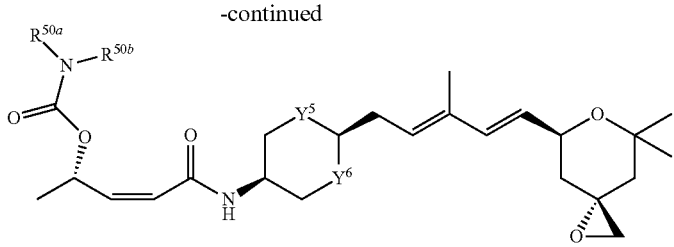
Compounds are represented in generic form, with substituents as noted in compound descriptions elsewhere herein. A more specific example is set forth below.
SCHEME 6B
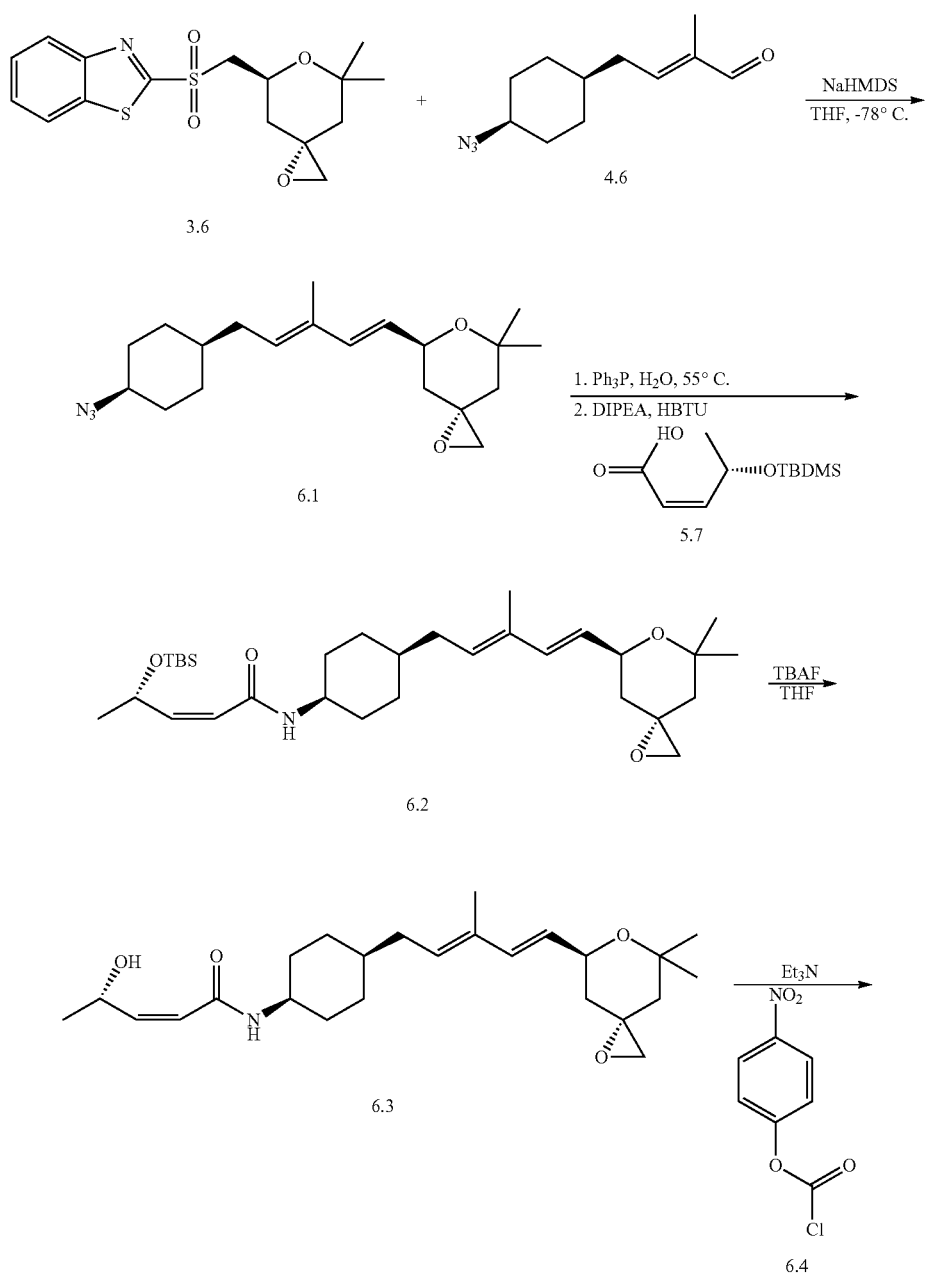

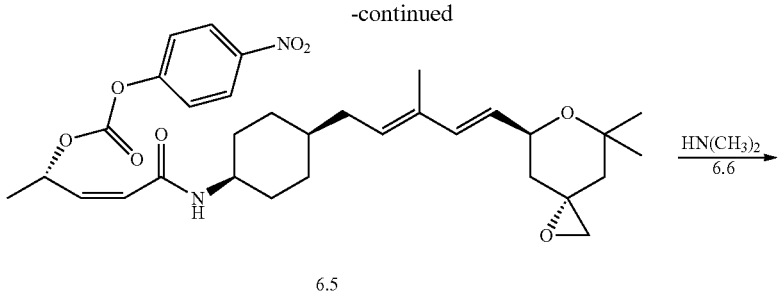

6.5

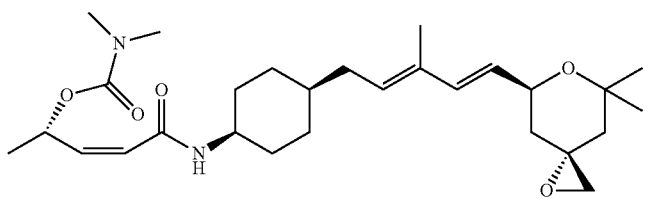

6.7

The above reactions can be carried out as generally outlined in the examples, although other suitable methods can be utilized as known to one skilled in the art.

It should also be understood that the synthetic methods disclosed herein can be used in connection with the compounds, compositions, and methods disclosed herein. Thus, the synthetic methods disclosed herein can be used to make the compounds disclosed herein.

7. Synthesis Route 7

In various aspects, substituted 7,7-dimethyl-1,6-dioxaspiro[2.5]octan-5-yl)-3-methylpenta-2,4-dien-1-yl)cyclohexyl)amino)-5-oxopent-3-en-2-yl carbamate analogues of the present invention can be prepared generically by the synthetic scheme as shown below.

SCHEME 7A

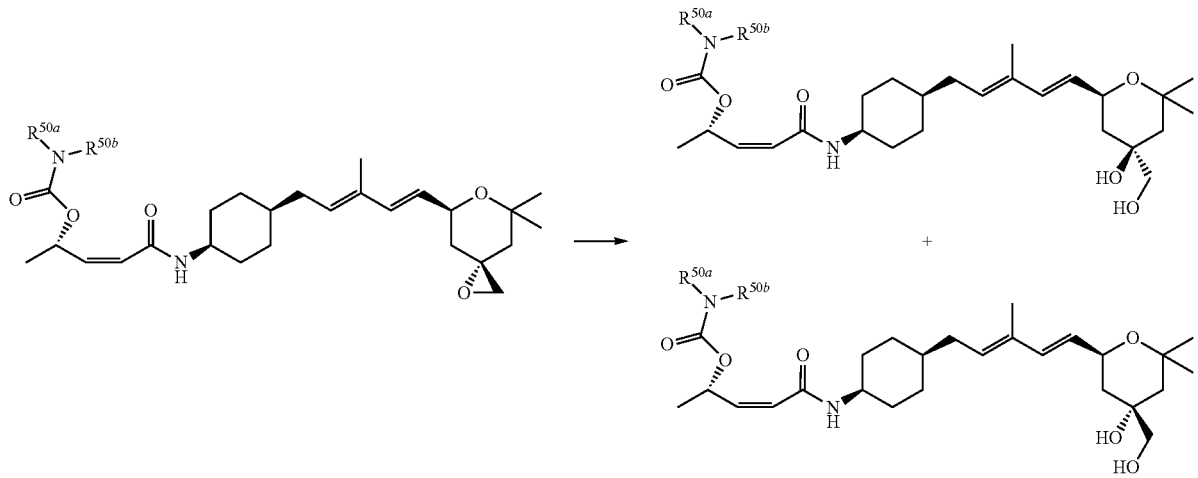

Compounds are represented in generic form, with substituents as noted in compound descriptions elsewhere herein. A more specific example is set forth below.

SCHEME 7B

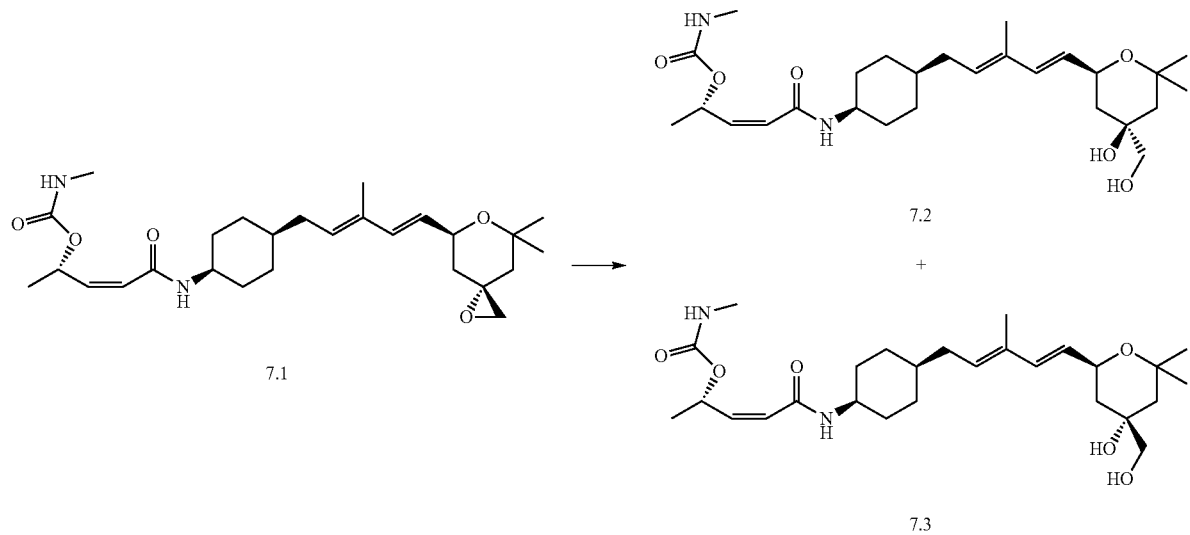

The above reactions can be carried out as generally outlined in the examples, although other suitable methods can be utilized as known to one skilled in the art.

It should also be understood that the synthetic methods disclosed herein can be used in connection with the compounds, compositions, and methods disclosed herein. Thus, the synthetic methods disclosed herein can be used to make the compounds disclosed herein.

D. Pharmaceutical Compositions

In one aspect, the invention pertains to pharmaceutical compositions comprising a therapeutically effective amount of one or more compounds having a structure represented by a formula:

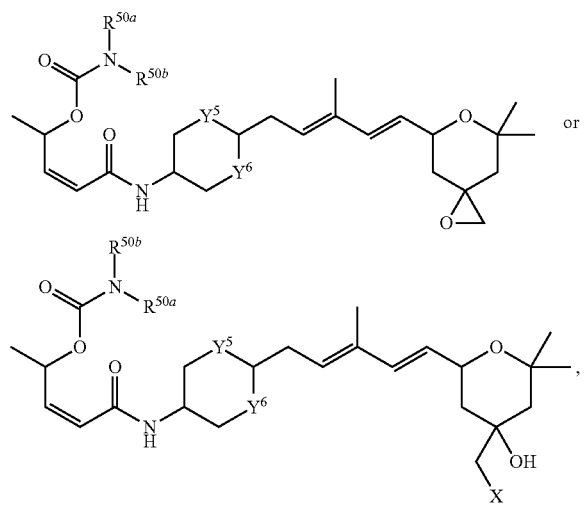

wherein each of $R^{50a}$ and $R^{50b}$ is independently selected from hydrogen, C1-C6 alkyl, C1-C6 monohaloalkyl, and C1-C6 polyhaloalkyl; wherein each of $Y^5$ and $Y^6$ is independently selected from —O— and —CH$_2$—; and wherein X is a leaving group; or a pharmaceutically acceptable salt, solvate, prodrug, or polymorph thereof, and a pharmaceutically acceptable carrier. In a further aspect, the therapeutically effective amount is effective for a mammal. In a still further aspect, the therapeutically effective amount is effective for a human. In a yet further aspect, the therapeutically effective amount is effective for a mouse.

In a further aspect, the pharmaceutical composition comprises a compound selected from:

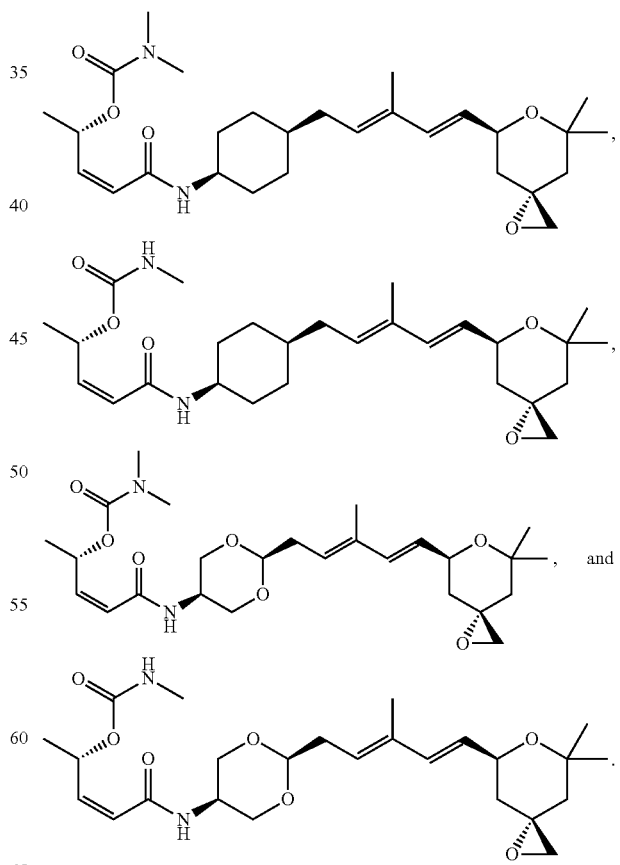

In a further aspect, the pharmaceutical composition comprises a compound selected from:

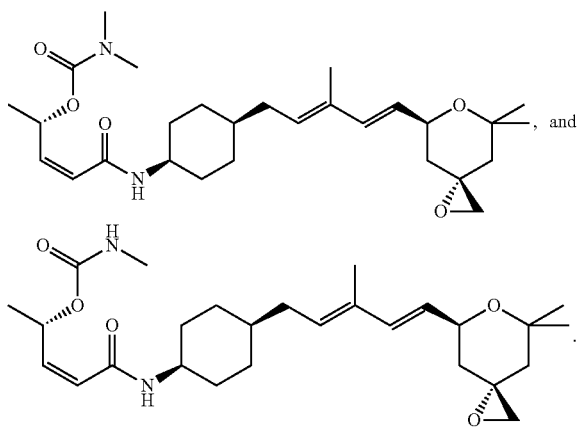

In a further aspect, the pharmaceutical composition comprises a compound selected from:

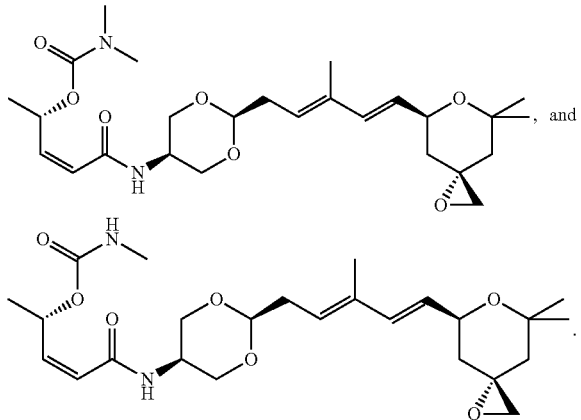

In a further aspect, the pharmaceutical composition comprises the compound:

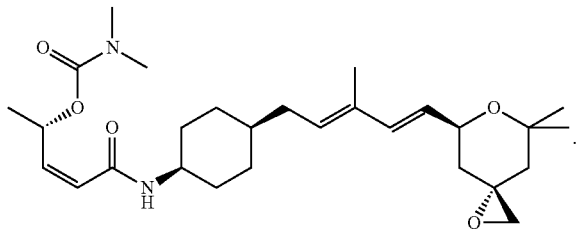 [SMILES: CC(/C=C/[C@@H]1C[C@]2(CO2)CC(C)(C)O1)=C\C[C@H]1CC[C@@H](NC(=O)/C=C\[C@H](C)OC(=O)N(C)C)CC1]

In a further aspect, the pharmaceutical composition comprises the compound:

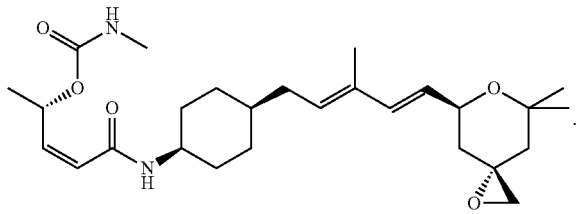 [SMILES: CNC(=O)O[C@@H](C)/C=C\C(=O)N[C@H]1CC[C@@H](C/C=C(C)/C=C/[C@@H]2C[C@]3(CO3)CC(C)(C)O2)CC1]

In a further aspect, the pharmaceutical composition comprises the compound:

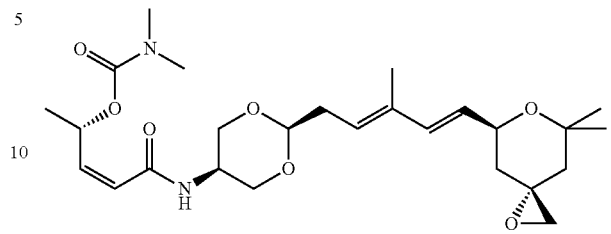

In a further aspect, the pharmaceutical composition comprises the compound:

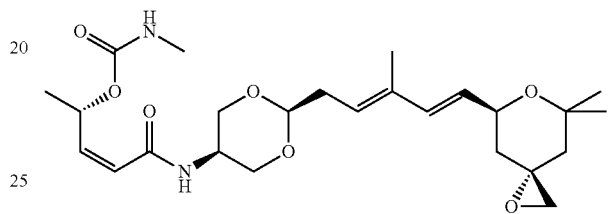

Also disclosed are pharmaceutical compositions, including dosage forms, comprising one or more disclosed compounds. The disclosed compounds can be administered alone or in combination with pharmaceutically acceptable carriers or excipients, in either single or multiple doses. The pharmaceutical compositions can be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

In one aspect, a dosage form can comprise a therapeutically effective amount of at least one product of the synthetic methods disclosed herein. In a further aspect, a dosage form for administration to a subject can comprise a therapeutically effective amount of any compound disclosed herein and a pharmaceutically acceptable carrier. In a specific aspect, the dosage form can comprise a therapeutically effective amount that can be effective for a mammal, e.g., a human or a mouse.

In one aspect, the term "pharmaceutically acceptable" can mean approved by a regulatory agency of the Federal or a state government or listed in the U. S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be a carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions can contain a therapeutically effective amount of one or more spliceosome inhibitors preferably in purified form, together with a suitable amount of carrier so as to provide the form for proper administration to the patient. The formulation should typically suit the mode of administration.

In one aspect, a composition can be formulated in accordance with routine procedures as a pharmaceutical composition adapted for intravenous administration to humans. Typically, compositions for intravenous administration are solutions in sterile isotonic aqueous buffer. Where necessary, the composition can also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

The pharmaceutical compositions can be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, creams, gels, inhalants, dermal patches, implants etc.

For parenteral administration, solutions of the compounds in sterile aqueous solution, aqueous propylene glycol or sesame or peanut oil can be employed. Such aqueous solutions should be suitable buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

It is understood that the pharmaceutical compositions can be used in connection with the methods and compounds disclosed herein.

E. Methods of Using the Compounds and Compositions

1. Treatment of a Disorder

Diseases and disorders involving uncontrolled cellular proliferation or cell overproliferation that can be treated or prevented include but are not limited to cancers, premalignant conditions (e.g., hyperplasia, metaplasia, and dysplasia), benign tumors, hyperproliferative disorders, and benign dysproliferative disorders. Cancer is characterized primarily by an increase in the number of abnormal cells derived from a given normal tissue, invasion of adjacent tissues by these abnormal cells, and lymphatic or blood-borne. Malignancies and related disorders that can be treated, prevented, managed, ameliorated, particularly metastatic cancer, by administration of a compound of the invention that inhibits ceramidase function as discussed below (for a review of such disorders, see Fishman et al., 1985, Medicine, 2d Ed., J. B. Lippincott Co., Philadelphia).

In one aspect, the disclosed compounds and/or compositions can be useful for the treatment of a cancer, including, but not limited to, leukemia, acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia, chronic lymphocytic leukemia, polycythemia vera, Lymphoma, Hodgkin's disease, non-Hodgkin's disease, multiple myeloma, Waldenstrom's macroglobulinemia, heavy chain disease, Solid tumors, sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. For a review of such disorders, see Fishman et al., 1985, Medicine, 2d Ed., J.B. Lippincott Co., Philadelphia).

In a further aspect, cancers and related disorders that can be treated or prevented by methods and compositions disclosed herein include but are not limited to the following: leukemia, including, but not limited to, acute leukemia, acute lymphocytic leukemia; acute myelocytic leukemia, including, but not limited to, myeloblastic, promyelocytic, myelomonocytic, monocytic, erythroleukemia and myelodysplastic syndrome; chronic leukemia, including, but not limited to, chronic myelocytic (granulocytic) leukemia, chronic lymphocytic leukemia, hairy cell leukemia; polycythemia vera; lymphomas, including, but not limited to, Hodgkin's lymphoma, non-Hodgkin's lymphoma; myeloma, including, but not limited, to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas, including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumor, including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer, including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including, but not limited to, pheochromocytom and adrenocortical carcinoma; thyroid cancer, including, but not limited to, papillary or follicular thyroid cancer, medullary thyroid cancer and anaplastic thyroid cancer; pancreatic cancer, including, but not limited to, insulinoma, gastrinoma, glucagonoma, vipoma, somatostatin-secreting tumor, and carcinoid or islet cell tumor; pituitary cancers, including, but not limited to, Cushing's disease, prolactin-secreting tumor, acromegaly, and diabetes insipius; eye cancer, including, but not limited to, ocular melanoma such as iris melanoma, choroidal melanoma, and ciliary body melanoma, and retinoblastoma; vaginal cancer, including, but not limited to, squamous cell carcinoma, adenocarcinoma, and melanoma; vulvar cancer, including, but not limited to, squamous cell carcinoma, melanoma, adenocarcinoma, basal cell carcinoma, sarcoma, and Paget's disease; cervical cancer, including, but not limited to, squamous cell carcinoma, and adenocarcinoma; uterine cancer, including, but not limited to, endometrial carcinoma and uterine sarcoma; ovarian cancers, including, but not limited to, ovarian epithelial carcinoma, borderline tumor, germ cell tumor, and stromal tumor; esophageal cancer, including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancer, including, but not limited to, adenocarcinoma, fungating (polypoid), ulcerating, superficial spreading, diffusely spreading, malignant lymphom, liposarcoma, fibrosarcoma, and carcinosarcoma; colon cancer; rectal cancer; liver cancer, including, but not limited to, hepatocellular carcinoma and hepatoblastoma, gallbladder cancer, including, but not limited to, adenocarcinoma; cholangiocarcinoma, including, but not limited to, papillary, nodular, and diffuse; lung cancer, including, but not limited to, non-small cell lung cancer, squamous cell carcinoma (epidermoid carcinoma), adenocarcinoma, large-cell carcinoma and small-cell lung cancer; testicular cancer, including, but not limited to, germinal tumor, seminoma, anaplastic, classic (typical), spermatocytic, nonseminoma, embryonal carcinoma, teratoma carcinoma, and choriocarcinoma (yolk-sac tumor); prostate cancer, including, but not limited to, adenocarcinoma, leiomyosarcoma, and rhabdomyosarcoma; penal cancers; oral cancer, including, but not limited to, squamous cell carcinoma; basal cancers; salivary gland cancer, including, but not limited to, adenocarcinoma, mucoepidermoid carcinoma, and adenoidcystic carcinoma; pharynx cancer, including, but not limited to, squamous cell cancer, and verrucous; skin cancer, including, but not limited to, basal cell carcinoma, squamous cell carcinoma and melanoma, superficial spreading melanoma, nodular melanoma, lentigo malignant melanoma, and acral lentiginous melanoma; kidney cancer, including, but not limited to, renal cell cancer, adenocarcinoma, hypernephroma, fibrosarcoma, and transitional cell cancer (renal pelvis and/or uterer); Wilms' tumor; bladder cancer, including, but not limited to, transitional cell carcinoma, squamous cell cancer, adenocarcinoma, carcinosarcoma. In addition, cancer includes myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In a further aspect, cancers and related disorders that can be treated or prevented by methods and compositions disclosed herein include, but are not limited, to triple negative breast cancer (i.e. any breast cancer that does not express the genes for estrogen receptor (ER), progesterone receptor (PR) and Her2/neu). In a still further aspect, cancers and related disorders that can be treated or prevented by methods and compositions disclosed herein include, but are not limited, are myc driven or c-myc associated cancers (e.g. cancers associated with over-expression of myc), such as breast cancer, prostate cancer, colon cancer, ovarian cancer, hepatocellular carcinoma, small cell lung cancer, non-small cell lung cancer, and pediatric cancers such as neuroblastoma.

a. Treating a Disorder of Uncontrolled Cellular Proliferation

In one aspect, the invention relates to a method of treating a disorder of uncontrolled cellular proliferation in a subject, comprising the step of administering to the subject a therapeutically effective amount of a compound having the structure represented by the formula:

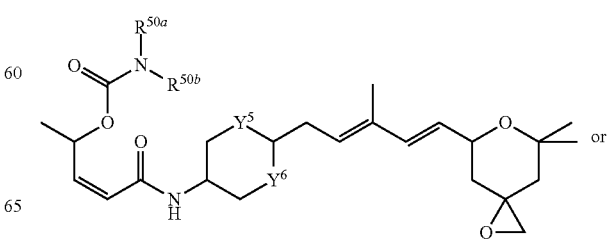

-continued

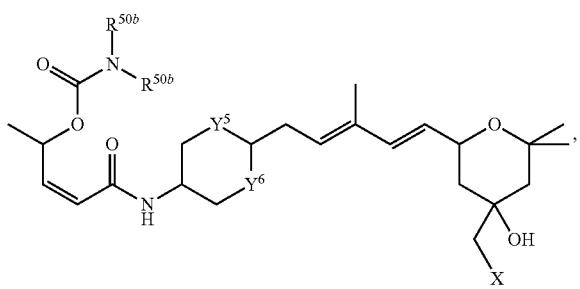

wherein each of $R^{50a}$ and $R^{50b}$ is independently selected from hydrogen, C1-C6 alkyl, C1-C6 monohaloalkyl, and C1-C6 polyhaloalkyl; wherein each of $Y^5$ and $Y^6$ is independently selected from —O— and —CH$_2$—; and wherein X is a leaving group; or a pharmaceutically acceptable salt, solvate, prodrug, or polymorph thereof.

In a further aspect, the compound is selected from:

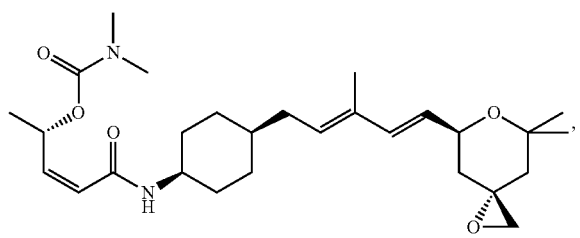 [SMILES: CC(/C=C/[C@@H]1C[C@]2(CO2)CC(C)(C)O1)=C\C[C@H]1CC[C@@H](NC(=O)/C=C\[C@H](C)OC(=O)N(C)C)CC1]

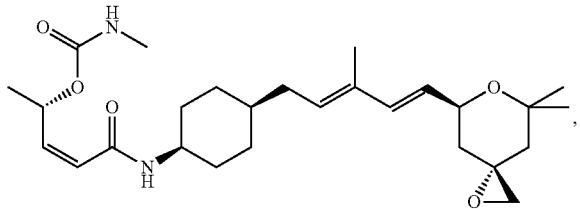

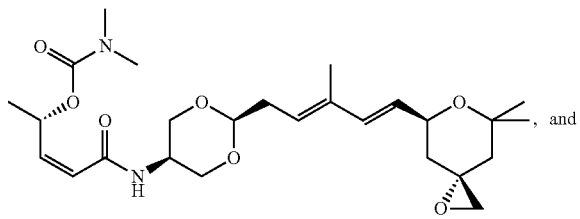

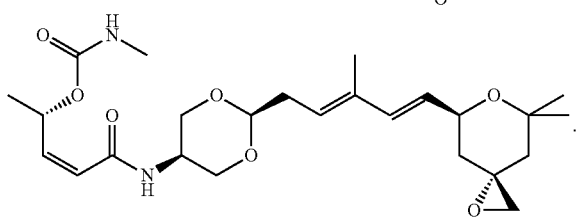

In a further aspect, the compound is selected from:

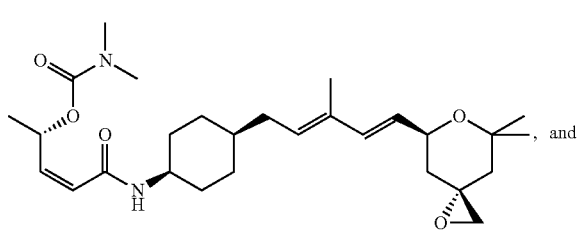

-continued

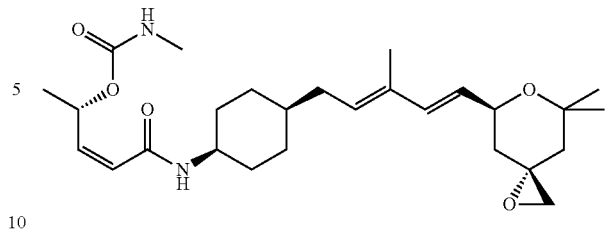

In a further aspect, the compound is selected from:

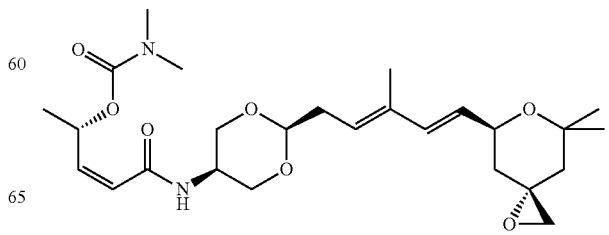

In a further aspect, the compound is:

[structure]

In a further aspect, the compound is:

[structure]

In a further aspect, the compound is:

[structure]

In a further aspect, the compound is:

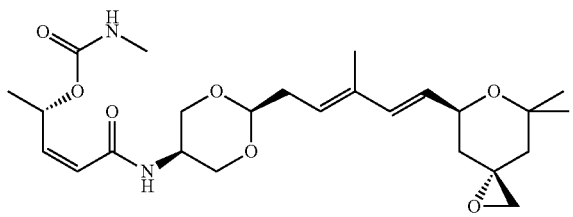

In a further aspect, the subject has been diagnosed with the disorder of uncontrolled cellular proliferation prior to the administering step. In a still further aspect, the method of treating a disorder of uncontrolled cellular proliferation in a subject further comprises the step of identifying a subject in need of treatment for a disorder of uncontrolled cellular proliferation.

In a further aspect, the step of administering occurs topically, parenterally, orally, intravenously, intramuscularly, subcutaneously or by aerosol. In a still further aspect, the step of administering occurs orally, parenterally, intramuscularly, or intravenously. In a yet further aspect, the step of administering occurs orally. In an even further aspect, step of administering occurs intravenously.

In a further aspect, the disorder of uncontrolled cellular proliferation is a cancer.

In a further aspect, the cancer is a sarcoma. In a still further aspect, the sarcoma is selected from fibrosarcoma, myxosarcoma, liposarcoma, chondrosarcoma, osteogenic sarcoma, chordoma, angiosarcoma, endotheliosarcoma, lymphangiosarcoma, leiomyosarcoma, rhabdomyosarcoma, and lymphangioendotheliosarcoma.

In a further aspect, the cancer is a carcinoma. In a still further aspect, the carcinoma is selected from colon carcinoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, bile duct carcinoma, choriocarcinoma, seminoma, embryonal carcinoma, lung carcinoma, small cell lung carcinoma, bladder carcinoma, and epithelial carcinoma.

In a further aspect, the cancer is selected from synovioma, mesothelioma, Ewing's tumor, pancreatic cancer, breast cancer, ovarian cancer, prostate cancer, hepatoma, Wilms' tumor, cervical cancer, testicular cancer, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In a further aspect, the cancer is triple negative breast cancer. In a still further aspect, the cancer is a myc driven or c-myc associated cancers. In a yet further aspect, the cancer is selected from breast cancer, prostate cancer, colon cancer, ovarian cancer, hepatocellular carcinoma, small cell lung cancer, and non-small cell lung cancer. In an even further aspect, the cancer is a pediatric cancer. In a still further aspect, the cancer is pediatric neuroblastoma.

In a further aspect, the cancer is a hematological cancer. In a still further aspect, the hematological cancer is selected from a leukemia, lymphoma, chronic myeloproliferative disorder, myelodysplastic syndrome, myeloproliferative neoplasm, plasma cell neoplasm (myeloma), solid tumor, sarcoma, and carcinoma.

In a further aspect, the hematological cancer is leukemia. In a still further aspect, the leukemia is selected from acute leukemia, acute lymphocytic leukemia, acute myelocytic leukemia, myeloblastic leukemia, promyelocytic leukemia, myelomonocytic leukemia, monocytic leukemia, erythroleukemia, chronic leukemia, chronic myelocytic (granulocytic) leukemia, and chronic lymphocytic leukemia.

In a further aspect, the hematological cancer is a lymphoma. In a still further aspect, the lymphoma is selected from AIDS-Related lymphoma, cutaneous T-Cell lymphoma, Hodgkin lymphoma, non-Hodgkin lymphoma, primary central nervous system lymphoma, mycosis fungoides and the Sézary Syndrome, heavy chain disease, and Waldenström macroglobulinemia. In a yet further aspect, the lymphoma is selected from Hodgkin's lymphoma and non-Hodgkin's lymphoma.

In a further aspect, the lymphoma is Hodgkin's lymphoma. In a still further aspect, the Hodgkin's lymphoma is classic Hodgkin lymphoma. In a yet further aspect, the classic Hodgkin's lymphoma is selected from nodular sclerosis Hodgkin lymphoma, mixed cellularity Hodgkin lymphoma, lymphocyte-depleted Hodgkin lymphoma, and Lymphocyte-rich classic Hodgkin lymphoma. In an even further aspect, the Hodgkin's lymphoma is nodular lymphocyte-predominant lymphoma.

In a further aspect, the lymphoma is non-Hodgkin's lymphoma. In a still further aspect, the non-Hodgkin's lymphoma is a B-cell type. In a yet further aspect, the B-cell type non-Hodgkin's lymphoma is selected from Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, and mantle cell lymphoma. In an even further aspect, the non-Hodgkin's lymphoma is a T-cell type. In a still further aspect, the T-cell type non-Hodgkin's lymphoma is selected from mycosis fungoides and the Sézary Syndrome, anaplastic large cell lymphoma, and precursor T-lymphoblastic lymphoma. In a yet further aspect, the non-Hodgkin's lymphoma is a NK-cell type.

In a further aspect, the hematological cancer is a chronic myeloproliferative disorder. In a still further aspect, the chronic myeloproliferative disorder is selected from chronic myelogenous leukemia, polycythemia vera, primary myelofibrosis, chronic idiopathic myelofibrosis, essential thrombocythemia, chronic neutrophilic leukemia, and chronic eosinophilic leukemia.

In a further aspect, the hematological cancer is a myeloplastic syndrome. In a still further aspect, the myeloplastic syndrome is selected from refractory anemia (RA), refractory anemia with ring sideroblasts (RARS), refractory anemia with excess blasts (RAEB), refractory cytopenia with multilineage dysplasia (RCMD), refractory cytopenia with unilineage dysplasia (RCUD), unclassifiable myelodysplastic syndrome (MDS-u), and myelodysplastic syndrome associated with an isolated del(5q).

In a further aspect, the hematological cancer is a myeloproliferative neoplasm. In a still further aspect, the myeloproliferative neoplasm is selected from chronic myelomonocytic leukemia (CMML), juvenile myelomonocytic leukemia (JMML), atypical chronic myeloid leukemia (aCML), and unclassifiable myelodysplastic/myeloproliferative neoplasm.

In a further aspect, the hematological cancer is a plasma cell neoplasm. In a still further aspect, the plasma cell neoplasm is selected from monoclonal gammopathy of undetermined significance (MGUS), isolated plasmacytoma of the bone, extramedullary plasmacytoma, and multiple myeloma.

In various aspects, the subject is a mammal. In a further aspect, the subject is a human. In a still further aspect, the subject is a mouse.

b. Treating a Genetic Disorder

In one aspect, the invention relates to a method of treating a genetic disorder in a subject, comprising the step of administering to the subject a therapeutically effective amount of a compound having the structure represented by the formula:

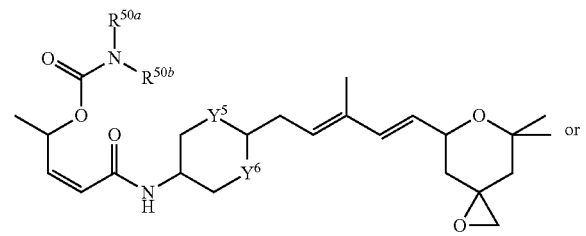

wherein each of $R^{50a}$ and $R^{50b}$ is independently selected from hydrogen, C1-C6 alkyl, C1-C6 monohaloalkyl, and C1-C6 polyhaloalkyl; wherein each of $Y^5$ and $Y^6$ is independently selected from —O— and —CH$_2$—; and wherein X is a leaving group; or a pharmaceutically acceptable salt, solvate, prodrug, or polymorph thereof.

In a further aspect, the compound is selected from:

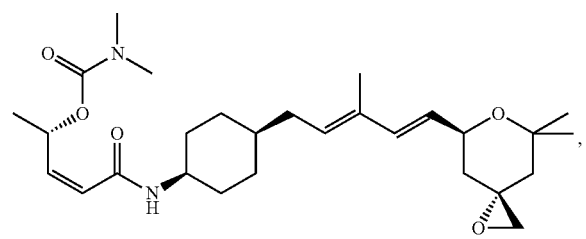

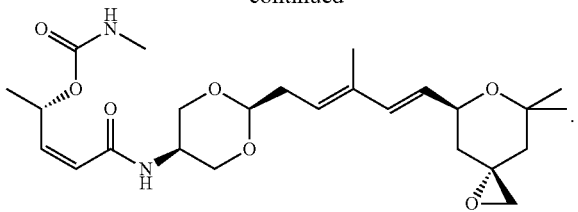

In a further aspect, the compound is selected from:

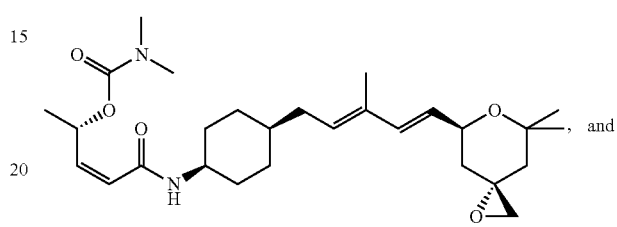

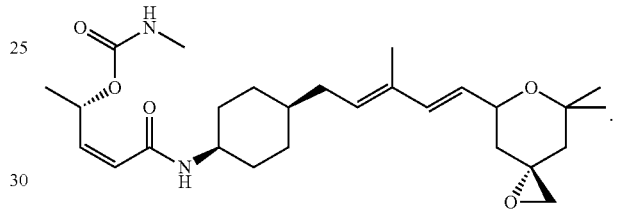

In a further aspect, the compound is selected from:

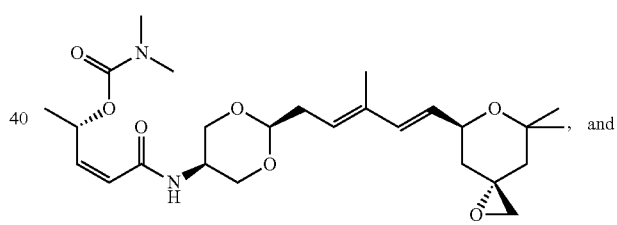

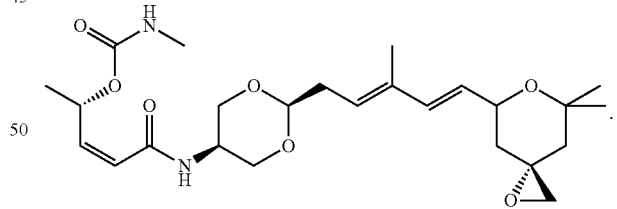

In a further aspect, the compound is:

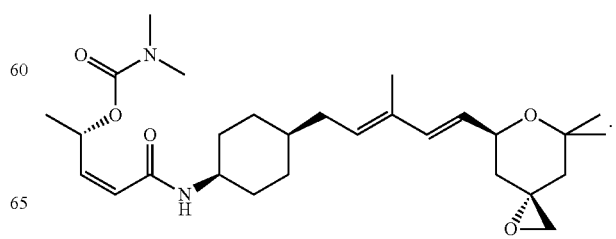

In a further aspect, the compound is:

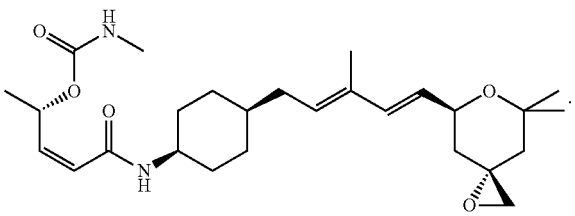 [SMILES: CNC(=O)O[C@@H](C)/C=C\C(=O)N[C@H]1CC[C@@H](C/C=C(C)/C=C/[C@@H]2C[C@]3(CO3)CC(C)(C)O2)CC1]

In a further aspect, the compound is:

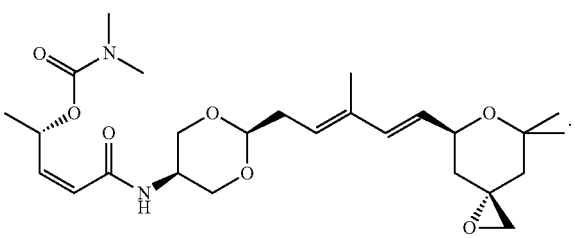 [SMILES: CC(/C=C/[C@@H]1C[C@]2(CO2)CC(C)(C)O1)=C\C[C@H]1OC[C@@H](NC(=O)/C=C\[C@H](C)OC(=O)N(C)C)CO1]

In a further aspect, the compound is:

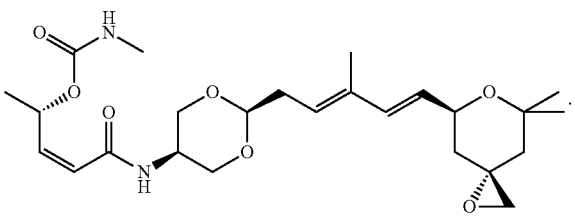 [SMILES: CNC(=O)O[C@@H](C)/C=C\C(=O)N[C@H]1CO[C@@H](C/C=C(C)/C=C/[C@@H]2C[C@]3(CO3)CC(C)(C)O2)OC1]

In a further aspect, the subject has been diagnosed with the genetic disorder prior to the administering step. In a still further aspect, the method of treating a genetic disorder further comprises the step of identifying a subject in need of treatment for a genetic disorder.

In a further aspect, the step of administering occurs topically, parenterally, orally, intravenously, intramuscularly, subcutaneously or by aerosol. In a still further aspect, the step of administering occurs orally, parenterally, intramuscularly, or intravenously. In a yet further aspect, the step of administering occurs orally. In an even further aspect, the step of administering occurs intravenously.

In a further aspect, the genetic disorder is associated with an abnormal pattern of pre-mRNA splicing. In a still further aspect, the genetic disorder is associated with uncontrolled cellular proliferation. In a yet further aspect, the uncontrolled cellular proliferation is a cancer.

In a further aspect, the cancer is a sarcoma. In a still further aspect, the sarcoma is selected from fibrosarcoma, myxosarcoma, liposarcoma, chondrosarcoma, osteogenic sarcoma, chordoma, angiosarcoma, endotheliosarcoma, lymphangiosarcoma, leiomyosarcoma, rhabdomyosarcoma, and lymphangioendotheliosarcoma.

In a further aspect, the cancer is a carcinoma. In a still further aspect, the carcinoma is selected from colon carcinoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, bile duct carcinoma, choriocarcinoma, seminoma, embryonal carcinoma, lung carcinoma, small cell lung carcinoma, bladder carcinoma, and epithelial carcinoma.

In a further aspect, the cancer is selected from synovioma, mesothelioma, Ewing's tumor, pancreatic cancer, breast cancer, ovarian cancer, prostate cancer, hepatoma, Wilms' tumor, cervical cancer, testicular cancer, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In a further aspect, the cancer is triple negative breast cancer. In a still further aspect, the cancer is a myc driven or c-myc associated cancers. In a yet further aspect, the cancer is selected from breast cancer, prostate cancer, colon cancer, ovarian cancer, hepatocellular carcinoma, small cell lung cancer, and non-small cell lung cancer. In an even further aspect, the cancer is a pediatric cancer. In a still further aspect, the cancer is pediatric neuroblastoma.

In a further aspect, the cancer is a hematological cancer. In a still further aspect, the hematological cancer is selected from a leukemia, lymphoma, chronic myeloproliferative disorder, myelodysplastic syndrome, myeloproliferative neoplasm, plasma cell neoplasm (myeloma), solid tumor, sarcoma, and carcinoma.

In a further aspect, the hematological cancer is leukemia. In a still further aspect, the leukemia is selected from acute leukemia, acute lymphocytic leukemia, acute myelocytic leukemia, myeloblastic leukemia, promyelocytic leukemia, myelomonocytic leukemia, monocytic leukemia, erythroleukemia, chronic leukemia, chronic myelocytic (granulocytic) leukemia, and chronic lymphocytic leukemia.

In a further aspect, the hematological cancer is a lymphoma. In a still further aspect, the lymphoma is selected from AIDS-Related lymphoma, cutaneous T-Cell lymphoma, Hodgkin lymphoma, non-Hodgkin lymphoma, primary central nervous system lymphoma, mycosis fungoides and the Sézary Syndrome, heavy chain disease, and Waldenström macroglobulinemia. In a yet further aspect, the lymphoma is selected from Hodgkin's lymphoma and non-Hodgkin's lymphoma.

In a further aspect, the lymphoma is Hodgkin's lymphoma. In a still further aspect, the Hodgkin's lymphoma is classic Hodgkin lymphoma. In a yet further aspect, the classic Hodgkin's lymphoma is selected from nodular sclerosis Hodgkin lymphoma, mixed cellularity Hodgkin lymphoma, lymphocyte-depleted Hodgkin lymphoma, and Lymphocyte-rich classic Hodgkin lymphoma. In an even further aspect, the Hodgkin's lymphoma is nodular lymphocyte-predominant lymphoma.

In a further aspect, the lymphoma is non-Hodgkin's lymphoma. In a still further aspect, the non-Hodgkin's lymphoma is a B-cell type. In a yet further aspect, the B-cell type non-Hodgkin's lymphoma is selected from Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, and mantle cell lymphoma. In an even further aspect, the non-Hodgkin's lymphoma is a T-cell type. In a still further aspect, the T-cell type non-Hodgkin's lymphoma is selected from mycosis fungoides and the Sézary Syndrome, anaplastic large cell lymphoma, and precursor T-lymphoblastic lymphoma. In a yet further aspect, the non-Hodgkin's lymphoma is a NK-cell type.

In a further aspect, the hematological cancer is a chronic myeloproliferative disorder. In a still further aspect, the chronic myeloproliferative disorder is selected from chronic myelogenous leukemia, polycythemia vera, primary myelofibrosis, chronic idiopathic myelofibrosis, essential thrombocythemia, chronic neutrophilic leukemia, and chronic eosinophilic leukemia.

In a further aspect, the hematological cancer is a myeloplastic syndrome. In a still further aspect, the myeloplastic syndrome is selected from refractory anemia (RA), refractory anemia with ring sideroblasts (RARS), refractory anemia with excess blasts (RAEB), refractory cytopenia with multilineage dysplasia (RCMD), refractory cytopenia with unilineage dysplasia (RCUD), unclassifiable myelodysplastic syndrome (MDS-u), and myelodysplastic syndrome associated with an isolated del(5q).

In a further aspect, the hematological cancer is a myeloproliferative neoplasm. In a still further aspect, the myeloproliferative neoplasm is selected from chronic myelomonocytic leukemia (CMML), juvenile myelomonocytic leukemia (JMML), atypical chronic myeloid leukemia (aCML), and unclassifiable myelodysplastic/myeloproliferative neoplasm.

In a further aspect, the hematological cancer is a plasma cell neoplasm. In a still further aspect, the plasma cell neoplasm is selected from monoclonal gammopathy of undetermined significance (MGUS), isolated plasmacytoma of the bone, extramedullary plasmacytoma, and multiple myeloma.

In various aspects, the subject is a mammal. In a further aspect, the subject is a human. In a still further aspect, the subject is a mouse.

In a further aspect, the genetic disorder is associated with a mutation in a gene selected from SF3B1, SRSF2, U2AF1, ZRSR2, SF3A1, PRPF40B, and SF1. In a still further aspect, the genetic disorder is associated with a mutation in the SRSF2 gene. In a yet further aspect, the genetic disorder is associated with a mutation in the U2AF1 gene. In an even further aspect, the genetic disorder is associated with a mutation in the ZRSR2 gene. In a still further aspect, the genetic disorder is associated with a mutation in the SF3A1 gene. In a yet further aspect, the genetic disorder is associated with a mutation in the PRPF40B gene. In an even further aspect, the genetic disorder is associated with a mutation in the SF1 gene.

In a further aspect, the genetic disorder is associated with a mutation in the SF3B1 gene. In a still further aspect, the mutation in the SF3B1 gene is selected from E491G, A590K, E592K, Y623C, R625H, N626D, N626Y, H662D, T663I, K666E, K700E, V701F, V701I, G740R, K741N, G742D, A744P, D781G, D894G, and A1188V. In a yet further aspect, the mutation in the SF3B1 gene is K700E. In an even further aspect, the mutation in the SF3B1 gene is V701F. In a still further aspect, the mutation in the SF3B1 gene is in a codon selected from 491, 590, 592, 623, 625, 626, 662, 663, 666, 700, 701, 740, 741, 742, 744, 781, 894, and 1188. In a yet further aspect, the mutation in the SF3B1 gene is in codon 626. In an even further aspect, the mutation in the SF3B1 gene is in codon 700. In a still further aspect, the mutation in the SF3B1 gene is in codon 701.

c. Inhibiting Cell Replication

In one aspect, the invention relates to a method for inhibiting cell replication in at least one cell, comprising the step of contacting at least one cell with an effective amount of a compound having the structure represented by the formula:

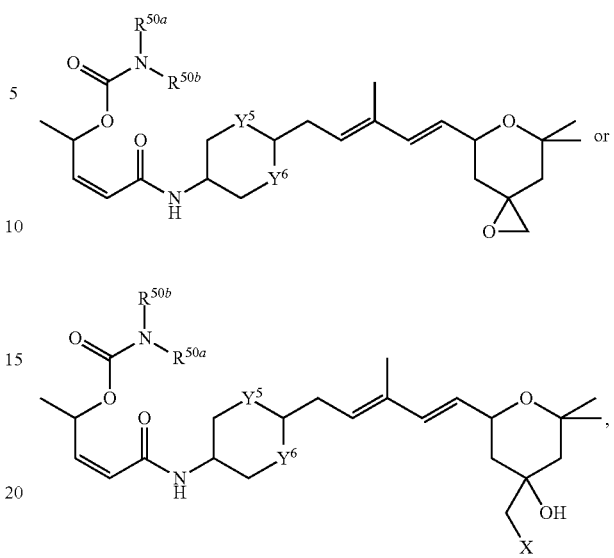

wherein each of $R^{50a}$ and $R^{50b}$ is independently selected from hydrogen, C1-C6 alkyl, C1-C6 monohaloalkyl, and C1-C6 polyhaloalkyl; wherein each of $Y^5$ and $Y^6$ is independently selected from —O— and —CH$_2$—; and wherein X is a leaving group; or a pharmaceutically acceptable salt, solvate, prodrug, or polymorph thereof.

In a further aspect, the compound is selected from:

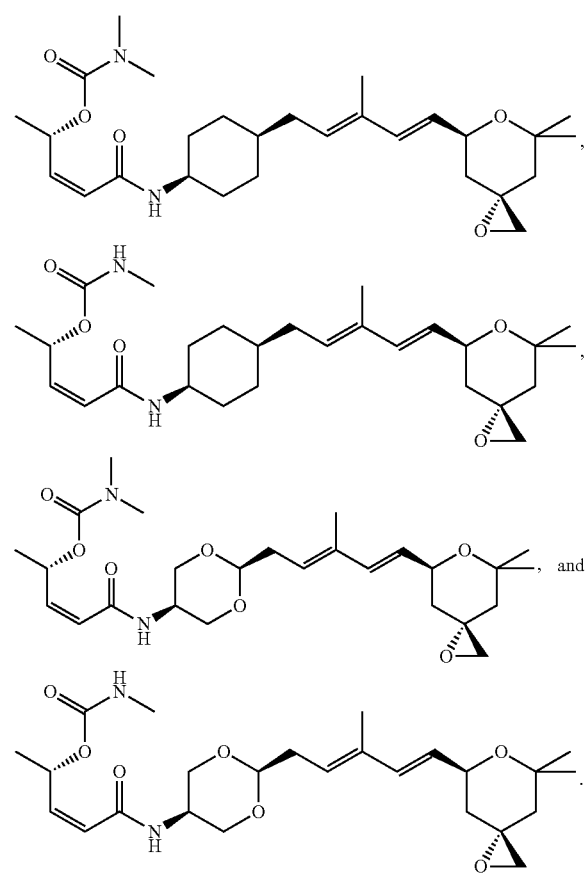

In a further aspect, the compound is selected from:

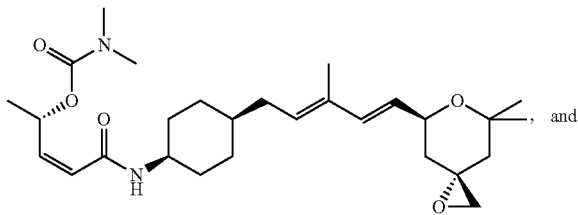
, and

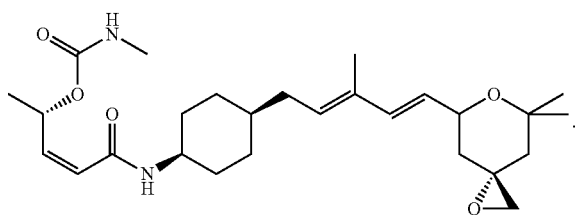
.

In a further aspect, the compound is selected from:

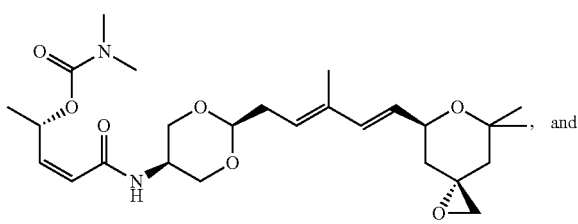
, and

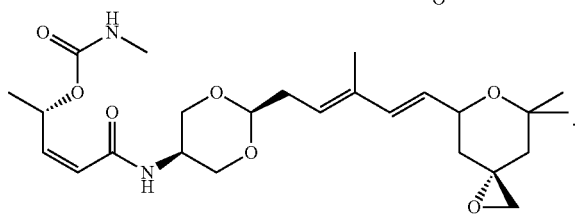
.

In a further aspect, the compound is:

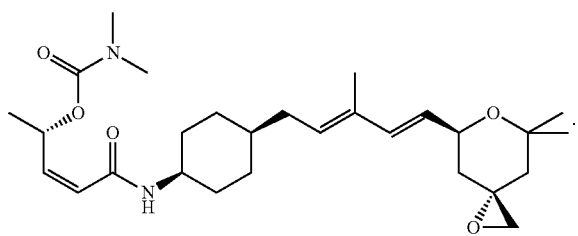 [SMILES: CC(/C=C/[C@@H]1C[C@]2(CO2)CC(C)(C)O1)=C\C[C@H]1CC[C@@H](NC(=O)/C=C\[C@H](C)OC(=O)N(C)C)CC1]
.

In a further aspect, the compound is:

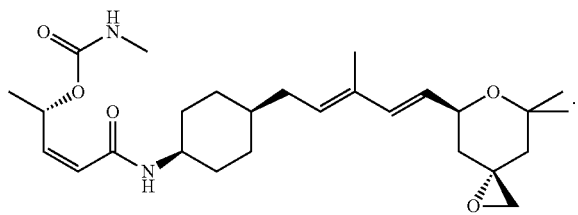 [SMILES: CNC(=O)O[C@@H](C)/C=C\C(=O)N[C@H]1CC[C@@H](C/C=C(C)/C=C/[C@@H]2C[C@]3(CO3)CC(C)(C)O2)CC1]
.

In a further aspect, the compound is:

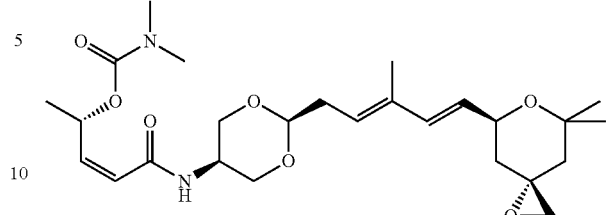
.

In a further aspect, the compound is:

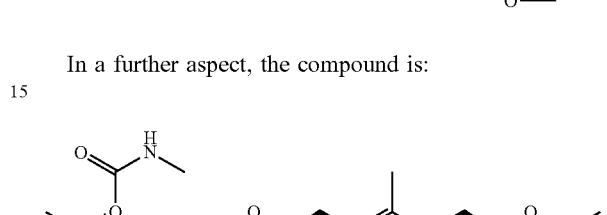
.

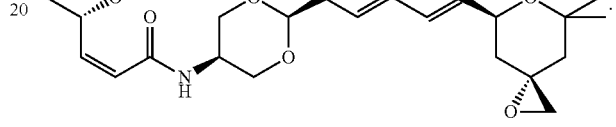

In a further aspect, inhibiting is preventing. In a still further aspect, the cell is mammalian. In a yet further aspect, the mammalian cell is human. In an even further aspect, the mammalian cell is murine. In a still further aspect, the cell is a cancer cell.

In a further aspect, the cancer cell is associated with a sarcoma. In a still further aspect, the sarcoma is selected from fibrosarcoma, myxosarcoma, liposarcoma, chondrosarcoma, osteogenic sarcoma, chordoma, angiosarcoma, endotheliosarcoma, lymphangiosarcoma, leiomyosarcoma, rhabdomyosarcoma, and lymphangioendotheliosarcoma.

In a further aspect, the cancer cell is associated with a carcinoma. In a still further aspect, the carcinoma is selected from colon carcinoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, bile duct carcinoma, choriocarcinoma, seminoma, embryonal carcinoma, lung carcinoma, small cell lung carcinoma, bladder carcinoma, and epithelial carcinoma.

In a further aspect, the cancer cell is associated with a cancer selected from synovioma, mesothelioma, Ewing's tumor, pancreatic cancer, breast cancer, ovarian cancer, prostate cancer, hepatoma, Wilms' tumor, cervical cancer, testicular cancer, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In a further aspect, the cancer is triple negative breast cancer. In a still further aspect, the cancer is a myc driven or c-myc associated cancers. In a yet further aspect, the cancer is selected from breast cancer, prostate cancer, colon cancer, ovarian cancer, hepatocellular carcinoma, small cell lung cancer, and non-small cell lung cancer. In an even further aspect, the cancer is a pediatric cancer. In a still further aspect, the cancer is pediatric neuroblastoma.

In a further aspect, the cancer cell is associated with a hematological cancer. In a still further aspect, the hematological cancer is selected from a leukemia, lymphoma, chronic myeloproliferative disorder, myelodysplastic syndrome, myeloproliferative neoplasm, plasma cell neoplasm (myeloma), solid tumor, sarcoma, and carcinoma.

In a further aspect, the hematological cancer is leukemia. In a still further aspect, the leukemia is selected from acute leukemia, acute lymphocytic leukemia, acute myelocytic leukemia, myeloblastic leukemia, promyelocytic leukemia, myelomonocytic leukemia, monocytic leukemia, erythroleukemia, chronic leukemia, chronic myelocytic (granulocytic) leukemia, and chronic lymphocytic leukemia.

In a further aspect, the hematological cancer is a lymphoma. In a still further aspect, the lymphoma is selected from AIDS-Related lymphoma, cutaneous T-Cell lymphoma, Hodgkin lymphoma, non-Hodgkin lymphoma, primary central nervous system lymphoma, mycosis fungoides and the Sézary Syndrome, heavy chain disease, and Waldenström macroglobulinemia. In a yet further aspect, the lymphoma is selected from Hodgkin's lymphoma and non-Hodgkin's lymphoma.

In a further aspect, the lymphoma is Hodgkin's lymphoma. In a still further aspect, the Hodgkin's lymphoma is classic Hodgkin lymphoma. In a yet further aspect, the classic Hodgkin's lymphoma is selected from nodular sclerosis Hodgkin lymphoma, mixed cellularity Hodgkin lymphoma, lymphocyte-depleted Hodgkin lymphoma, and Lymphocyte-rich classic Hodgkin lymphoma. In an even further aspect, the Hodgkin's lymphoma is nodular lymphocyte-predominant lymphoma.

In a further aspect, the lymphoma is non-Hodgkin's lymphoma. In a still further aspect, the non-Hodgkin's lymphoma is a B-cell type. In a yet further aspect, the B-cell type non-Hodgkin's lymphoma is selected from Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, and mantle cell lymphoma. In an even further aspect, the non-Hodgkin's lymphoma is a T-cell type. In a still further aspect, the T-cell type non-Hodgkin's lymphoma is selected from mycosis fungoides and the Sézary Syndrome, anaplastic large cell lymphoma, and precursor T-lymphoblastic lymphoma. In a yet further aspect, the non-Hodgkin's lymphoma is a NK-cell type.

In a further aspect, the hematological cancer is a chronic myeloproliferative disorder. In a still further aspect, the chronic myeloproliferative disorder is selected from chronic myelogenous leukemia, polycythemia vera, primary myelofibrosis, chronic idiopathic myelofibrosis, essential thrombocythemia, chronic neutrophilic leukemia, and chronic eosinophilic leukemia.

In a further aspect, the hematological cancer is a myeloplastic syndrome. In a still further aspect, the myeloplastic syndrome is selected from refractory anemia (RA), refractory anemia with ring sideroblasts (RARS), refractory anemia with excess blasts (RAEB), refractory cytopenia with multilineage dysplasia (RCMD), refractory cytopenia with unilineage dysplasia (RCUD), unclassifiable myelodysplastic syndrome (MDS-u), and myelodysplastic syndrome associated with an isolated del(5q).

In a further aspect, the hematological cancer is a myeloproliferative neoplasm. In a still further aspect, the myeloproliferative neoplasm is selected from chronic myelomonocytic leukemia (CMML), juvenile myelomonocytic leukemia (JMML), atypical chronic myeloid leukemia (aCML), and unclassifiable myelodysplastic/myeloproliferative neoplasm.

In a further aspect, the hematological cancer is a plasma cell neoplasm. In a still further aspect, the plasma cell neoplasm is selected from monoclonal gammopathy of undetermined significance (MGUS), isolated plasmacytoma of the bone, extramedullary plasmacytoma, and multiple myeloma.

In a further aspect, the cell has been isolated from a human prior to the contacting step. In a still further aspect, the step of contacting occurs in vitro. In a yet further aspect, the step of contacting occurs in vivo.

In a further aspect, the step of contacting occurs via administration of the compound to a subject. In a still further aspect, the step of contacting occurs via administration of the compound to a subject, wherein the subject is a mammal. In a yet further aspect, the step of contacting occurs via administration of the compound to a subject, wherein the subject is a human. In an even further aspect, the step of contacting occurs via administration of the compound to a subject, wherein the subject is a mouse.

In a further aspect, the step of contacting occurs via administration of the compound to a subject, wherein the administration occurs topically, parenterally, orally, intravenously, intramuscularly, subcutaneously, or by aerosol. In a still further aspect, the step of contacting occurs via administration of the compound to a subject, wherein the administration occurs orally, parenterally, intramuscularly, or intravenously. In a yet further aspect, the step of contacting occurs via administration of the compound to a subject, wherein the administration occurs orally. In an even further aspect, the step of contacting occurs via administration of the compound to a subject, wherein the administration occurs intravenously.

In a further aspect, the step of contacting occurs via administration of the compound to a subject, wherein the subject has been diagnosed with a need for inhibiting cell replication prior to the administering step. In a still further aspect, the step of contacting occurs via administration of the compound to a subject, wherein the subject has been diagnosed with a need for treatment of a disorder of uncontrolled cellular proliferation prior to the administering step.

d. Modulating mRNA Splicing

In one aspect, the invention relates to a method for modulating mRNA splicing in at least one cell, comprising the step of contacting the cell with an effective amount of a compound having the structure represented by the formula:

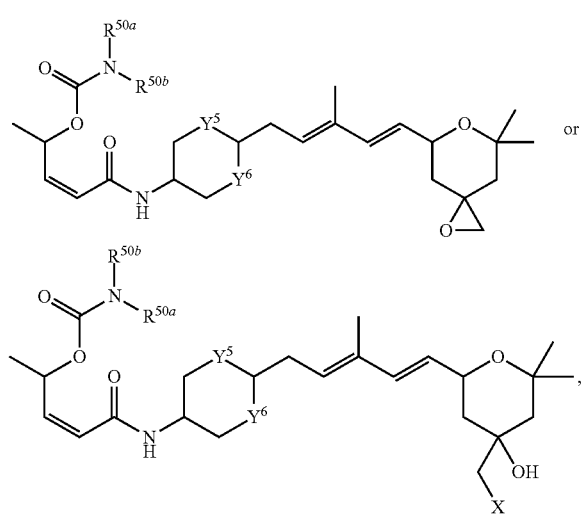

wherein each of $R^{50a}$ and $R^{50b}$ is independently selected from hydrogen, C1-C6 alkyl, C1-C6 monohaloalkyl, and C1-C6 polyhaloalkyl; wherein each of $Y^5$ and $Y^6$ is independently selected from —O— and —CH$_2$—; and wherein X is a leaving group; or a pharmaceutically acceptable salt, solvate, prodrug, or polymorph thereof.

In a further aspect, the compound is selected from:

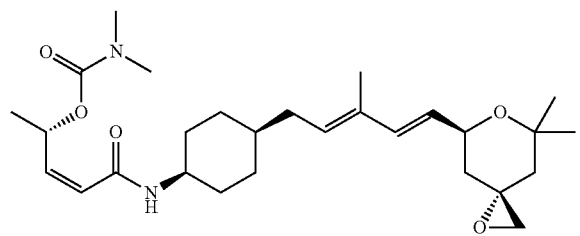
,

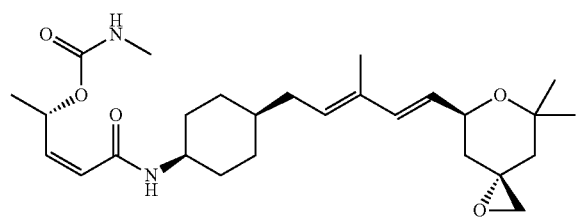
,

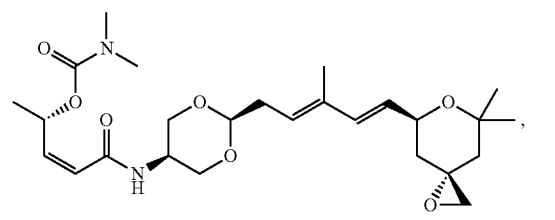
, and

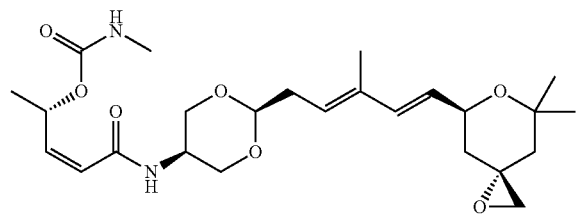
.

In a further aspect, the compound is selected from:

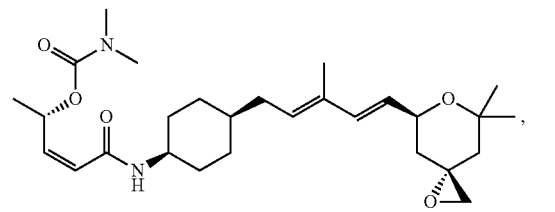
, and

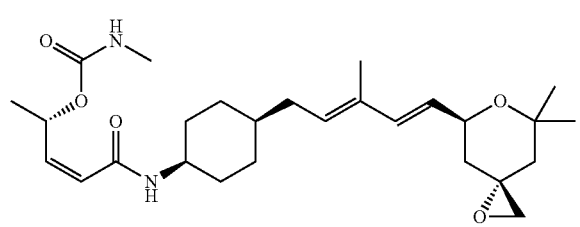
.

In a further aspect, the compound is selected from:

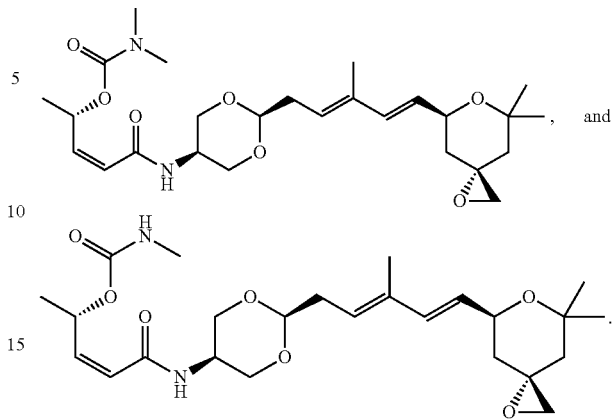

In a further aspect, the compound is:

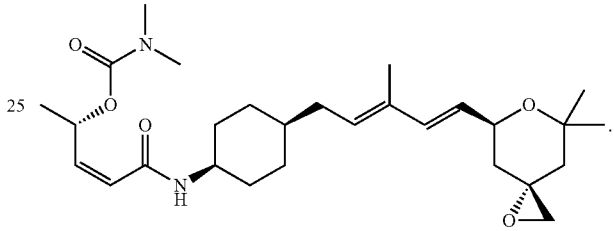

In a further aspect, the compound is:

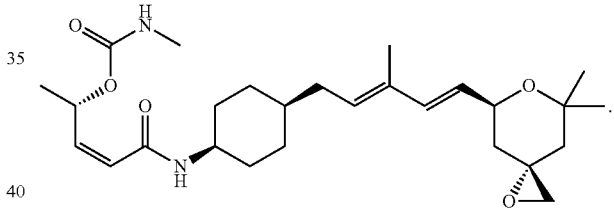

In a further aspect, the compound is:

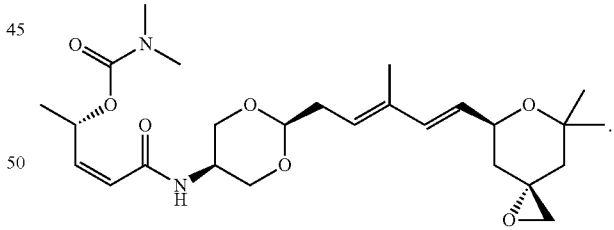

In a further aspect, the compound is:

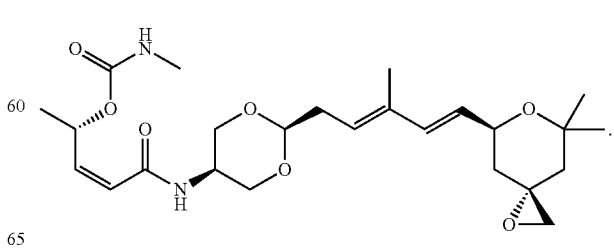

In a further aspect, the modulation of mRNA splicing results from direct impairment of at least one spliceosome in the cell. In a still further aspect, the impairment of the spliceosome is impairment of assembly of the spliceosome. In a yet further aspect, the impairment of the spliceosome is impairment of activity of the spliceosome. In an even further aspect, the splicing defect results from altered gene expression of at least one splicing factor or regulator within the cell.

In a further aspect, contacting the cell results in an accumulation of at least one truncated p27 cyclin-dependent kinase. In a still further aspect, the at least one truncated p27 cyclin-dependent kinase has biological activity. In a yet further aspect, the at least one truncated p27 cyclin-dependent kinase contributes to a cell cycle arrest of the cell.

In a further aspect, the cell is mammalian. In a still further aspect, the mammalian cell is human. In a yet further aspect, the mammalian cell is murine. In an even further aspect, the cell is a cancer cell.

In a further aspect, the cancer cell is associated with a sarcoma. In a still further aspect, the sarcoma is selected from fibrosarcoma, myxosarcoma, liposarcoma, chondrosarcoma, osteogenic sarcoma, chordoma, angiosarcoma, endotheliosarcoma, lymphangiosarcoma, leiomyosarcoma, rhabdomyosarcoma, and lymphangioendotheliosarcoma.

In a further aspect, the cancer cell is associated with a carcinoma. In a still further aspect, the carcinoma is selected from colon carcinoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, bile duct carcinoma, choriocarcinoma, seminoma, embryonal carcinoma, lung carcinoma, small cell lung carcinoma, bladder carcinoma, and epithelial carcinoma.

In a further aspect, the cancer cell is associated with triple negative breast cancer. In a still further aspect, the cancer is a myc driven or c-myc associated cancers. In a yet further aspect, the cancer cell is associated with a cancer selected from breast cancer, prostate cancer, colon cancer, ovarian cancer, hepatocellular carcinoma, small cell lung cancer, and non-small cell lung cancer. In an even further aspect, the cancer cell is associated with a pediatric cancer. In a still further aspect, the cancer cell is associated with pediatric neuroblastoma.

In a further aspect, the cancer cell is associated with a cancer selected from synovioma, mesothelioma, Ewing's tumor, pancreatic cancer, breast cancer, ovarian cancer, prostate cancer, hepatoma, Wilms' tumor, cervical cancer, testicular cancer, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In a further aspect, the cancer cell is associated with a hematological cancer. In a still further aspect, the hematological cancer is selected from a leukemia, lymphoma, chronic myeloproliferative disorder, myelodysplastic syndrome, myeloproliferative neoplasm, plasma cell neoplasm (myeloma), solid tumor, sarcoma, and carcinoma.

In a further aspect, the hematological cancer is leukemia. In a still further aspect, the leukemia is selected from acute leukemia, acute lymphocytic leukemia, acute myelocytic leukemia, myeloblastic leukemia, promyelocytic leukemia, myelomonocytic leukemia, monocytic leukemia, erythroleukemia, chronic leukemia, chronic myelocytic (granulocytic) leukemia, and chronic lymphocytic leukemia.

In a further aspect, the hematological cancer is a lymphoma. In a still further aspect, the lymphoma is selected from AIDS-Related lymphoma, cutaneous T-Cell lymphoma, Hodgkin lymphoma, non-Hodgkin lymphoma, primary central nervous system lymphoma, mycosis fungoides and the Sézary Syndrome, heavy chain disease, and Waldenström macroglobulinemia. In a yet further aspect, the lymphoma is selected from Hodgkin's lymphoma and non-Hodgkin's lymphoma.

In a further aspect, the lymphoma is Hodgkin's lymphoma. In a still further aspect, the Hodgkin's lymphoma is classic Hodgkin lymphoma. In a yet further aspect, the classic Hodgkin's lymphoma is selected from nodular sclerosis Hodgkin lymphoma, mixed cellularity Hodgkin lymphoma, lymphocyte-depleted Hodgkin lymphoma, and Lymphocyte-rich classic Hodgkin lymphoma. In an even further aspect, the Hodgkin's lymphoma is nodular lymphocyte-predominant lymphoma.

In a further aspect, the lymphoma is non-Hodgkin's lymphoma. In a still further aspect, the non-Hodgkin's lymphoma is a B-cell type. In a yet further aspect, the B-cell type non-Hodgkin's lymphoma is selected from Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, and mantle cell lymphoma. In an even further aspect, the non-Hodgkin's lymphoma is a T-cell type. In a still further aspect, the T-cell type non-Hodgkin's lymphoma is selected from mycosis fungoides and the Sézary Syndrome, anaplastic large cell lymphoma, and precursor T-lymphoblastic lymphoma. In a yet further aspect, the non-Hodgkin's lymphoma is a NK-cell type.

In a further aspect, the hematological cancer is a chronic myeloproliferative disorder. In a still further aspect, the chronic myeloproliferative disorder is selected from chronic myelogenous leukemia, polycythemia vera, primary myelofibrosis, chronic idiopathic myelofibrosis, essential thrombocythemia, chronic neutrophilic leukemia, and chronic eosinophilic leukemia.

In a further aspect, the hematological cancer is a myeloplastic syndrome. In a still further aspect, the myeloplastic syndrome is selected from refractory anemia (RA), refractory anemia with ring sideroblasts (RARS), refractory anemia with excess blasts (RAEB), refractory cytopenia with multilineage dysplasia (RCMD), refractory cytopenia with unilineage dysplasia (RCUD), unclassifiable myelodysplastic syndrome (MDS-u), and myelodysplastic syndrome associated with an isolated del(5q).

In a further aspect, the hematological cancer is a myeloproliferative neoplasm. In a still further aspect, the myeloproliferative neoplasm is selected from chronic myelomonocytic leukemia (CMML), juvenile myelomonocytic leukemia (JMML), atypical chronic myeloid leukemia (aCML), and unclassifiable myelodysplastic/myeloproliferative neoplasm.

In a further aspect, the hematological cancer is a plasma cell neoplasm. In a still further aspect, the plasma cell neoplasm is selected from monoclonal gammopathy of undetermined significance (MGUS), isolated plasmacytoma of the bone, extramedullary plasmacytoma, and multiple myeloma.

In a further aspect, the cell has been isolated from a human prior to the contacting step. In a still further aspect, the step of contacting occurs in vitro. In a yet further aspect, the step of contacting occurs in vivo.

In a further aspect, the step of contacting occurs via administration of the compound to a subject. In a still further aspect, the step of contacting occurs via administration of the compound to a subject, wherein the subject is a mammal. In a yet further aspect, the step of contacting occurs via administration of the compound to a subject, wherein the subject is a human. In an even further aspect, the step of contacting occurs via administration of the compound to a subject, wherein the subject is a mouse.

In a further aspect, the step of contacting occurs via administration of the compound to a subject, wherein the administration occurs topically, parenterally, orally, intravenously, intramuscularly, subcutaneously, or by aerosol. In a still further aspect, the step of contacting occurs via administration of the compound to a subject, wherein the administration occurs orally, parenterally, intramuscularly, or intravenously. In a yet further aspect, the step of contacting occurs via administration of the compound to a subject, wherein the administration occurs orally. In an even further aspect, the step of contacting occurs via administration of the compound to a subject, wherein the administration occurs intravenously.

In a further aspect, the step of contacting occurs via administration of the compound to a subject, wherein the subject has been diagnosed with a need for inhibiting cell replication prior to the administering step. In a still further aspect, the step of contacting occurs via administration of the compound to a subject, wherein the subject has been diagnosed with a need for treatment of a disorder of uncontrolled cellular proliferation prior to the administering step.

e. Modulating the Activity of a Spliceosome

In one aspect, the invention relates to a method for modulating the activity of at least one spliceosome in at least one cell, comprising the step of contacting the cell with an effective amount of a compound having the structure represented by the formula:

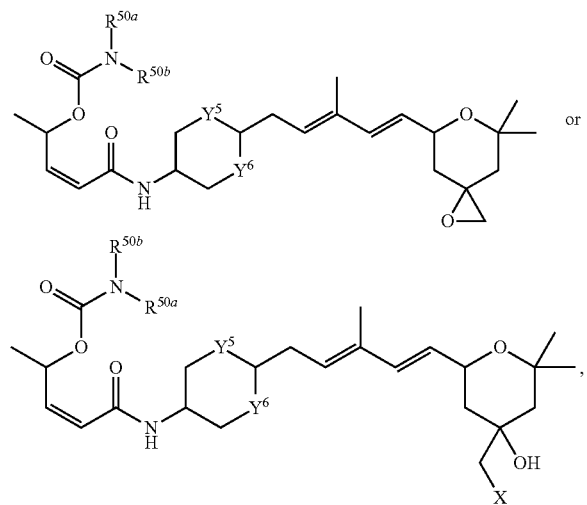

wherein each of $R^{50a}$ and $R^{50b}$ is independently selected from hydrogen, C1-C6 alkyl, C1-C6 monohaloalkyl, and C1-C6 polyhaloalkyl; wherein each of $Y^5$ and $Y^6$ is independently selected from —O— and —CH$_2$—; and wherein X is a leaving group; or a pharmaceutically acceptable salt, solvate, prodrug, or polymorph thereof.

In a further aspect, the compound is selected from:

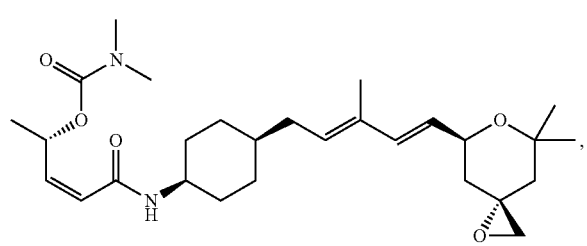

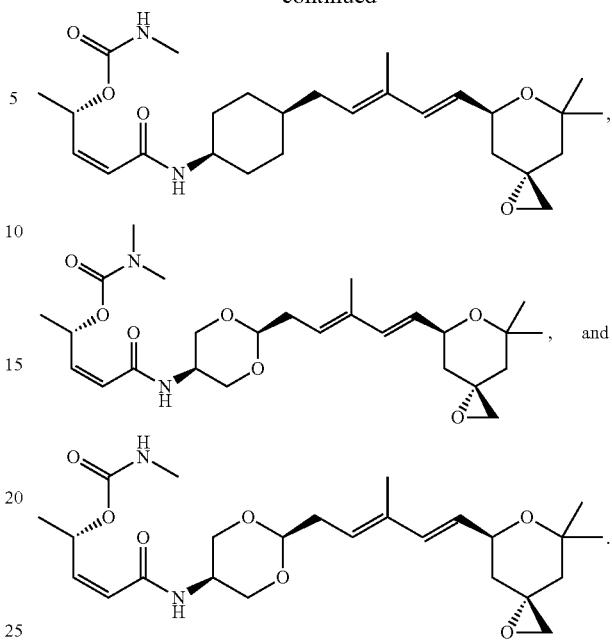

In a further aspect, the compound is selected from:

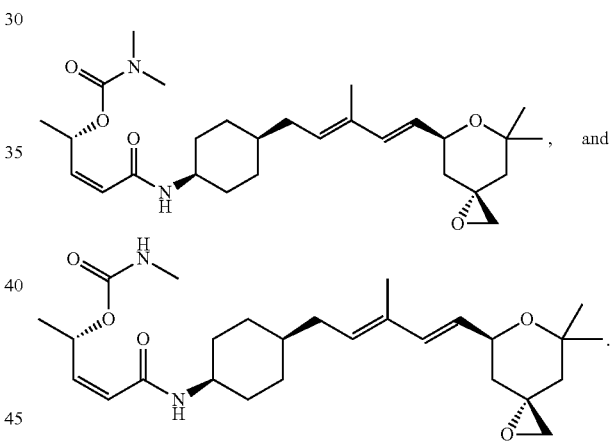

In a further aspect, the compound is selected from:

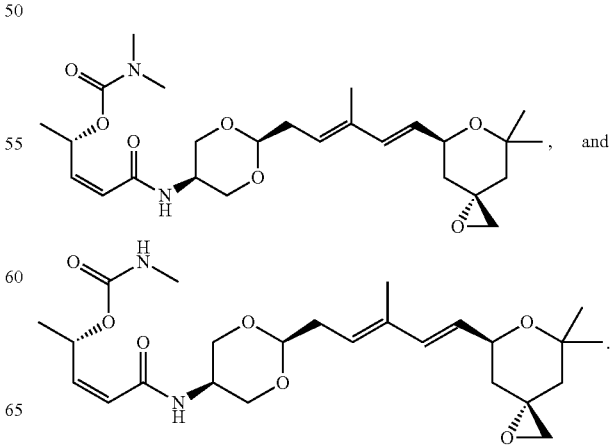

In a further aspect, the compound is:

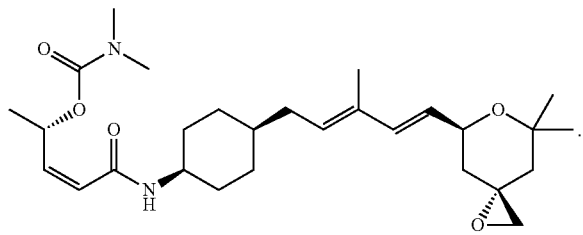 [SMILES: CC(/C=C/[C@@H]1C[C@]2(CO2)CC(C)(C)O1)=C\C[C@H]1CC[C@@H](NC(=O)/C=C\[C@H](C)OC(=O)N(C)C)CC1]

In a further aspect, the compound is:

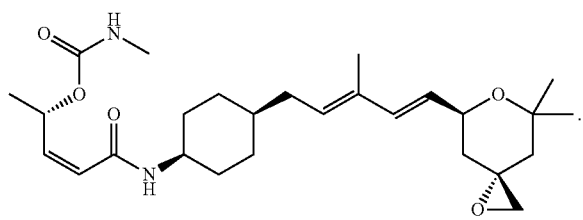

In a further aspect, the compound is:

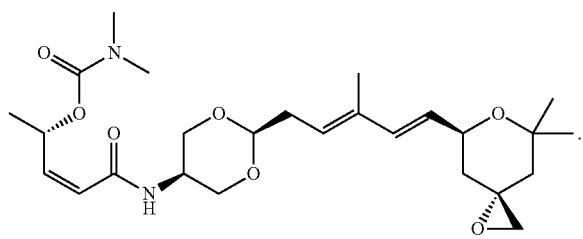 [SMILES: CC(/C=C/[C@@H]1C[C@]2(CO2)CC(C)(C)O1)=C\C[C@H]1OC[C@@H](NC(=O)/C=C\[C@H](C)OC(=O)N(C)C)CO1]

In a further aspect, the compound is:

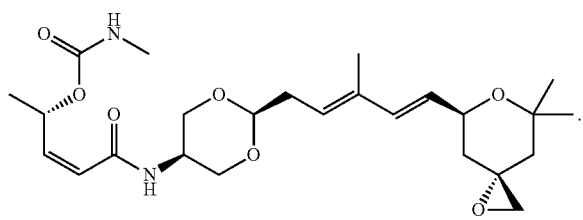

In a further aspect, the compound binds to a SF3b subunit of the spliceosome. In a still further aspect, the compound interferes with the assembly of the SF3b subunit of the spliceosome. In a yet further aspect, the compound destabilizes the SF3b subunit. In an even further aspect, the compound interferes with the integration of the SF3b subunit into a U2 snRNP particle. In a still further aspect, the compound interferes with the U2 snRNP recruitment of the at least one spliceosome. In a yet further aspect, the compound binds to a SAP130 or a SAP155 protein of the SF3b subunit. In an even further aspect, the compound binds to a SAP130 protein of the SF3b subunit. In a still further aspect, the compound binds to a SAP155 protein of the SF3b subunit.

In a further aspect, the cell is mammalian. In a still further aspect, the mammalian cell is human. In a yet further aspect, the mammalian cell is murine. In an even further aspect, the cell is a cancer cell.

In a further aspect, the cancer cell is associated with a sarcoma. In a still further aspect, the sarcoma is selected from fibrosarcoma, myxosarcoma, liposarcoma, chondrosarcoma, osteogenic sarcoma, chordoma, angiosarcoma, endotheliosarcoma, lymphangiosarcoma, leiomyosarcoma, rhabdomyosarcoma, and lymphangioendotheliosarcoma.

In a further aspect, the cancer cell is associated with a carcinoma. In a still further aspect, the carcinoma is selected from colon carcinoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, bile duct carcinoma, choriocarcinoma, seminoma, embryonal carcinoma, lung carcinoma, small cell lung carcinoma, bladder carcinoma, and epithelial carcinoma.

In a further aspect, the cancer cell is associated with a cancer selected from synovioma, mesothelioma, Ewing's tumor, pancreatic cancer, breast cancer, ovarian cancer, prostate cancer, hepatoma, Wilms' tumor, cervical cancer, testicular cancer, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In a further aspect, the cancer cell is associated with triple negative breast cancer. In a still further aspect, the cancer is a myc driven or c-myc associated cancers. In a yet further aspect, the cancer cell is associated with a cancer selected from breast cancer, prostate cancer, colon cancer, ovarian cancer, hepatocellular carcinoma, small cell lung cancer, and non-small cell lung cancer. In an even further aspect, the cancer cell is associated with a pediatric cancer. In a still further aspect, the cancer cell is associated with pediatric neuroblastoma.

In a further aspect, the cancer cell is associated with a hematological cancer. In a still further aspect, the hematological cancer is selected from a leukemia, lymphoma, chronic myeloproliferative disorder, myelodysplastic syndrome, myeloproliferative neoplasm, plasma cell neoplasm (myeloma), solid tumor, sarcoma, and carcinoma.

In a further aspect, the hematological cancer is leukemia. In a still further aspect, the leukemia is selected from acute leukemia, acute lymphocytic leukemia, acute myelocytic leukemia, myeloblastic leukemia, promyelocytic leukemia, myelomonocytic leukemia, monocytic leukemia, erythroleukemia, chronic leukemia, chronic myelocytic (granulocytic) leukemia, and chronic lymphocytic leukemia.

In a further aspect, the hematological cancer is a lymphoma. In a still further aspect, the lymphoma is selected from AIDS-Related lymphoma, cutaneous T-Cell lymphoma, Hodgkin lymphoma, non-Hodgkin lymphoma, primary central nervous system lymphoma, mycosis fungoides and the Sézary Syndrome, heavy chain disease, and Waldenström macroglobulinemia. In a yet further aspect, the lymphoma is selected from Hodgkin's lymphoma and non-Hodgkin's lymphoma.

In a further aspect, the lymphoma is Hodgkin's lymphoma. In a still further aspect, the Hodgkin's lymphoma is classic Hodgkin lymphoma. In a yet further aspect, the classic Hodgkin's lymphoma is selected from nodular sclerosis Hodgkin lymphoma, mixed cellularity Hodgkin lymphoma, lymphocyte-depleted Hodgkin lymphoma, and Lymphocyte-rich classic Hodgkin lymphoma. In an even further aspect, the Hodgkin's lymphoma is nodular lymphocyte-predominant lymphoma.

In a further aspect, the lymphoma is non-Hodgkin's lymphoma. In a still further aspect, the non-Hodgkin's lymphoma is a B-cell type. In a yet further aspect, the B-cell type non-Hodgkin's lymphoma is selected from Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, and mantle cell lymphoma. In an even further aspect, the non-Hodgkin's lymphoma is a T-cell type. In a still further aspect, the T-cell type non-Hodgkin's lymphoma is selected from mycosis fungoides and the Sézary Syndrome, anaplastic large cell lymphoma, and precursor T-lymphoblastic lymphoma. In a yet further aspect, the non-Hodgkin's lymphoma is a NK-cell type.

In a further aspect, the hematological cancer is a chronic myeloproliferative disorder. In a still further aspect, the chronic myeloproliferative disorder is selected from chronic myelogenous leukemia, polycythemia vera, primary myelofibrosis, chronic idiopathic myelofibrosis, essential thrombocythemia, chronic neutrophilic leukemia, and chronic eosinophilic leukemia.

In a further aspect, the hematological cancer is a myeloplastic syndrome. In a still further aspect, the myeloplastic syndrome is selected from refractory anemia (RA), refractory anemia with ring sideroblasts (RARS), refractory anemia with excess blasts (RAEB), refractory cytopenia with multilineage dysplasia (RCMD), refractory cytopenia with unilineage dysplasia (RCUD), unclassifiable myelodysplastic syndrome (MDS-u), and myelodysplastic syndrome associated with an isolated del(5q).

In a further aspect, the hematological cancer is a myeloproliferative neoplasm. In a still further aspect, the myeloproliferative neoplasm is selected from chronic myelomonocytic leukemia (CMML), juvenile myelomonocytic leukemia (JMML), atypical chronic myeloid leukemia (aCML), and unclassifiable myelodysplastic/myeloproliferative neoplasm.

In a further aspect, the hematological cancer is a plasma cell neoplasm. In a still further aspect, the plasma cell neoplasm is selected from monoclonal gammopathy of undetermined significance (MGUS), isolated plasmacytoma of the bone, extramedullary plasmacytoma, and multiple myeloma.

In a further aspect, the cell has been isolated from a human prior to the contacting step. In a still further aspect, the step of contacting occurs in vitro. In a yet further aspect, the step of contacting occurs in vivo.

In a further aspect, the step of contacting occurs via administration of the compound to a subject. In a still further aspect, the step of contacting occurs via administration of the compound to a subject, wherein the subject is a mammal. In a yet further aspect, the step of contacting occurs via administration of the compound to a subject, wherein the subject is a human. In an even further aspect, the step of contacting occurs via administration of the compound to a subject, wherein the subject is a mouse.

In a further aspect, the step of contacting occurs via administration of the compound to a subject, wherein the administration occurs topically, parenterally, orally, intravenously, intramuscularly, subcutaneously, or by aerosol. In a still further aspect, the step of contacting occurs via administration of the compound to a subject, wherein the administration occurs orally, parenterally, intramuscularly, or intravenously. In a yet further aspect, the step of contacting occurs via administration of the compound to a subject, wherein the administration occurs orally. In an even further aspect, the step of contacting occurs via administration of the compound to a subject, wherein the administration occurs intravenously.

In a further aspect, the step of contacting occurs via administration of the compound to a subject, wherein the subject has been diagnosed with a need for inhibiting cell replication prior to the administering step. In a still further aspect, the step of contacting occurs via administration of the compound to a subject, wherein the subject has been diagnosed with a need for treatment of a disorder of uncontrolled cellular proliferation prior to the administering step.

2. Determining a Therapeutically Effective Amount

Toxicity and therapeutic efficacy of the disclosed compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices can be desirable. While compounds that exhibit toxic side effects can be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage for use in humans. The dosage of such compounds lies preferably within a range of circulating concentrations that include the $ED_{50}$ with little or no toxicity. Dosages can vary within this range depending upon the dosage form employed and the route of administration utilized. For any compound used in disclosed herein, the therapeutically effective dose can be estimated initially from cell culture assays. A dose can be formulated in animal models to achieve a circulating plasma concentration range that includes the $IC_{50}$ as determined in cell culture experiments. Such information can be used to more accurately determine useful doses in humans. Levels in plasma can be measured, for example, by high performance liquid chromatography.

Suitable daily doses for the treatment or prevention of a disorder described herein can be readily determined by those skilled in the art. A recommended dose of a compound of a compound disclosed herein can be from about 0.1 mg to about 1000 mg per day, e.g., from about 0.1 to about 500 mg/kg/day, 0.1 to about 250 mg/kg/day, or 0.1 to about 100 mg/kg/day, per kg of body weight, given as a single dose, a single once-a-day dose, or as divided doses throughout a selected time period.

The anti-cancer activity of the disclosed therapies can be determined by using various experimental animal models of such as the SCID mouse model or nude mice with human tumor grafts known in the art and described in Yamanaka, 2001, Microbiol Immunol 2001; 45 (7): 507-14.

The disclosed protocols and compositions can be tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which a patient tissue sample is grown in culture, and exposed to or otherwise administered a protocol, and the effect of such protocol upon the tissue sample is observed.

A lower level of proliferation or survival of the contacted cells can indicate that the therapy can be effective to treat a selected disorder in a subject. Alternatively, instead of culturing cells from a patient, protocols can be screened using cells of a tumor or malignant cell line. Many assays known in the art can be used to assess such survival and/or growth; for example, cell proliferation can be assayed by measuring 3H-thymidine incorporation, by direct cell count, by detecting changes in transcriptional activity of known genes such as proto-oncogenes or cell cycle markers; cell viability can be assessed by trypan blue staining, while differentiation can be assessed visually based on changes in morphology, etc.

Compounds for use in therapy can be tested in suitable animal model systems prior to testing in humans, including but not limited to in rats, mice, chicken, cows, monkeys, rabbits, etc. The principle animal models for cancer known in the art and widely used include mice, such as described in Hann et al., 2001, Curr Opin Cell Biol 2001, 13 (6): 778-84, which is incorporated herein by reference in its entirety.

Further, any assays known to those skilled in the art can be used to evaluate the prophylactic and/or therapeutic utility of the combinatorial therapies disclosed herein for treatment, prophylaxis, management or amelioration of one or more symptoms associated with the disease or disorder as described hereinabove.

3. Co-Therapeutic Use

In one aspect, other cancer treatments can be used in combination with the administration of one or more compounds disclosed herein. Such treatments include the use of one or more molecules, or compounds for the treatment of cancer (i.e., cancer therapeutics). Some examples include, but are not limited to, chemoagents, immunotherapeutics, cancer vaccines, anti-angiogenic agents, cytokines, hormone therapies, gene therapies, biological therapies, and radiotherapies. While maintaining or enhancing efficacy of treatment, preferably the methods of the present invention increase patient compliance, improve therapy and/or reduce unwanted or adverse effects.

In one aspect, the methods of the invention includes the administration of one or more angiogenesis inhibitors such as but not limited to: angiostatin (plasminogen fragment); antiangiogenic antithrombin III; angiozyme; ABT-627; Bay 12-9566; benefin; bevacizumab; BMS-275291; cartilage-derived inhibitor (CDI); CAI; CD59 complement fragment; CEP-7055; Col 3; combretastatin A-4; endostatin (collagen XVIII fragment); fibronectin fragment; Gro-beta; halofuginone; heparinases; heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); marimastat; metalloproteinase inhibitors (TIMPs); 2-methoxyestradiol; MMI 270 (CGS 27023A); MoAb IMC-1C11; neovastat; NM-3; panzem; PI-88; placenta ribonuclease inhibitor; plasminogen activator inhibitor; platelet factor-4 (PF4); prinomastat; prolactin 16 kD fragment; proliferin-related protein (PRP); PTK 787/ZK 222594; retinoids; solimastat; squalamine; SS3304; SU5416; SU6668; SU11248; tetrahydrocortisol-S; tetrathiomolybdate; thalidomide; thrombospondin-1 (TSP-1); TNP-470; transforming growth factor-beta (TGF-b); vasculostatin; vasostatin (calreticulin fragment); ZD6126; ZD 6474; farnesyl transferase inhibitors (FTI); and bisphosphonates.

Additional examples of anti-cancer agents that can be used in the various aspects disclosed herein, including pharmaceutical compositions and dosage forms disclosed herein, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-I receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. These two agents are particularly useful when used in methods employing thalidomide and a topoisomerase inhibitor.

In a further aspect, the treatment methods disclosed herein includes the administration of one or more immunotherapeutic agents, such as antibodies and immunomodulators, which include, but are not limited to, HERCEPTINS, RITUXANS, OVAREX™, PANOREX@, BEC2, IMC-C225, VITAMIN, CAMPATH@ I/H, Smart MI95, LYMPHOCIDE™, Smart I D10, and ONCOLYM™, rituximab, gemtuzumab, or trastuzumab.

In a still further aspect, the treatment methods disclosed herein includes administering one or more anti-angiogenic agents, which include, but are not limited to, angiostatin, thalidomide, kringle 5, endostatin, other Serpins, antithrombin, 29 kDa N-terminal and 40 kDa C-terminal proteolytic fragments of fibronectin, 16 kDa proteolytic fragment of prolactin, 7.8 kDa proteolytic fragment of platelet factor-4, a 13-amino acid peptide corresponding to a fragment of platelet factor-4 (Maione et al., 1990, Cancer Res. 51: 2077), a 14-amino acid peptide corresponding to a fragment of collagen I (Tolma et al., 1993, J. Cell Biol. 122: 497), a 19 amino acid peptide corresponding to a fragment of Thrombospondin I (Tolsma et al., 1993, J Cell Biol. 122: 497), a 20-amino acid peptide corresponding to a fragment of SPARC (Sage et al., 1995, J: Cell. Biochem. 57: 1329-), or any fragments, family members, or derivatives thereof, including pharmaceutically acceptable derivatives thereof.

In one aspect, the treatment methods disclosed herein can comprise the use of radiation.

In a further aspect, the treatment methods further comprises the administration of one or more cytokines, which includes, but is not limited to, lymphokines, tumor necrosis factors, tumor necrosis factor-like cytokines, lymphotoxin-α, lymphotoxin-β, interferon-α, interferon-β, macrophage inflammatory proteins, granulocyte monocyte colony stimulating factor, interleukins (including, but not limited to, interleukin-1, interleukin-2, interleukin-6, interleukin-12, interleukin-15, interleukin-18), OX40, CD27, CD30, CD40 or CD137 ligands, Fas-Fas ligand, 4-1BBL, endothelial monocyte activating protein or any fragments, family members, or derivatives thereof, including pharmaceutically acceptable salts thereof.

In a further aspect, the treatment method comprises hormonal treatment. Hormonal therapeutic treatments comprise hormonal agonists, hormonal antagonists (e.g., flutamide, tamoxifen, leuprolide acetate (LUPRON™), LH-RH antagonists), inhibitors of hormone biosynthesis and processing, steroids (e.g., dexamethasone, retinoids, betamethasone, cortisol, cortisone, prednisone, dehydrotestosterone, glucocorticoids, mineralocorticoids, estrogen, testosterone, progestins), antigestagens (e.g., mifepristone, onapristone), antiandrogens (e.g., cyproterone acetate), and the like.

In a further aspect, the disclosure also relates to kits comprising at least one disclosed compound and one or more other therapeutically active compounds, which are usually applied in the treatment of the above mentioned conditions. For example, the disclosed kits can comprise therapeutically effective amounts of one or more disclosed compound and one or anti-cancer agents. The kits can be co-packaged, co-formulated, and/or co-delivered with the anti-cancer agents. For example, a drug manufacturer, a drug reseller, a physician, or a pharmacist can provide a disclosed kit for delivery to a patient.

4. Prophylactic Treatment

In a further aspect, the disclosed compounds, compositions, and methods can be used prophylactically, i.e., to prevent progression to a neoplastic or malignant state, including but not limited to those disorders listed above. Such prophylactic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W.B. Saunders Co., Philadelphia, pp. 68-79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

5. Kits

In one aspect, the invention relates to a kit comprising at least one compound having a structure represented by a formula:

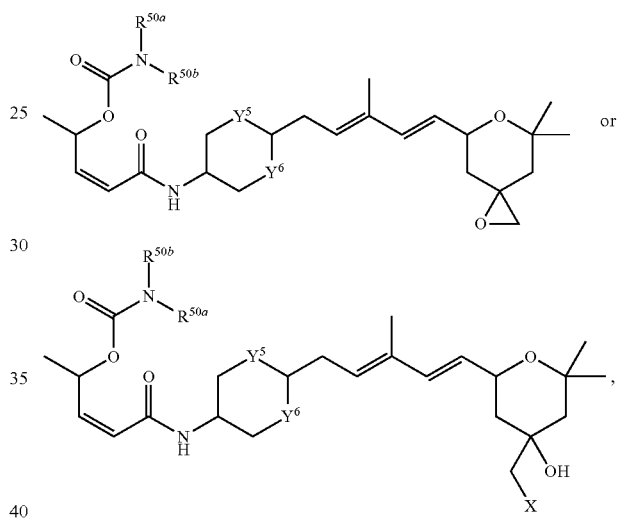

wherein each of $R^{50a}$ and $R^{50b}$ is independently selected from hydrogen, C1-C6 alkyl, C1-C6 monohaloalkyl, and C1-C6 polyhaloalkyl; wherein each of $Y^5$ and $Y^6$ is independently selected from —O— and —CH$_2$—; and wherein X is a leaving group; or a pharmaceutically acceptable salt, solvate, prodrug, or polymorph thereof; and one or more of: (a) at least one agent known to increase spliceosome activity; (b) at least one agent known to decrease spliceosome activity; (c) at least one agent known to treat a disorder of uncontrolled cellular proliferation; or (d) instructions for treating a disorder of uncontrolled cellular proliferation.

In a further aspect, the at least one compound is selected from:

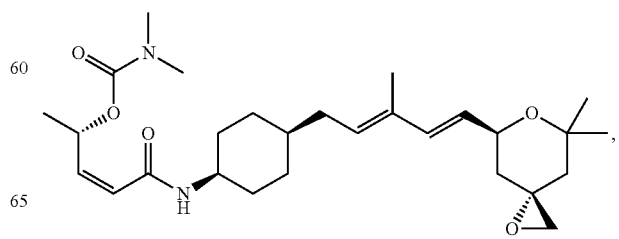

-continued

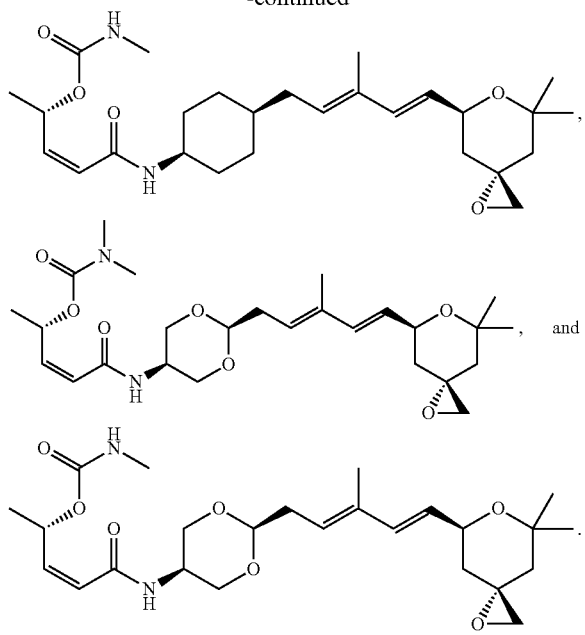

In a further aspect, the at least one compound is selected from:

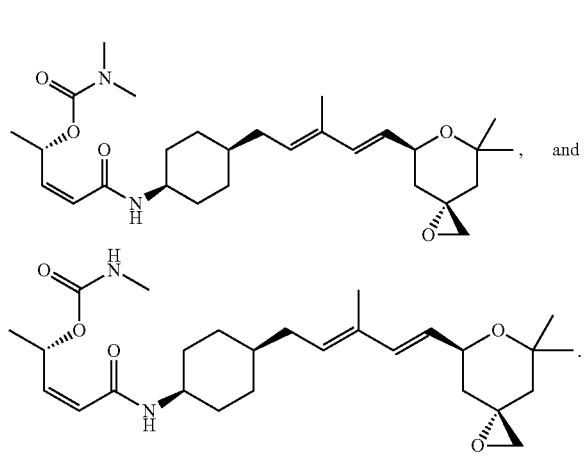

In a further aspect, the at least one compound is selected from:

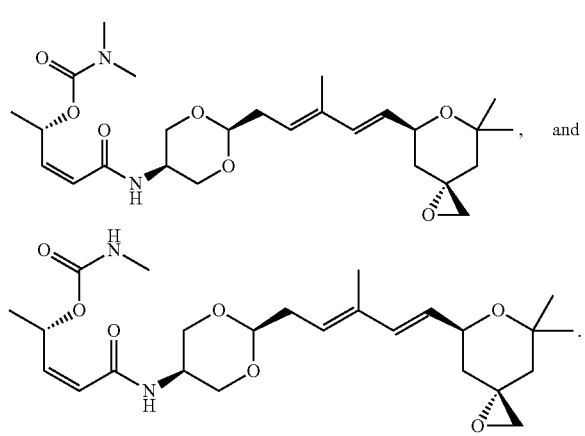

In a further aspect, the at least one compound is:

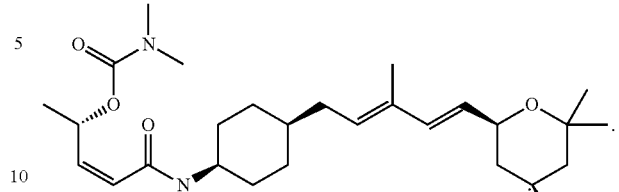

In a further aspect, the at least one compound is:

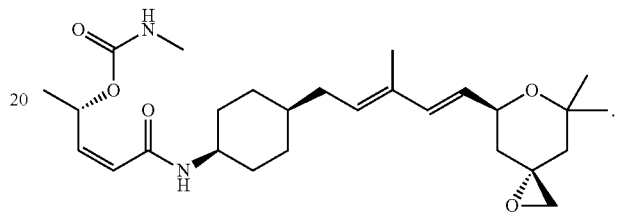

In a further aspect, the at least one compound is:

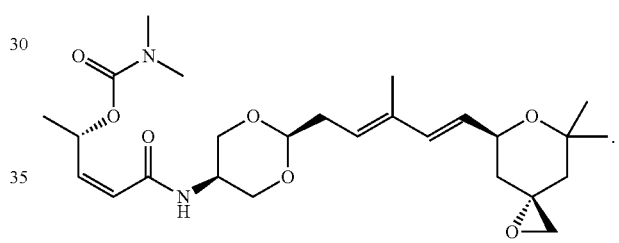

In a further aspect, the at least one compound is:

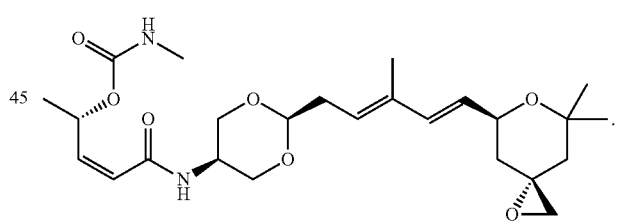

In a further aspect, the at least one compound and the at least one agent are co-formulated. In a still further aspect, the at least one compound and the at least one agent are co-packaged.

In a further aspect, the at least one agent is a hormone therapy agent. In a still further aspect, the hormone therapy agent is selected from one or more of the group consisting of leuprolide, tamoxifen, raloxifene, megestrol, fulvestrant, triptorelin, medroxyprogesterone, letrozole, anastrozole, exemestane, bicalutamide, goserelin, histrelin, fluoxymesterone, estramustine, flutamide, toremifene, degarelix, nilutamide, abarelix, and testolactone, or a pharmaceutically acceptable salt, hydrate, solvate, or polymorph thereof.

In a further aspect, the at least one agent is a chemotherapeutic agent. In a still further aspect, the chemotherapeutic agent is selected from one or more of the group consisting of an alkylating-like agent, an antimetabolite agent, an antineoplastic antibiotic agent, a mitotic inhibitor agent, an mTor inhibitor agent or other chemotherapeutic agent.

In a further aspect, the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt, hydrate, solvate, or polymorph thereof.

In a further aspect, the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt, hydrate, solvate, or polymorph thereof.

In a further aspect, the alkylating-like agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt, hydrate, solvate, or polymorph thereof.

In a further aspect, the mitotic inhibitor agent is selected from one or more of the group consisting of etopside, vincristine, ixabepilone, vinorelbine, vinblastine, and teniposide, or a pharmaceutically acceptable salt, hydrate, solvate, or polymorph thereof.

In a further aspect, the mTor inhibitor agent is selected from one or more of the group consisting of everolimus, siroliumus, and temsirolimus, or a pharmaceutically acceptable salt, hydrate, solvate, or polymorph thereof.

In a further aspect, the kit further comprises instructions to provide the compound in connection with surgery. In a still further aspect, the kit further comprises instructions to provide the compound in connection with surgery, wherein the instructions provide that surgery is performed prior to the administering of at least one compound. In a yet further aspect, the kit further comprises instructions to provide the compound in connection with surgery, wherein the instructions provide that surgery is performed after the administering of at least one compound. In an even further aspect, the kit further comprises instructions to provide the compound in connection with surgery, wherein the instructions provide that surgery is performed after the administering of at least one compound, and wherein the instructions provide that the administering of at least one compound is to effect presurgical debulking of a tumor. In a still further aspect, the kit further comprises instructions to provide the compound in connection with surgery, wherein the instructions provide that surgery is performed after the administering of at least one compound, and wherein the instructions provide that surgery is performed at about the same time as the administering of at least one compound.

In a further aspect, the kit further comprises instructions to provide the compound in connection with radiotherapy. In a still further aspect, the kit further comprises instructions to provide the compound in connection with radiotherapy, wherein the instructions provide that radiotherapy is performed prior to the administering of at least one compound. In a yet further aspect, the kit further comprises instructions to provide the compound in connection with radiotherapy, wherein the instructions provide that radiotherapy is performed after the step of the administering of at least one compound. In an even further aspect, the kit further comprises instructions to provide the compound in connection with radiotherapy, wherein the instructions provide that radiotherapy is performed at about the same time as the step of the administering of at least one compound.

In a further aspect, the kit further comprises a plurality of dosage forms, the plurality comprising one or more doses; wherein each dose comprises a therapeutically effective amount of the compound and the at least one agent. In a still further aspect, the kit further comprises a plurality of dosage forms, the plurality comprising one or more doses; wherein each dose comprises a therapeutically effective amount of the compound and the at least one agent, and wherein each dose of the compound and the at least one agent are co-formulated. In a yet further aspect, the kit further comprises a plurality of dosage forms, the plurality comprising one or more doses; wherein each dose comprises a therapeutically effective amount of the compound and the at least one agent, and wherein each dose of the compound and the at least one agent are co-packaged.

In a further aspect, the kit further comprises a plurality of dosage forms, the plurality comprising one or more doses; wherein each dose comprises a therapeutically effective amount of the compound and the at least one agent, and wherein the dosage forms are formulated for oral administration and/or intravenous administration. In a still further aspect, the kit further comprises a plurality of dosage forms, the plurality comprising one or more doses; wherein each dose comprises a therapeutically effective amount of the compound and the at least one agent, and wherein the dosage forms are formulated for oral administration. In a yet further aspect, the kit further comprises a plurality of dosage forms, the plurality comprising one or more doses; wherein each dose comprises a therapeutically effective amount of the compound and the at least one agent, and wherein the dosage forms are formulated for intravenous administration.

In a further aspect, the kit further comprises a plurality of dosage forms, the plurality comprising one or more doses; wherein each dose comprises a therapeutically effective amount of the compound and the at least one agent; and wherein the dosage form for the compound is formulated for oral administration and the dosage form for the at least one agent is formulated for intravenous administration. In a still further aspect, the kit further comprises a plurality of dosage forms, the plurality comprising one or more doses; wherein each dose comprises a therapeutically effective amount of the compound and the at least one agent; and wherein the dosage form for the compound is formulated for intravenous administration and the dosage form for the at least one agent is formulated for oral administration.

In a further aspect, the instructions for treating a disorder of uncontrolled cellular proliferation provide instructions for treating a cancer.

In a further aspect, the cancer is triple negative breast cancer. In a still further aspect, the cancer is a myc driven or c-myc associated cancers. In a yet further aspect, the cancer is selected from breast cancer, prostate cancer, colon cancer, ovarian cancer, hepatocellular carcinoma, small cell lung cancer, and non-small cell lung cancer. In an even further aspect, the cancer is a pediatric cancer. In a still further aspect, the cancer is pediatric neuroblastoma.

In a further aspect, the cancer is a hematological cancer.

In a further aspect, wherein the hematological cancer is selected from a leukemia, lymphoma, chronic myeloproliferative disorder, myelodysplastic syndrome, myeloproliferative neoplasm, and plasma cell neoplasm (myeloma).

In a further aspect, the cancer is a sarcoma. In a still further aspect, the sarcoma is selected from fibrosarcoma, myxosarcoma, liposarcoma, chondrosarcoma, osteogenic sarcoma, chordoma, angiosarcoma, endotheliosarcoma, lymphangiosarcoma, leiomyosarcoma, rhabdomyosarcoma, and lymphangioendotheliosarcoma.

In a further aspect, the cancer is a carcinoma. In a still further aspect, the carcinoma is selected from colon carcinoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, bile duct carcinoma, choriocarcinoma, seminoma, embryonal carcinoma, lung carcinoma, small cell lung carcinoma, bladder carcinoma, and epithelial carcinoma.

In a further aspect, the cancer is selected from synovioma, mesothelioma, Ewing's tumor, pancreatic cancer, breast cancer, ovarian cancer, prostate cancer, hepatoma, Wilms' tumor, cervical cancer, testicular cancer, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In a further aspect, the cancer is a hematological cancer. In a still further aspect, the hematological cancer is selected from a leukemia, lymphoma, chronic myeloproliferative disorder, myelodysplastic syndrome, myeloproliferative neoplasm, plasma cell neoplasm (myeloma), solid tumor, sarcoma, and carcinoma.

In a further aspect, the hematological cancer is leukemia. In a still further aspect, the leukemia is selected from acute leukemia, acute lymphocytic leukemia, acute myelocytic leukemia, myeloblastic leukemia, promyelocytic leukemia, myelomonocytic leukemia, monocytic leukemia, erythroleukemia, chronic leukemia, chronic myelocytic (granulocytic) leukemia, and chronic lymphocytic leukemia.

In a further aspect, the hematological cancer is a lymphoma. In a still further aspect, the lymphoma is selected from AIDS-Related lymphoma, cutaneous T-Cell lymphoma, Hodgkin lymphoma, non-Hodgkin lymphoma, primary central nervous system lymphoma, mycosis fungoides and the Sézary Syndrome, heavy chain disease, and Waldenström macroglobulinemia. In a yet further aspect, the lymphoma is selected from Hodgkin's lymphoma and non-Hodgkin's lymphoma.

In a further aspect, the lymphoma is Hodgkin's lymphoma. In a still further aspect, the Hodgkin's lymphoma is classic Hodgkin lymphoma. In a yet further aspect, the classic Hodgkin's lymphoma is selected from nodular sclerosis Hodgkin lymphoma, mixed cellularity Hodgkin lymphoma, lymphocyte-depleted Hodgkin lymphoma, and Lymphocyte-rich classic Hodgkin lymphoma. In an even further aspect, the Hodgkin's lymphoma is nodular lymphocyte-predominant lymphoma.

In a further aspect, the lymphoma is non-Hodgkin's lymphoma. In a still further aspect, the non-Hodgkin's lymphoma is a B-cell type. In a yet further aspect, the B-cell type non-Hodgkin's lymphoma is selected from Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, and mantle cell lymphoma. In an even further aspect, the non-Hodgkin's lymphoma is a T-cell type. In a still further aspect, the T-cell type non-Hodgkin's lymphoma is selected from mycosis fungoides and the Sézary Syndrome, anaplastic large cell lymphoma, and precursor T-lymphoblastic lymphoma. In a yet further aspect, the non-Hodgkin's lymphoma is a NK-cell type.

In a further aspect, the hematological cancer is a chronic myeloproliferative disorder. In a still further aspect, the chronic myeloproliferative disorder is selected from chronic myelogenous leukemia, polycythemia vera, primary myelofibrosis, chronic idiopathic myelofibrosis, essential thrombocythemia, chronic neutrophilic leukemia, and chronic eosinophilic leukemia.

In a further aspect, the hematological cancer is a myeloplastic syndrome. In a still further aspect, the myeloplastic syndrome is selected from refractory anemia (RA), refractory anemia with ring sideroblasts (RARS), refractory anemia with excess blasts (RAEB), refractory cytopenia with multilineage dysplasia (RCMD), refractory cytopenia with unilineage dysplasia (RCUD), unclassifiable myelodysplastic syndrome (MDS-u), and myelodysplastic syndrome associated with an isolated del(5q).

In a further aspect, the hematological cancer is a myeloproliferative neoplasm. In a still further aspect, the myeloproliferative neoplasm is selected from chronic myelomonocytic leukemia (CMML), juvenile myelomonocytic leukemia (JMML), atypical chronic myeloid leukemia (aCML), and unclassifiable myelodysplastic/myeloproliferative neoplasm.

In a further aspect, the hematological cancer is a plasma cell neoplasm. In a still further aspect, the plasma cell neoplasm is selected from monoclonal gammopathy of undetermined significance (MGUS), isolated plasmacytoma of the bone, extramedullary plasmacytoma, and multiple myeloma.

6. Subjects

The compounds, compositions, and methods disclosed herein can be useful for the treatment or prevention of one or more disorders associated with cell splicing in a subject, as discussed hereinabove. In general, a subject can be any age, including a fetus. A subject to which a compound or compositions disclosed herein can be administered can be an animal, including but not limited to a mammal, such as a non-primate mammal (e.g., cows, pigs, sheep, goats, horses, chickens, dogs, rats, etc.) and a primate (e.g., a monkey such as a acynomolgous monkey and a human). A subject can also be a laboratory animal (e.g., a mouse, rabbit, guinea pig, fruit fly, etc.).

In one aspect, a subject can be diagnosed with one or more disorders as discussed herein elsewhere. In a specific aspect, a subject can be diagnosed with one or more disorders as discussed herein elsewhere before the step of administering to the subject a therapeutically effective amount of one more compounds disclosed herein.

In a further aspect, a subject can be a subject in need of treatment for disorder of uncontrolled cellular proliferation, e.g., cancer. In a still further aspect, a subject can have cancer or a related disorder, as discussed hereinbefore. In one aspect, a subject can be treated prophylactically with a compound or composition disclosed herein, as discussed herein elsewhere.

One or more compounds or compositions disclosed herein can be utilized for the prevention of a variety of cancers, e.g, in individuals who are predisposed as a result of familial history or in individuals with an enhanced risk to cancer due to environmental factors.

The methods and compositions of the invention can be used in patients who are treatment naive, in patients who have previously received or are currently receiving treatment with other pharmaceutical agents or combinations, including but not limited to anti-cancer agents. Other subjects can include patients that have metastasis or no metastasis.

The methods and compositions of the invention are useful not only in untreated patients but are also useful in the treatment of patients partially or completely un-responsive to other treatments. In various aspects, the disclosure provides methods and compositions useful for the treatment of diseases or disorders in patients that have been shown to be or can be refractory or non-responsive to therapies comprising the administration of other agents.

In one aspect, subjects that can be treated with the compositions disclosed herein include those subjects displaying the presence of one or more characteristics of a transformed phenotype, or of a malignant phenotype, displayed in vivo or displayed in vitro by a cell sample from a subject, can indicate the desirability of prophylactic/therapeutic administration of a compound or composition disclosed herein. As mentioned hereinabove, such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 Dalton cell surface protein, etc.

In a further aspect, a subject that exhibits one or more of the following predisposing factors for malignancy can be treated by administration of an effective amount of a compound disclosed herein: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, Basic Pathology, 2d Ed., W.B. Saunders Co., Philadelphia, pp. 112-113) etc.)

7. Manufacture of a Medicament

Also provided is a method for the manufacture of a medicament for treatment of a disorder in a subject (e.g., a mammal), for modulating spliceosome activity, comprising at least one compound having a structure represented by a formula:

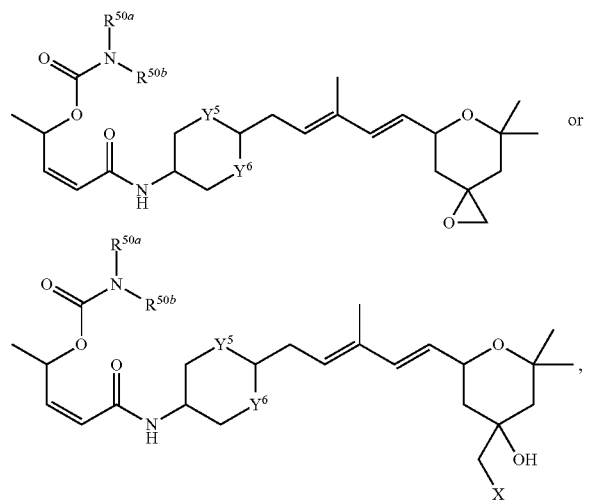

wherein each of $R^{50a}$ and $R^{50b}$ is independently selected from hydrogen, C1-C6 alkyl, C1-C6 monohaloalkyl, and C1-C6 polyhaloalkyl; wherein each of $Y^5$ and $Y^6$ is independently selected from —O— and —CH$_2$—; and wherein X is a leaving group; or a pharmaceutically acceptable salt, solvate, prodrug, or polymorph thereof.

In a further aspect, the medicament comprises a compound selected from:

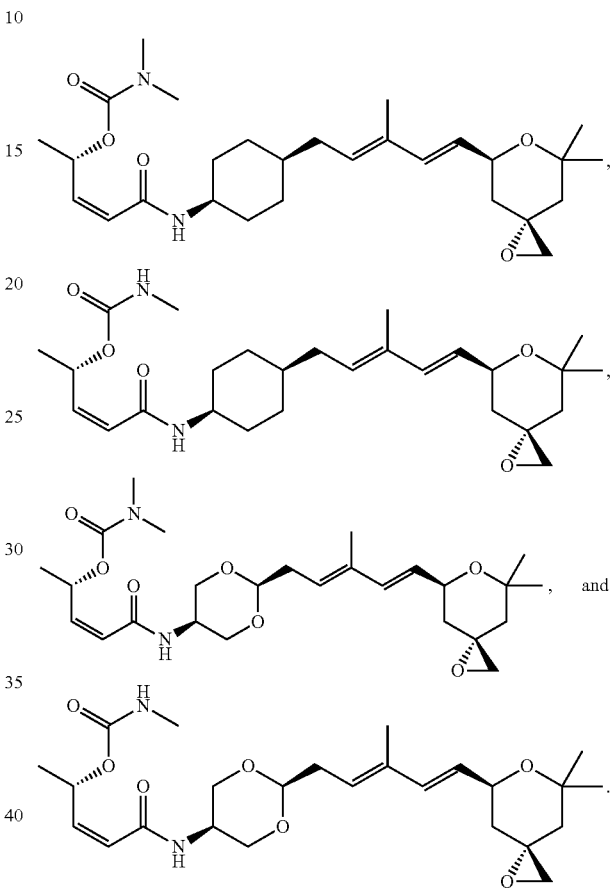

In a further aspect, the medicament comprises a compound selected from:

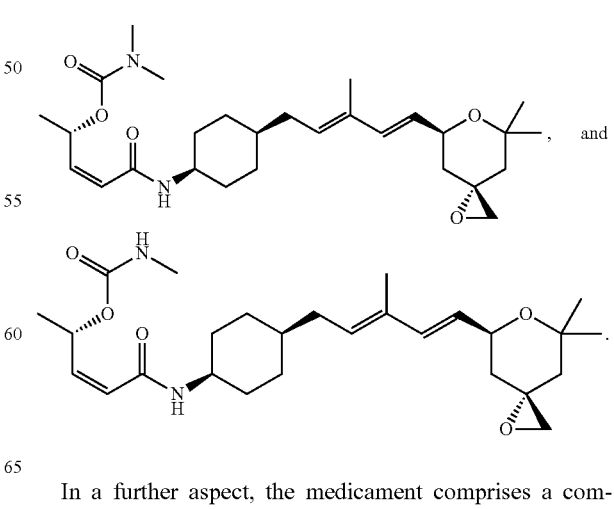

In a further aspect, the medicament comprises a compound selected from:

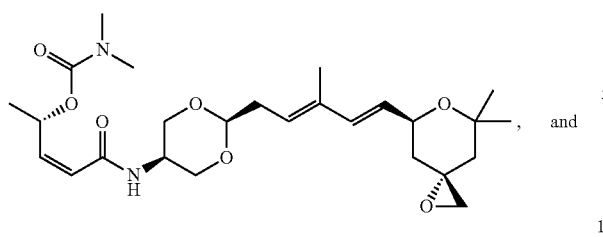, and

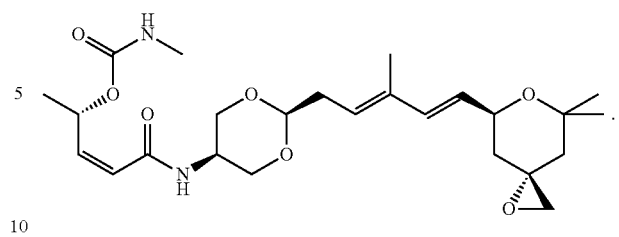

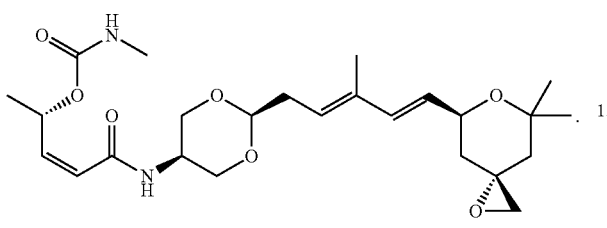

In a further aspect, the medicament comprises the compound:

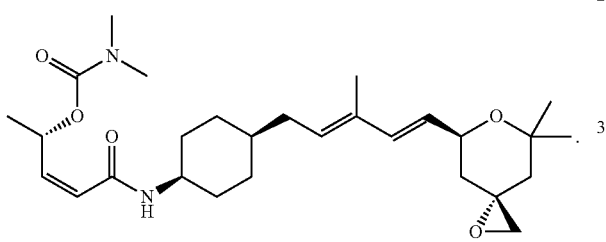

In a further aspect, the medicament comprises the compound:

8. Use of Compounds

Also provided are uses of the disclosed compounds. For example, provided is the use of a compound having a structure represented by a formula:

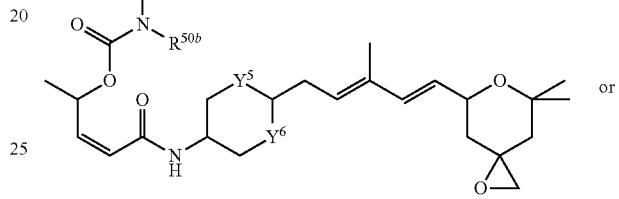 or wherein each of $R^{50a}$ and $R^{50b}$ is independently selected from hydrogen, C1-C6 alkyl, C1-C6 monohaloalkyl, and C1-C6 polyhaloalkyl; wherein each of $Y^5$ and $Y^6$ is independently selected from —O— and —CH$_2$—; and wherein X is a leaving group; or a pharmaceutically acceptable salt, solvate, prodrug, or polymorph thereof.

In a further aspect, provided is the use of a compound selected from:

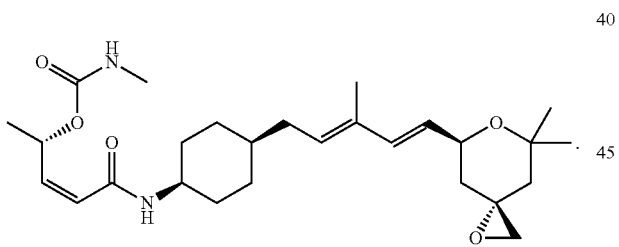

In a further aspect, the medicament comprises the compound:

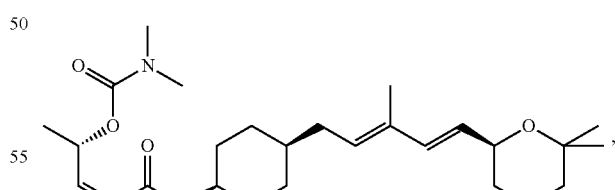

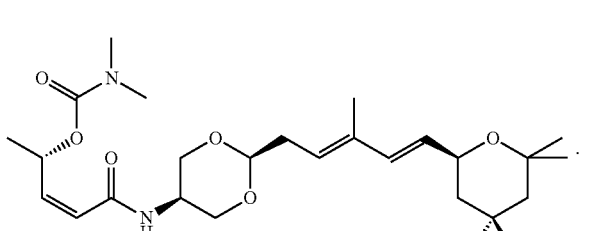

In a further aspect, the medicament comprises the compound:

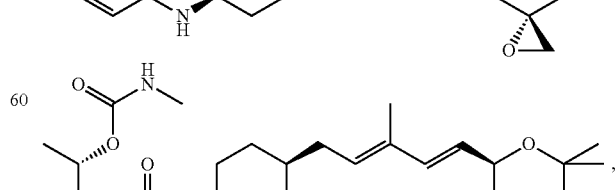

-continued

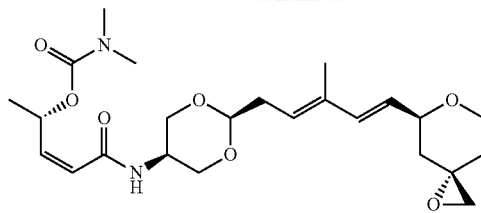, and

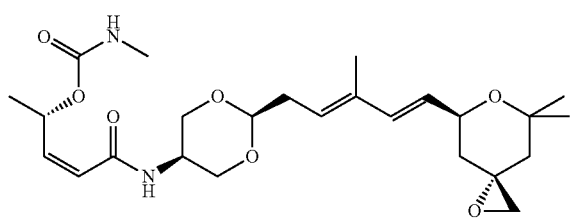.

In a further aspect, provided is the use of a compound selected from:

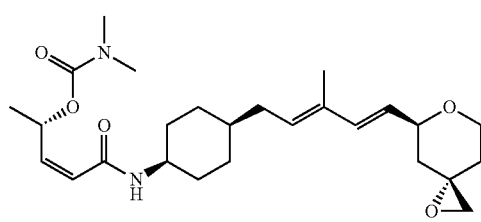, and

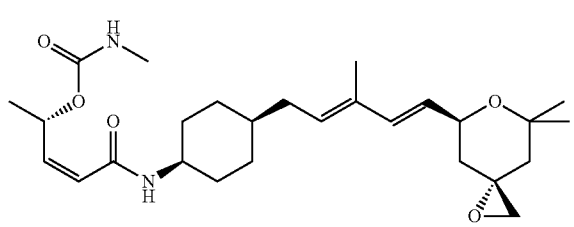.

In a further aspect, provided is the use of a compound selected from:

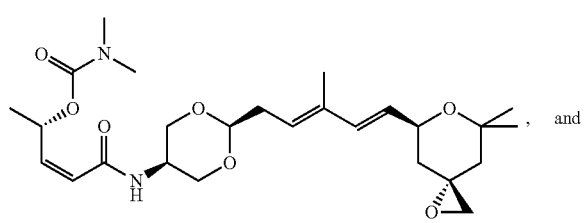, and

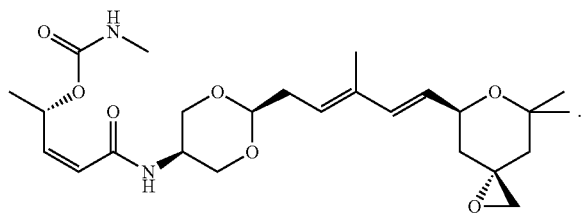 [SMILES: CNC(=O)O[C@@H](C)/C=C\C(=O)N[C@H]1CO[C@@H](C/C=C(C)/C=C/[C@@H]2C[C@]3(CO3)CC(C)(C)O2)OC1].

In a further aspect, provided is the use of the compound:

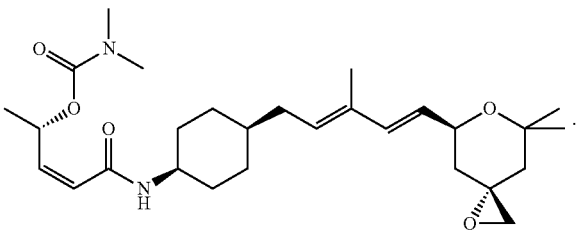 [SMILES: CC(/C=C/[C@@H]1C[C@]2(CO2)CC(C)(C)O1)=C\C[C@H]1CC[C@@H](NC(=O)/C=C\[C@H](C)OC(=O)N(C)C)CC1].

In a further aspect, provided is the use of the compound:

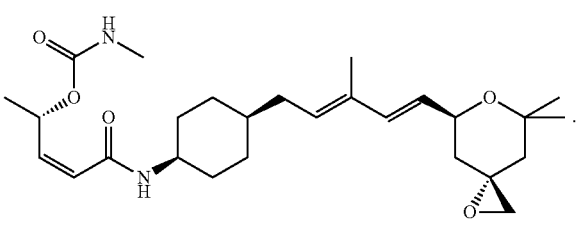 [SMILES: CNC(=O)O[C@@H](C)/C=C\C(=O)N[C@H]1CC[C@@H](C/C=C(C)/C=C/[C@@H]2C[C@]3(CO3)CC(C)(C)O2)CC1].

In a further aspect, provided is the use of the compound:

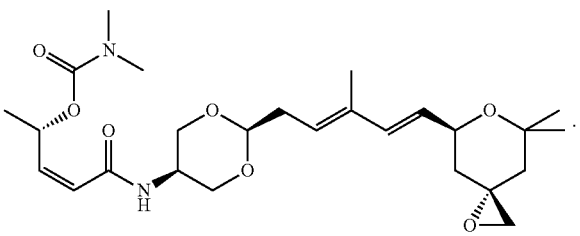 [SMILES: CC(/C=C/[C@@H]1C[C@]2(CO2)CC(C)(C)O1)=C\C[C@H]1OC[C@@H](NC(=O)/C=C\[C@H](C)OC(=O)N(C)C)CO1].

In a further aspect, provided is the use of the compound:

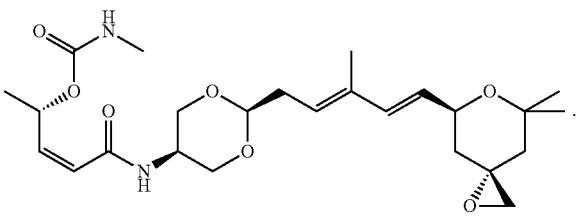 [SMILES: CNC(=O)O[C@@H](C)/C=C\C(=O)N[C@H]1CO[C@@H](C/C=C(C)/C=C/[C@@H]2C[C@]3(CO3)CC(C)(C)O2)OC1].

In one aspect, the use relates to the treatment of a disorder in a subject, e.g., a mammal, including a human.

F. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. General Methods

All materials and reagents were used as is unless otherwise indicated. Air- or moisture-sensitive reactions were carried out under a nitrogen atmosphere. THF, toluene, acetonitrile, N,N-dimethyl formamide and $CH_2Cl_2$ were distilled before use. All compounds were purified on Biotage pre-packed silica gel columns. TLC analysis was performed using glass TLC plates (0.25 mm, 60 F-254 silica gel). Visualization of the developed plates was accomplished by staining with ethanolic phosphomolybdic acid, ceric ammonium molybdate, or ethanolic ninhydrin followed by heating on a hot plate (120° C.). All tested compounds possessed a purity of >95% as determined by ultra-high pressure liquid chromatography on a Waters Acquity UPLC/PDA/ELSD/MS system carried out with a BEH C18 2.1×50 mm column using gradient elution with stationary phase: BEH C18, 1.7 mm, solvents: A: 0.1% formic acid in water, B: 0.1% formic acid in acetonitrile. NMR spectra were obtained on Bruker Avance II 400 MHz. The values $d_H$ 7.26 and $d_C$ 77.0 ppm were used as references for NMR spectroscopy in $CDCl_3$. The coupling constants deduced in $^1H$ NMR data cases were obtained by first-order coupling analysis. Analytical and preparative SFC (Supercritical Fluid Chromatography) systems (AD-H) were used for analysis and purification. IR spectra were collected using a Nicolet IR 100 (FT IR). FT IR analyses were prepared as neat and neat films on KBr plates, and the data are reported in wave-numbers ($cm^{-1}$) unless specified otherwise. Melting points (mp) were obtained on a Buchi apparatus and are uncorrected. The University of Illinois Mass Spectroscopy Laboratories and High Throughput Analytical Center at St. Jude Children's Research Hospital collected the high resolution mass spectral data.

2. Synthesis of Intermediates a. Synthesis of (S)-Butyl 6,6-Dimethyl-4-Oxotetrahydro-2H-Pyran-2-Carboxylate (1)

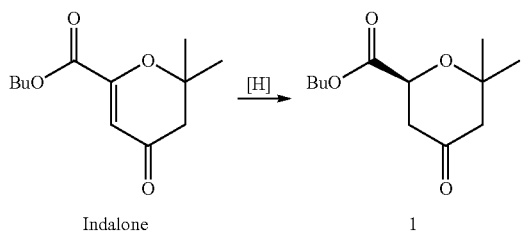

A solution of commercially available indalone (29 g, 129 mmol) and (2R,5R)-5-butylmethyl-2-(5-methylfuran-2-yl) imidazolidin-4-one (6.3 g, 23.2 mmol) in anhydrous $Et_2O$ (580 mL) was stirred and cooled at ice bath temperature (0-4° C.) as di-tert-butyl 2,6-dimethyldicarboxylate (45.9 g, 145 mmol) and trichloroacetic acid (TCA) (3.8 g, 23.2 mmol) were sequentially added. The resulting yellow solution was allowed to stir for 6 days in the cold room (~4° C.) by which time $^1HNMR$ showed all of starting material has been consumed. The reaction mixture was passed through a short pad of silica gel and eluted with $Et_2O$ (400 mL). Concentration and purification of the residue on silica gel (750 g, 5-24% EtOAc in hexane) gave 27 g (93%) of keto ester 1 as an oil. All analytical data for this compound was reported in our earlier publication.

b. Synthesis of (3R,5S)-Butyl 7,7-Dimethyl-1,6-Dioxaspiro[2.5]Octane-5-Carboxylate (2)

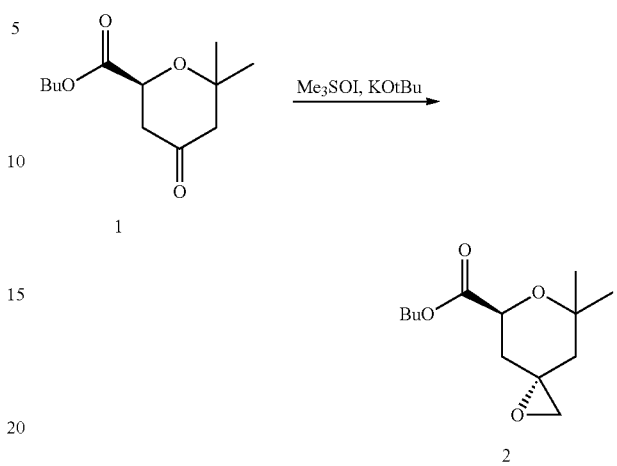

Trimethylsulfoxonium iodide (788 mg, 3.51 mmol) and t-BuOK (0.310 ml, 2.76 mmol) were added to a 25 mL 2-neck round bottom flask. Anhydrous DMSO (5 mL) was added to the reaction flask which was under $N_2$ at room temp. The reaction was stirred for 1 hr and then cooled to 15° C. (S)-butyl 6,6-dimethyl-4-oxotetrahydro-2H-pyran-2-carboxylate (500 mg, 2.190 mmol) dissolved in 3 mL anhydrous DMSO was added to the reaction flask drop wise. A small aliquot was taken from the reaction flask, quenched with water and EtOAc. The sample was analyzed by TLC in 10% EtOAc/Hexane (eluted twice). The reaction was complete and was quenched after 30 min with ice water (5 mL). The product was extracted with EtOAc (3×20 mL). The organic layers were combined, washed with water (20 mL) and brine (20 mL) and dried over $Na_2SO_4$. The organic solution was concentrated and chromatographed using a 5-30% gradient of EtOAc/Hex to yield 403 mg (76%).

c. Synthesis of 7,7-Dimethyl-1,6-Dioxaspiro[2.5] Octan-5-Yl)Methanol (3)

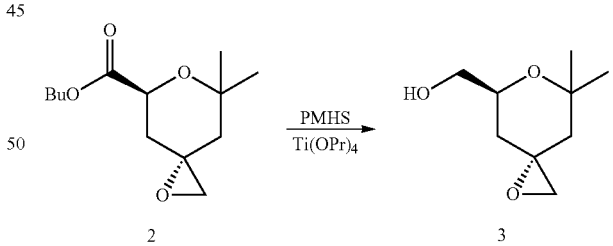

In a 500 mL RB flask, the ester 2 (34.5 g, 141 mmol) and polymethylhydrosiloxane (PMHS) (22.3 g, 356 mmol) were mixed and cooled to 0° C. $Ti(OPr)_4$ (43 mL, 141 mmol) was added via an addition funnel to the above neat solution over 30 min, and stirred for 24 h at rt. The reaction mixture was diluted with THF (400 mL) and transferred to a 1 L RB flask, which was cooled with a cold water bath. This was then allowed to rapidly stir and slowly treated with 4M aqueous NaOH (114 mL). The mixture was stirred until the evolution of gas had ceased and then for an additional 2 h at rt. The resulting cloudy white mixture was then extracted with ether (2×550 mL, 2×300 30% EtOAc in ether). The combined organic layers were then washed with water (150 mL) and dried over Na$_2$SO$_4$. Concentration and purification of the residue on silica gel (340 g, 7-40% acetone in hexane) gave 22 g (88%) of alcohol 3 as an oil. [α]$_D^{24}$+56.2° (c=2.2, CHCl$_3$); the analytical data for this compound was identical to that reported in our earlier publication.

d. Synthesis of 2-((((3R,5S)-7,7-Dimethyl-1,6-Dioxaspiro[2.5]Octan-5-yl)Methyl)Thio)Benzo[D]Thiazole (4)

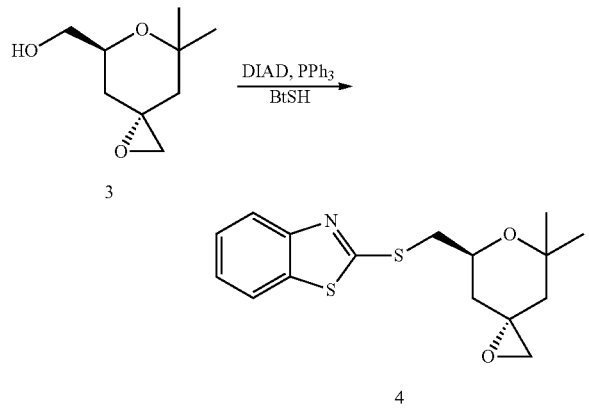

A solution of alcohol 3 (19.5 g, 113 mmol) in THF (750 mL) was treated with Ph$_3$P (32.7 g, 6.31 mmol) and 2-mercapto benzothiazole (20.5 g, 119 mmol) and allowed to stir at rt. After 15 min, the reaction solution was cooled to 0° C. as diisopropyl azodicarboxylate (26 mL, 125 mmol) in toluene (70 mL) was added drop-wise. The resulting yellow suspension was allowed to stir for 1 h at 0° C. by which time TLC indicated that all of starting material was consumed. The reaction mixture was concentrated and the residue was triturated with 10% EtOAc in hexane (500 mL). The solids were filtered and washed with 7.5% EtOAc in hexane (3×100 mL). The filtrate was then evaporated and the resulting residue was purified by flash chromatography (750 g, 5-30% EtOAc in hexane) to give 27.6 g (76%) of sulfide derivative 4 as a viscous oil. [α]$_D^{24}$+49.9° (c=1.3, CHCl$_3$); $^1$H NMR (400 MHz, CDCl$_3$) δ 7.87-7.82 (m, 1H), 7.76-7.72 (m, 1H), 7.44-7.37 (m, 1H), 7.32-7.27 (m, 1H), 4.35-4.24 (m, 1H), 3.54 (ddd, J=19.8, 13.2, 5.8 Hz, 2H), 2.57 (q, J=4.6 Hz, 2H), 2.03-1.92 (m, 2H), 1.42-1.34 (m, 4H), 1.25 (s, 3H), 1.16 (dd, J=13.9, 1.9 Hz, 1H); $^{13}$C NMR (101 MHz, CDCl$_3$) δ 167.14, 153.17, 135.33, 125.98, 124.16, 121.46, 120.95, 73.58, 67.46, 55.56, 50.94, 42.42, 38.76, 37.04, 31.26, 23.72; IR (Neat Film) 2973, 2910, 1459, 1428, 1252, 1090, 1055, 1020 cm$^{-1}$; HRMS (ESI) m/z Calculated for C$_{16}$H$_{19}$NO$_2$S$_2$ (M+1)$^+$ 322.0935. found 322.0930.

e. Synthesis of 2-((((3R,5S)-7,7-Dimethyl-1,6-Dioxaspiro[2.5]Octan-5-yl)Methyl)Sulfonyl)Benzo[D]Thiazole (5)

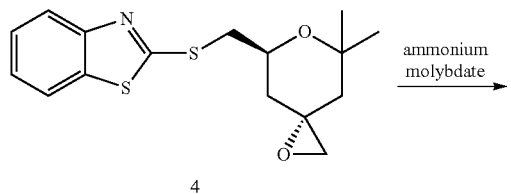

A solution of sulfide 4 (29 g, 90 mmol) in EtOH (700 mL) at 0° C. was treated with a mixture of ammonium molybdate 4H$_2$O (33.4 g, mmol) and 30% H$_2$O$_2$ (123 mL, 1.08 mol) which was adjusted to pH 4-5 with 7.0 phosphate buffer (49 mL, 0.26 M) at 0° C., before the addition. The resulting suspension was allowed to stir for 14 h at room temperature by which time SFC and LC/MS analysis showed that all of starting material has been consumed. The reaction solution was divided into two portions for further work-up. Each portion was diluted with water (400 mL) and CH$_2$Cl$_2$ (400 mL) and the aqueous layer was extracted with CH$_2$Cl$_2$ (2×300 mL), washed with brine (1×300 mL). The two organic portions were combined and dried over Na$_2$SO$_4$. The solvent was evaporated under reduced pressure to give the crude product as a white viscous solid. This was crystallized using methylene chloride and hexane to give 29 g (91%) of pure sulfone 5 as a white solid. Melting point=124-126° C.; [α]$_D^{24}$+4.5° (c=1.1, CHCl$_3$); $^1$H NMR (400 MHz, CDCl$_3$) δ 8.25-8.17 (m, 1H), 8.04-7.97 (m, 1H), 7.67-7.52 (m, 2H), 4.62-4.54 (m, 1H), 3.91 (dd, J=14.8, 9.2 Hz, 1H), 3.43 (dd, J=14.7, 2.8 Hz, 1H), 2.53 (dd, J=17.9, 4.5 Hz, 2H), 1.96-1.74 (m, 2H), 1.25 (s, 3H), 1.23-1.20 (m, 1H), 1.01 (dd, J=14.0, 1.8 Hz, 1H), 0.59 (s, 3H); $^{13}$C NMR (101 MHz, CDCl$_3$) δ 167.14, 153.17, 135.33, 125.98, 124.16, 121.46, 120.95, 73.58, 67.46, 55.56, 50.94, 42.42, 38.76, 37.04, 31.26, 23.72; IR (Neat Film) 2973, 2916, 1475, 1423, 1325, 1147, 1088, 1027 cm$^{-1}$; HRMS (ESI) m/z Calculated for C$_{16}$H$_{19}$NO$_4$S$_2$ (M+1)$^+$ 354.0834. found 354.0843.

f. Synthesis of Tert-Butyl((1S,4S)-4-(2-Hydroxyethyl)Cyclohexyl)Carbamate (6)

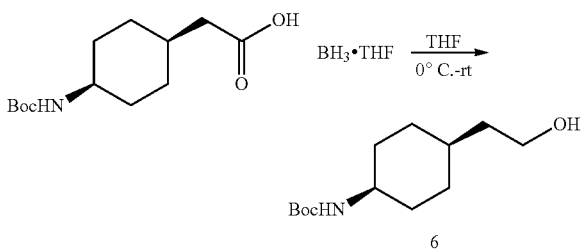

A stirred solution of acid (15.6.0 g, 60.3 mmol) in anhydrous THF (250 mL) and cooled to 0° C. as BH$_3$.THF (158 mL, 65.3 mmol, 1.0 M in THF) was added drop-wise over 1 h. The resulting homogenous solution was stirred for 3 h at room temperature at which time the TLC indicated that the acid has been consumed. The reaction was cooled to 0° C. and aqueous 3N NaOH (52 mL) was added to destroy the excess borane. The resulting mixture was allowed to stir for additional 1.5 h at rt. The solvent was removed under reduced pressure and the resulting residue was diluted with EtOAc (200 mL) and saturated aqueous NaHCO$_3$ (80 mL). The organic layer was separated and the aqueous layer was then extracted with EtOAc (2×200 mL). The combined organic layers were washed with water (200 mL) and brine (150 mL), dried over MgSO₄. Concentrated and the resulting viscous solid was crystallized using methylene chloride and hexane to give 12.2 g (86%) of alcohol 6 as a white solid. Melting point=78-79° C.; $^1$H NMR (400 MHz, CDCl₃) δ 4.65 (s, 1H), 3.74 (bs, 1H), 3.71 (dd, 3H, J=6.4, 11.6 Hz), 1.58 (m, 8H), 1.47 (s, 9H), 1.25 (s, 3H); $^{13}$C NMR (CDCl₃, 100 MHz) δ 155.2, 79.1, 60.8, 46.4, 38.4, 29.7, 28.6, 27.8; IR (Neat) 3424, 3308, 2929, 2858, 1674, 1531, 1448, 1395, 1318, 1249, 1162, 1049 cm$^{-1}$; HRMS (ESI) m/z Calculated for C₁₃H₂₆NO₃ (M+1)⁺ 244.1913. found 244.1916.

g. Synthesis of 2-((1S,4S)-4-Azidocyclohexyl)Ethanol (7)

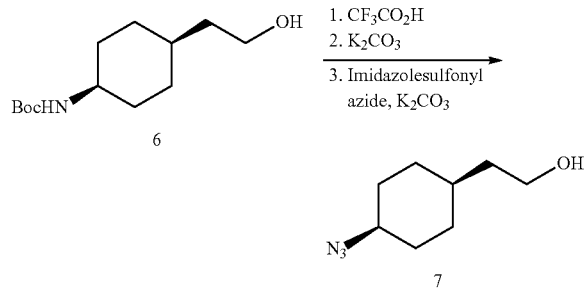

A solution of NHBoc alcohol derivative 6 (10 g, 41.1 mmol) in methylene chloride (160 mL) at 0° C. as trifluoroacetic acid (35.1 mL, 431 mmol) was added drop wise. The resulting solution was allowed to warm to room temperature and stirred for additional 4 h at which time TLC showed that all of the stating material has been consumed. The solvent was evaporated under reduced pressure and the resulting residue was dissolved in MeOH (200 mL), cooled to 0° C. and solid K₂CO₃ (17.0 g, 123 mmol) was then added to the resulting solution. This mixture was allowed to stir for 1 h, filtered through sintered funnel and washed with methylene chloride (2×50 mL). The filtrate was concentrated to give free amine (5.8 g) as oil. The crude amine used in the next step without further purification.

To a stirred solution of amine derivative (5.8 g, 40.5 mmol) in MeOH (225 mL) was sequentially added K₂CO₃ (12.5 g, 91 mmol) and CuSO₄ 5H₂O (0.1 g, 0.4 mmol). The mixture was cooled to 0° C. and 1H-imidazole-1-sulfonylazide HCl (9.4 g, 54.7 mmol) was added portion-wise to the resulting suspension. The reaction was warmed to room temperature and stirred for overnight. The reaction mixture was concentrated under vacuum and diluted with water (100 mL). The product was extracted with EtOAc (2×250 mL) and the combined organic layers were dried over Na₂SO₄. Concentrated and the resulted residue was purified on silica column (160 g, 6-40% acetone in hexane) to give 5 g (73%) of the azide derivative 7 as colorless oil. $^1$H NMR (400 MHz, CDCl₃) δ 3.84-3.74 (m, 1H), 3.69 (t, J=6.1 Hz, 2H), 1.88-1.72 (m, 2H), 1.66-1.43 (m, 8H), 1.40-1.18 (m, 2H); $^{13}$C NMR (101 MHz, CDCl₃) δ 60.57, 57.92, 39.01, 32.67, 29.14, 27.45; IR (Neat Film) 3274, 2872, 2802, 2061, 1419, 1236, 1032 cm$^{-1}$; HRMS (ESI) m/z Calculated for C₈H₁₅N₃O (M+1)⁺ 170.1288. found 170.1281.

h. Synthesis of (E)-Ethyl 4-((1S,4S)-4-Azidocyclohexyl)-2-Methylbut-2-Enoate (8)

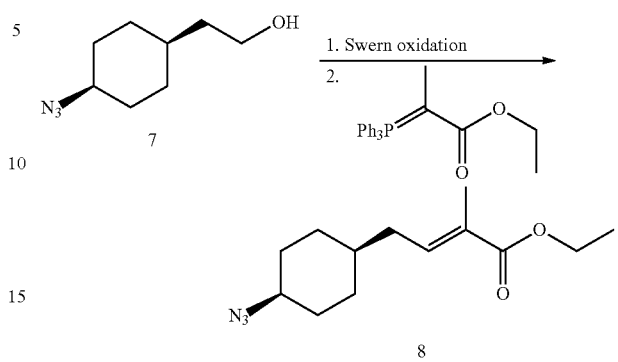

A cold (−78° C.) stirred solution of oxalyl chloride (20.6 mL, 2M in methylene chloride, 41.4 mmol) in anhydrous methylene chloride (80 mL) was treated with DMSO (4.2 mL, 59.1 mmol) drop-wise. After the resultant mixture was stirred for 15 min at −78° C., a solution of alcohol 7 (5 g, 29.5 mmol) in methylene chloride (60 mL) was added. The resultant slurry was stirred at −78° C. for 60 min and then treated with diisopropylethylamine (26.3 mL, 148 mmol). The cooling bath was removed, and the reaction mixture was stirred at room temperature for 1 h to afford a yellow solution of aldehyde. This solution was cooled to 0° C. and treated with stable ylide (16.0 g, 44.3 mmol) at 0° C. for 10 min. The resulting suspension was allowed to warm to room temperature and stirred overnight. Water (100 mL) and ether (300 mL) were added to the reaction mixture. The organic layer was separated and washed sequentially with water (100 mL), brine (50 mL) and dried over Na₂SO₄. Concentrated and the resulting residue was purified on silica column (160 g, 2-20% EtOAc in hexane) to give 7 g (94%) of conjugated ester 8 as oil. $^1$H NMR (400 MHz, CDCl₃) δ 6.75 (tq, J=7.7, 1.5 Hz, 1H), 4.29-4.14 (q, J=7.1 Hz, 2H), 3.86-3.72 (m, 1H), 2.11 (t, J=7.5 Hz, 2H), 1.87-1.76 (m, 5H), 1.62-1.48 (m, 5H), 1.35-1.30 (m, 2H), 1.31 (t, J=7.1 Hz 3H); $^{13}$C NMR (101 MHz, CDCl₃) δ 168.19, 140.43, 128.69, 60.45, 57.70, 36.43, 35.39, 29.22, 27.40, 14.30, 12.54; IR (Neat Film) 2874, 2804, 2061, 1677, 1236 cm$^{-1}$; HRMS (ESI) m/z Calculated for C₁₃H₂₁N₃O₂ (M+1)⁺ 250.1707. found 250.1716.

i. Synthesis of (E)-4-((1S,4S)-4-Azidocyclohexyl)-2-Methylbut-2-En-1-ol (9)

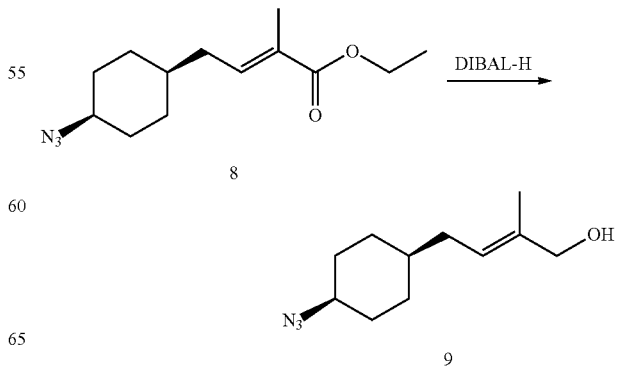

A solution of DIBAL-H (66 mL, 1.0 M in hexanes) was added drop-wise to cold (−78° C.) solution of conjugated ester 8 in methylene chloride (150 mL). The resulting mixture was allowed to stir at −78° C. for 2.5 h by which time the TLC showed all of starting material has been consumed. The reaction was quenched with MeOH (9 mL) and diluted with saturated sodium potassium tartrate tetrahydrate (150 mL) and EtOAc (160 mL). The resulting mixture was vigorously stirred for 2 h at room temperature to get a clear solution. The aqueous layer was extracted with EtOAc (2×200 mL) and the combined organic layers were dried over $Na_2SO_4$. Concentrated and the residue was purified on silica column (160 g, 5-40% EtOAc in hexane) to give 5.3 g (91%) of pure alcohol 9 as oil. $^1H$ NMR (400 MHz, $CDCl_3$) δ 5.41 (t, J=7.2 Hz, 1H), 4.01 (s, 2H), 3.83-3.73 (m, 1H), 1.97 (t, J=6.9 Hz, 2H), 1.85-1.75 (m, 4.3 Hz, 2H), 1.66 (s, 3H), 1.60-1.48 (m, 2H), 1.41-1.23 (m, 4H); $^{13}C$ NMR (101 MHz, $CDCl_3$) δ 135.69, 124.36, 68.96, 57.95, 36.85, 29.25, 27.32, 13.85; IR (Neat Film) 3275, 2870, 2801, 2060, 1418, 1236, 993 $cm^{-1}$; HRMS (ESI) m/z Calculated for $C_{11}H_{19}N_3O$ $(M+Na)^+$ 232.1426. found 232.1423.

j. Synthesis of (E)-4-((1S,4S)-4-Azidocyclohexyl)-2-Methylbut-2-Enal (10)

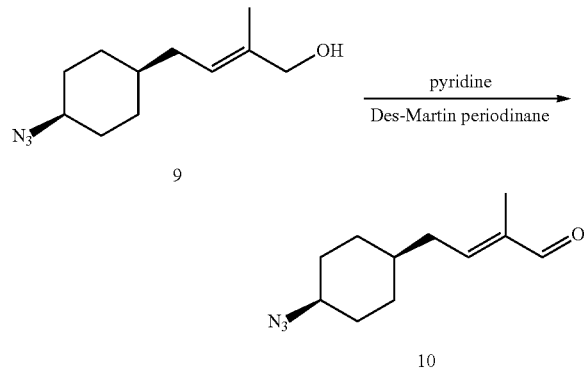

A solution of alcohol 9 (3.3 g, 15.7 mmol) and pyridine (12 mL) in anhydrous methylene chloride (80 mL) at 0° C. as Dess-Martin periodinate (12.4 g, 23.6 mmol) was added in portions. The resulting solution was stirred for 2 h at room temperature and added 1:1 mixture (300 mL) of saturated aqueous $NaHCO_3$ solution and saturated aqueous sodium thiosulfate solution. The mixture was stirred for 30 min at rt. The aqueous layer was separated and extracted with EtOAc (2×400 mL) and the combined fractions were dried over $Na_2SO_4$. Concentrated and the resulting residue purified on silica column (2-20% EtOAc in hexane) to give 3.0 g (92%) of aldehyde 10 as an oil. $^1H$ NMR (400 MHz, $CDCl_3$) δ 9.41 (s, 1H), 6.50 (td, J=7.6, 1.0 Hz, 1H), 3.88-3.78 (m, 1H), 2.30 (t, J=6.9 Hz, 2H), 1.89-1.79 (m, 2H), 1.75 (d, J=0.4 Hz, 3H), 1.64-1.51 (m, 5H), 1.44-1.29 (dt, J=14.5, 11.2 Hz, 2H); $^{13}C$ NMR (101 MHz, $CDCl_3$) δ 195.16, 152.83, 140.31, 57.50, 36.46, 35.72, 29.22, 27.33, 9.41; IR (Neat Film) 2874, 2803, 2061, 1659, 1418, 1236 $cm^{-1}$; HRMS (ESI) m/z Calculated for $C_{11}H_{17}N_3O$ $(M+1)^+$ 208.1445. found 208.1455.

k. Synthesis of (S)-Ethyl 2-((Tert-Butyldimethylsilyl)Oxy)Propanoate (11)

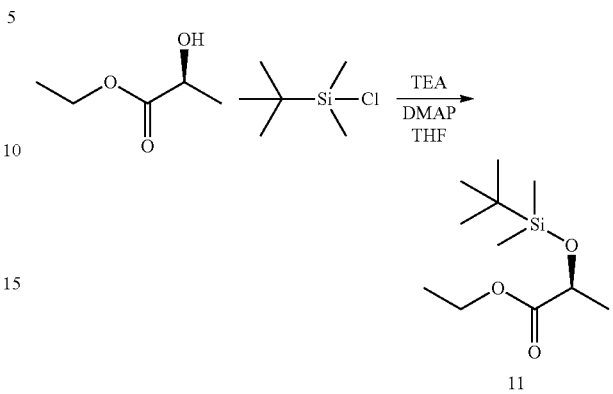

A stirred solution of (S)-ethyl 2-hydroxypropanoate (120 g, 1.0 mol) in THF (1.5 L) at room temperature as DMAP (12.4 g, 0.1 mol) and triethylamine (1.5 L, 2.0 mol) were sequentially added. The resulting solution was stirred for 10 min and cooled to 0° C. TBSCl (205 g, 1.3 mol) was added portion-wise to the above solution for 30 minutes. The resulting white suspension was allowed to warm to room temperature and stirred for overnight. The reaction mixture filtered through a sintered funnel to remove salts and washed with tert-butyl methyl ether (1.4 L). The filtrate was divided into two 700 mL portions which were each washed with 15% cold AcOH (500 mL), water (500 mL), saturated aqueous $NaHCO_3$ (350 mL), water (500 mL), brine (400 mL), and dried over $MgSO_4$. Concentrated and the resulted residue was purified on silica column (2% t-Butyl methyl ether/hexane) to give 200 g (85%) of silyl ether 11 as a colorless oil. All analytical data for this compound was identical with the reported data in literature (see Massad, S. K., Hawkins, L. D. and Baker, D. C. A series of (2S)-2-O-protected-2-hydroxypropanals (L-lactaldehydes) suitable for use as optically active intermediates. The Journal of Organic Chemistry 48, 5180-5182 (1983)).

l. Synthesis of (S)-2-((Tert-Butyldimethylsilyl)Oxy) Propanal (12)

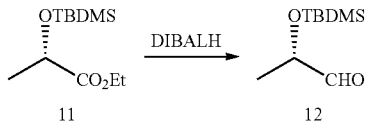

The ester 11 (100 g, 430 mmol) was dissolved in hexane (600 mL) in a two-neck round bottom flask (2 L) and cooled to −78° C. DIBAL-H (572 mL, 1M in hexane, 572 mmol) was added to reaction solution drop-wise using additional funnel. The internal temperature was monitored and not allowed to exceed −71° C. The resulting suspension was stirred for additional 1 h at −78° C. Water (200 mL) was added drop-wise at −78° C. and stirred for 10 minutes after which the reaction mixture was allowed to warm to rt. tert-butyl methyl ether (400 mL) was added and the resulting mixture was filtered to remove the salts. The residue was washed with ether (2×200 mL). The aqueous layer was extracted with ether (2×200 mL). All organic layers were combined and dried over Na$_2$SO$_4$. The solvent was concentrated on rotovap at 30° C. and 200 mbar and the resulted crude product was chromatographed on silica gel (1:1 CH$_2$Cl$_2$/Hexane) to give 81 g (87%) of pure aldehyde 12 as an oil.

m. Synthesis of (S,Z)-Methyl 4-((Tert-Butyldimethylsilyl)Oxy)Pent-2-Enoate (13)

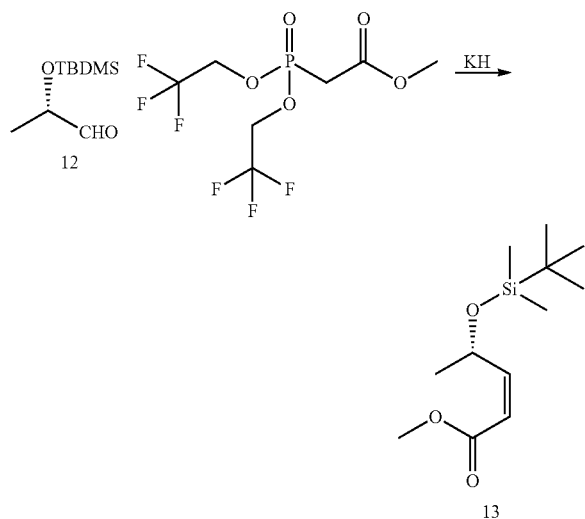

In a dry 3 L 3-neck flask, KH (49 g, 30% wt. in mineral oil) was taken and washed with hexane (4×20 mL and 1×50 mL). The dried KH (15.1 g, 377 mmol) was taken in anhydrous THF (640 mL) and cooled to −78° C. After 10 min, methyl 2-(bis(2,2,2-trifluoroethoxy)acetate (126 g, 377 mmol) in THF (185 mL) was added drop-wise to the reaction mixture over 2 hrs. The reaction mixture was stirred at −78° C. for 1 hr as the aldehyde 12 (68 g, 361 mmol) in THF (200 mL) was slowly added and stirred for additional 3 hrs. The reaction mixture was quenched with cold water (500 mL) and diluted with tert-Butyl methyl ether (250 mL). The aqueous layer was separated and extracted again with tert-Butyl methyl ether (1×500 mL, 2×250 mL). The combined organic layers were washed with water, brine and dried over Na2SO4. Concentrated and the residue was purified on silica column (2% tert-Butyl methyl ether in hexane) to give 65 g (74%) conjugated ester 13 as an oil.

n. Synthesis of (S,Z)-4-((Tert-Butyldimethylsilyl)Oxy)Pent-2-Enoic Acid (14)

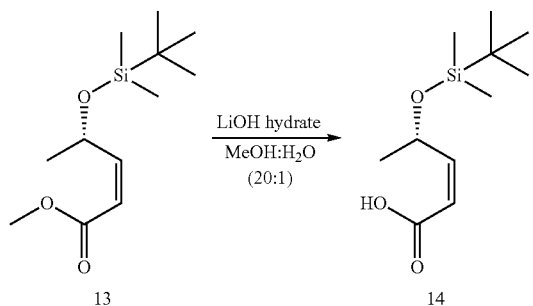 [SMILES: COC(=O)/C=C\[C@H](C)O[Si](C)(C)C(C)(C)C ; C[C@@H](/C=C\C(=O)O)O[Si](C)(C)C(C)(C)C]

To a stirred solution of the methyl ester 13 (21.1 g, 87 mmol) in MeOH:H$_2$O (420 mL, 20:1) at 0° C. was added LiOH hydrate (18.2 g, 434 mmol). The reaction suspension was allowed to warm to room temperature and stirred for 36-40 h. The reaction mixture was concentrated on the rotovap at 25° C. until half of the solvent had evaporated. There was approximately 200 mL of solvent when it was removed from the rotovap. The resulted solution was cooled to 0° C. and acidified to pH 5 using 1 N citric acid (~170 mL). The product was extracted with EtOAc (400 mL, 2×100 mL). The organic fractions were combined, washed with brine and dried over MgSO$_4$. The solvent was evaporated to give 17 g (89%) of acid derivative 14 as viscous oil. All analytical data for this compound was identical with the reported data in literature (see Motoyoshi, H., Horigome, M., Watanabe, H. and Kitahara, T. Total synthesis of FR901464: second generation. Tetrahedron 62, 1378-1389 (2006)).

o. Synthesis of (3R,7S)-7-((1E,3E)-5-((1S,4R)-4-Azidocyclohexyl)-3-Methylpenta-1,3-Dien-1-Yl)-5,5-Dimethyl-1,6-Dioxaspiro[2.5]Octane (15)

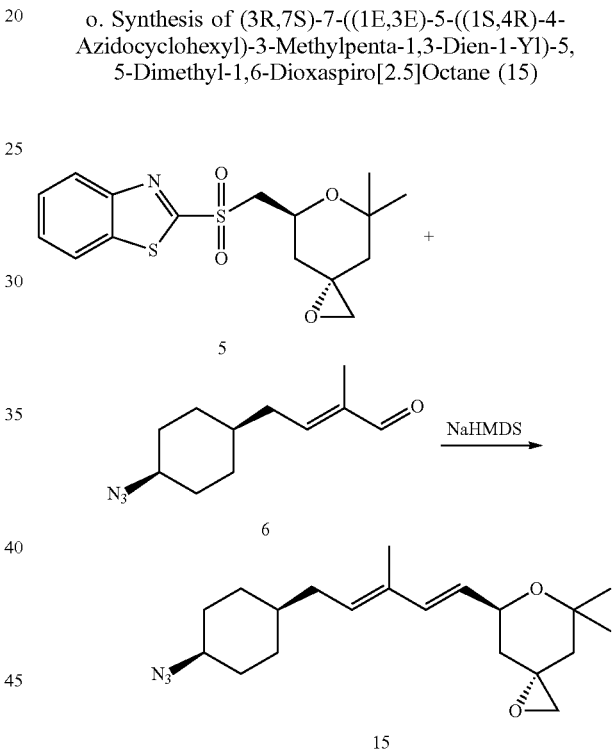

A mixture of sulfone 5 (4.7 g, 13.4 mmol) and aldehyde 10 (2.4 g, 11.8 mmol) was azeotroped with benzene (2×25 ml), dissolved in anhydrous THF (80 ml), and cooled to −78° C. The reaction solution was treated drop-wise with NaHMDS (14.7 ml, 1M in THF, 14.7 mmol) over 10 min. The resulting yellow suspension was stirred at −78° C. for 60 min, then warmed to 0° C. for 15 min, and finally at room temperature for 0.5 h. The reaction mixture was quenched with pH 7 buffer solution (120 ml) and extracted with Et$_2$O (3×150 mL). The organic layer was dried (Na$_2$SO$_4$), filtered and concentrated in vacuo. The solids were removed by addition of 10% CH$_2$Cl$_2$ in hexane. The resulted residue was purified on silica column (100 g, 2-20% EtOAc in hexane) to give 3.3 g (81%) of diene 15 (E/Z ratio 95:5) as an oil. $^1$H NMR (400 MHz, CDCl$_3$) δ 6.26 (d, J=15.5 Hz, 1H), 5.54 (dd, J=15.7, 6.7 Hz, 1H), 5.46 (t, J=7.7 Hz, 1H), 4.51-4.39 (m, 1H), 3.82-3.72 (m, 1H), 2.57 (s, 2H), 2.10-2.02 (m, 2H), 2.02-1.86 (m, 2H), 1.84-1.73 (m, 3H), 1.71 (s, 3H), 1.59-

1.46 (m, 4H), 1.42-1.38 (s, 3H), 1.30-1.24 (m, 2H), 1.27 (s, 3H), 1.25-1.12 (m, 2H); $^{13}$C NMR (101 MHz, CDCl$_3$) δ 136.19, 133.93, 131.74, 127.02, 73.01, 69.59, 57.94, 55.67, 51.03, 42.45, 38.62, 37.03, 34.88, 31.53, 29.24, 27.37, 27.32, 23.76, 12.50; IR (Neat Film) 2916, 2872, 2802, 2060, 1418, 1253, 956 cm$^{-1}$; HRMS (ESI) m/z Calculated for C$_{20}$H$_{31}$N$_3$O$_2$ (M+1)$^+$ 346.2489. found 346.2492.

p. Synthesis of (S,Z)-4-((Tert-Butyldimethylsilyl)Oxy)-N-((1R,4R)-4-((2E,4E)-5-((3R,5S)-7,7-Dimethyl-1,6-Dioxaspiro[2.5]Octan-5-Yl)-3-Methylpenta-2,4-Dien-1-Yl)Cyclohexyl)Pent-2-Enamide (16)

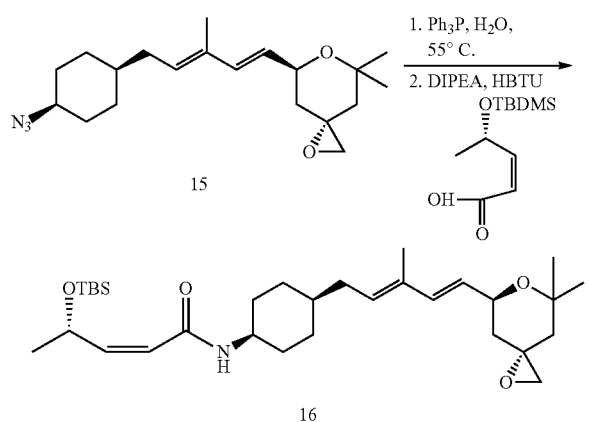

The azide diene 15 (3.3 g, 9.57 mmol) was azeotroped with benzene (2×20 mL), dissolved again in anhydrous benzene (44 mL) and treated with Ph$_3$P (4.5 g, 17.2 mmol) at rt. The reaction solution was degassed with nitrogen and heated at 55° C. for 1.5 h by which time LC/MS showed that all of starting material has been consumed. Water (1.6 mL) was added and heated again at 55° C. for another 1.5 h by the time LC/MS showed the formation of free amine. The reaction mixture was cooled to room temperature and diluted with a mixture of CH$_2$Cl$_2$ and ether (8:2, 150 mL). This mixture was shaken vigorously, dried over Na$_2$SO$_4$, filtered, and concentrated. The resulted amine intermediate was used in the next step without further purification.

To a stirred solution of crude amine in acetonitrile (45 mL) were added N,N'-diisopropylethylamine (6.6 mL, 37.3 mmol) and a solution of carboxylic acid 14 (3 g, 13.1 mmol) in acetonitrile (22 mL). This mixture was cooled to 0° C. and HBTU (3.1 g, 12.3 mmol) was portion wise added to the resultant solution. The reaction suspension was stirred for 30 min at 0° C. and then warm to room temperature. Stirred another 2 h at room temperature and then diluted with EtOAc (200 mL). After successive washing with saturated aqueous NaHCO$_3$ solution (50 mL), saturated aqueous NH$_4$Cl solution (50 mL), saturated NaHCO$_3$ solution (50 mL) and brine (50 mL), the organic layer was dried over Na$_2$SO$_4$. The solvent was evaporated and the residue was mixed with 18% EtOAc in hexane (30 mL) and the resultant solids were filtered through sintered funnel. The solids were then washed successively with 18% EtOAc in hexane (50 mL) and hexane (50 mL). The filtrate was concentrated and the residue was purified on silica gel (4-40% EtOAc in hexane) to give 4.3 g (83%) of amide 16 as a viscous liquid. All analytical data for this compound was as previously reported (see Lagisetti, C. et al. Antitumor Compounds Based on a Natural Product Consensus Pharmacophore. J. Med. Chem. 51, 6220-6224 (2008)).

q. Synthesis of (S,Z)—N-((1R,4R)-4-((2E,4E)-5-((3R,5S)-7,7-Dimethyl-1,6-Dioxaspiro[2.5]Octan-5-Yl)-3-Methylpenta-2,4-Dien-1-Yl)Cyclohexyl)-4-Hydroxypent-2-Enamide (17)

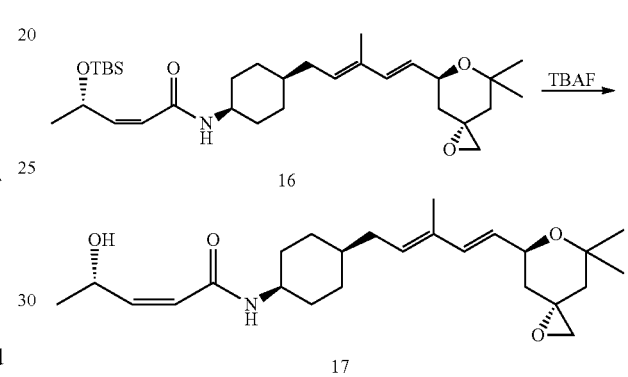

A solution of TBS protected amide 16 (4.1 g, 7.7 mmol) in THF (37 mL) at −5-0° C. as TBAF (9.2 mL, 9.2 mmol, 1.0 M in THF) was slowly added using syringe for 5 minutes. The light yellow solution was allowed to stir for 30 min at 0° C. and after that stir for additional 2 h at room temperature by which time TLC and LC/MS showed the starting material has been consumed. THF was evaporated and the resulted residue was diluted with EtOAc (200 mL), water (30 mL) and saturated aqueous NaHCO$_3$ (30 mL). The organic layer was separated and washed with water (50 mL) and brine (50 mL) and dried over Na$_2$SO$_4$. Concentrated and the crude residue was purified by SFC-80 using AD-H column (20% MeOH) to give 2.6 g (81%) of alcohol 17 as viscous oil. All analytical data for this compound was as previously reported (see Lagisetti, C. et al. Antitumor Compounds Based on a Natural Product Consensus Pharmacophore. J. Med. Chem. 51, 6220-6224 (2008)).

r. Synthesis of (S,Z)-5-(((1R,4R)-4-((2E,4E)-5-((3R,5S)-7,7-Methyl-1,6-Dioxaspiro[2.5]Octan-5-Yl)-3-Methylpenta-2,4-Dien-1-Yl)Cyclohexyl)Amino)-5-Oxopent-3-En-2-Yl (4-Nitrophenyl)Carbonate (18)

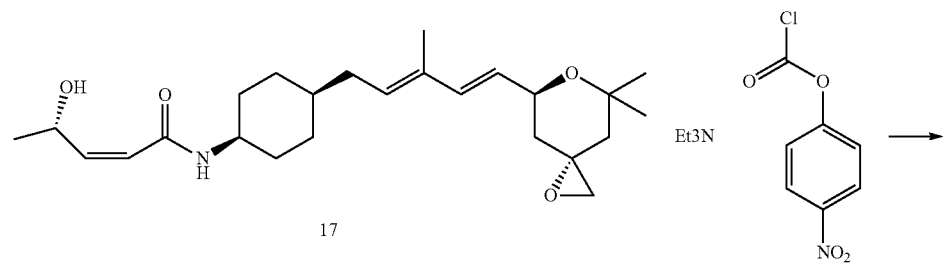

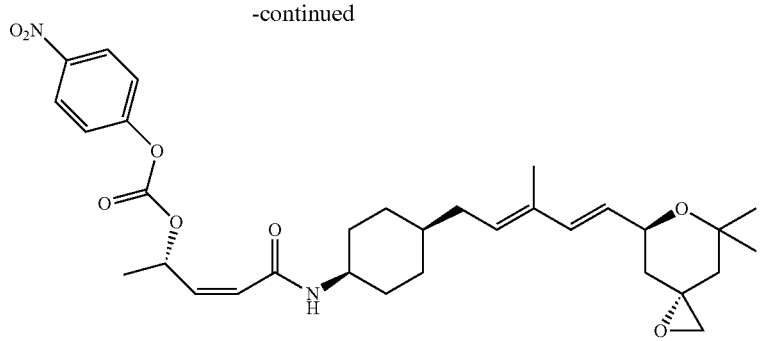

18

A solution of alcohol 17 (2 g, 4.7 mmol) in $CH_2Cl_2$ (70 mL) was stirred at room temperature as triethyl amine (2.6 mL, 19.1 mmol) was added. After 5-10 min, the reaction was cooled with ice-bath as p-nitrophenylchloroformate (2 g, 9.8 mmol) was added. After 10 min stirring at 0° C., TLC and LC/MS indicated that all of the starting material has been consumed. Cold water (100 mL) was added to the mixture and diluted with methylene chloride (100 mL). The organic layer was separated and the aqueous layer was extracted with methylene chloride (2×75 mL). The combined solvents were washed with water (100 mL), brine (90 mL) and dried over $Na_2SO_4$. Evaporation and purification of the residue on silica gel (100 g, 10-50% EtOAc in hexane) gave 2.5 g (90%) of carbonate 18 as a fluffy solid. All analytical data for this compound was as previously reported (see Lagisetti, C. et al. Synthetic mRNA Splicing Modulator Compounds with in Vivo Antitumor Activity. *J. Med. Chem.* 52, 6979-6990 (2009)).

3. Analog Synthesis

A stirred solution of the activated carbamate (0.1 mmol) in dichloroethane (2 mL) was cooled in an ice-bath and the corresponding amine (3 mmol) was added dropwise. The resulting yellow solution was allowed to stir at ambient temperature until TLC indicated completion of the reaction. The solvent was then removed under reduced pressure. The yellow viscous crude was dissolved in a minimum volume of methylene chloride and treated with hexane. The resulting yellow solids were filtered and washed with 5% methylene chloride in hexane (5 mL). The filtrate was concentrated and purified on silica gel to give the corresponding carbamate derivative.

a. Synthesis of (S,Z)-5-(((1R,4R)-4-((2E,4E)-5-((3R,5S)-7,7-Methyl-1,6-Dioxaspiro[2.5]Octan-5-Yl)-3-Methylpenta-2,4-Dien-1-Yl)Cyclohexyl)Amino)-5-Oxopent-3-En-2-Yl Dimethylcarbamate (19)

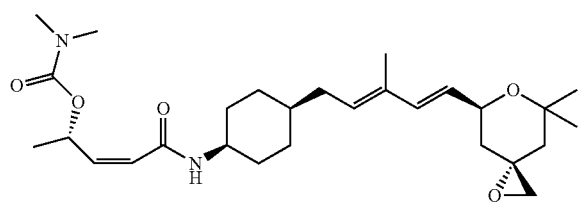

19

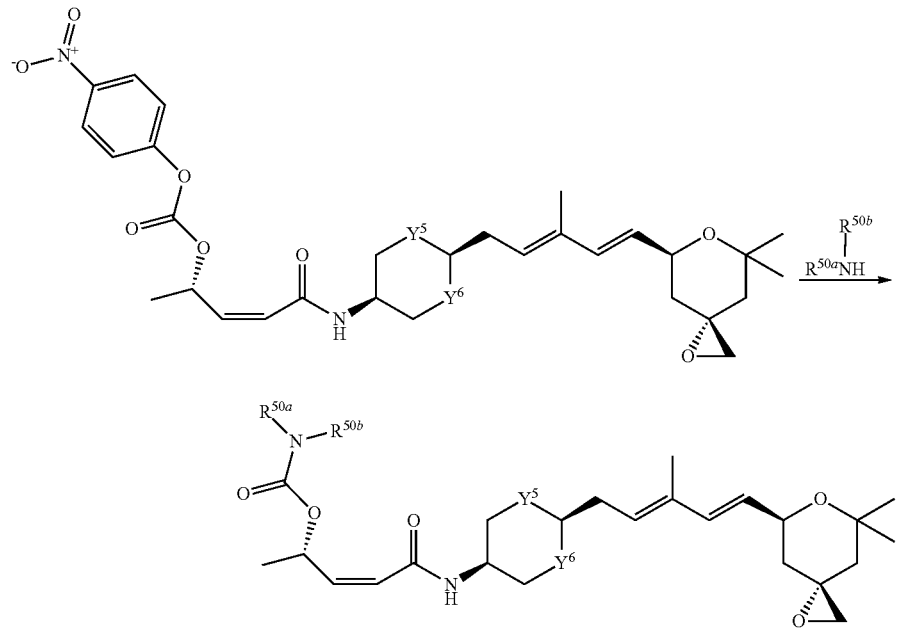

Yield: 755 mg (90%) of 19 as a fluffy solid. ¹H NMR (400 MHz, CDCl₃) δ 8.23 (d, J=8.0 Hz, 1H), 6.27 (d, J=15.6 Hz, 1H), 5.82 (d, J=11.4 Hz, 1H), 5.64-5.46 (m, 4H), 4.51-4.39 (m, 1H), 4.18-4.06 (m, 1H), 2.91 (s, 6H), 2.57 (s, 2H), 2.14-2.04 (td, J=7.0, 4.6 Hz, 2H), 2.04-1.85 (m, 3H), 1.75-1.65 (m, 2H), 1.71 (s, 3H), 1.63-1.51 (m, 4H), 1.42-1.32 (s, 2H), 1.39 (s, 3H), 1.34 (d, J=6.1 Hz, 3H), 1.28 (s, 3H), 1.24-1.10 (m, 2H); ¹³C NMR (101 MHz, CDCl₃) δ 165.15, 156.45, 136.36, 136.27, 133.60, 132.30, 126.85, 126.27, 73.02, 69.61, 69.53, 55.67, 51.03, 45.24, 42.45, 38.63, 36.66, 36.26, 35.89, 34.55, 31.53, 29.64, 29.50, 27.76, 27.43, 23.76, 20.66, 12.44; IR (Neat Film) 3267, 2874, 2804, 1656, 1635, 1511, 1370, 1172, 1038 cm⁻¹; HRMS (ESI) m/z Calculated for $C_{28}H_{44}N_2O_5$ (M+1)⁺ 489.3323. found 489.3334.

b. Synthesis of (S,Z)-5-(((1R,4R)-4-((2E,4E)-5-((3R,5S)-7,7-Methyl-1,6-Dioxaspiro[2.5]Octan-5-Yl)-3-Methylpenta-2,4-Dien-1-Yl)Cyclohexyl) Amino)-5-Oxopent-3-En-2-Yl Methylcarbamate (20)

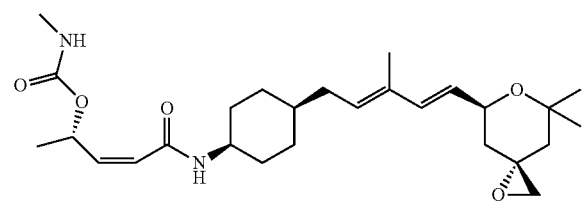

20

Yield: 75 mg (92%) of 20 as a white viscous solid. ¹H NMR (400 MHz, CDCl₃) δ 7.94 (d, J=7.7 Hz, 1H), 6.26 (d, J=15.7 Hz, 1H), 5.82 (d, J=10.8 Hz, 1H), 5.66-5.44 (m, 4H), 4.77 (s, 1H), 4.52-4.39 (m, 1H), 4.18-4.06 (m, 1H), 2.78 (d, J=5.0 Hz, 3H), 2.57 (s, 2H), 2.09 (t, J=7.1 Hz, 2H), 2.05-1.87 (m, 2H), 1.80-1.67 (m, 2H), 1.72 (s, 3H), 1.65-1.49 (m, 4H), 1.48-1.41 (m, 1H), 1.40 (s, 3H), 1.38-1.34 (m, 2H), 1.31 (d, J=5.8 Hz, 3H), 1.28 (s, 3H), 1.24-1.12 (m, 2H); ¹³C NMR (101 MHz, CDCl₃) δ 165.17, 157.03, 136.66, 136.16, 133.70, 132.10, 126.80, 126.06, 73.06, 69.52, 69.15, 55.68, 51.04, 45.36, 42.46, 38.57, 36.62, 34.42, 31.52, 29.57, 29.44, 27.68, 27.39, 27.33, 23.76, 20.60, 12.44; HRMS (ESI) m/z Calculated for $C_{27}H_{42}N_2O_5$ (M+1)⁺ 475.3172. found 475.3188.

c. Synthesis of (S,Z)-5-(((2R,5R)-2-((2E,4E)-5-((3R,5S)-7,7-Methyl-1,6-Dioxaspiro[2.5]Octan-5-Yl)-3-Methylpenta-2,4-Dien-1-Yl)-1,3-Dioxan-5-Yl) Amino)-5-Oxopent-3-En-2-Yl Dimethyl Carbamate (22)

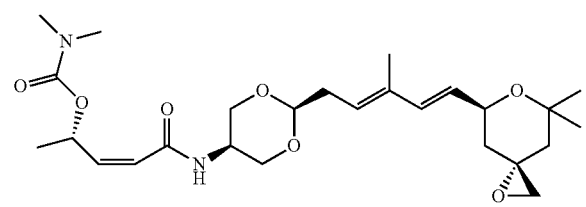

22

Yield: 1.72 g (86%) of 22 as a fluffy solid. ¹H NMR (400 MHz, CDCl₃) δ 7.93 (d, J=8.2 Hz, 1H), 6.27 (d, J=15.8 Hz, 1H), 5.91-5.84 (m, 1H), 5.84-5.78 (m, 2H), 5.58 (dd, J=15.7, 6.6 Hz, 1H), 5.50 (t, J=7.2 Hz, 1H), 4.58 (t, J=5.3 Hz, 1H), 4.45 (ddd, J=11.0, 6.6, 1.8 Hz, 1H), 4.06-3.87 (m, 5H), 2.89 (s, 6H), 2.58-2.54 (m, 2H), 2.54-2.47 (m, 2H), 2.03-1.86 (m, 2H), 1.73 (d, J=0.9 Hz, 3H), 1.41-1.35 (m, 6H), 1.27 (s, 3H), 1.24-1.11 (m, 2H); ¹³C NMR (101 MHz, CDCl3) δ 165.23, 156.30, 141.45, 135.70, 135.48, 127.86, 125.92, 123.67, 102.04, 73.04, 70.15, 70.12, 69.50, 69.39, 55.66, 51.05, 43.80, 42.45, 38.59, 36.31, 35.90, 34.20, 31.54, 23.77, 20.44, 12.59; HRMS (ESI) m/z Calcd for $C_{26}H_{40}N_2O_7Na$ (M+Na)⁺ 515.2733. found 515.2734.

d. Synthesis of (S,Z)-5-(((2R,5R)-2-((2E,4E)-5-((3R,5S)-7,7-Dimethyl-1,6-Dioxaspiro[2.5]Octan-5-Yl)-3-Methylpenta-2,4-Dien-1-Yl)-1,3-Dioxan-5-Yl) Amino)-5-Oxopent-3-En-2-Yl Butylcarbamate (23)

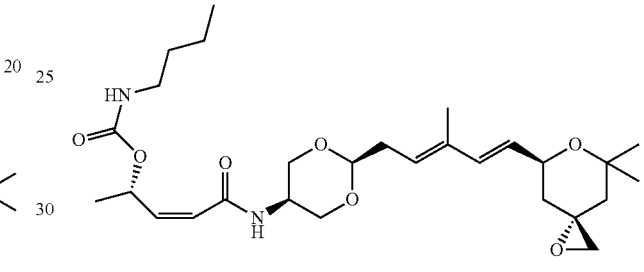

23

Yield: 5.3 mg (75%) of 23 as an oil. ¹H NMR (400 MHz, CDCl₃) δ 7.73 (d, J=8.1 Hz, 1H), 6.27 (d, J=15.7 Hz, 1H), 5.97-5.77 (m, 3H), 5.59 (dd, J=15.7, 6.6 Hz, 1H), 5.51 (t, J=7.2 Hz, 1H), 4.75 (bt, J=7.3 Hz, 1H), 4.60 (t, J=5.2 Hz, 1H), 4.50-4.41 (m, 1H), 4.07-3.88 (m, 5H), 3.15 (q, J=6.7 Hz, 2H), 2.57 (s, 2H), 2.49 (dd, J=7.2, 5.3 Hz, 2H), 2.02-1.86 (m, 2H), 1.73 (d, J=1.3 Hz, 3H), 1.51-1.41 (m, 2H), 1.40 (s, 3H), 1.37-1.31 (m, 5H), 1.28 (s, 3H), 1.27-1.12 (m, 2H), 0.90 (t, J=7.3 Hz, 3H); ¹³C NMR (101 MHz, CDCl₃) δ 165.18, 156.28, 141.59, 135.66, 135.50, 127.82, 125.82, 123.61, 102.06, 73.07, 70.12, 69.46, 68.85, 55.69, 51.07, 43.85, 43.46, 42.46, 40.71, 38.60, 34.16, 32.00, 31.54, 23.77, 20.39, 19.93, 13.75, 12.60; HRMS (ESI) m/z Calcd for $C_{28}H_{45}N_2O_7$(M+H)⁺ 521.3227. found 521.3220.

e. Synthesis of (S,Z)-5-(((2R,5R)-2-((2E,4E)-5-((3R,5S)-7,7-Methyl-1,6-Dioxaspiro[2.5]Octan-5-Yl)-3-Methylpenta-2,4-Dien-1-Yl)-1,3-Dioxan-5-Yl) Amino)-5-Oxopent-3-En-2-Yl Diethylcarbamate (24)

24

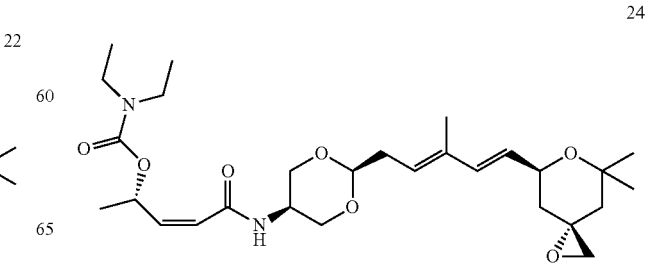

Yield: 4.2 mg (62%) of 24 as an oil. $^1$H NMR (400 MHz, Chloroform-d) δ 7.92 (d, J=8.3 Hz, 1H), 6.27 (d, J=15.7 Hz, 1H), 5.96-5.87 (m, 1H), 5.86-5.77 (m, 2H), 5.59 (dd, J=15.7, 6.6 Hz, 1H), 5.50 (t, J=7.3 Hz, 1H), 4.58 (t, J=5.3 Hz, 1H), 4.49-4.41 (m, 1H), 4.07-3.86 (m, 5H), 3.38-3.18 (m, 4H), 2.57 (s, 2H), 2.49 (dd, J=7.3, 5.4 Hz, 2H), 2.02-1.85 (m, 2H), 1.73 (d, J=1.3 Hz, 3H), 1.39 (s, 3H), 1.37 (d, J=6.3 Hz, 3H), 1.28 (s, 3H), 1.26-1.13 (m, 4H), 1.11 (t, J=7.1 Hz, 6H); $^{13}$C NMR (101 MHz, CDCl$_3$) δ 165.28, 155.59, 141.76, 135.70, 135.50, 127.87, 125.92, 123.47, 102.05, 73.04, 70.12, 69.50, 69.08, 55.67, 51.05, 43.82, 42.46, 38.58, 34.20, 31.53, 23.76, 21.07, 20.45, 14.22, 12.60; HRMS (ESI) m/z Calcd for C$_{28}$H$_{45}$N$_2$O$_7$(M+H)$^+$ 521.3227. found 521.3223.

f. Synthesis of (S,Z)-5-(((2R,5R)-2-((2E,4E)-5-((3R, 5S)-7,7-Methyl-1,6-Dioxaspiro[2.5]Octan-5-Yl)-3-Methylpenta-2,4-Dien-1-Yl)-1,3-Dioxan-5-Yl) Amino)-5-Oxopent-3-En-2-Yl Tert-Butylcarbamate (25)

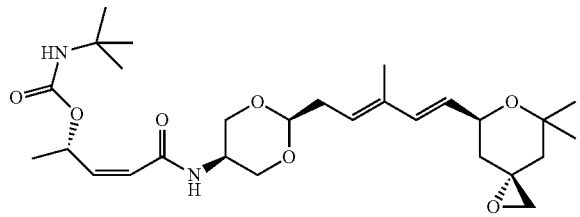

25

Yield: 3.8 mg (54%) of 25 as a viscous oil. $^1$H NMR (400 MHz, Chloroform-d) δ 7.71 (s, 1H), 6.28 (dt, J=15.7, 0.9 Hz, 1H), 5.92-5.76 (m, 3H), 5.59 (dd, J=15.7, 6.5 Hz, 1H), 5.54 (t, J=7.3 Hz, 1H), 4.68 (s, 1H), 4.59 (t, J=5.2 Hz, 1H), 4.51-4.41 (m, 1H), 4.05-3.95 (m, 2H), 3.97-3.87 (m, 3H), 2.57 (s, 2H), 2.48 (dd, J=7.2, 5.3 Hz, 2H), 2.02-1.87 (m, 2H), 1.73 (s, 3H), 1.40 (s, 3H), 1.34 (d, J=5.9 Hz, 3H), 1.30 (s, 9H), 1.28 (s, 3H), 1.24-1.13 (m, 2H); $^{13}$C NMR (101 MHz, CDCl$_3$) δ 165.23, 154.44, 142.09, 135.63, 135.42, 127.78, 125.82, 123.29, 102.03, 73.04, 70.02, 69.42, 68.36, 55.66, 51.03, 50.43, 43.87, 42.43, 38.59, 34.17, 31.52, 28.95, 23.75, 20.35, 12.58; HRMS (ESI) m/z Calcd for C$_{28}$H$_{45}$N$_2$O$_7$ (M+H)$^+$ 521.3227. found 521.3232.

g. Synthesis of (S,Z)-5-(((2R,5R)-2-((2E,4E)-5-((3R,5S)-7,7-Methyl-1,6-Dioxaspiro[2.5]Octan-5-Yl)-3-Methylpenta-2,4-Dien-1-Yl)-1,3-Dioxan-5-Yl) Amino)-5-Oxopent-3-En-2-Yl Methyl(Propyl) Carbamate (26)

26

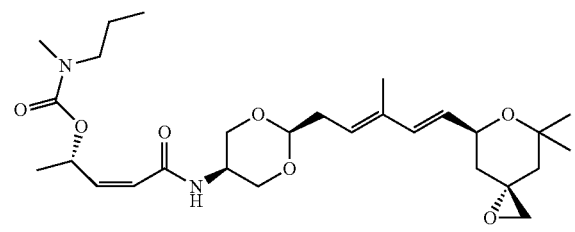

Yield: 4.2 mg (52%) of 26 as a viscous oil. $^1$H NMR (400 MHz, CDCl$_3$) δ 7.91 (bd, 1H), 6.27 (d, J=15.8 Hz, 1H), 5.95-5.77 (m, 3H), 5.59 (dd, J=15.7, 6.6 Hz, 1H), 5.50 (t, J=7.1 Hz, 1H), 4.59 (t, J=5.2 Hz, 1H), 4.51-4.42 (m, 1H), 4.06-3.87 (m, 5H), 3.18 (dd, J=14.2, 7.0, 2H), 2.88 (s, 3H), 2.57 (s, 2H), 2.50 (s, 2H), 2.03-1.86 (m, 2H), 1.73 (d, J=0.8 Hz, 3H), 1.54 (dd, J=14.8, 7.4 Hz, 2H), 1.40 (s, 3H), 1.37 (d, J=6.2 Hz, 3H), 1.28 (s, 3H), 1.23-1.13 (m, 2H), 0.94-0.80 (m, 3H); $^{13}$C NMR (101 MHz, CDCl$_3$) δ 165.23, 156.15, 141.54, 135.67, 135.45, 127.83, 125.89, 123.60, 102.01, 73.01, 70.09, 70.06, 69.47, 69.25, 55.63, 51.02, 50.54, 43.79, 42.42, 38.55, 34.17, 33.91, 31.51, 23.74, 21.10, 20.39, 12.57, 11.12; HRMS (ESI) m/z Calcd for C$_{28}$H$_{45}$N$_2$O$_7$(M+H)$^+$ 521.3227. found 521.3231.

h. Synthesis of (S,Z)-5-(((2R,5R)-2-((2E,4E)-5-((3R,5S)-7,7-Methyl-1,6-Dioxaspiro[2.5]Octan-5-Yl)-3-Methylpenta-2,4-Dien-1-Yl)-1,3-Dioxan-5-Yl) Amino)-5-Oxopent-3-En-2-Yl (2-Methoxyethyl) Carbamate (27)

27

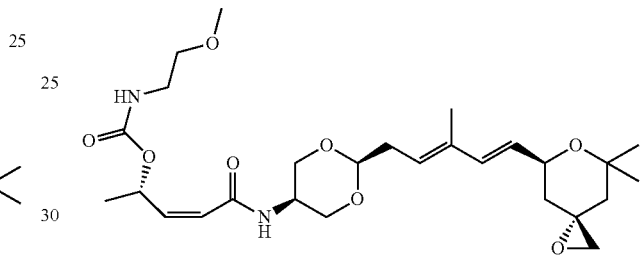

Yield: 3.6 mg (50%) of 27 as a viscous oil. $^1$H NMR (400 MHz, Chloroform-d) δ 7.64 (d, J=8.1 Hz, 1H), 6.32-6.23 (m, 1H), 6.00-5.90 (m, 1H), 5.89-5.78 (m, 2H), 5.59 (dd, J=15.7, 6.6 Hz, 1H), 5.50 (t, J=7.3 Hz, 1H), 5.09 (t, J=5.8 Hz, 1H), 4.59 (t, J=5.2 Hz, 1H), 4.51-4.42 (m, 1H), 4.06-3.87 (m, 5H), 3.43 (dd, J=5.5, 4.5 Hz, 2H), 3.34 (d, J=0.8 Hz, 5H), 2.57 (d, J=0.8 Hz, 2H), 2.49 (dd, J=7.3, 5.3 Hz, 2H), 2.03-1.85 (m, 2H), 1.77-1.71 (m, 3H), 1.40 (s, 3H), 1.35 (d, J=6.4 Hz, 3H), 1.28 (s, 3H), 1.24-1.12 (m, 2H); $^{13}$C NMR (101 MHz, CDCl$_3$) δ 165.12, 156.17, 141.80, 135.64, 135.53, 127.89, 125.78, 123.48, 102.07, 73.07, 71.38, 70.14, 69.46, 69.12, 58.77, 55.69, 51.07, 43.83, 42.46, 40.71, 38.59, 34.17, 31.54, 23.77, 20.36, 12.60; HRMS (ESI) m/z Calcd for C$_{27}$H$_{43}$N$_2$O$_8$ (M+H)$^+$ 523.3019. found 523.3013.

i. Synthesis of (S,Z)-5-(((2R,5R)-2-((2E,4E)-5-((3R, 5S)-7,7-Methyl-1,6-Dioxaspiro[2.5]Octan-5-Yl)-3-Methylpenta-2,4-Dien-1-Yl)-1,3-Dioxan-5-Yl) Amino)-5-Oxopent-3-En-2-Yl Butyl(Methyl) Carbamate (28)

28

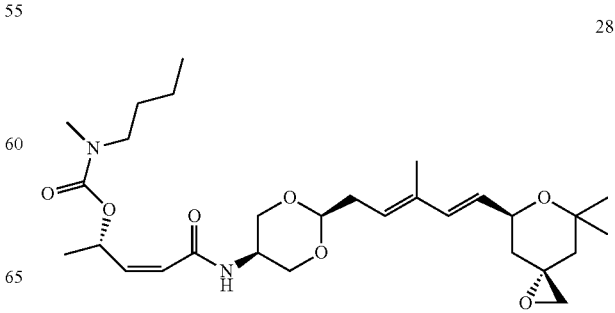

Yield: 4.2 mg (46%) of 28 as a viscous oil. $^1$H NMR (400 MHz, CDCl$_3$) δ 7.85 (bd, 1H), 6.20 (dt, J=16.1, 1.0 Hz, 1H), 5.89-5.67 (m, 3H), 5.52 (dd, J=15.7, 6.6 Hz, 1H), 5.43 (t, J=7.3 Hz, 1H), 4.52 (t, J=5.1 Hz, 1H), 4.45-4.30 (m, 1H), 4.01-3.77 (m, 5H), 3.25-3.10 (m, 2H), 2.81 (s, 3H), 2.50 (s, 2H), 2.44 (d, J=6.4 Hz, 2H), 1.97-1.77 (m, 2H), 1.67 (d, J=1.4 Hz, 3H), 1.42 (p, J=7.4, 6.2 Hz, 2H), 1.33 (s, 3H), 1.30 (d, J=6.2 Hz, 3H), 1.25-1.17 (m, 5H), 1.16-1.06 (m, 2H), 0.90-0.80 (m, 3H); $^{13}$C NMR (101 MHz, CDCl$_3$) δ 165.27, 156.12, 141.47, 135.68, 135.45, 127.84, 125.88, 123.58, 102.02, 73.02, 70.05, 69.47, 69.26, 55.64, 51.02, 48.30, 43.82, 42.42, 38.55, 34.36, 34.17, 31.50, 29.95, 23.74, 20.39, 19.75, 13.83, 12.56; HRMS (ESI) m/z Calcd for C$_{29}$H$_{47}$N$_2$O$_7$(M+H)$^+$ 535.3383. found 535.3379.

j. Synthesis of (S,Z)-5-(((2R,5R)-2-((2E,4E)-5-((3R, 5S)-7,7-Methyl-1,6-Dioxaspiro[2.5]Octan-5-Yl)-3-Methylpenta-2,4-Dien-1-Yl)-1,3-Dioxan-5-Yl) Amino)-5-Oxopent-3-En-2-Yl Isopropyl(Methyl) Carbamate (29)

29

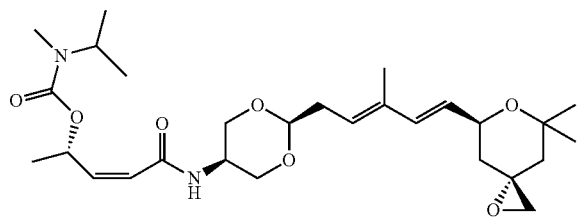

Yield: 4.5 mg (50%) of 29 as an oil. $^1$H NMR (400 MHz, CDCl$_3$) δ 7.99 (s, 1H), 6.26 (dd, J=15.7, 1.1 Hz, 1H), 5.96-5.75 (m, 3H), 5.58 (dd, J=15.7, 6.6 Hz, 1H), 5.49 (t, J=7.3 Hz, 1H), 4.58 (t, J=5.3 Hz, 1H), 4.52-4.19 (m, 2H), 4.03-3.87 (m, 5H), 2.73 (s, 3H), 2.55 (s, 2H), 2.48 (t, J=6.4 Hz, 2H), 2.06-1.82 (m, 2H), 1.72 (d, J=1.3 Hz, 3H), 1.38 (s, 3H), 1.36 (d, J=6.2 Hz, 3H), 1.26 (s, 3H), 1.22-1.12 (m, 2H), 1.08 (d, J=6.6 Hz, 6H); $^{13}$C NMR (101 MHz, CDCl$_3$) δ 165.26, 155.77, 141.66, 135.66, 135.45, 127.84, 125.90, 123.52, 102.00, 73.01, 70.09, 69.46, 69.20, 55.63, 51.01, 46.36, 43.78, 42.43, 38.56, 34.17, 31.51, 26.91, 23.74, 20.43, 19.83, 12.56; HRMS (ESI) m/z Calcd for C$_{28}$H$_{45}$N$_2$O$_7$(M+H)$^+$ 521.3227. found 521.322.

k. Synthesis of (S,Z)-5-(((2R,5R)-2-((2E,4E)-5-((3R,5S)-7,7-Methyl-1,6-Dioxaspiro[2.5]Octan-5-Yl)-3-Methylpenta-2,4-Dien-1-Yl)-1,3-Dioxan-5-Yl) Amino)-5-Oxopent-3-En-2-Yl Tert-Butyl(Methyl) Carbamate (30)

30

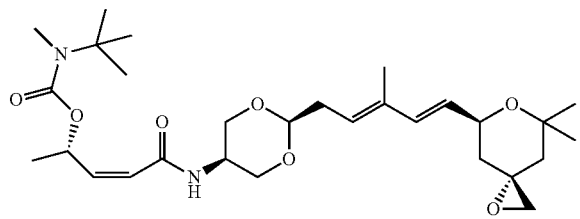

Yield: 5.4 mg (59%) of 30 as an oil. $^1$H NMR (400 MHz, Chloroform-d) δ 8.04 (d, J=8.1 Hz, 1H), 6.27 (dt, J=15.7, 1.0 Hz, 1H), 5.91-5.73 (m, 3H), 5.59 (dd, J=15.7, 6.6 Hz, 1H), 5.50 (t, J=7.3 Hz, 1H), 4.58 (t, J=5.3 Hz, 1H), 4.52-4.39 (m, 1H), 4.07-3.97 (m, 2H), 3.98-3.82 (m, 3H), 2.91 (s, 3H), 2.57 (s, 2H), 2.53-2.40 (m, 2H), 2.02-1.87 (m, 2H), 1.73 (d, J=1.3 Hz, 3H), 1.41-1.36 (m, 15H), 1.28 (s, 3H), 1.23-1.13 (m, 2H); $^{13}$C NMR (101 MHz, CDCl$_3$) δ 165.36, 156.19, 141.63, 135.71, 135.42, 127.82, 125.96, 123.47, 102.04, 73.02, 70.07, 70.02, 69.49, 69.08, 55.65, 55.57, 51.04, 43.86, 42.44, 38.57, 34.21, 31.52, 31.32, 28.79, 23.75, 20.42, 12.58; HRMS (ESI) m/z Calcd for C$_{29}$H$_{47}$N$_2$O$_7$(M+H)$^+$ 535.3383. found 535.3392.

l. Synthesis of (S,Z)-5-(((2R,5R)-2-((2E,4E)-5-((3R, 5S)-7,7-Methyl-1,6-Dioxaspiro[2.5]Octan-5-Yl)-3-Methylpenta-2,4-Dien-1-Yl)-1,3-Dioxan-5-Yl) Amino)-5-Oxopent-3-En-2-Yl Methylcarbamate (31)

31

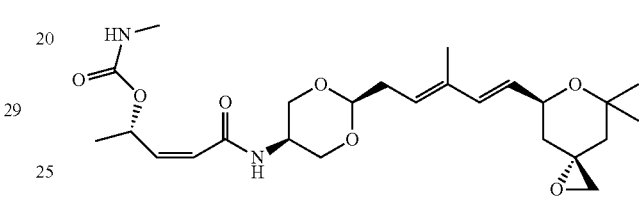

Yield: 3 mg (52%) of 31 as an oil. $^1$H NMR (400 MHz, CDCl$_3$) δ 7.79 (d, J=7.8 Hz, 1H), 6.27 (d, J=15.7 Hz, 1H), 5.96-5.88 (m, 1H), 5.86-5.79 (m, 2H), 5.59 (dd, J=15.7, 6.6 Hz, 1H), 5.52 (t, J=7.1 Hz, 1H), 4.74 (s, 1H), 4.61 (t, J=5.1 Hz, 1H), 4.50-4.42 (m, 1H), 4.06-3.89 (m, 5H), 2.77 (d, J=4.9 Hz, 3H), 2.57 (s, 2H), 2.50 (t, J=6.2 Hz, 2H), 2.07-1.86 (m, 2H), 1.73 (s, 3H), 1.40 (s, 3H), 1.34 (d, J=6.3 Hz, 3H), 1.29 (s, 3H), 1.26-1.11 (m, 2H); $^{13}$C NMR (101 MHz, CDCl$_3$) δ 165.22, 156.78, 141.26, 135.66, 135.50, 127.77, 125.82, 123.80, 102.04, 73.09, 70.12, 69.47, 68.96, 55.70, 51.08, 43.87, 42.47, 38.59, 34.15, 31.54, 29.30, 27.47, 23.78, 20.41, 12.59; HRMS (ESI) m/z Calcd for C$_{25}$H$_{39}$N$_2$O$_7$ (M+H)$^+$ 479.2757. found 479.2763.

m. Synthesis of (S,Z)-5-(((2R,5R)-2-((2E,4E)-5-((3R,5S)-7,7-Methyl-1,6-Dioxaspiro[2.5]Octan-5-Yl)-3-Methylpenta-2,4-Dien-1-Yl)-1,3-Dioxan-5-Yl) Amino)-5-Oxopent-3-En-2-Yl Carbamate (32)

32

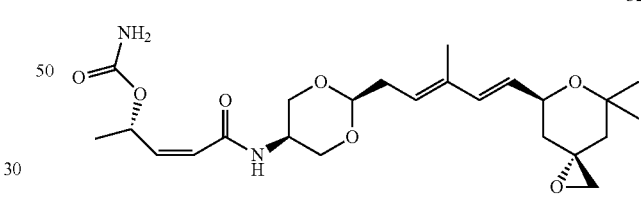

Yield: 6 mg (95%) of 32 as a oil. $^1$H NMR (400 MHz, CDCl$_3$) δ 7.76 (d, J=8.0 Hz, 1H), 6.28 (d, J=15.7 Hz, 1H), 5.97-5.87 (m, 1H), 5.86-5.80 (m, 2H), 5.64-5.50 (m, 2H), 4.74 (s, 2H), 4.61 (t, J=4.9 Hz, 1H), 4.52-4.41 (m, 1H), 4.09-3.87 (m, 5H), 2.57 (s, 2H), 2.49 (t, J=7.2 Hz, 2H), 2.02-1.86 (m, 2H), 1.74 (s, 3H), 1.39 (s, 3H), 1.37 (d, J=6.3 Hz, 3H), 1.28 (s, 3H), 1.23-1.09 (m, 2H); $^{13}$C NMR (101 MHz, CDCl$_3$) δ 165.18, 156.46, 140.64, 135.73, 135.47, 127.72, 125.81, 124.03, 102.03, 73.11, 70.14, 70.08, 69.48, 69.35, 55.72, 51.09, 43.89, 42.45, 38.60, 34.10, 31.54, 23.79, 20.35, 12.61; HRMS (ESI) m/z Calcd for C$_{24}$H$_{37}$N$_2$O$_7$(M+H)$^+$ 465.2601. found 465.2610.

n. Synthesis of (S,Z)-5-(((1R,4R)-4-((2E,4E)-5-((3R,5S)-7,7-Dimethyl-1,6-Dioxaspiro[2.5]Octan-5-Yl)-3-Methylpenta-2,4-Dien-1-Yl)Cyclohexyl)Amino)-5-Oxopent-3-En-2-Yl (2-(Dimethylamino)Ethyl)(Methyl)Carbamate (33)

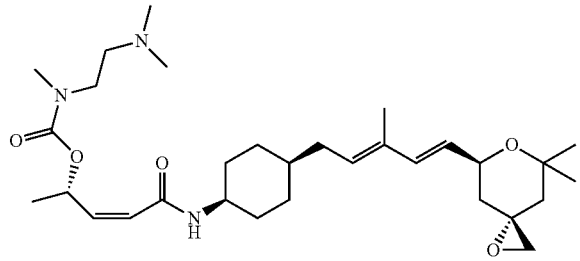

33

Yield: Yield: 8 mg (34%) of 33 as a viscous oil. $^1$H NMR (400 MHz, CDCl$_3$) δ 8.22-8.05 (m, 1H), 6.20 (d, J=15.7 Hz, 1H), 5.82-5.70 (m, 1H), 5.58-5.39 (m, 4H), 4.45-4.33 (m, 1H), 4.06 (s, 1H), 3.51-3.21 (m, 2H), 2.86 (s, 3H), 2.50 (s, 2H), 2.41-2.32 (m, 2H), 2.22-2.17 (m, 6H), 2.05-1.95 (m, 2H), 1.96-1.80 (m, 2H), 1.73-1.58 (m, 5H), 1.55-1.45 (m, 4H), 1.37-1.31 (m, 4H), 1.30-1.27 (m, 2H), 1.28 (d, J=6.1 Hz, 3H), 1.22 (s, 3H), 1.18-1.05 (m, 2H); $^{13}$C NMR (101 MHz, CDCl$_3$) δ 165.12, 156.13, 136.47, 136.26, 133.60, 132.32, 126.87, 126.15, 73.02, 69.60, 69.55, 57.17, 56.78, 55.68, 51.03, 46.86, 45.71, 45.35, 42.45, 38.64, 36.76, 34.78, 34.53, 31.53, 29.59, 29.46, 27.88, 27.59, 23.76, 20.65, 12.48; HRMS (ESI) m/z Calcd for $C_{31}H_{51}N_3O_5$ (M+H)$^+$ 546.3907. found 546.3932.

o. Synthesis of (S,Z)-5-(((1R,4R)-4-((2E,4E)-5-((3R,5S)-7,7-Methyl-1,6-Dioxaspiro[2.5]Octan-5-Yl)-3-Methylpenta-2,4-Dien-1-Yl)Cyclohexyl)Amino)-5-Oxopent-3-En-2-Yl Carbamate (34)

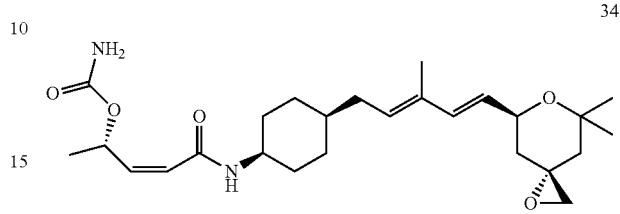

34

Yield: 16 mg (81%) of 18d as a viscous oil. $^1$H NMR (400 MHz, CDCl$_3$) δ 7.62 (d, J=7.7 Hz, 1H), 6.28 (d, J=15.7 Hz, 1H), 5.87-5.75 (m, 1H), 5.70-5.46 (m, 4H), 4.74 (s, 2H), 4.50-4.42 (m, 1H), 4.12-4.06 (m, 1H), 2.57 (s, 2H), 2.15-2.06 (m, 2H), 2.01-1.87 (m, 2H), 1.78-1.67 (m, 5H), 1.63-1.52 (m, 4H), 1.50-1.42 (m, 1H), 1.39 (s, 3H), 1.37-1.29 (m, 5H), 1.27 (s, 3H), 1.22-1.12 (m, 2H); $^{13}$C NMR (101 MHz, CDCl$_3$) δ 165.03, 156.62, 136.70, 136.35, 133.78, 131.98, 126.77, 126.03, 73.08, 69.57, 69.51, 55.68, 51.04, 45.41, 42.45, 38.58, 36.62, 34.22, 31.52, 29.52, 29.44, 27.66, 27.35, 23.77, 20.50, 12.48; HRMS (ESI) m/z Calcd for $C_{26}H_{41}N_2O_5$ (M+H)$^+$ 461.3015. found 461.3020.

p. Synthesis of Sudemycin D6 Diols (20A and 20B)

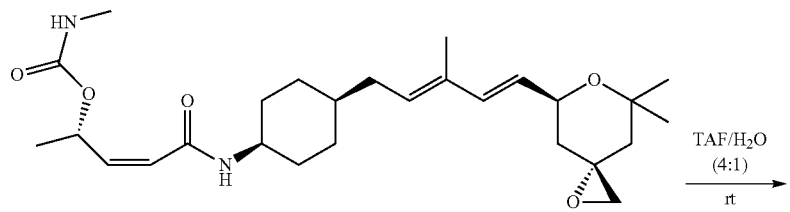

20

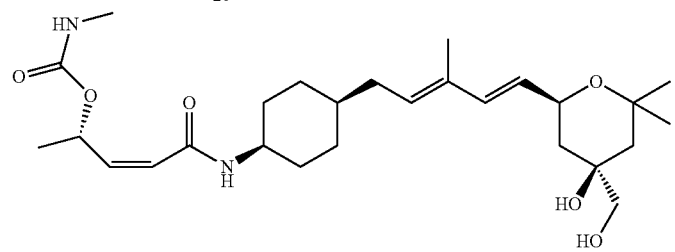

20A

+

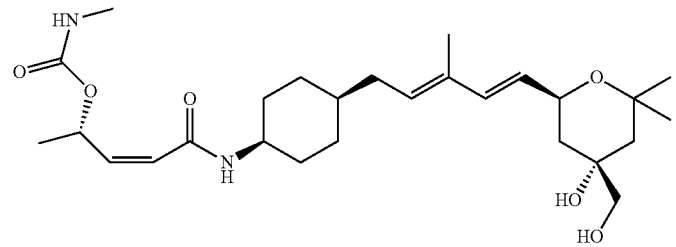

20B

An ice-cooled stirred solution of compound 20 (75 mg, 0.15 mmol) in a mixture of THF and water (1 mL, 4:1) was slowly treated with a solution of trifluoroacetic acid (0.47 mL, 1M in THF). The reaction was allowed to warm to room temp and stirred overnight. UPLC and SFC showed the formation of two products with the correct mass for the diasteriomeric diols. Saturated aqueous NaHCO$_3$ (4 mL) was added and the product was extracted with EtOAc (3×10 mL). The combined organic layers were dried over Na$_2$SO$_4$ and the solvent was evaporated under vacuum. The residue was initially purified by silica column (2-10% MeOH in methylene chloride) and gave diol (60 mg) as a mixture of two diastereomers. These two diastereomers were separated by prep-SFC using an OD-H column (25% MeOH) to give diol 20A (25 mg, 32%) and diol B (20 mg, 26%) as viscous oils. Data for Diol A: $^1$H NMR (400 MHz, Chloroform-d) δ 8.09 (d, J=8.1 Hz, 1H), 6.24 (d, J=15.7 Hz, 1H), 5.81 (d, J=11.1 Hz, 1H), 5.62 (t, J=10.3 Hz, 1H), 5.56-5.46 (m, 3H), 4.90 (s, 1H), 4.15-4.01 (m, 2H), 3.67 (dd, J=56.2, 11.0 Hz, 2H), 2.77 (d, J=4.2 Hz, 3H), 2.42 (s, 2H), 2.09 (t, J=7.1 Hz, 2H), 1.92 (d, J=13.2 Hz, 1H), 1.80 (d, J=13.8 Hz, 1H), 1.74-1.68 (m, 2H), 1.71 (s, 3H), 1.62-1.52 (m, 5H), 1.48-1.36 (m, 4H), 1.30 (s, 6H), 1.22 (s, 3H); $^{13}$C NMR (101 MHz, CDCl$_3$) δ 165.31, 157.07, 136.77, 136.09, 133.72, 132.02, 126.81, 125.95, 72.41, 71.18, 69.65, 69.10, 67.80, 45.43, 44.97, 40.57, 36.63, 34.40, 33.20, 29.56, 29.42, 27.62, 27.40, 27.26, 24.99, 20.62, 12.47; HRMS (ESI) m/z Calcd for C$_{27}$H$_{45}$N$_2$O$_6$ (M+H)$^+$ 493.3278. found 493.3275. Data for Diol 20B: $^1$H NMR (400 MHz, Chloroform-d) δ 8.03 (d, J=7.6 Hz, 1H), 6.27 (d, J=15.7 Hz, 1H), 5.81 (d, J=11.1 Hz, 1H), 5.66-5.52 (m, 3H), 5.48 (t, J=7.6 Hz, 1H), 4.88 (q, J=4.6 Hz, 1H), 4.58-4.43 (m, 1H), 4.10 (m, 1H), 3.38 (d, J=2.2 Hz, 2H), 2.77 (d, J=4.8 Hz, 3H), 2.09 (t, J=7.1 Hz, 3H), 1.75-1.66 (m, 2H), 1.71 (d, J=1.2 Hz, 3H), 1.69-1.61 (m, 2H), 1.60-1.52 (m, 5H), 1.46 (s, 3H), 1.38-1.28 (m, 4H), 1.30 (d, J=5.7 Hz, 3H), 1.24 (s, 3H); $^{13}$C NMR (101 MHz, CDCl$_3$) δ 165.28, 157.07, 136.75, 135.80, 133.86, 131.63, 127.34, 125.99, 72.18, 71.89, 71.07, 69.12, 67.41, 45.42, 42.72, 39.62, 36.67, 34.44, 32.82, 29.58, 29.44, 27.60, 27.40, 27.24, 24.57, 20.63, 12.46; HRMS (ESI) m/z Calcd for C$_{22}$H$_{45}$N$_2$O$_6$(M+H)$^+$ 493.3278. found 493.3274.

4. Cell Culture Procedure

The A549 lung cancer, WiDr colorectal cancer, MCF-7 breast cancer, PC-3 prostate cancer, and OVCAR-3 ovarian cancer cell lines were purchased from the American Type Culture Collection (ATCC, Manassas, Va.) and were maintained in growth media as recommended by the ATCC. The JeKo-1 and JVM-2 mantle cell lymphoma cell lines were purchased from the DSMZ (Brunswick, Germany) and were maintained in growth media as recommended by the vendor. The pediatric rhabdomyosarcoma Rh18 cell line was provided y Dr. P. Houghton (Ohio State University—Nationwide Children's Hospital, Columbus, Ohio) and were maintained in growth media as recommended by Dr. Houghton. All cell culture media were supplemented with L-glutamine and penicillin/streptomycin. All cells were grown under standard culture conditions in CO$_2$ incubators, at 37° C., with 5% CO$_2$, and 100% relative humidity.

5. In Vitro Cytoxicity Analysis

Cell viabilities were determined by measuring the cleavage of (sodium 3'-[1-(phenylaminocarbonyl)-3,4-tetrazolium]-bis(4-methoxy-6-nitro)benzene sulfonic acid hydrate) (XTT) to a water-soluble orange formazan by mitochondrial dehydrogenase, following the manufacturer's instructions (Roche Applied Science, Indianapolis, Ind.). Briefly, cell lines were seeded at various cell densities depending on the cell type. The adherent cell lines were allowed to adhere overnight before compound addition, whereas the suspension cell lines were seeded the day of compound addition. Stock concentrations of the compounds were made in DMSO, diluted in culture media and subsequently added to the plates at various final concentrations, then incubated for 72 hours. After the incubation period, the XTT labeling reagent, containing the electron-coupling reagent, was added to each well and incubated for 4 hours. The absorbance of each well was then read at 490 nm with a reference wavelength of 690 nm using a VersaMax™ microplate reader (Sunnyvale, Calif.). Data are expressed as the percentage of growth compared to vehicle-treated cells, as calculated from absorbance and corrected for background absorbance. The IC$_{50}$ is defined as the drug concentration that inhibits growth to 50% of the vehicle-treated control; IC$_{50}$ values were calculated from sigmoidal analysis of the dose response curves using Origin v7.5 software (Northampton, Mass.).

Alternatively, cell lines were seeded in 100 µL cell culture medium in 96-well plates. Depending on the cell proliferation rate, cells were seeded at 4,000 to 6,000 cells/well. Suspension cell cultures were initiated with 20,000 cells/well. The cells were incubated overnight at 37° C., and then the drug treatments were started by adding 50 µL medium containing the corresponding drug dilution and DMSO. The final concentration of DMSO onto the cells was 0.5% v/v in all wells. The cells viability was determined using the CellTiter-Glo Luminescent Cell Viability Assay (Promega, Madison, Wis.). The CellTiter-Glo reagent was prepared according to the manufacturer's instructions, and then 50 µL reagent was added to each well for 1 h at rt. The luminescence was measured on an Envision Multilabel Plate Reader (PerkinElmer, Waltham, Mass.). The IC$_{50}$ values were calculated from the dose-response curve analysis with GraphPad Prism 6.01 (GraphPad Software, La Jolla, Calif.) using the nonlinear regression model 4 Parameter Logistic. Nine concentrations were generated by 1:2 serial dilutions for each IC$_{50}$ assay. Each drug concentration was evaluated in triplicate or quadruplicate.

6. Cell Cycle Analysis

Cell cycle analysis was performed by treating A549, JeKo-1, and WiDr cancer cell lines with a range of compound 1 concentrations overnight for 18 hours. After the incubation period, the cells were harvested and fixed with ethanol, then incubated with RNAse A and propidium iodide (PI). Fluorescence was detected using the BD FACSCalibur flow cytometer and analyzed using Cell Quest Pro software (both from BD Biosciences, San Jose, Calif.). Analysis of the percentage of cells in each of the cell cycle phases (G1, S, or G2/M) was calculated by measuring the DNA content in each sample. The data shown represent the average determinations.

7. Cell Proliferation Assays for Short-Term Exposure to a Compound

The cell were seeded in of 100 µl of medium into 96-well plates (HeLa at 4×10$^4$ cell/well; SK_MEL_2 at 6×10$^4$ cell/well), they were allowed to attach overnight, and then treatments started by adding 50 µl of medium containing Sudemycin D6 to produce a final concentration of 1 µM and DMSO to 0.5% v/v final into the experimental well. Continuous drug treatments were run in the same plate, using concentrations of 0, 62.5, 125, 250, 500 & 1000 nM final. DMSO was added into all wells, including non-treated wells to 0.5% v/v final concentration. For wells where the drug was withdrawn, the medium was carefully aspirated after 1, 2, 3 and 4 hours after the addition of the drug, the cells were washed once with PBS and then 150 µl of fresh cell culture medium containing 0.5% v/v DMSO was added into all washed out wells. After 72 hours of the addition of drug, the cell viability was determined using CellTiter-Glo luminescent cell viability assay (Promega, Madison, Wis.), and Sudemycin D6 cytotoxicity was calculated as the percentage of cell proliferation inhibition against the control treatment DMSO.

8. Drug Combination Assays

Preliminary cytotoxic screenings for each drug used in drug combination assays were performed to determine their cytotoxic dose range. The drug combination assays were initiated at a dose that was 4 or more times higher than the concentration of each drug required for the $IC_{50}$ value. Eight concentrations were established by 1:3 serial dilutions of the single drugs and their combinations with the splicing modulators. All drug concentrations were evaluated in triplicate in 96-well cell culture plates. Assays of individual drugs and drug combinations were run on the same tissue culture plate. Cell viability was determined using the CellTiter-Glo reagent. Drug interactions, in terms of synergism, additive effect, or antagonism, were based on the drugs' Combination Index (CI) (Chou et al., *Adv. Enzyme Regul.* 1984, 22, 27).

9. Combination Index for Constant-Ratio Drug Combinations

Luminescence data obtained from the cell viability determinations were formatted per the requirements of the analytical software (viability data range: >0 and <1). The formatted data were analyzed with the software CalcuSyn 2.1 (Biosoft, Cambridge, UK), which provides quantitative CI values for the drug interaction analyses (see ranges in Supplementary Table S2). All CI values were calculated at the combination dose that produced a cytotoxic effect in 50% of the cells ($ED_{50}$). Neither AUDA nor NCND alone produced a cytotoxic effect, so it was not possible to determine a CI for those drugs. Therefore, in these two cases the drug interaction was evaluated by comparing the $IC_{50}$ value of Sudemycin with that of the $IC_{50}$ values resulting from the serial dilutions of the splicing modulator combined with a constant dose of the non-toxic drug.

10. In Vitro Alternative Splicing Assay

Figure 9:
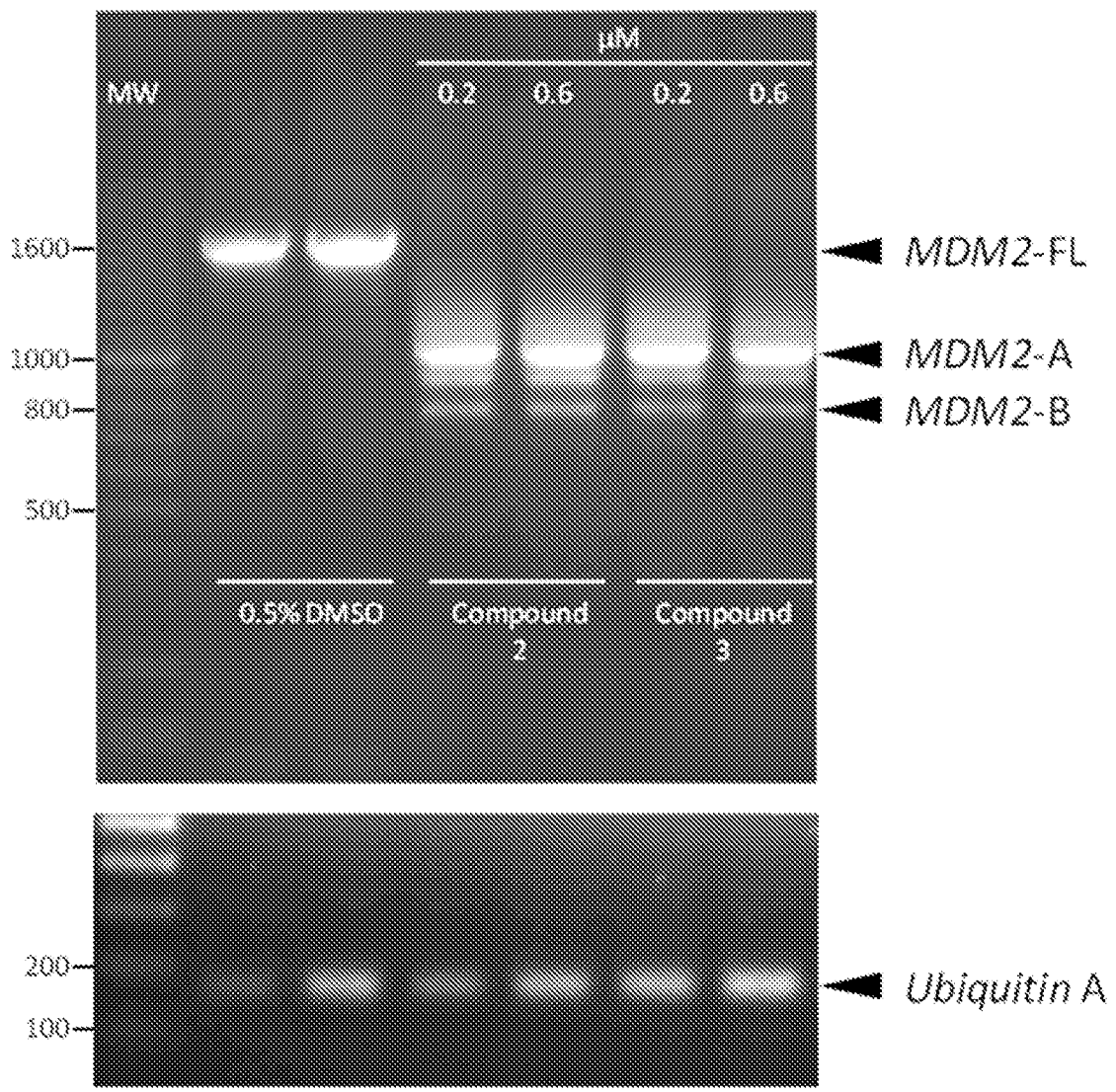
FIG. 9 shows the induction of alternative MDM2 splicing in Rh18 by compounds 19 and 20. The upper panel of the figure shows the PCR results of the MDM2 alternative splicing. The lower panel of the figure shows the amplification of ubiquitin A, a gene that serves as a loading control because it is an amplified transcript that is not affected by splicing modulators. The cells were exposed to the indicated drug treatments for 8 h.
Figure 10:
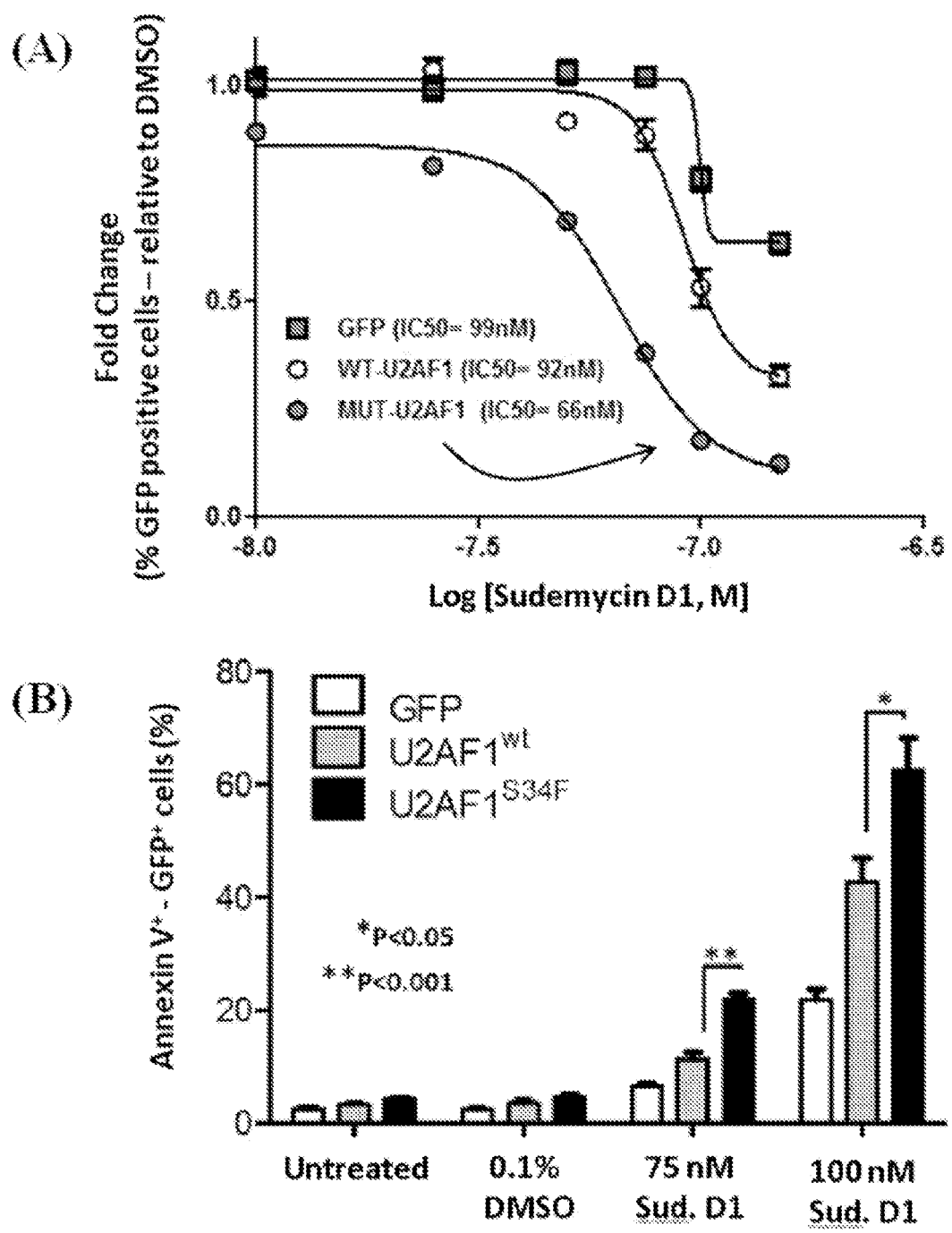
FIG. 10 shows representative data showing the effect of a representative disclosed compound on splicing in U2AF1$^{S34F}$ transduced cells. Bone marrow was collected from C57BL/6 mice and pooled together in a single solution, and then c-kit positive cells were selected. The c-kit positive cells were cultured with media enriched with stem cell factor (SCF), Flt-3, IL3, and thromboprotein (TPO), and other cytokines. Murine stem cell virus (MSCV) was used to transduce these cells with one of three constructs as indicated in the figure: GFP (control), U2AF1-IRES-GFP (indicated as WT-U2AF1 in the figure), or U2AF1$^{S34F}$-IRES-GFP (indicated as MUT-U2AF1 in the figure). The transduced cells carry a construct that expresses GFP and as indicated wild-type or mutant U2AF1. The control cells construct expresses only GFP. The left panel (Panel A) shows the concentration dependent effect of a representative test compound, sudemycin D1, on the expression of GFP in the three indicated transduced cell types. The data show that the test compound affects the expression of GFP from the splicing construct in cells expressing both the wild-type U2AF1 and the mutant U2AF1 (S34F mutation), with greater sensitivity realized in the mutant U2AF1 cells. The apparent IC$_{50}$ is as indicated in the figure panel. The right panel (Panel B) shows the effect of either 75 or 100 nM sudemycin D1 compared to control cells on the apoptosis. The assay data are expressed as the percentage of annexin V stained cells among the GFP positive cells. The data show that cells expressing either the wild-type U2AF1 or the mutant U2AF1 are more sensitive to the effects of the treatment with the test compound, sudemycin D1, with the cells expressing mutant U2AF1 the most sensitive. These cells show an increased tendency to apoptosis (i.e. increased expression of annexin V) in the GFP positive cells.
Figure 11:
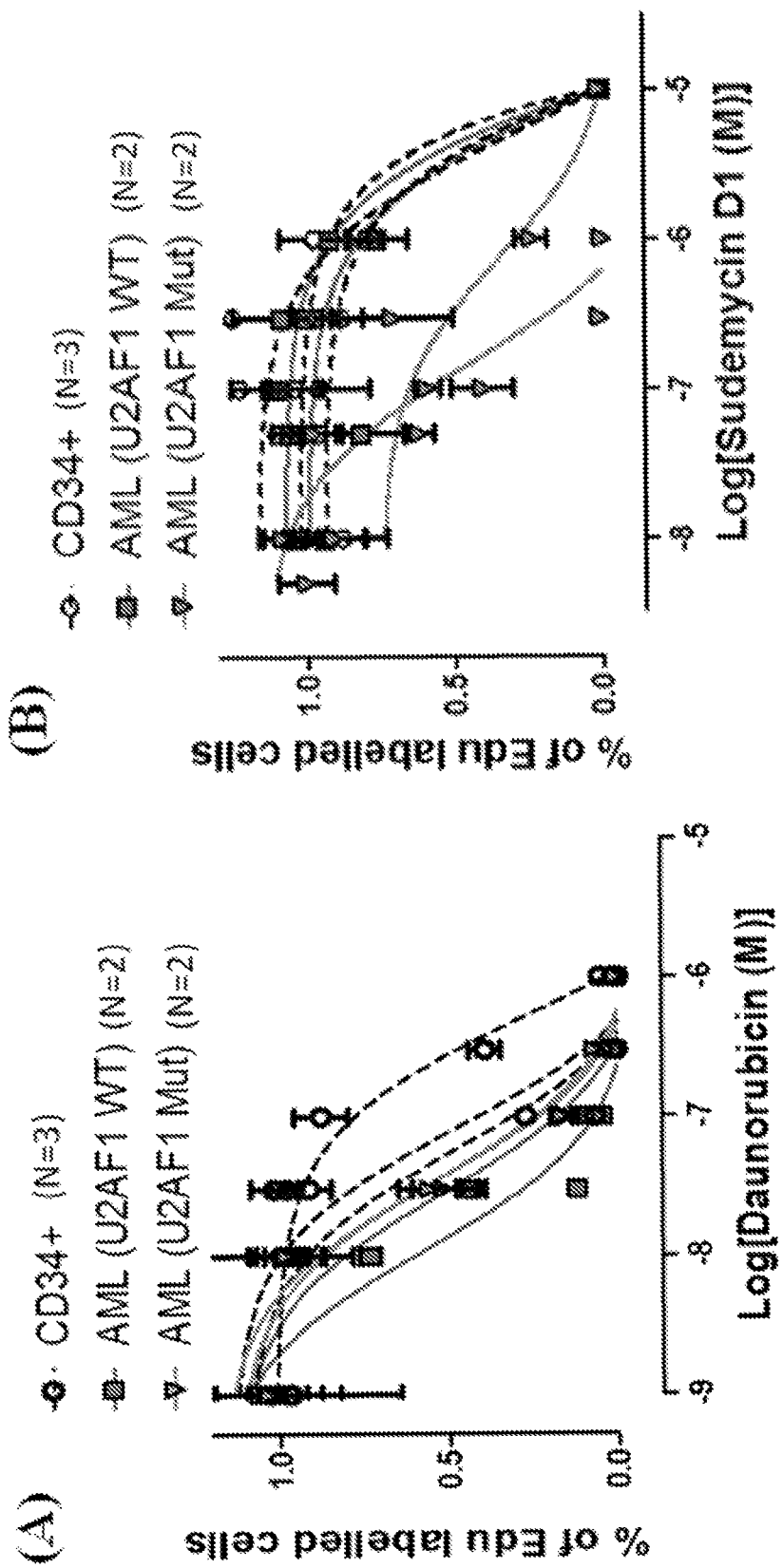
FIG. 11 shows representative data for the effect of a representative disclosed compound, sudemycin D1, on replication of U2AF1 wild-type AML blast cells and AML blast cells with mutant U2AF1 S34F compared to CD34+ cells. Replication was determined from incorporation of 5-ethynyl-2'-deoxyuridine using standard assay techniques. The left panel shows a control experiment showing the effect of daunorubicin on cells (CD34 positive cells, AML blast cells with wild-type U2AF1, and AML blast cells with mutant S34F U2AF1 as indicated). The right panel shows the concentration dependent effect of the test compound, sudemycin D1, on replication. The data show that the cells expressing mutant U2AF1 are extremely sensitive to the effects of the test compared to either wild-type U2AF1 or CD34+ cells.

In vitro evaluation of MDM2 alternative-splicing reactions was performed as previously described (*ACS Chem. Biol.*, 2011, 6, 582) using Rh18 cells. Briefly, following an 8 h exposure of exponentially growing cells to drug, total RNA was isolated using TRIzol reagent (Invitrogen, Carlsbad, Calif.). Total RNA (1 µg) was used to convert the mRNA to cDNA by using random primers, Oligo(dT)$_{16}$ and Omniscript Reverse Transcription Kit (Qiagen, Germantown, Md.). PCR analyses were performed using specific oligonucleotides (see Table I) and standard amplification protocols. PCR products were separated by agarose gel electrophoresis, visualized by ethidium bromide staining on an UV transilluminator, and recorded. PCR band sizes were calculated by comparing them to the standard EZ Load 100-bp PCR Molecular Ruler (BioRad Laboratories, Hercules, Calif.). The identities of specific transcripts were verified by sequencing, as previously described (*ACS Chem. Biol*, 2011, 6, 582). Representative data are shown in FIG. 9.

11. Bioanalysis of Compound 20 in C.B-17 Scid Mouse Plasma by LC-MS/MS

A sensitive and specific LC-MS/MS assay was developed for quantification of compound 20 in plasma for application in a murine pharmacokinetic study. Calibrators and quality controls (QCs) were prepared using 100% methanol stocks in blank C.B-17 scid mouse plasma with lithium heparin anticoagulant. The calibrators and QCs, 25 µL each, were stored briefly on wet ice and then protein precipitated with 75 µL of ice cold compound 19 internal standard processing solution. The supernatants, 100 µL of each, were mixed with 100 µL of methanol-10 mM ammonium bicarbonate, pH 7.0 (50:50 v/v) and injected from the 96-well plate to the LC-MS/MS system via a CTC HTS PAL autosampler. Chromatography was performed using a Phenomenex Synergi Fusion-RP C18 column (4.0 µM, 50 mm×2.0 mm) maintained at 35° C., and a linear gradient mobile phase consisting of water:methanol:acetonitrile (22.5:57.5:22.5, v/v) to methanol: acetonitrile (70:30, v/v) and back. Retention times of 0.47 and 0.59 min were observed for compounds 20 and 19, respectively. Detection was performed with an AB Sciex 5500 QTRAP LC-MS/MS System equipped with a Turbo IonSpray® source using the positive multiple-reaction monitoring (MRM) mode. The transitions monitored included m/x 475->288 for compound 20 and m/x 489->400 for compound 19, which served as an internal standard. The lower limit of quantitation was 1 ng/mL (5× S:N ration, <20% CV); intra-run precision and accuracy was ≤11.2% CV and 96.5-103%, respectively. The calibration curve was linear from 1 to 500 ng/mL (R=0.9968) and QC samples above the limit of quantitation (500 ng/mL) were precisely and accurately diluted into the linear range with blank C.B-17 scid mouse plasma.

12. In Vivo Plasma Pharmacokinetic (PK) Study of Compound 20 in C.B-Scid Mice

A plasma PK study of compound 20 in male C.B-17 scid mice receiving a continuous i.v. infusion of compound 20 (100 mg/kg over 30 min) was performed. Compound 20 was formulated in 15% Captisol®/50 mM Na$_2$HPO$_4$/NaH$_2$PO$_4$ solution at 3 mg/mL and infused with a syringe pump at a rate of 20 µL/min via a jugular vein catheter. Blood samples (1 to 2 samples per mouse, 18 samples from 11 total mice) were collected by either retro-orbital sinus bleeding or terminal cardiac puncture at the following times after the start of infusion: 7.5, 15, 30 (end of infusion), 35, 45, and 60 minutes. The samples were immediately processed to plasma by centrifugation at 2000 g for 5 min; the resultant volume of plasma was then protein precipitated with a 3:1 volume of ice cold IS processing solution. The supernatants were immediately placed on dry ice and then stored at −80° C. until analysis.

13. Pharmacokinetic Analysis

The concentration-time data for compound 20 in mice was analyzed using the MLEM population estimation

TABLE I

| Gene | Primer | Sequence | Isoform; expected product size (bp) |
|---|---|---|---|
| MDM2 (NM_002392) | mdm2-F | CTGGGGAGTCTTGAGGGACC | MDM2-FL; 1604 |
| | msm2-R | CAGGTTGTCTAAATTCCTAG | MDM2-A; 1019 |
| | | | MDM2-B; 785 |
| Ubiquitin A (NM_001033930) | UbA-F | ACCTGACCAGCAGCGTCTGATATT | UbA-FL; 165 |
| | UbA-R | TCGCAGTTGTATTTCTGGGCAAGC | | method as implemented in ADAPTS (D'Argenio, D. Z. and Schumitzky, A., *Wang ADAPT 5 User's Guide: Pharmacokinetic/Pharmacodynamic Systems Analysis Software*; Biomedical Simulations Resource: Los Angeles, Calif., USA, 2009). A linear, one-compartment PL model was fit to the data, and the adequacy of the fit was assessed by the −2 log likelihood value, visual predictive checks, and the residual plots. Inter-individual variability in plasma clearance (CL) and volume of distributions (V) was assumed to be log-normally distributed with the covariance matrix constrained to diagonal elements. The residual, intra-individual error was described using an additive and proportional model, with the additive term fixed to the lower limit of quantitation of the LC-MS/MS assay (LLOQ, 1 ng/mL). Beal's M3 method was used to handle data that was below the LLOQ (Beal, S. L., *J. Pharmacokinet. Pharmacodyn.* 2001, 28, 481). Other secondary parameters, such as the area under the plasma concentration-time curve to infinity ($AUC_{inf}$), maximum plasma concentration ($C_{max}$), and the time of $C_{max}$ ($T_{max}$) were derived for the population using standard formulae (Pharmacokinetics, Second Edition; Gibaldi, M.; Perrier, D., Eds.; $2^{nd}$ ed.; CRC Press, 1982).

14. Infusions in Tumor Bearing Mice

Xenograft tumors were first established from an SK-MEL-2 cell culture at the St. Jude Children's Research Hospital Xenograft Core. After these tumors were established as a mouse xenograft model, they were routinely maintained in the C.B-17 scid strain (Taconic Farms, Germantown, N.Y.). Experimental animals were prepared by transplanting small pieces of dissected tumors from donor animals into recipient mice. All animal studies were performed in accordance with the St. Jude Children's Research Hospital Animal Care and Use Committee. SK-MEL-2 xenograft tumors were transplanted into male C.B-17 scid mice on Day −21. On Days −7 to −5, a jugular vein catheter was surgically implanted into each mouse. Beginning on Day 1, the animals (8 for vehicle, 9 for drug-treatment) received daily infusions of vehicle (10% [(2-hydroxypropyl)-β-cyclodextrin] dissolved in 50 mM $Na_2HPO_4$/$NaH_2PO_4$, pH 7.4) or 100 mg/kg of compound 20 for 5 consecutive days. Infusions were carried out by placing the animals inside a continuous infusion system (Instech Laboratories, Plymouth Meeting, Pa.), and delivering the vehicle or drug solution via the jugular catheter at a rate of 4 µL/min with a SP230iw syringe pump (WPI, Sarasota, Fla.). The total volume infused into the animals did not exceed 850 µL per day. Tumors were continuously measured during and after infusion periods, 5 times per week (weekdays). Tumor volumes were determined based on the following equation: $Tu_{vol} = (\delta_1/2 + \delta_2/2)^{1.5708}$, where $\delta_1$ and $\delta_2$ are diameters measured with a caliper at right angles of each other. The size of the tumors ranged from 0.2 to 0.5 $cm^3$ at the times the infusions were initiated.

15. Characterization of Representative Compounds

Representative compounds of the present invention were synthesized using the methods as described herein above. The compounds were characterized using the methods as described herein above (see Table II). Without wishing to be bound by a particular theory, the data suggest the presence of a compact and relatively non-polar pocket near (or on) the SF3B subunit, as activity decreases with both the size of hydrophobic groups and with increasing polarity.

TABLE II

| Compound Structure | MDM2 Splicing Effects | JeKo1 $IC_{50}$ (µM) | Plasma Stability* | Buffer Soluble† | Rapid Onset†† |
|---|---|---|---|---|---|
|  | Yes | 0.10 | No | No | Yes |
|  | Yes | 0.047 | No | No | Yes |
|  | Yes | 0.22 | No | Yes | No |

TABLE II-continued

| Compound Structure | MDM2 Splicing Effects | JeKo1 IC$_{50}$ (μM) | Plasma Stability* | Buffer Soluble† | Rapid Onset†† |
|---|---|---|---|---|---|
| (structure) | Yes | 0.30 | Yes | Yes | No |
| (structure) | Yes | 0.041 | Yes | No | Yes |
| (structure) | ND | 0.17 | ND | Yes | ND |
| (structure) | Yes | 0.022 | Yes | Yes | Yes |
| (structure) | ND | 0.10 | ND | ND | ND |

*"Yes" indicates mouse plasma stability is >5 hours in mouse plasma at 37° C. as determined by HPLC.
†"Yes" indicates the compound's solubility (as determined by HPLC) is >10 μM in phosphate buffered saline.
††"Yes" indicates maximum cytotoxicity or splicing modulation is seen within 5 hours of drug treatment.
"ND" indicates that the experimental parameter was not determined.

16. Cytotoxicity of Representative Compounds

The compounds were characterized using the in vitro cytotoxicity assay as described herein above (see Table III).

TABLE III

| Compound Structure | JeKo1 IC$_{50}$ (μM) | PC3 IC$_{50}$ (μM) |
|---|---|---|
| (structure) | >1 | >10 |

TABLE III-continued

| Compound Structure | JeKo1 IC$_{50}$ (μM) | PC3 IC$_{50}$ (μM) |
|---|---|---|
| (structure) | >1 | >10 |
| (structure) | >1 | 7.3 |
| (structure) | 0.61 | 3.2 |
| (structure) | >1 | >10 |
| (structure) | 0.69 | 3.2 |

TABLE III-continued

| Compound Structure | JeKo1 IC$_{50}$ (μM) | PC3 IC$_{50}$ (μM) |
|---|---|---|
| [structure: N-methyl-N-isopropyl carbamate derivative] | 0.7 | 3.4 |
| [structure: N-methyl-N-tert-butyl carbamate derivative] | 0.78 | 2.7 |
| [structure: N,N-dimethyl carbamate derivative] | 0.3 | 4.4 |
| [structure: N-methyl carbamate derivative] | 0.9 | >10 |
| [structure: NH$_2$ carbamate derivative] | 1.9 | >10 |

17. Drug Synergy Studies

The in vitro anticancer activity of compounds 19 and 20 in combination with successive members of a panel of 23 diverse types of clinically useful anticancer drugs and bioactive agents was evaluated using the drug combination assay as described herein above (see Table IV). The ranges of the Combination Index (CI) used are illustrated in Table V.

TABLE IV

| Drug | Mechanism of Action | Interaction Type | CI in SK-MEL-2 with compound 19 |
|---|---|---|---|
| 5-Fluorouracil | Nucleoside metabolic Inhibitor | Ineffective[a] | — |
| AUDA | Inhibitor of sEH | Synergism | n.d.[b] |
| BEZ 235 | Dual inhibitor of PI3K and mTOR | Strong synergism | 0.21 |
| BIBR 1532 | Telomerase inhibitor | Ineffective | — |
| Bortezomib | Proteasome inhibitor | Antagonism | n.d. |
| Camptothecin | DNA topoisomerase I inhibitor | Antagonism | 0.74 |
| Doxorubicin | Antibiotic inhibitor of DNA topoisomerase II | Ineffective | — |
| Etoposide | Topoisomerase II inhibitor | Ineffective | — |

TABLE IV-continued

| Drug | Mechanism of Action | Interaction Type | CI in SK-MEL-2 with compound 19 |
|---|---|---|---|
| Harringtonine | Inhibitor of protein synthesis | Antagonism | n.d. |
| Hydroxyurea | Antimetabolite | Ineffective | — |
| Imatinib | Competitive tyrosine kinase inhibitor | Antagonism | n.d. |
| Lonidamine | Mitochondrial hexokinase inhibitor | Ineffective | — |
| Mitomycin C | DNA cross-linker, alkylating agent | Ineffective | — |
| NCND | Inhibitor of sEH | Slightly additive | — |
| Nutlin-3 | Inhibit the interaction with MDM2-p53 | Ineffective | — |
| Oxythiamine | Transketolase inhibitor | Ineffective | — |
| Panobinostat | Broad-spectrum HDAC inhibitor | Antagonism | 0.76 |
| PX-866 | Irreversible inhibitor of PI3K | Synergism | 0.57 |
| Silibinin | Inhibitor of P-glycoprotein-mediated cellular efflux & cytochrome P450 | Moderate synergism | 0.89 |
| Sorafenib | Multikinase inhibitor | Synergism | 0.43 |
| SU 9516 | Cyclin-dependent kinase-2 inhibitor | Antagonism | 0.83 |
| Taxol | Microtubule inhibitor | Antagonism | n.d. |
| Temsirolimus | Inhibitor of mTORC1 | Synergism | 0.68 |

$^a$Ineffective interaction indicates that the concentration of drug required for the IC$_{50}$ is much higher than 1 μM.
$^b$The notation n.d. indicates that the CI value was not determined. Drug interaction was established by combination of various concentrations of compound 19 combined with the indicated drug at a constant concentration.

TABLE V.

| Range of CI | Interaction |
|---|---|
| <0.1 | Very strong synergism |
| 0.1-0.3 | Strong synergism |
| 0.3-0.7 | Synergism |
| 0.7-0.85 | Moderate synergism |
| 0.85-0.90 | Slight synergism |
| 0.90-1.10 | Nearly additive |
| 1.10-1.20 | Slight antagonism |
| 1.20-1.45 | Moderate antagonism |
| 1.45-3.3 | Antagonism |
| 3.3-10 | Strong antagonism |
| >10 | Very strong antagonism |

Figure 2:
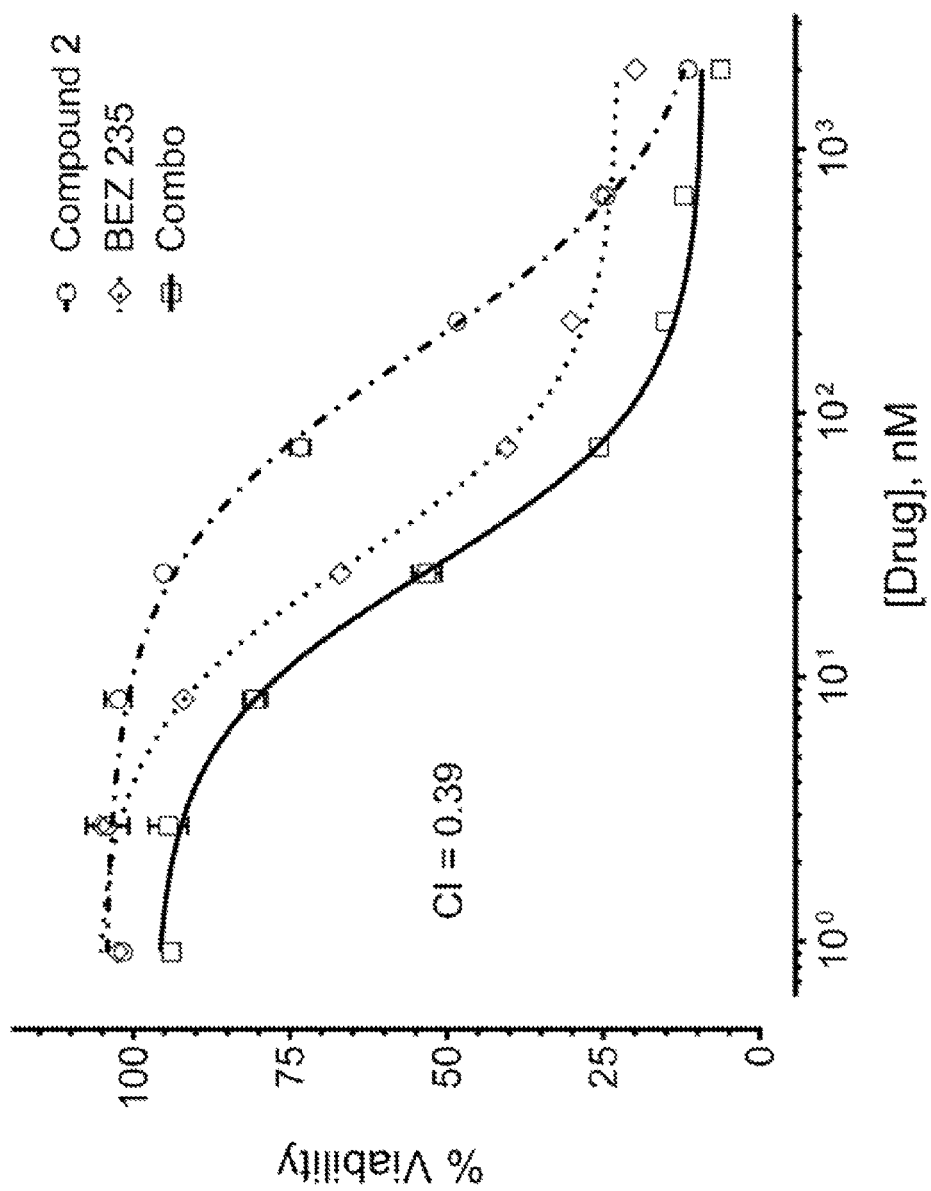
FIG. 2 shows the concentration-effect curve of compound 19 and BEZ 235. The interactions between compound 19 and BEZ 235 result in strong synergism. The $IC_{50}$ curve of the drug combination in the neuroblastoma cell line SK-NA-S is plotted. Each experimental condition was carried out in triplicate; error bars represent the SEM. Drug interactions were assessed with the software CalcuSyn 2.1 (Biosoft, Cambridge, UK). The program is based on Chou-Talalay's Combination Index theorem, which renders a quantitative definition of the drugs' interaction defined as the Combination Index (CI) (Cou et al., Adv. Enzyme Regul. 1984, 22, 27).
Figure 3:
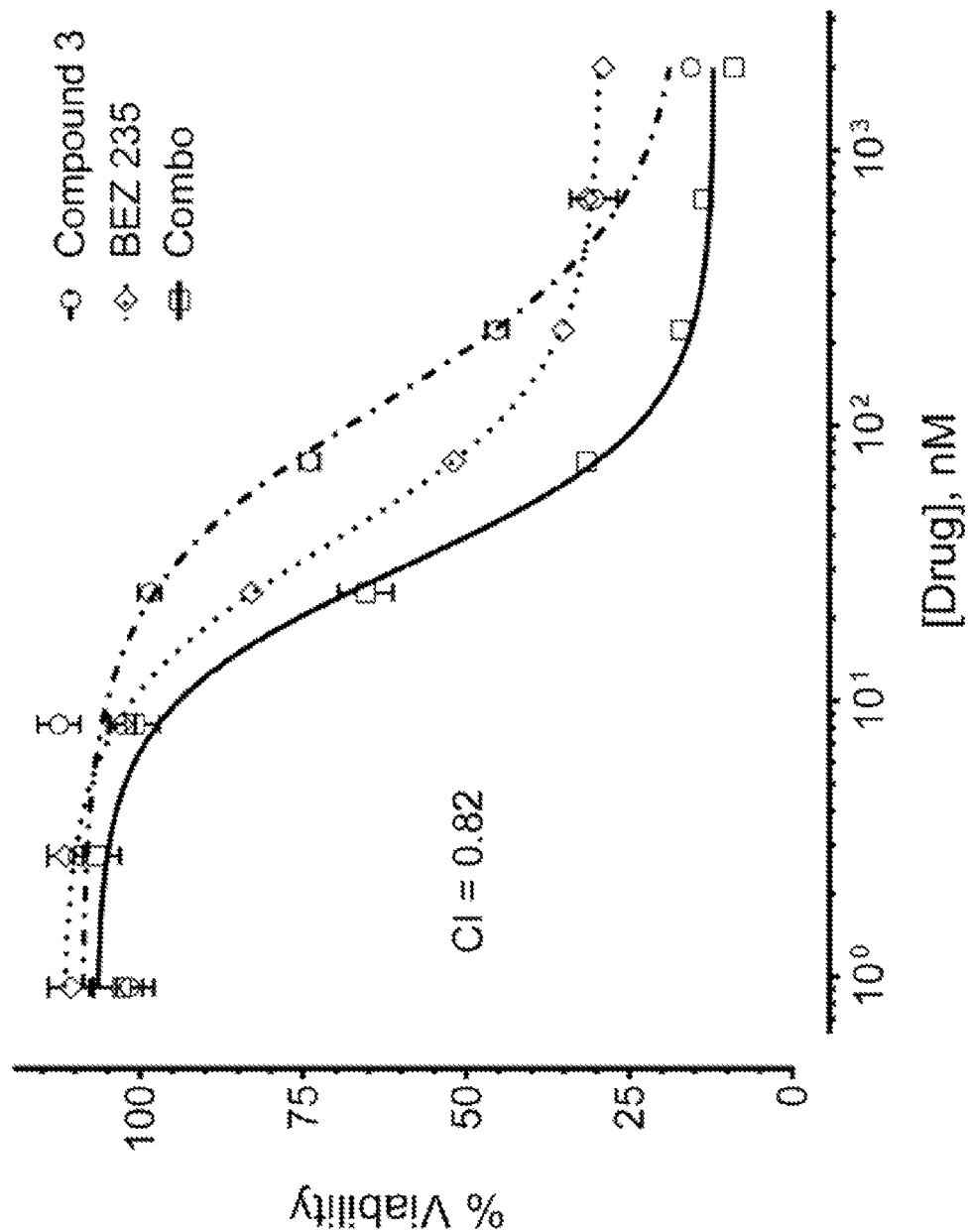
FIG. 3 shows the concentration-effect curve of compound 20 and BEZ 235. The interactions between compound 20 and BEZ 235 result in strong synergism. The $IC_{50}$ curve of the drug combination in the neuroblastoma cell line SK-NA-S is plotted. Each experimental condition was carried out in triplicate; error bars represent the SEM. Drug interactions were assessed with the software CalcuSyn 2.1 (Biosoft, Cambridge, UK).

The strongest synergy was observed with BEZ235, a dual inhibitor of phosphatidylinositol-3-kinase (PI3K) and the mammalian target of rapamycin (mTOR) (Maira et al., *Mol. Cancer Ther.* 2008, 7, 1851) (Table VI). BEZ235 is currently under investigation in numerous clinical trials. Given the strong synergy observed with this compound, the combined effects of selective inhibitors of the two individual targets, PI3K and mTOR, were further investigated (LoPiccolo et al, *Drug Res. Updat.* 2008, 11, 32). Specifically, PS-866 and temsirolimus were evaluated. Interestingly, both of these agents demonstrated synergy with compound 20. This synergy is also seen for both compounds 19 and 20 in all cell lines investigated (see FIGS. 2 and 3). The second strongest synergistic agent was the multi-kinase inhibitor sorafenib, which is also reported to have off-target inhibition of soluble epoxide hydrolase (sEH) (Liu et al., *Mol. Cancer Ther.* 2009, 8, 2193). Some mammalian epoxide hydrolases are known to be important in the metabolism of epoxide containing xenobiotics (Decker et al., *Arch. Toxicol.* 2009, 83, 297). Since the sudemycins (and related drugs) have an epoxide group as a critical feature of their pharmacophore (Lagisetti et al., *J. Med. Chem.* 2008, 51, 6220), it is possible that this group is metabolized and inactivated by epoxide hydrolases present in tumor cells during the course of the cytotoxicity screening. The diol product of epoxide ring opening of compound 20 was subsequently prepared, but offered no detectable activity at a concentration of 10 μM. It was thus hypothesized that EH inhibitors may stabilize this class of drugs. Evaluation of the EH inhibitor AUDA indicates synergy with compound 19, supporting the possibility that this epoxide metabolic pathway is significant for these drugs in vitro and potentially in vivo.

TABLE VI

| | CI of 19 + inhibitor | |
|---|---|---|
| Cell Line | PI3K inhibitor (PC-866) | mTOR inhibitor (Temsirolimus) |
| HeLa | 0.49 | 0.35 |
| JeKo-1 | n.d. | 0.37 |
| PC-3 | 0.67 | 0.57 |
| SK-MEL-2 | 0.57 | 0.68 |
| Sk-N-AS | 0.65 | 0.58 |
| WiDr | 0.33 | 0.44 |

18. Population Plasma PK Parameters of Intravenous Compound 20 in C.B-27 Scid Mice The compounds were characterized using the MLEM population estimation method as described herein above. The mean population pharmacokinetic ("PK") parameter estimates are listed in Table VII.

TABLE VII

| Parameter | Estimate | RSE (%) | IIV (% CV) | RSE (%) |
|---|---|---|---|---|
| CL (mL/min/kg) | 280 | 28.6 | 5.21 | 504 |
| V (L/kg) | 0.877 | 195 | 113 | 68.7 |
| T$_{1/2}$ (min) | 2.18 | — | 113 | — |
| σ$_{add}$ (μM) | 0.00211$^a$ | — | — | — |
| σ$_{prop}$ (%) | 36.4 | 47.4 | — | — |
| C$_{max}$ (μM) | 24.1 | — | — | — |
| T$_{max}$ (min) | 30.0 | — | — | — |
| AUC$_{inf}$ (μM-min) | 752 | — | — | — |

$^a$Fixed to assay LLOQ (1 ng/mL)

Figure 7:
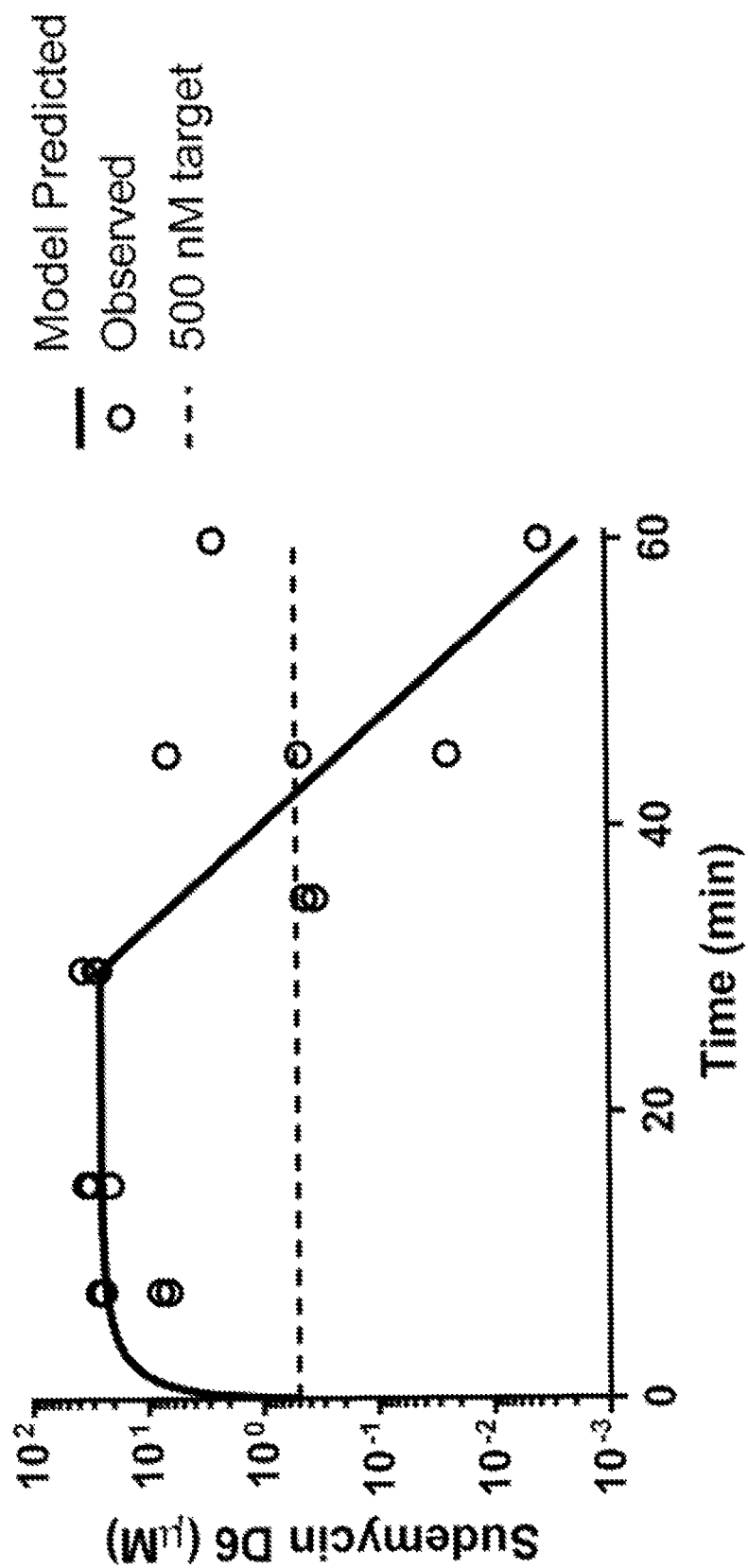
FIG. 7 shows the plasma concentration-time profile of intravenous Sudemycin D6 (compound 20) in C.B-17 scid Mice.

The one-compartment model adequately described the mean population compound 20 plasma concentration-time data, with good concordance between observed and predicted population concentrations (see FIG. 7). After a 30-minute infusion of compound 20 at 50 mg/kg in C.B-17 scid mice, the mean CL value of 280 mL/min/kg was considered high, as it exceeded hepatic blood flow by 3-fold. The mean V value exceeded total body water (>0.6 L/kg), suggesting distribution to the peripheral tissues, but was highly variable between mice. The overall PK variability was moderate-to-high, particularly at time points after the end of infusion. The population mean terminal elimination half-life (T$_{1/2}$) was 2.18 minutes, with post-hoc individual estimates ranging from 50 seconds to 12 minutes. The high CL and variability may result from the differential expression of enzymes responsible for the metabolism of compound 20. Moreover, both the amount and tissue location of these enzymes and their activity may vary both within and between mice. Despite rapid CL and PK variability, the target plasma concentration of 500 nM, a concentration associated with tumor spliceosome inhibition in flank xenograft models and in cellular systems, was far exceeded and maintained for an adequate time period.

19. Maximum Tolerated Dose Studies

Figure 8:
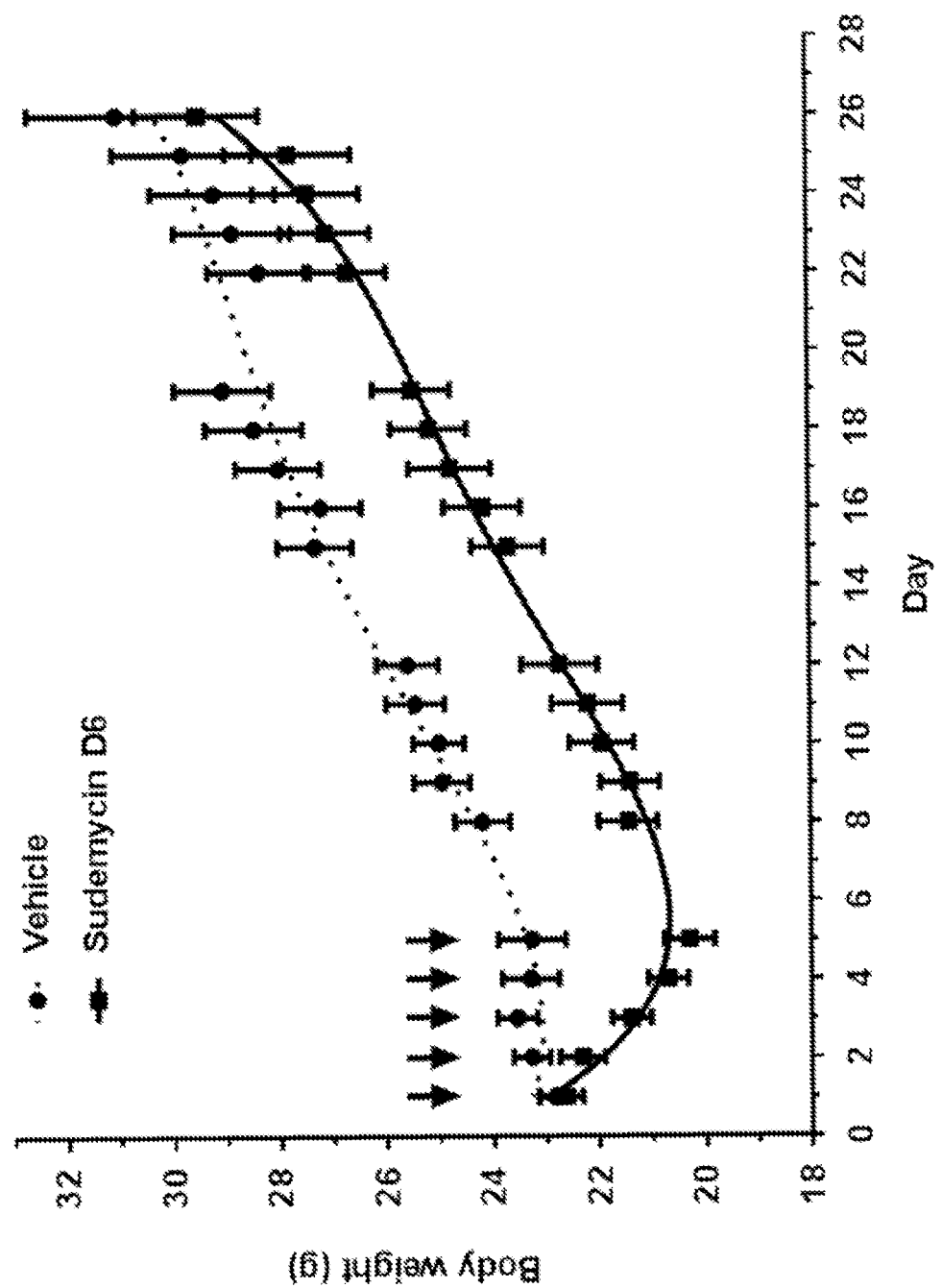
FIG. 8 shows that Sudemycin D6 (compound 20) causes weight loss in C.B-17 scid mice. The arrows indicate the days where a four hour infusion of 50 mg/kg of either vehicle of compound 20 was given to each mouse. Animals' weight was measured daily 5 times per week. N=8 for the vehicle group and n=9 for the drug treated group. Error bars represent the SEM. Treatment with compound 20 induced a rapid weight loss from the beginning of the drug administration. The weight loss continues during all of the infusion period of compound 20. The average weight loss in the animals treated with compound 20 was 12.7% at day 5 of infusion. Shortly after the drug is no longer administered, the animals in the drug-treated group began to gain weight sustainably, with basically the same rate as the mice infused with the vehicle.

The in vivo effects, e.g. weight loss, of compound 20 were evaluated in mice using the methods described herein above. Briefly, mice (C.B-17 scid) were infused over four hours with either vehicle or 50 mg/kg compound 20 daily over a period of five days. Weight of the test animals was determined daily (5 weight measurements/week). The group sizes were eight animals for the vehicle group and nine animals for the drug treated group. The data shown in FIG. 8 indicate that treatment with compound 20 correlated with weight loss during the drug infusion period, i.e. drug treatment induced a rapid weight loss from the beginning of the drug administration; and the loss of weight continued during all the infusion period of compound 20. The average weight loss in the treated animals was 12.7%, at day 5 of infusion. Following termination of drug treatment, the animals in the drug-treated group began to gain weight sustainably at essentially the same rate of weight gain as the mice infused with the vehicle.

20. In Vivo Tumor Xenograft Studies

Figure 4:
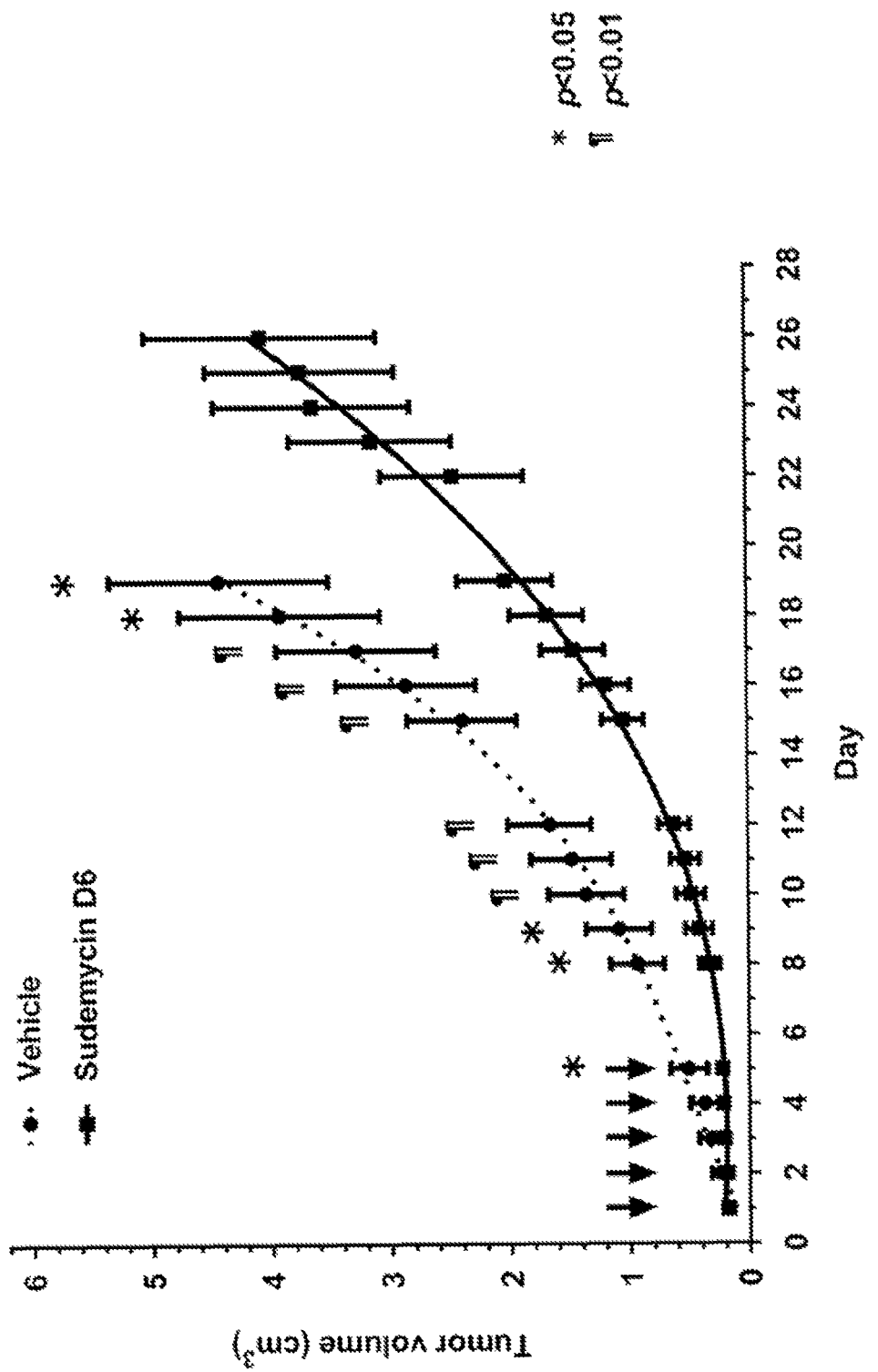
FIG. 4 shows the ability of compound 20 to inhibit SK-MEL-2 tumor growth in a mouse xenograft model. The arrows indicate a four hour infusion of 50 mg/kg of either vehicle of compound 20. Tumor growth was monitored daily 5 times per week. N=8 for the vehicle group and n=9 for the drug treated group. Mice were euthanized when the tumor burden reached the size limit (>4 cm$^3$). Error bars represent the SEM. Statistical evaluations were assessed using one-tailed t-Test, and the symbols above the lines indicate significant differences at: *=p<0.05; ¶=p<0.01.
Figure 5:
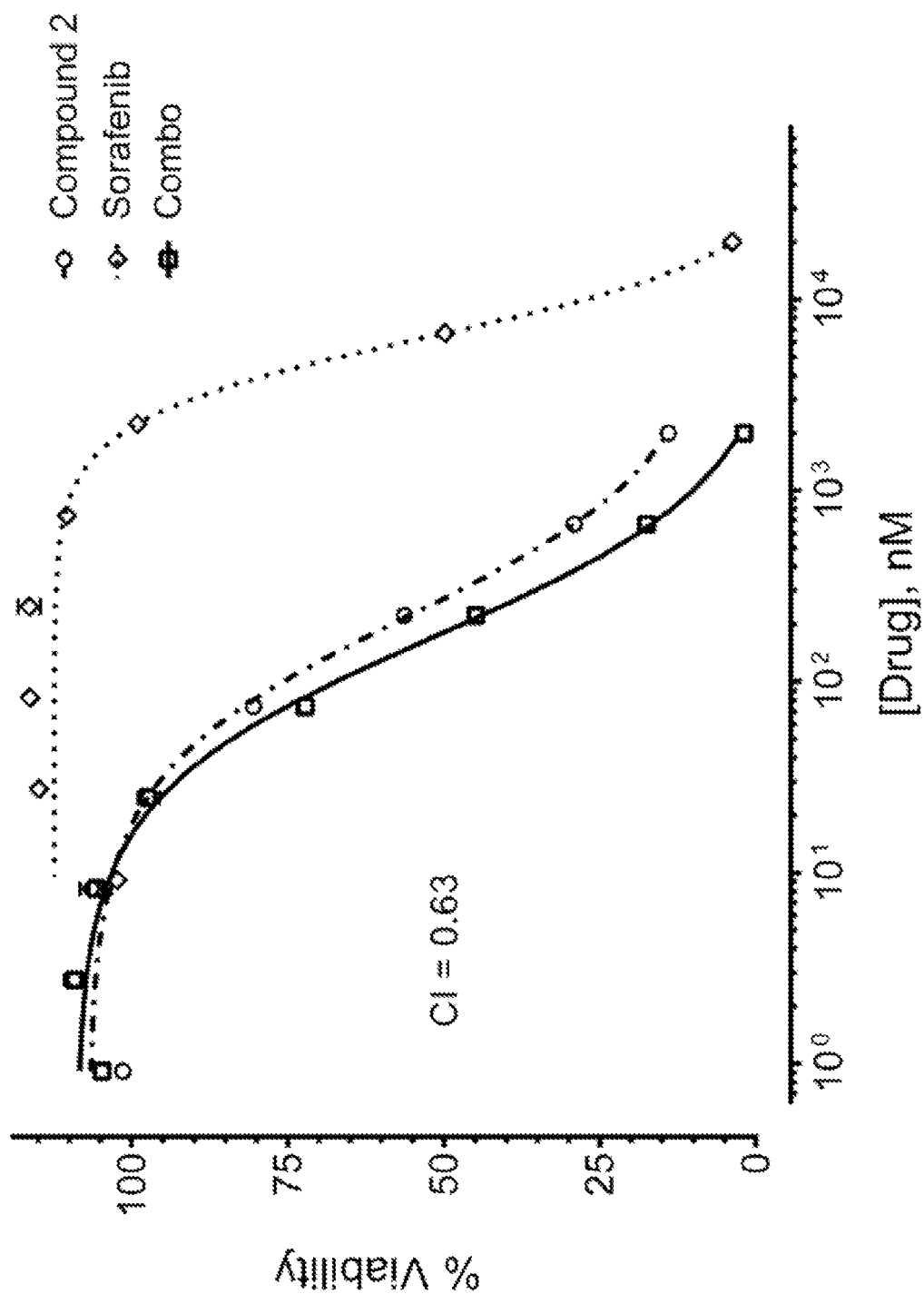
FIG. 5 shows the concentration-effect curve of compound 19 and Sorafenib. The interaction between compound 19 and Sorafenib is predominantly synergistic. The $IC_{50}$ curve of the drug combination in the neuroblastoma cell line SK-NA-S is plotted. Each experimental condition was carried out in triplicate; error bars represent the SEM. Drug interactions were assessed with the software CalcuSyn 2.1 (Biosoft, Cambridge, UK).
Figure 6:
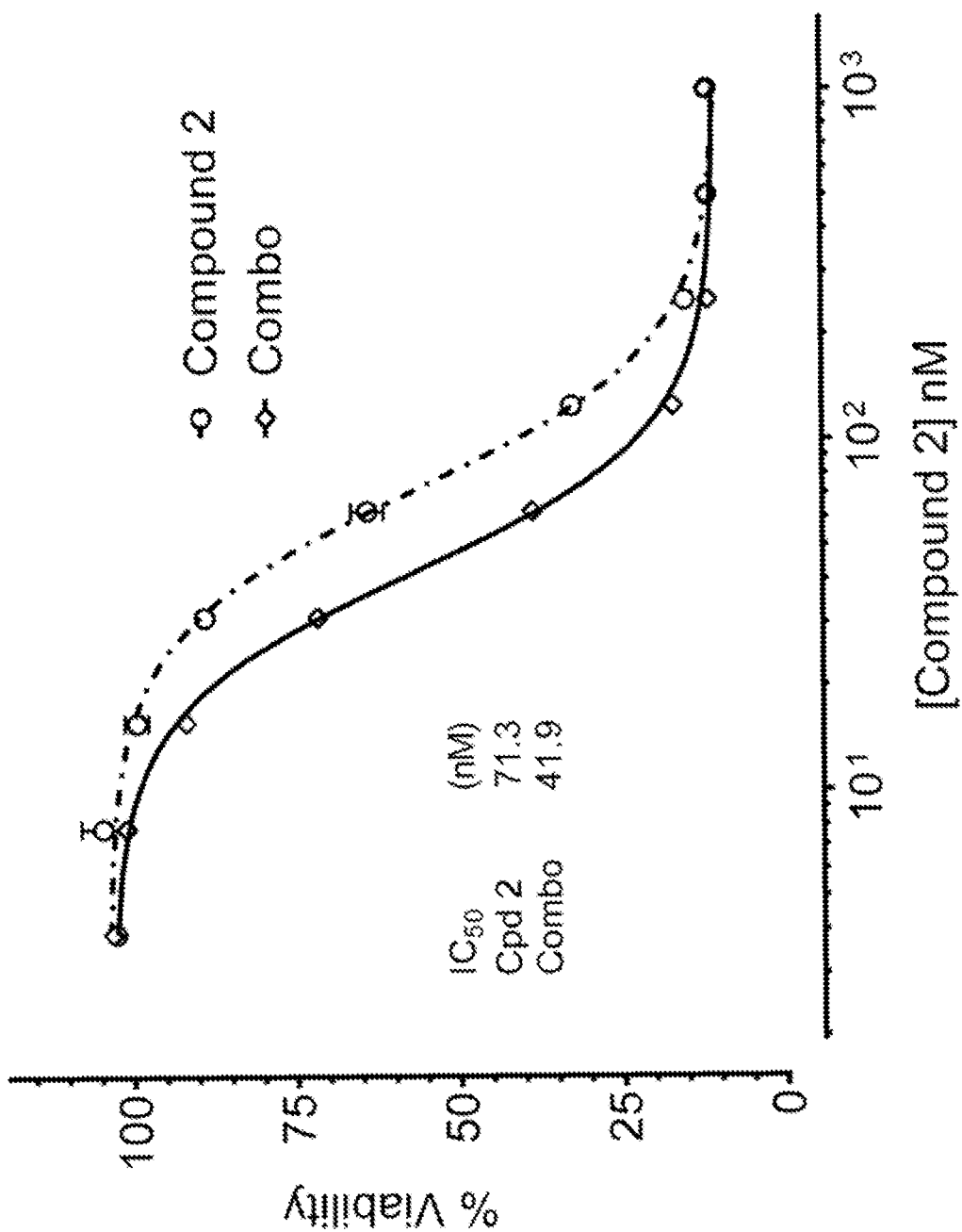
FIG. 6 shows that the inhibition of soluble epoxide hydrolase improves the $IC_{50}$ of compound 20. $IC_{50}$ curves of drug combinations in HeLa cells are shown. The combination index (CI) cannot be calculated, because AUDA (15 μM) alone is not cytotoxic. The drug doses required to inhibit 50% of cell proliferation ($IC_{50}$) were calculated based on the dose-response nonlinear regression 4 Parameter Logistic curve models. Each experimental condition was carried out in quadruplicate; error bars represent the SEM.

The efficacy of compound 20 in the inhibition of tumor growth in mice was evaluated using the methods as described herein above. Thus, SK-MEL-2 tumors were transplanted into male C.B-17 scid mice. The animals were subsequently infused over 4 h with either vehicle (8 mice) or compound 20 (9 mice) for 5 consecutive days. No differences in fatalities or behavioral changes were observed between the control infusion and the drug treatment groups. In the drug treated group (50 mg/kg of compound 20 over 4 h, once a day for 5 days) 100% inhibition of tumor growth was observed during the infusion period and significant inhibition observed subsequent to this dosing period (see FIG. 4). This demonstrates the single agent antitumor effects of splicing modulator 20 in this xenograft model of an aggressive metastatic human melanoma.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

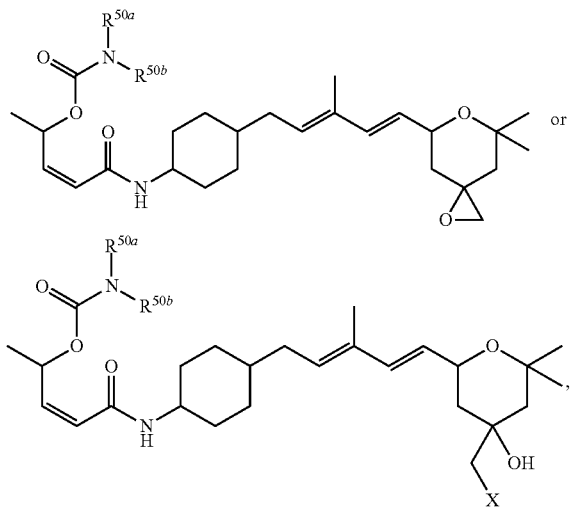

wherein $R^{50a}$ is selected from C1-C6 alkyl, C1-C6 monohaloalkyl, and C1-C6 polyhaloalkyl;

wherein $R^{50b}$ is selected from hydrogen, C1-C6 alkyl, C1-C6 monohaloalkyl, and C1-C6 polyhaloalkyl;

and wherein X is a leaving group;

or a pharmaceutically acceptable salt thereof.

2. The compound of claim 1, wherein $R^{50a}$ is selected from methyl, —$CH_2F$, —$CHF_2$, and —$CF_3$, and wherein $R^{50b}$ is selected from hydrogen, methyl, —$CH_2F$, —$CHF_2$, and —$CF_3$.

3. The compound of claim 1, wherein each of $R^{50a}$ and $R^{50b}$ is methyl.

4. The compound of claim 1, wherein $R^{50b}$ is hydrogen.

5. The compound of claim 1, wherein $R^{50b}$ is hydrogen and $R^{50a}$ is methyl is hydrogen and $R^{50b}$ is methyl.

6. The compound of claim 1, wherein X is selected from chloro, bromo, and iodo.

7. The compound of claim 1, having a structure represented by a formula:

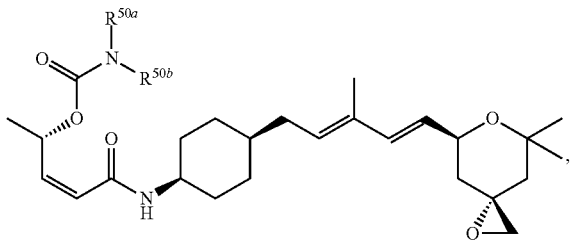

or a pharmaceutically acceptable salt thereof.

8. A pharmaceutical composition comprising a therapeutically effective amount of a compound having a structure represented by a formula:

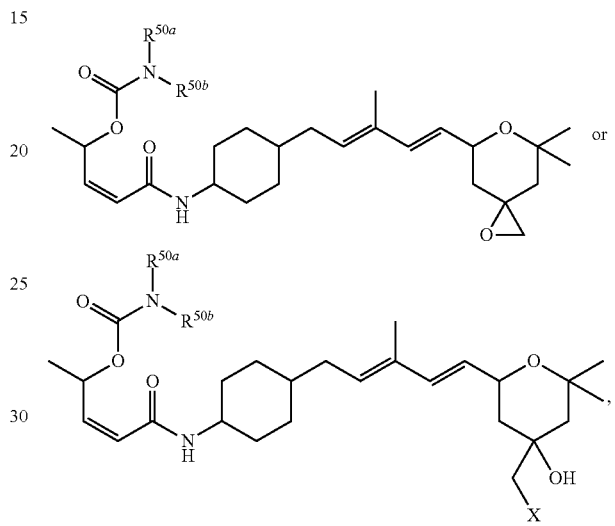

wherein $R^{50a}$ is selected from C1-C6 alkyl, C1-C6 monohaloalkyl, and C1-C6 polyhaloalkyl;

wherein $R^{50b}$ is selected from hydrogen, C1-C6 alkyl, C1-C6 monohaloalkyl, and C1-C6 polyhaloalkyl; and wherein X is a leaving group;

or a pharmaceutically acceptable salt thereof, and a pharmaceutically acceptable carrier.

9. The compound of claim 1, having a structure represented by a formula:

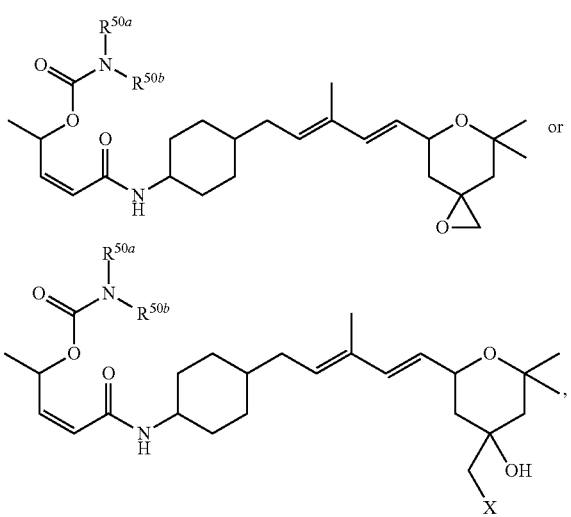

or a pharmaceutically acceptable salt thereof.

10. The compound of claim 1, having a structure represented by a formula:

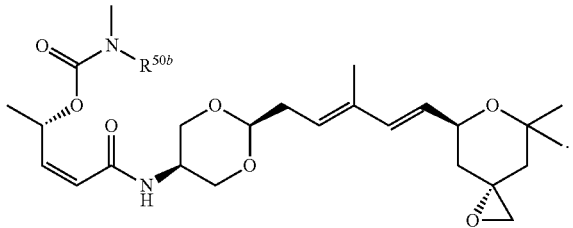

wherein $R^{50b}$ is hydrogen or C1-C4 alkyl,
or a pharmaceutically acceptable salt thereof.

11. The compound of claim 1, having a structure represented by a formula:

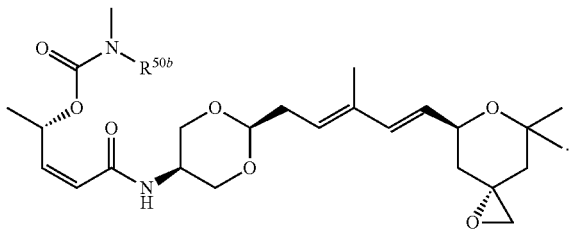

or a pharmaceutically acceptable salt thereof.

12. The compound of claim 1, wherein $R^{50b}$ is selected from hydrogen and C1-C6 alkyl.

13. The compound of claim 1, wherein $R^{50b}$ is C1-C6 alkyl.

14. The compound of claim 1, wherein $R^{50b}$ is selected from hydrogen and C1-C4 alkyl.

15. The compound of claim 1, wherein $R^{50b}$ is C1-C4 alkyl.

16. The composition of claim 8, wherein the compound has a structure represented by a formula:

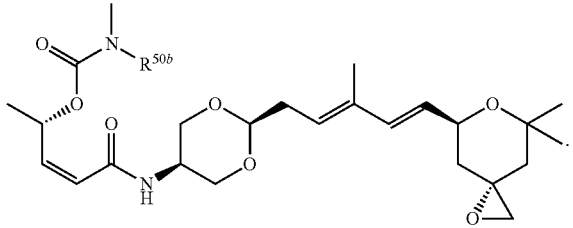

wherein $R^{50b}$ is hydrogen or methyl,
or a pharmaceutically acceptable salt thereof.

17. A method of treating leukemia or lymphoma in a subject, comprising the step of administering to the subject a therapeutically effective amount of a compound having a structure represented by a formula:

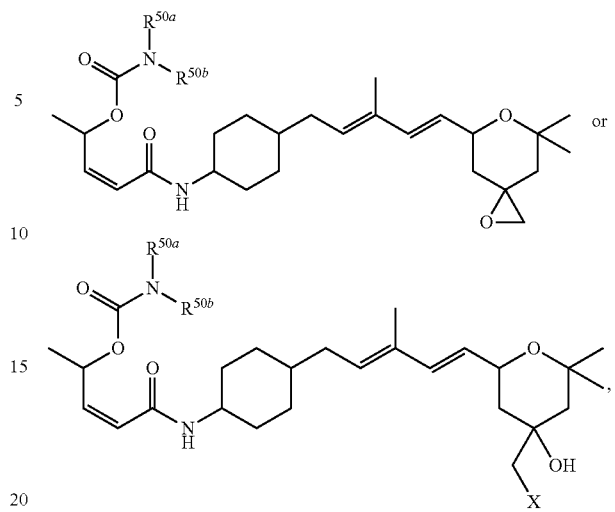

wherein $R^{50a}$ is selected from C1-C6 alkyl, C1-C6 monohaloalkyl, and C1-C6 polyhaloalkyl;
wherein $R^{50b}$ is selected from hydrogen, C1-C6 alkyl, C1-C6 monohaloalkyl, and C1-C6 polyhaloalkyl; and
wherein X is a leaving group;
or a pharmaceutically acceptable salt thereof.

18. The method of claim 17, wherein the leukemia is selected from acute leukemia, acute lymphocytic leukemia, acute myelocytic leukemia, myeloblastic leukemia, promyelocytic leukemia, myelomonocytic leukemia, monocytic leukemia, erythroleukemia, chronic leukemia, chronic myelocytic (granulocytic) leukemia, and chronic lymphocytic leukemia.

19. The method of claim 17, wherein the lymphoma is selected from AIDS-Related lymphoma, cutaneous T-Cell lymphoma, Hodgkin lymphoma, non-Hodgkin lymphoma, primary central nervous system lymphoma, mycosis fungoides and the Sézary Syndrome, heavy chain disease, and Waldenström macroglobulinemia.

20. The method of claim 17, wherein the compound has a structure represented by a formula:

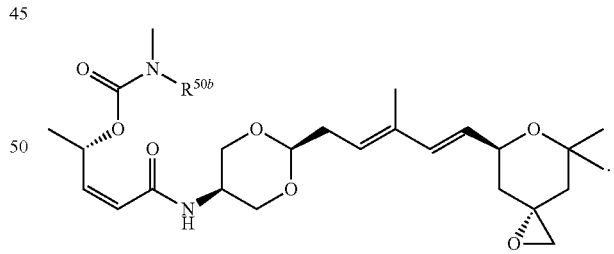

wherein $R^{50b}$ is hydrogen or methyl,
or a pharmaceutically acceptable salt thereof.

* * * * *

UNITED STATES PATENT AND TRADEMARK OFFICE
CERTIFICATE OF CORRECTION

PATENT NO.        : 9,682,993 B2
APPLICATION NO.   : 14/650826
DATED             : June 20, 2017
INVENTOR(S)       : Thomas R. Webb and Chandraiah Lagisetti Page 1 of 1

It is certified that error appears in the above-identified patent and that said Letters Patent is hereby corrected as shown below:

In the Specification

Column 1, Line 16 – Line 20:
Replace:
"The invention was made in part with government support under grant number CA014074, awarded by the National Institutes of Health. The government has certain rights in the invention."

With:
-- This invention was made with government support under grant CA014074 awarded by the National Institutes of Health. The government has certain rights in the invention. --

Signed and Sealed this
Tenth Day of July, 2018

Andrei Iancu
*Director of the United States Patent and Trademark Office*